United States Patent
Dranoff et al.

(10) Patent No.: US 7,250,291 B1
(45) Date of Patent: Jul. 31, 2007

(54) TUMOR ANTIGENS AND USES THEREOF

(75) Inventors: Glenn Dranoff, Lexington, MA (US); Jan Schmollinger, Berlin (DE); F. Stephen Hodi, Farmingham, MA (US); Joseph Mollick, Palo Alto, CA (US)

(73) Assignee: Dana-Farber Cancer Institute, Boston, MA (US)

( * ) Notice: Subject to any disclaimer, the term of this patent is extended or adjusted under 35 U.S.C. 154(b) by 0 days.

(21) Appl. No.: 09/762,577

(22) PCT Filed: Aug. 6, 1999

(86) PCT No.: PCT/US99/17738

§ 371 (c)(1),
(2), (4) Date: Aug. 29, 2002

Related U.S. Application Data

(60) Provisional application No. 60/095,766, filed on Aug. 7, 1998.

(51) Int. Cl.
*C12N 15/85* (2006.01)

(52) U.S. Cl. .................. 435/325; 435/320.1; 536/23.1; 536/24.3; 530/350

(58) Field of Classification Search ............... 536/23.1, 536/24.3; 435/320.1, 326; 514/44
See application file for complete search history.

(56) References Cited

U.S. PATENT DOCUMENTS 5,840,708 A * 11/1998 Weiss ........................ 514/44
6,472,172 B1 * 10/2002 Deng et al. ................ 435/69.1

OTHER PUBLICATIONS

Bowie et al (Science, 1990, 257:1306-1310).*
Burgess et al (J of Cell Bio. 111:2129-2138, 1990).*
Lazar et al (Molecular and Cellular Biology, 1988, 8:1247-1252).*
Miller (1995, FASEB J., vol. 9, pp. 190-199).*
Deonarain (1998, Expert Opin. Ther. Pat., vol. 8, pp. 53-69).*
Verma (Sep. 1997, Nature, vol. 389, pp. 239-242).*
Crystal (1995, Science, vol. 270, pp. 404-410).*
Branch, AD, 1998, TIBS 23: 45-50.*
Gura (Science, 1995, 270:575-577).*
MPSRCH search report, 2006, us09-762-577b-11.rni, pp. 2-3; and.*
MPSRCH search report, 2006, us-09-762-577b-12.p2n.rni, pp. 2-3.*
White et al, 2001 (Ann Rev Med, 52: 125-145).*
Boon, 1992 (Adv Can Res, 58:177-210).*
Ezzell, 1995 (J. NIH Res, 7:46-49).*
Spitler, 1995 (Cancer Biotherapy, 10:1-3).*
Gura, 1997, (Science, 278:1041-1042).*
Jain, 1994 (Sci. Am., 271:58-65).*
Curti, 1993 (Crit. Rev. in Oncology/Hermatology, 14:29-39).*
Hartwell et al (Science, 1997, 278:1064-1068).*
Dranoff et al., "Vaccination with irradiated tumor cells engineered to secrete murine granulocyte-macrophage colony-stimulating factor stimulates potent, specific, and long-lasting anti-tumor immunity," Proc. Natl. Acad. Sci. U.S.A. 90:3539-3543, 1993.
Dranoff et al., "A phase I study of vaccination with autologous, irradiated melanoma cells engineered to secrete human granulocyte-macrophage colony stimulating factor," Human Gene Therapy 7:111-123, 1997.
Ellem et al., "A case report: Immune responses and clinical course of the first human use of granulocyte/macrophage-colony-stimulating-factor-transduced autologous melanoma cells for immunotherapy," Cancer Immunol. Immunother. 44:10-20, 1997.
Jäger et al., "Strategies for the development of vaccines to treat breast cancer," Recent Results Cancer Res. (Germany) 152:94-102, 1998.
Scanlan et al., "Characterization of human colon cancer antigens recognized by autologous antibodies," Int. J. Cancer 76:652-658, 1998.
Simons et al., "Bioactivity of autologous irradiated renal cell carcinoma vaccines generated by ex vivo granulocyte-macrophage colony-stimulating factor gene transfer," Cancer Research 57:1537-1546, 1997.
Soffer et al., "Vaccination with irradiated autologous melanoma cells engineered to secrete human granulocyte-macrophage colony-stimulating factor generates potent antitumor immunity in patients with metastatic melanoma," Proc. Natl. Acad. Sci. U.S.A. 95:13141-13146, 1998.
Takahashi et al., "707-AP peptide recognized by human antibody induces human leukocyte antigen A2-restricted cytotoxic T lymphocyte killing of melanoma," Clin. Cancer Res. 3:1363-1370, 1997.
Genbank Accession No. AI459806, Hillier et al., WashU-NCI human EST Project, Mar. 9, 1999.
Genbank Accession No. AI590782, NCI-CGAP http://www.ncbi.nih.gov/ncicgap, National Cancer Institute, Cancer Genoma Anatomy Project (CGAP), Tumor Gene Index, May 14, 1999.
Genbank Accession No. AI115047, Marra et al., The WashU-HHMI Mouse EST Project, Sep. 2, 1998.

* cited by examiner

*Primary Examiner*—Shanon Foley
*Assistant Examiner*—Minh-Tam Davis
(74) *Attorney, Agent, or Firm*—Bromberg & Sunstein LLP

(57) ABSTRACT

The invention features tumor antigens; tumor antigen-encoding nucleic acids; antibodies specific for tumor antigens and methods of using the antibodies; methods of identifying tumor antigens and the nucleic acids that encode them; methods of monitoring or diagnosing tumors in patients; methods of testing patients for the increased likelihood of developing a tumor; and methods and compositions for treatment of a tumor or prophylaxis against developing a tumor.

5 Claims, 23 Drawing Sheets

Cell Cycle Analysis
293 WT Cells        293 MAIAP Transfected Cells
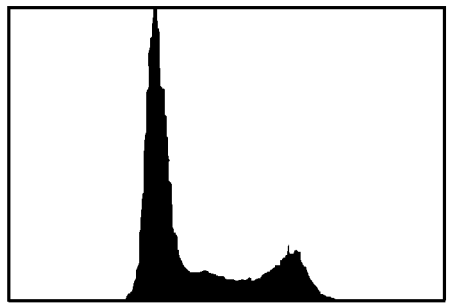
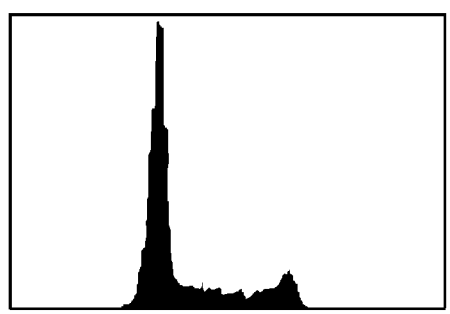
1 hr. after irradiation
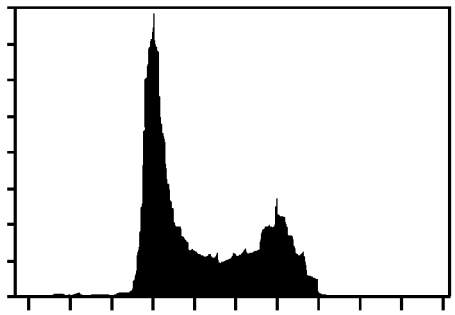
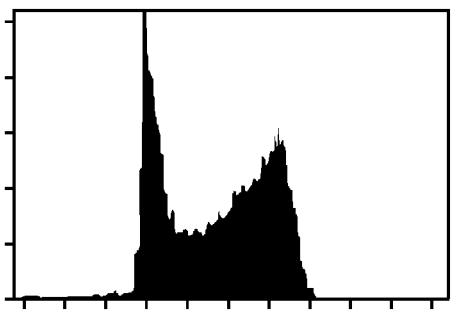
24 hrs. after irradiation
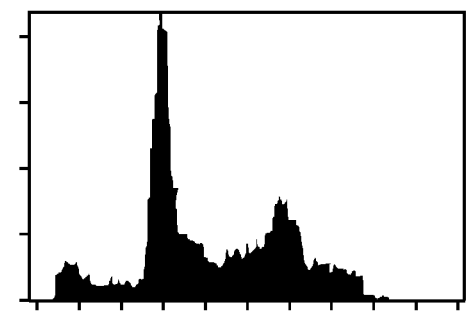
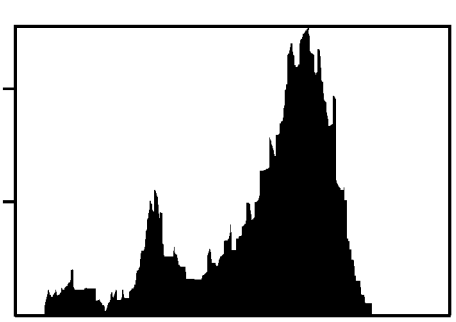
48 hrs. after irradiation
*FIG. 5*

```
ATGACAGGGTCCAGAAACTGGCGAGCCACGAGGGACATGTGTAGGTATCG
GCACAACTATCCGGATCTGGTGGAACGAGACTGCAATGGGGACACGCCAA
ACCTGAGTTTCTACAGAAATGAGATCCGCTTCCTGCCCAACGGCTGTTTC
ATTGAGGACATTCTTCAGAACTGGACGGACAACTATGACCTCCTTGAGGA
CAATCACTCCTACATCCAGTGGCTGTTTCCTCTGCGAGAACCAGGAGTGA
ACTGGCATGCCAAGCCCCTCACGCTCAGGGAGGTCGAGGTGTTTAAAAGC
TCCCAGGAGATCCAGGAGCGGCTTGTCCGGGCCTACGAGCTCATGCTGGG
CTTCTACGGGATCCGGCTGGAGGACCGAGGCACGGGCACGGTGGGCCGAG
CACAGAACTACCAGAAGCGCTTCCAGAACCTGAACTGGCGCAGCCACAAC
AACCTCCGCATCACACGCATCCTCAAGTCGCTGGGTGAGCTGGGCCTCGA
GCACTTCCAGGCGCCGCTGGTCCGCTTCTTCCTGGAGGAGACGCTGGTGC
GGCGGGAGCTGCCGGGGGTGCGGCAGAGTGCCCTGGACTACTTCATGTTC
GCCGTGCGCTGCCGACACCAGCGCCGCCAGCTGGTGCACTTCGCCTGGGA
GCACTTCCGGCCCCGCTGCAAGTTCGTCTGGGGGCCCCAAGACAAGCTGC
GGAGGTTCAAGCCCAGCTCTCTGCCCCATCCGCTCGAGGGCTCCAGGAAG
GTGGAGGAGGAAGGAAGCCCCGGGGACCCCGACCACGAGGCCAGCACCCA
GGGTCGGACCTGTGGGCCAGAGCATAGCAAGGGTGGGGGCAGGGTGGACG
AGGGGCCCCAGCCACGGAGCGTGGAGCCCCAGGATGCGGGACCCCTGGAG
AGGAGCCAGGGGGATGAGGCAGGGGGCCACGGGGAAGATAGGCCGGAGCC
CTTAAGCCCCAAAGAGAGCAAGAAGAGGAAGCTGGAGCTGAGCCGGCGGG
AGCAGCCGCCCACAGAGCCAGGCCCTCAGAGTGCCTCAGAGGTGGAGAAG
ATCGCTCTGAATTTGGAGGGGTGTGCCCTCAGCCAGGGCAGCCTCAGGAC
GGGGACCCAGGAAGTGGGCGGTCAGGACCCTGGGGAGGCAGTGCAGCCCT
GCCGCCAACCCCTGGGAGCCAGGGTGGCCGACAAGGTGAGGAAGCGGAGG
AAGGTGGATGAGGGTGCTGGGGACAGTGCTGCGGTGGCCAGTGGTGGTGC
CCAGACCTTGGCCCTTGCCGGGTCCCTGCCCCATCGGGGCACCCCAAGG
CTGGACACAGTGAGAACGGGGTTGAGGAGGACACAGAAGGTCGAACGGGG
CCCAAAGAAGGTACCCCTGGGAGCCCATCGGAGACCCCAGGCCCCCGCCC
AGCAGGACCTGCAGGGGACGAGCCAGCCGAGAGCCCATCGGAGACCCCAG
GCCCCAGCCCGGCAGGACCTACAAGGGATGAGCCAGCCGAGAGCCCATCG
GAGACCCCAGGCCCCGCCCGGCAGGACCTGCAGGGACGAGCCAGCCGA
GAGCCCATCGGAGACCCCAGGCCCCGCCCGGCAGGACCTGCAGGGGACG
AGCCAGCCGAGAGCCCATCGGAGACCCCAGGCCCCAGCCCGGCAGGACCT
ACAAGGGATGAGCCAGCCAAGGCGGGGAGGCAGCAGAGTTGCAGGACGC
AGAGGTGGAGTCTTCTGCCAAGTCTGGGAAGCCTTAA
```

FIG. 6

MTGSRNWRATRDMCRYRHKYPDLVERDCNGDTPNLSFYRNEIRFLPNGCFIEDIL
QNWTDNYDLLEDNHSYIQWLFPLREPGVNWHAKPLTLREVEVFKSSQEIQERLV
RAYELMLGFYGIRLEDRGTGTVGRAQNYQKRFQNLNWRSHNNLRITRILKSLGEL
GLEHFQAPLVRFFLEETLVRRELPGVRQSALDYFMFAVRCRHQRRQLVHFAWEH
FRPRCKFVWGPQDKLRRFKPSSLPHPLEGSRKVEEEGSPGDPDHEASTQGRTCGPE
HSKGGGRVDEGPQPRSVEPQDAGPLERSQGDEAGGHGEDRPEPLSPKESKKRKLEL
SRREQPPTEPGPQSASEVEKIALNLEGCALSQGSLRTGTQEVGGQDPGEAVQPCRQP
LGARVADKVRKRRKVDEGAGDSAAVASGGAQTLALAGSPAPSGHPKAGHSEN
GVEEDTEGRTGPKEGTPGSPSETPGPRPAGPAGDEPAESPSETPGPSPAGPTRDEPAE
SPSETPGPRPAGPAGDEPAESPSETPGPRPAGPAGDEPAESPSETPGPSPAGPTRDEP
AKAGEAAELQDAEVESSAKSGKP

FIG. 7

MRVLGTVLRWPVVVPRPWPLPGPLPHRGTPRLDTVRTGLRRTQKVERGPKKVPL
GAHRRPQAPAQQDLQGTSQPRAHRRPQAPARQDLQGMSQPRAHRRPQAPARQDL
QGTSQPRAHRRPQAPARQDLQGTSQPRAHRRPQAPARQDLQGMSQPRRGRQQSC
RTQRWSLLPSLGSL

FIG. 8

| Treatment Day | IL- pg/ml | IL-4 pg/ml | IL-5 pg/ml | IL-6 pg/ml | IL-10 pg/ml | GM-CSF pg/ml | γ-IFN g/ml | TNF-β pg/m |
|---|---|---|---|---|---|---|---|---|
| Tumor | 0 | 0 | 0 | 0 | 0 | 0 | 0 | 0 |
| Day 6 | 0 | 0 | 0 | 2.78 | 0 | 0 | 50 | 0 |
| Day 28 | 163 | 0 | 6.45 | 3.71 | 20 | 724 | 0 | 50 |
| Day 56 | 411 | 45 | 15.81 | 1.91 | 204 | 804 | 0 | 0 |
| Day 150 | 831 | 45 | 21.17 | 2.23 | 127 | 1,027 | 0 | 0 |

| Source | IL-4 pg/ml | IL-5 pg/ml | IL-6 pg/ml | IL-10 pg/ml | GM-CSF pg/ml | γ-IFN g/ml |
|---|---|---|---|---|---|---|
| TTLs | 166 | 7.7 | 2.9 | 2095 | 241 | 171 |
| Metastatis | 0 | 0 | 1.12 | 8.4 | 0 | 0 |

| Serum → <br> ↓ Tumor | K08 | K016 | K017 | K023 | K027 | K029 | K032 |
|---|---|---|---|---|---|---|---|
| K008 M | ++ | + | + | ++ | +++ | ++ | + |
| K016 V | ND | 0 | ND | ND | ND | ND | ND |
| K017 V | 0 | ND | + | ND | ND | + | ND |
| K023 V | ND | ND | ND | 0 | ++ | 1/2+ | ND |
| K023 M | 1/2+ | ND | ND | + | ND | 0 | + |
| K027 M | +++ | + | 0 | 0 | 0 | 0 | + |
| K029 V | ++ | 0 | 1/2+ | 0 | + | 0 | 0 |
| K029 M | + | 0 | 1/2+ | 0 | + | 0 | 0 |

TRAAM (a novel gene; 5' end)
TTCGGTTTCGCTTCCGCCTCCAGCGCGAGCCCCGCCGCCGCCGAGCATGGACGACCCCGA
CTGCGACTCCACCTGGGAGGAGGACGAGGAGGATGCGGAGGACGCGGAGGACGAGGACTG
CGAGGACGGCGAGGCCGCCGGCGCGAGGGACGCGGACGCAGGGGACGAGGACGAGGAGTC
GGAGGAGCCGCGGGCGGCGCGGCCCAGCTCGTTCCAGTCCAGAATGACAGGGTCCAGAAA
CTGGCGAGCCACGAGGGACATGTGTAGGTATCGGCACAACTATCCGGATCTGGTGGAACG
AGACTGCAATGGGGACACGCCAAACCTGAGTTTCTACAGAAATGAGATCCGCTTCCTGCC
CAACGGCTGTTTCATTGAGGACATTCTTCAGAACTGGACGGACAACTATGACCTCCTTGA
GGACAATCACTCCTACATCCAGTGGCTGTTTCCTCTGCGAGAACCAGGAGTGAACTGGCA
TGCCAAGCCCCTCACGCTCAGGGAGGTCGAGGTGTTTAAAAGCTCCCAGGAGATCCAGGA
GCGGCTTGTCCGGGCCTACGAGCTCATGCTGGGCTTCTACGGGATCCGGCTGGAGGACCG
AGGCACGGGCACGGTGGGCCGAGCACAGAACTACCAGAAGCGCTTCCAGAACCTGAACTG
GCGCAGCCACAACAACCTCCGCATCACACGCATCCTCAAGTCGCTGGGTGAGCTGGGCCT
CGAGCACTTCCAGGCGCCGCTGGTCCGCTTCTTCCTGGAGGAGACGCTGGTGCGGCGGGA
GCTGCCGGGGGTGCGGCAGAGTGCCCTGGACTACTTCATGTTCGCCGTGCGCTGCCGACA
CCAGCGCCGCCAGCTGGTGCACTTCGCCTGGGAGCACTTCCGGCCCCGCTGCAAGTTCGT
CTGGGGGCCCCAAGACAAGCTGCGGAGGTTCAAGCCCAGCTCTCTGCCCCATCCGCTCGA
GGGCTCCAGGAAGGTGGAGGAGGAAGGAAGCCCCGGGGACCCCGACCACGAGGCCAGCAC
CCAGGGTCGGACCTGTGGGCCAGAGCATAGCAAGGGTGGGGGCAGGGTGGACGAGGGGCC
CCAGCCACGGAGCGTGGAGCCCCAGGATGCGGGACCCCTGGAGAGGAGCCAGGGGGATGA
GGCAGGGGGCCACGGGGAAGATAGGCCGGAGCCCTTAAGCCCCAAAGAGAGCAAGAAGAG
GAAGCTGGAGCTGAGCCGGCGGGAGCAGCCGCCCACAGAGCCAGGCCCTCAGAGTGCCTC
AGAGGTGGAGAAGATCGCTCTGAATTTGGAGGGGTGTGCCCTCAGCCAGGGCAGCCTCAG
GACGGGGACCCAGGAAGTGGGCGGTCAGGACCCTGGGGAGGCAGTGCAACCCTGCCGGCA
ACCCCTGGGAGCCAGGGTGGCCGACAAGGTGAGGAAACCGGAGGAAGGTGGAT

TRAAM (amino terminus)
SVSLPPPARAPPPPSMDDPDCDSTWEEDEEDAEDAEDEDCEDGEAAGARDADAGDEDE
ESEEPRAARPSSFQSRMTGSRNWATRDMCRYRHNYPDLVERDCNGDTPNLSFYRNEIR
FLPNGCFIEDILQNWTDNYDLLEDNHSYIQWLFPLREPGVNWHAKPLTLREVEVFKSSQ
EIQERLVRAYELMLGFYGIRLEDRGTGTVGRAQNYQKRFQNLNWRSHNNLRITRILKSL
GELGLEHFQAPLVRFFLEETLVRRELPGVRQSALDYFMFAVRCRHQRRQLVHFAWEHF
RPRCKFVWGPQDKLRRFKPSSLPHPLEGSRKVEEEGSPGDPDHEASTQGRTCGPEHSKG
GGRVDEGPQPRSVEPQDAGPLERSQGDEAGGHGEDRPEPLSPKESKKRKLELSRREQPP
TEPGPQSASEVEKIALNLEGCALSQGSLRTGTQEVGGQDPGEAVQPCRQPLGARVADKV
RKPEEGG

TRAAM (3' end; sequence represents the coding strand of the gene, presented 5' to 3')
CGCGGTGGCTAGTGGTGGTGCCCAGACCTTGGCCCTTGCCGGGTCCCCTGCCCCATCGGG
GCACCCCAAGGCTGGACACAGTGAGAACGGGGTTGAGGAGGACACAGAAGGTCGAACGGG
GCCCAAAGAAGGTACCCCTGGGAGCCCATCGGAGACCCCAGGCCCCAGCCCAGCAGGACC
TGCAGGGGACGAGCCAGCCGAGAGCCCATCGGAGACCCCAGGCCCCGCCCAGCAGGACC
TGCAGGGGACGAGCCGGCCGAGAGCCCATCGGAGACCCCAGGCCCCGCCCAGCAGGACC
TGCAGGGGACGAGCCAGCCAAGACCCCATCGGAGACCCCAGGCCCCAGCCCGGCAGGACC
TACAAGGGATGAGCCAGCCGAGAGCCCATCGGAGACCCCAGGCCCCGCCCGGCAGGACC
TGCAGGGGACGAGCCAGCCGAGAGCCCATCGGAGACCCCAGGCCCCGCCCGGCAGGACC
TGCAGGGGACGAGCCAGCCGAGAGCCCATCGGAGACCCCAGGCCCCAGCCCGGCAGGACC
TACAAGGGATGAGCCAGCCAAGGCGGGGAGGCAGCAGAGTTGCAGGACGCAGAGGTGGA
GTCTTCTGCCAAGTCTGGGAAGCCTTAAGGAAAGGAGTGCCCGTCGGCGTCTTGGTCCTC
CTGTCCCTGCTGCAGGGGCTGGGGCCTCCGGAGCTGCTGCGGGCTCCCCTCAGGCTCTGC
TTCGTGACCCGTGACCCATGACCCACAGTGCTGGCCTCCTGTGGGGCCACTATAGCAGCC
ACCAGAAGCCGCGAGGCCCTCAGGGAAGCCCAAGGCCTGCAGAAGCCTCCTGGCCTGGCT
GTGTCTTCCCCACCCAGCTCTCCCCTGCGCCCCTGTCTTTGTAAATTGACCCTTCTGGAG
TGGGGGGCGGCGGGCAGGGCTGCTTTTCTTAGTCTGATGCCAAGCAAGGCCTTTTCTGAA
TAAATTCATTTGACTTTG

*FIG. 17A*

TRAAM (carboxy terminus)
RWLVVVPRPWPLPGPLPHRGTPRLDTVRTGLRRTQKVERGPKKVPLGAHRRPQAPAQQ
DLQGTSQPRAHRRPQAPAQQDLQGTSRPRAHRRPQAPAQQDLQGTSQPRPHRRPQAPA
RQDLQGMSQPRAHRRPQAPARQDLQGTSQPRAHRRPQAPARQDLQGTSQPRAHRRPQ
APARQDLQGMSQPRRGRQQSCRTQRWSLLPSLGSLKERSARRRLGPPVPAAGAGASGA
AAGSPQALLRDP KIAA0603 (in the database as a human brain cDNA of unknown function;
the human homolog of mouse TBC)
GAACTGAGGAGCTTGTGGAGAAAAGCTATACACCAACAAATCTTGTTACTTCGAATGGAA
AAAGAAAACCAGAAACTTGAAGCAAGCAGAGATGAACTCCAGTCCAGAAAAGTTAAATTA
GACTATGAAGAAGTTGGTGCATGTCAGAAAGAGGTCTTAATAACTTGGGATAAGAAGTTG
TTAAACTGCAGAGCTAAAATCAGATGTGATATGGAAGATATTCATACTCTTCTTAAAGAA
GGAGTTCCCAAAAGTCGACGAGGAGAAATTTGGCAGTTTCTGGCTTTACAGTACCGACTC
AGACACAGATTGCCTAATAAACAACAGCCTCCTGACATATCCTATAAGGAACTTTTGAAG
CAGCTCACTGCTCAGCAGCATGCGATTCTTGTGGATTTAGGAAGGACGTTTCCTACTCAC
CCTTACTTTTCAGTACAGCTTGGGCCAGGACAGCTGTCACTGTTTAACCTCCTGAAAGCC
TATTCATTCTTTGCTGGACAAAGAATGGGATACTGTCAGGGGATCAGCTTTGTGGCTGGA
GTCCTGCTTCTGCACATGAGTGAAGAGCAAGCCTTTGAAATGCTGAAATTCCTCATGTAT
GACCTCGGCTTCCGCAAGCAGTACAGACCTGACATGATGTCGCTGCAGATTCAAATGTAC
CAGCTGTCCAGGCTCCTTCATGACTATCACAGAGATCTCTACAATCACCTTGAAGAAAAT
GAAATCAGCCCCAGTCTTTATGCTGCCCCCTGGTTCCTCACATTGTTTGCCTCTCAGTTT
TCATTAGGATTTGTAGCCAGAGTTTTTGATATTATTTTCTTCAGGGAACTGAAGTTATA
TTCAAGGTTGCACTCAGCCTACTGAGCAGCCAAGAGACACTTATAATGGGAATGTGAGAG
CTTTGAAAATATTGTTGAGTTTCTTAAAAACACGCTACCTGATATGAATACCTCTGAAAT
GGAAAAAATTATTACCCAGGTTTTTGAGATGGATATTTCTAAGCAGTTGCATGCCTATGA
GGTGGAATATCATGTGCTACAGGATGAGCTTCAGGAATCTTCATATTCCTGTGAGGATAG
TGAAACTTTGGAGAAGCTGGAGAGGGCCAATAGCCAACTGAAAAGACAAAACATGGACCT
CCTAGAAAAATTACAGGTAGCTCATACTAAAATCCAGGCCTTGGAATCAAACCTGGAAAA
TCTTTTGACGAGAGAGACCAAAATGAAGTCTTTAATCCGGACCCTGGAACAAGAAAAAT
GGCTTATCAAAAGACAGTGGAGCAACTCCGGAAGCTGCTGCCCGCGGATGCTCTAGTCAA
TTGTGACCTGTTGCTGAGAGACCTAAACTGCAACCCTAACAACAAAGCCAGATAGGAAAT
AAGCCATAATTGAAGAGCCAGGCTCAGCAGAAAGTGCTCCTTAGAATACTACAGAGAGGA
AGAGCCTGCATGTCGCTGGCCCAAGGCTGGACCCTGAAGCTGATGGAACCACCTAATACT
GGTGCTGAGCTCCTAGTCACAGCAGGTGGACCTCGTGCTCATCAGAGCATGCCAATCTAA
GCCCATTGGACATAGTAGACTGGTTTTTGTTGTTGCTATGACATATAAATATATATATAA
AATGAACATAGTTCATGCTTTCAGATAAAATGAGTAGATGTATATTTAGATTAATTTTTT
TAGTCAGAACTTCATGAAATCCACACCAAAGGAAAGGTAAACTGAAATTTCCCTTGGACA
TATGTGAAATCTTTTTGTCTTTATAGTGAAACAAAGCCAGAGCATCTTTGTATATTGCAA
TATACTTGAAAAAAATGAATGTATTTTTTTCTCCAAAGAACAGCATGTTTCACTCAATGG
TGAAAAGGTGGAAACATTTATGTTAACTTTATGTGTTCTGTCTTGATATCTACTGACATT
GTCTATATGAGGAAAATGATTACTGGTCATGCTCCTGTGATTTTTGGGAAGGTAGGGTC
ATTTCTCCCTGCCTGCTTTGTGCCAACTAGCATGTTGCATCTACTGCATTATGAATCTGG
TGGCTTACTTTTAAACATACTAAAAACAGTAGGACTTGGCTGAATCTACCCCCAGGTAAA
GGAGAATGTTGCTTATTTTTAGCAAACTAACAGCCTTATTCTCAACTAAAATATCACAC
CTGAAAAATTTAATTTTTTGGTGCCACAGTCACCAAATGACAAGGATTTGCCACTTTCCC
ACCAAATTGTGAGTGCTTGTAATTTAGGTCTCTCTACCTTAAATTCAGTATAAGGAAACG
TAATTATGATTGATTTTTTCCAAAGATGACAAGCTGTGTTGAAATACATTTTTCTTTTGA
CCAATTGACAGAATCTAATAAGCTTTAATAATCTTCCCCTTTTATGTGAAAAGTTTTGAG
AACTGTGAAATGTTTAGGAACAAACTGTTGAAATCCATTGGAAGGGAAAAAAGAAAGTGG
TACCAGTGTTACCAGCTCAACTAAAACCTGCAATTGTGCATTTCAACTTTTCACTTCCTC
AGCATACAAATAGCTCATTAGAAGACATTCACGCATGGTGGGTATAGGCAAGGAAAGTAA
TTTTCAAAGTACATTTGCAGTTCTCTTTTTCAGAGATGATTCTATGATAGCGCCTCTGAA
AGTTGATGCAGCATTTTCGCCTTTCCAAAAAGTATTTATCCTCACTGCTTTTGCAGTAC
TTGTATTTTCACAGATGGATTATCTGGGGTAATTTTCTTCAAAGGGAGTTTGTTATACAC
AGTGAAAATGTATTATAGAGTAGAATAGTAAAGCTCTAGGGGTTTCAGAAAGCTTTGATG

FIG. 17B

```
AACAGATGACAAACATCTGAAACCCCCTCCGCACTGTTACCCAGTGTGTATATAATGACT
TGTTATAGCTCAGTGTGCCCTTGAATCCATACAGTTTCTTAAAAGACAATAAAATCTTAT
TAATAAAGTTAATGTAACTTCTAAGTTCTAGAAAATGCTGATTCTGTCTGCCCCATTCAA
TTGGGGGCTACTAATTGATTTGTTGCTTGGATTTCCTGAGAATTTCTCTATTTGTAGGAG
GGGTTTTTTCTTTTTACGGTCTGTTGATGACAATTACTTTATGGGTGTGATGCACCGATG
GTAGCCAAGGAATCTGTTGGGGAAGTTCGGAAAGAAACCTTTTCTTTCTTTTATTCAGTT
TAAAGTAAACTTTATCCTGGATGTTTAGAATCAACATTAAGAGTTATATTATGGTGTTCA
GAGATTAAGCTGACTTGGATACAATATTTTCTTTTGAAAATGAATTTTCTTTTTCATTTG
TGATTTTTAAAAAATGTTGCACCAGTTATGCTTCATGCATCGTTACATCTTCATCAGGTT
TGTAAAATGTCTAGTTCCTTTGCAATAAATATATTGCTGC
```

UBP-3 (a novel nuclear ubiquitin-specific protease)
```
MTVRNIASICNMGTNASALEKDIGPEQFPINEHYFGLVNFGNTCYCNSVLQALYFCRPFR
ENVLAYKAQQKKKENLLTCLADLFHSIATQKKKVGVIPPKKFISRLRKENDLFDNYMQQ
DAHEFLNYLLNTIADILQEEKKQEKQNGKLKNGNMNEPAENNKPELTWVHEIFQGTLTN
ETRCLNCETVSSKDEDFLDLSVDVEQNTSITHCLRDFSNTETLCSEQKYYCETCCSKQEA
QKRMRVKKLPMILALHLKRFKYMEQLHRYTKLSYRVVFPLELRLFNTSSDAVNLDRMY
DLVAVVVHCGSGPNRGHYITIVKSHGFWLLFDDDIVEKIDAQAIEEFYGLTSDISKNSESG
YILFYQSRE
```

**TPR/UBP-3 (a novel translocation; the 5' end is identical to the nucleoporin
TPR and the 3' end is a novel nuclear ubiquitin-specific protease)**
```
GAGAACTACAAAAAAGAAAAAGCAGAAAATGAAAAAATACAAAATGAGCAGCTTGAGAAA
CTTCAAGAACAAGTTACAGATTTGCGATCACAAAATACCAAAATTTCTACCCAGCTAGAT
TTTGCTTCTAAACGTTATGAAATGCTGCCAGATAATGTTGAAGGATATCGTCGAGAAATA
ACATCACTTCCTGAGAGAAATCAGAAACTCACTGCCACAACTCCAAAGCCAGAACAGATT
ATCCATACGATGACTCCGATTTGAGAGGAGCCAATGAGAAGCTAGCTGTCGCCGAAGTTT
GAGCCGAAAATTTGAAGAAGGAAAAGGAAATGCTTAAATTGTCTGAAGTTCGTCTTTCTC
AGCAAAGAGAGTCTTTGTTAGCTGAACAAAGGGGGCAAAACTTACTGCTAACTAATCTGC
AAACAATTCAGGGAATACTGGAGCGATCTGAAACAGAAACCAAACAAAGGCTTAGTAGCC
AGATAGAAAAACTGGAACATGAGATCTCTCATCTAAAGAAGAAGTTGGAAAATGAGGTGG
AACAAAGGCATACACTTACTAGAAATCTAGATGTTCAACTTTTAGATACAAAGAGACAAC
TGGATACAGAGACAAATCTTCATCTTAACACAAAAGAACTATTAAAAAATGCTCAAAAAG
AAATTGCCACATTGAAACAGCACCTCAGTAATATGGAAGTCCAAGTTGCTTCTCAGTCTT
CACAGAGAACTGGTAAAGGTCGGCCTAGCAACAAAGAAGATGTGGATGATCTTGTGAGTC
TGCTAAGACAGACAGAAGAGCAGGTGAATGACTTAAAGGAGAGACTCAAAAAAAACAAGT
ACGAGCAATGTGGAACAATATCAAGCAATGGTTACTAGTTTAGAAGAATCCCTGAACAAG
GAAAAACAGGTGACAGAAGAAGTGCGTAAGAATATTGAAGTTCGTTTAAAAGAGTCAGCT
GAATTTCAGACACAGTTGGAAAAGAAGTTGATGGAAGTAGAGAAGGAAAAACAAGAACTT
CAGGATGATAAAAGAAGAGCCATAGAGAGCATGGAACAACAGTTATCTGAATTGAAGAAA
ACACTTTCCTAGTGTTCAGAATGAAGTACAAGAAGCTCTTCAGAGAGCAAGCACAGCTTT
AAGTAATGAGCAGCAAGCCAGACGTGACTGTCAGGAACAAGCTAAAATAGCTGTGGAAGC
TCAGAATAAGTATGAGAGAGAATTGATGCTGCATGCTGCTGATGTTGAAGCTCTACAAGC
TGCGAAGGAGCAGGTTTCAAAAATGGCATCAGTCCGTCAGCATTTGGAAGAAACAACACA
GAAAGCAGAATCACAGTTGTTGGAGTGTAAAGCATCTTGGGAGGAAAGAGAGAGAATGTT
AAAGGATGAAGTTTCCAAATGTGTATGTCGCTGTGAAGATCTGGAGAAACAAAACAGATT
ACTTCATGATCAGATCGAAAAATTAAGTGACAAGGTCGTTGCCTCTGTGAAGGAAGGTGT
ACAAGGTCCCACTGAATGTATCTCTCAGTGAAGAAGGAAAATCTCAAGAACAAATTTTGG
AAATTCTCAGATTTATACGACGAGAAAAGAAATTGCTGAAACTAGGTTTGAGGTGGCTC
AGGTTGAGAGTCTGCGTTATCGACAAAGGGTTGAACTTTTAGAAAGAGAGCTGCAGGAAC
TGCAAGATAGTCTAAATGCTGAAAGGGAGAAAGTCCAGGTAACTGCAAAAACAATGGCTC
AGCATGAAGAACTGATGAAGAAAACTGAAACAATGAATGTAGTTATGGAGACCAATAAAA
TGCTAAGAGAAGAGAAGGAGAGACTAGAACAGGATCTACAGCAAATGCAAGCAAAGGTGA
```

*FIG. 17C*

```
GGAAACTGGAGTTAGATATTTTACCCTTACAAGAAGCAAATGCTGAGCTGAGTGAGAAAA
GCGGTATGTTGCAGGCAGAGAAGAAGCTCTTAGAAGAGGATGTCAAACGTTGGAAAGCAC
GTAACCAGCATCTAGTAAGTCAACAGAAAGATCCAGATACAGAAGAATATCGGAAGCTCC
TTTCTGAAAAGGAAGTTCATACTAAGCGTATTCAACAATTGACAGAAGAAATTGGTAGAC
TTAAAGCTGAAATTGCAAGATCAAATGCATCTTTGACTAACAACCAGAACTTAATTCAGA
GTCTGAAGGAAGATCTAAATAAAGTAAGAACTGAAAAGGAAACCATCCAGAAGGACTTAG
ATGCCAAAATAATTGATATCCAAGAAAAGTCAAAACTATTACTCAAGTTAAGAAAATTG
GACGTAGGTACAAGACTCAATATGAAGAACTTAAAGCACAACAGGATAAGGTTATGGAGA
CATCGGCTCAGTCTTCTGGAGACCATCAGGAGCAGCATGTTTCAGTCCAGGAAATGCAGG
AACTCAAAGAAACGCTCAACCAAGCTGAAACAAAATCAAAATCACTTGAAAGTCAAGTAG
AGAATTTGCAGAAGACATTATTTGAAAAAGAGACAGAAGCAAGAAATCTCCAGGAACAGA
CTGTGCAACTTCAGTCTGAACTTTCACGACTTTGTCAGGATTTTCAAGATAGAACCACAC
AGGAGGAGCAGCTCCGACAACAGATAACTAAAAAAAAAAAACTCGTGCCGAATTCGGCAC
GAGCTCCCAGCCAAATTGAAAGCCGGACCCCAGGCCGCCGCGTTGCCGCCCGGCCTCCCC
GCCAGCGCGCCACCATGGGCAGTCCCGGTTTCCCCTTGTAAAGATGGCGGTGAGGGATCG
CTGCAACCTTTAGATTAATGACTCTCCGAAACATCGCCTCCCATCTGTAATATGGGCACC
CAATGCTTTTGTTTTGGAAAAAGACATTGGTCCAGAGCAGTTTCCAATCAATGAACACTA
TTTCGGATTGGTCAATTTTGGAAACACATGCTACTGTAACTCCGTGCTTCAGGCATTGTA
CTTCTGCCGTCCATTCCGGGAGAATGTGTTGGCATACAAGGCCCAGCAAAAGAAGAAGGA
AAACTTGCTGACGTGCCTGGCGGACCTTTTCCACAGCATTGCCACACAGAAGAAGAAGGT
TGGCGTCATCCCACCAAAGAAGTTCATTTCAAGGCTGAGAAAAGAGAATGATCTCTTTGA
TAACTACATGCAGCAGGATGCTCATGAATTTTTAAATTATTTGCTAAACACTATTGCGGA
CATCCTTCAGGAGGAGAAGAAACAGGG
```

BRAP-2/H$^+$-ATPase (5' portion nearly identical with BRAP-2; 3' end identical to a portion of an accessory unit of H$^+$-ATPase)

```
AACAGATGGAAAAATAGTACAGTATGAATGTGAGGGGGATACTTGCCAGGAAGAGAAAAT
AGATGCCTTACAGTTAGAGTATTCATATTTACTAACAAGCCAGCTGGAATCTCAGCGAAT
CTACTGGGAAAACAAGATAGTTCGGATAGAGAAGGACACAGCAGAGGAAATTAACAACAT
GAAGACCAAGTTTAAAGAAACAATTGAGAAGTGTGATAATCTAGAGCACAAACTAAATGA
TCTCCTAAAAGAAAAGCAGTCTGTGGAAAGAAAGTGCACTCAGCTAAACACAAAAGTGGC
CAAACTCACCAACGAGCTCAAAGAGGAGCAGGAAATGAACAAGTGTTTGCGAGCCAACCA
AGTCCTCCTGCAGAACAAGCTAAAAGAGGAGGAGAGGGTGCTGAAGGAGACCTGTGACCA
AAAAGATCTGCAGATCACCGAGATCCAGGAGCAGCTGCGTGACGTCATGTTCTACCTGGA
GACACAGCAGAAGATCAACCATCTGCCTGCCGAGACCCGGCAGGAAATCCAGGAGGGACA
GATCAACATCGCCATGGCCTCGGCCTCGAGCCCTGCCTCTTCGGGGGGCAGTGGGAAGTT
GCCCTCCAGGAAGGGCCGCAGCAAGAGGGGCAAGTGACCTTCAGAGCAACAGACATCCCT
GAGACTGTTCTCCCTGACACTGTGAGAGTGTGCTGGGACCTTCAGCTAAATGTGAGGGTG
GGCCCTAATAAGTACAAGTGAGGATCAAGCCACAGTTGTTTGGCTCTTTCATTTGCTAGT
GTGTGATGTAGTGAATGTAAAGGGTGCTGACTGGAGAGCTGATAGAAAGGCGCTGCGTTC
GAAAAGGTCTTAAGAGTTCACTAACCTCACATTCTAATGACCATTTTGCCTTCCTGCTTG
GTAGAAGCCCCAACTCTGCTGTGCATTTTTCCATTGTATTTATGGAGTTGGCGTATTTGA
CATTCAGTTCTGGGGTAGGTTTAAGATGTTAAGTTATTTCTTGTAACCTCAAAGGTAAGG
TTATCTAGCACTAAAGCACCAAACCTCTCTGAGGGCATAACAGCTGCTTTAAAGAGAGGT
TTCCATTGGCTATTAAGGAGTTATGAAAACTCCCTAGCAATAGTGTCATATCATTATCAT
CTCCCCCTTCCTCTGGGGAGTGGAAGAATTGCTTGAATGTTATCTGAAAAGAGGCCTGGT
AGTAAACCAGGCCCTGGCTCTTTACCAGCAGTCATCTCTTCTTGCTCTGGGGCCAGCCAG
GAAAAACAAACAACCCGGGGCACATTGGGTAGACTCAGTGTAGGAAAAATGGTGGCAGCT
CCACTGTTTATTTTTGGTGACTTCGTACGTCATTATGAACCGCAATTAAGGAGGAGGCTT
AATGGCTGTTCCCAAACTCAAATCTCAGAGTGGGTATCCTAGCATCTAGCAAGACTGAGT
GGGGAGATTTCTCATCCGTGTGAAAATGTAGAGTGAGGCCTCTGACTAGCTAATTGTGTA
TTTTGTTGGGTTTAGTATTTTCTAAATGTTTACAAAATATTGGGCTGCATGTTCAGGTTG
```

FIG. 17D

```
CAGCTAGAGGGAGCTTGGGCAGATTTTCAATTACGCTTTCAAGATATAACCAAAAGCTGT
TTCTAAATCCTAAAATTAGAATTTCAACAGAGCCCCCTTTAGAACAGTCATATAACGCTT
GTGTGGGCCAACAGAGGGGCTGTGTACTCTCTCTGGAACCATAAATGTCAAATAATTTAT
AACCTGCAGTAATTGAGCAAACTTAAAATAAGACCTGTGTTGGAATTTAGTTTCTTGAAG
AGGTAGAGGGATAGGTTAGTAAGATGTATTGTTAAACAACAGGTTTTAGTTTTTGCTTTA
TAATTAGCCACAGGTTTTCAAATGATCACATTTCAGAATAGGTTTTTAGCCTGTAATTAG
GCCTCATCCCCTTTGACCTAAATGTCTTACATGTTACTTGTTAGCACATCAACTGTATCA
CTAATCACCATCTGTTTTTGTGGGATGTGCTGCAGCATTTCCCAAAAAACTTTACGTGTA
ATGTTGCAAAATGAATGTACTCAGACATTCTTAATTTTTACTTAGGGCAGACCAACTCTT
TGAGTCTCTCTTGGACTTATATATACAGATATCTTAAGAGTGGGAATGTAAAGCATAACC
TAATTCTCTTTCCTATAGAGATTCTATTTTATTTAAAATCTATTTTTACACTAGTTAGAA
TCCTGCTGTTTTGGATCAAGTACTTGTCTTGCATGTCTGACCTTGCAGAAGCTGGGGTGG
ATCATAGCATACTAATGAAGAGAATTAGAAGTAGTTTACAAAGCTCGCTCACTCCTCATT
TCTCTGTGATCCCTTCTATCCAGTGGCCCCACCACCACCTGGGAAAACAGATTTTTCAGT
ACAGGTGGGATAAATGCTCTGAAAGGCTGTGCCCAGAGGAATGAGCAAATAGGCAAGTGT
TTCCAAACTACTTGGAGGTTTACAAAAAATATGTCCCAGAAAAAAAAAAACTCGTGCCGA
ATTCGGCACGAGGGAGGACCTGACTCCCCTCACCTTTGGGGTGCAGGAACTCAACCTGAC
TGGCTCCTTCTGGAATGACTCCTTTGCCAGGCTCTCACTGACCTATGAACGACTCTTTGG
TACCACAGTGACATTCAAGTTCATTCTGGCCAACCGCCTCTACCCAGTGTCTGCCCGGCA
CTGGTTTACCATGGAGCGCCTCGAAGTCCACAGCAATGGCTCCGTCGCCTACTTCAATGC
TTCCCAGGTCACAGGGCCCAGCATCTACTCCTTCCACTGCGAGTATGTCAGCAGCCTGAG
CAAGAAGGGTAGTCTCCTCGTGGCCCGCACGCAGCCCTCTCCCTGGCAGATGATGCTTCA
GGACTTCCAGATCCAGGCTTTCAACGTAATGGGGAGCAGTTCTCCTACGCCAGCGACTG
TGCCAGCTTCTTCTCCCCCGGCATCTGGATGGGGCTGCTCACCTCCTGTTCATGCTCTT
CATCTTCACCTATGGCCTGCACATGATCCTCAGCCTCAAGACCATGGATCGCTTTGATGA
CCACAAGGGCCCCACTATTTCTTTGACCCAGATTGTGTGACCCTGTGCCAGTGGGGGGGT
TGAGGGTGGGACGGTGTCCGTGTTGTTGCTTTCCCACCCTGCAGCGCACTGGACTGAAGA
GCTTCCCTCTTCCTACTGCAGCATGAACTGCAAGCTCCCCTCAGCCCATCTTGCTCCCTC
TTCAGCCCGCTGAGGAGCTTTCTTGGGCTGCCCCATCTCTCCCAACAAGGTGTACATAT
TCTGCGTAGATGCTAGACCAACCAGCTTCCCAGGGTTCGTCGCTGTGAGGCGTAAGGGAC
ATGAATTCTAGGGTCTCCTTTCTCCTTATTTATTCTTGTGGCTACATCATCCCTGGCTGT
GGATAGTGCTTTTGTGTAGCAAATGCTCCCTCCTTAAGGTTATAGGGCTCCCTGAGTTTG
GGAGTGTGGAAGTACTACTTAACTGTCTGTCCTGCTTGGCTGTCGTTATCGTTTTCTGGT
GATGTTGTGCTAACAATAAGAAGTACACGGGTTTATTTCTGTGGCCTGAGAAGGAAGGGA
CCTCCACGACAGGTGGGCTGGGTGCGATCGCCGGCTGTTTGGCATGTTCCCACCGGGAGT
GCCGGGCAGGAGCATGGGGTGCT
```

K008-1 (a novel gene whose product bears homology to ankyrin containing proteins)

```
AAATATAGATCTCGACCTCGAAATTGTACAGTCTTTGCAGCATGGTCATGGAGGATGGAC
TGATGGAATGTTTGAGACTTTAACTACAACTGGAACTGTTTGTGGCATTGATGAAGATCA
TGACATTGTAGTACAGTATCCAAGTGGCAATAGGTGGACCTTCAATCCTGCTGTTCTCAC
TAAAGCGAACATTGTCCGAAGTGGAGATGCTGCTCAGGGTGCAGAAGGAGGCACCTCGCA
GTTTCAAGTGGGTGATCTTGTACAAGTTTGTTATGACCTGGAACGAATTAAACTTCTACA
AAGAGGACATGGAGAATGGGCTGAAGCGATGCTTCCAACTTTAGGTAAAGTTGGCCGAGT
ACAACAGATTTATTCAGACAGTGATTTAAAGGTGGAAGTTTGTGGAACATCTTGGACATA
CAATCCAGCAGCAGTTTCCAAGGTGGCATCTGCAGGATCAGCCATTAGCAATGCATCTGG
TGAAAGACTCTCACAACTCCTGAAGAAATTATTTGAAACCCAAGAATCTGGTGACCTCAA
TGAAGAATTAGTTAAGGCTGCTGCCAATGGAGATGTTGCTAAAGTGGAAGATTTGCTTAA
AAGACCAGATGTGGATGTAAATGGGCAATGTGCTGGCCACACAGCTATGCAAGCTGCTAG
TCAGAATGGACATGTTGACATTTTGAAGTTACTTTTGAAGCAAAACGTGGATGTCGAAGC
```

*FIG. 17E*

```
AGAGGATAAAGATGGTGATAGAGCAGTTCACCATGCAGCTTTTGGAGATGAAGGCGCTGT
TATAGAAGTACTACATCGAGGTAGTGCTGATTTGAATGCTCGAAACAAGCGCCGACAGAC
ACCACTTCATATTGCTGTCAATAAAGGTCATCTTCAAGTTGTGAAGACTTTATTGGACTT
TGGCTGTCATCCCAGTCTCCAGGATTCTGAAGGTGATACCCCTCTTCATGATGCAATAAG
TAAGAAACGTGATGATATCCTAGCAGTTCTTTTGGAAGCTGGAGCAGATGTTACCATCAC
AAACAATAATGGATTTAATGCTCTGCATCATGCTGCACTAAGGGGAAATCCCAGTGCAAT
GCGTGTTTTACTATCTAAATTACCAAGACCATGGATTGTGGATGAGAAGAAAGATGATGG
TTATACTGCCTTACATCTGGCTGCCCTTAATAATCACGTAGAAGTGGCTGAACTGTTGGT
ACATCAGGGTAATGCAAACCTGGATATCCAGAATGTGAACCAACAAACTGCCCTACACCT
TGCTGTTAACGACAGCATACCCAGATTGTTAGGCTTTTGGTCCGTGCAGGTGCCAAGCT
TGATATTCAGGATAAGGATGGGGATACTCCTTTGCATGAAGCTCTAAGGCATCACACTTT
GTCTCAGCTACGTCAGCTCCAAGATATGCAAGATGTGGGGAAGGTGGATGCTGCCTGGGA
GCCATCCAAAAACACGTTAATAATGGGACTTGGTACCCAGGGGGCAGAGAAGAAGAGTGC
AGCATCTATTGCCTGTTTCTTGGCAGCCAATGGTGCTGACCTGAGCATTCGAAATAAGAA
GGGTCAATCGCCACTTGATCTCTGTCCTGATCCGAATCTCTGCAAAGCACTGGCAAAGTG
TCATAAGGAAAAAGTCAGTGGTCAAGTGGGTTCTCGGAGTCCTTCTATGATTAGTAATGA
TTCTGAAACCTTAGAAGAGTGTATGGTGTGCTCAGATATGAAGAGAGATACTCTTTTTGG
TCCATGTGGACATATTGCTACCTGTTCTTTATGTTCTCCACGTGTCAAGAAATGCCTCAT
CTGTAAAGAACAGGTTCAATCCAGGACAAAGATTGAAGAATGTGTGGTATGCTCTGACAA
GAAAGCAGCTGTTCTTTTTCAACCCTGTGGCCACATGTGTGCTTGTGAGAACTGTGCTAA
CCTGATGAAAAAGTGTGTGCAGTGTCGAGCAGTAGTTGAACGAAGAGTGCCTTTCATTAT
GTGCTGTGGAGGGAAAAGTTCAGAAGATGCCACTGATGATATCTCAAGTGGGAATATTCC
AGTATTACAAAAGGACAAGGATAATACCAATGTCAATGCAGATGTGCAAAAGTTGCAGCA
ACAGTTACAAGACATTAAAGAGCAGACAATGTGCCCTGTGTGTCTAGATCGTCTGAAGAA
TATGATTTTCCTTTGTGGTCACGGAACCTGTCAACTCTGTGGAGACCGCATGAGTGAATG
TCCTATCTGTCGCAAGGCTATTGAACGAAGGATTCTTTTGTATTAACTAAGACACATGGT
GTATTTTGTTAGCTAATGTATCTAGTCATGAGATCTTAATAGGCTTTTGATCTAGTTGGA
AGTTCTGATGAGTTAATTTCTAATATCATAGTTTCTTTACTAGAGTATAATTGGGCTGTA
AATGTACCAGAACAAAAAACCCTACAAAATGGTGTTGGAAATTGTGTTTTTTGTTTTTGT
TTTAAATTTGAAACATCAAATTCATGTAACTCATAGGATAATTTACCTTTGGCTTCTAAG
AGGAAAGTCCTTTAAGGATATCCTTTTTTAAAAAATTGCATTTTTCTCTTATAATTTGTA
AATTTGTTGGATCTCAAAAGACATAATTCTTTGTGATCAGTTATCCTTCATTTCATCGTG
GTTTTACACAGTGAGTTGATAACAGGTTCTCTGAGAAGTCATGCATCAAATAAAAGAGGC
AGGTCAAACAATTATGTCACATGGTAAATTATAAAATGACAGTACAAGTTCCAGATAGTT
AAGGGAATACCGAAGGGATGATTCTTTTTTTAAGATAACAGGAAGTTACCCACATGTTTG
TTTCTGAATTCTTAGAGTAAATGGAAGCATAGAATGAGGGAATAATGACTTTGCATTTCT
CTTGTTTTCTAGATTCAAAAGGAACATTGTTTAACTTGAATCAGATTACCAGTTTCAAGG
TGACTGATAGACAAGAAAGGAAAATAAGCAATAATAGTGGGCAACTGAAGAGAAAAAA
AAAACGAGTATCTATTAACTGGCCACTAACAGTTGCCTTTCTTACATTAATTTATACACT
ATTTTGTTCAGCCAGTGTTTTAAAAAAAATCTATGAAAAGTGTACTTCCGGTTTTCTGT
GATTACTTATCTGGGCTTGATCTGACCAGTGAAATGACATTGCCCTATTTGGACCTCTGA
GGTTCTATTTAGCTTTGCAGATGTACATAGTATCCCAGTGATCTGCAAAATTAATGCCTT
TTCCAAGAAAAATCTTTTCTTCTCTGTATCAGTTAATTCTGACAGTGTTAGTGATTCTG
TCTTCATTATAGGCCTTATTTCCATTATCTCTTTCTTTATAGTATTTTTTGTTATAAAGA
AAACAGTCTTTCTGTGTATACCTACGGATGAGGGTATTATTTAAACTGCCAACAATATCC
AAGACATGGTCAATAACCTAATTATAAATACTTTAGAAAGAGTGACCAGGACATGTATAG
AAATGTCTGCTTACCTGTAGACTTT
```

NIDLDLEIVQSLQHGHGGWTDGMFETLTTTGTVCGIDEDHDIVVQYPSGNRWTFNPAVL
TKANIVRSGDAAQGAEGGTSQFQVGDLVQVCYDLERIKLLQRGHGEWAEAMLPTLGKVG
RVQQIYSDSDLKVEVCGTSWTYNPAAVSKVASAGSAISNASGERLSQLLKKLFETQESG
DLNEELVKAAANGDVAKVEDLLKRPDVDVNGQCAGHTAMQAASQNGHVDILKLLLKQNV
DVEAEDKDGDRAVAAAAFGDEGAVIEVLHRGSADLNARNKRRQTPLHIAVNKGHLQVVK
TLLDFGCHPSLQDSEGDTPLHDAISKKRDDILAVLLEAGADVTITNNNGFNALHHAALR
GNPSAMRVLLSKLPRPWIVDEKKDDGYTALHLAALNNHVEVAELLVHQGNANLDIQNVN
QQTALHLAVERQHTQIVRLLVRAGAKLDIQDKDGDTPLHEALRHHTLSQLRQLQDMQDV
GKVDAAWEPSKNTLIMGLGTQGAEKKSAASIACFLAANGADLSIRNKKGQSPLDLCPDP
NLCKALAKCHKEKVSGQVGSRSPSMISNDSETLEECMVCSDMKRDTLFGPCGHIATCSL
CSPRVKKCLICKEQVQSRTKIEECVVCSDKKAAVLFQPCGHMCACENCANLMKKCVQCR
AVVERRVPFIMCCGGKSSEDATDDISSGNIPVLQKDKDNTNVNADVQKLQQQLQDIKEQ
TMCPVCLDRLKNMIFLCGHGTCQLCGDRMSECPICRKAIERRILLYZLRHMVYFVSZCI
ZSZDLNRLLIZLEVLMSZFLISZFLYZSIIGLZMYQNKKPYKMVLEIVFFVFVLNLKHQ
IHVTHRIIYLWLLRGKSFKDILFZKIAFFSYNLZICWISKDIILCDQLSFISSWFYTVS
ZZQVLZEVMHQIKEAGQTIMSHGKLZNDSTSSRZLREYRRDDSFFKITGSYPHVCFZIL
RVNGSIEZGNNDFAFLLFSRFKRNIVZLESDYQFQGDZZTRKGKISNNSGQLKRKKKRV
SINWPLTVAFLTLIYTLFCSASVFKKNLZKVYFRFSVITYLGLIZPVKZHCPIWTSEVL
FSFADVHSIPVICKINAFSKKKSFLLCISZFZQCZZFCLHYRPYFHYLFLYSIFCYKEN
SLSVYTYGZGYYLNCQQYPRHGQZPNYKYFRKSDQDMYRNVCLPVDF

MAIAP (a novel member of the "inhibitor of apoptosis" family)

CGGCACGAGCTCGTGCCGGGCAGGCCTGTGCCTATCCCTGCTGTCCCCAGGGTGGGCCCC
GGGGGTCAGGAGCTCCAGAAGGGCCAGCTGGGCATATTCTGAGATTGGCCATCAGCCCCC
ATTTCTGCTGCAAACCTGGTCAGAGCCAGTGTTCCCTCCATGGGACCTAAAGACAGTGCC
AAGTGCCTGCACCGTGGACCACAGCCGAGCCACTGGGCAGCCGGTGATGGTCCCACGCAG
GAGCGCTGTGGACCCCGCTCTCTGGGCAGCCCTGTCCTAGGCCTGGACACCTGCAGAGCC
TGGGACCACGTGGATGGGCAGATCCTGGGCCAGCTGCGGCCCCTGACAGAGGAGGAAGAG
GAGGAGGGCGCCGGGGCCACCTTGTCCAGGGGGCCTGCCTTCCCCGGCATGGGCTCTGAG
GAGTTGCGTCTGGCCTCCTTCTATGACTGGCCGCTGACTGCTGAGGTGCCACCCGAGCTG
CTGGCTGCTGCCGGCTTCTTCCACACAGGCCATCAGGACAAGGTGAGGTGCTTCTTCTGC
TATGGGGGCCTGCAGAGCTGGAAGCGCGGGGACGACCCCTGGACGGAGCATGCCAAGTGG
TTCCCCAGCTGTCAGTTCCTGCTCCGGTCAAAAGGAAGAGACTTTGTCCACAGTGTGCAG
GAGACTCACTCCCAGCTGCTGGGCTCCTGGGACCCGTGGGAAGAACCGGAAGACGCAGCC
CCTGTGGCCCCCTCCGTCCCTGCCTCTGGGTACCCTGAGCTGCCCACACCCAGGAGAGAG
GTCCAGTCTGAAAGTGCCCAGGAGCCAGGAGCCAGGGATGTGGAGGCGCAGCTGCGGCGG
CTGCAGGAGGAGAGGACGTGCAAGGTGTGCCTGGACCGCGCCGTGTCCATCGTCTTTGTG
CCGTGCGGCCACCTGGTCTGTGCTGAGTGTGCCCCCGGCCTGCAGCTGTGCCCCATCTGC
AGAGCCCCCGTCCGCAGCCGCGTGCGCACCTTCCTGTCCTAGGCCAGGTGCCATGGCCGG
CCAGGTGGGCTGCAGAGTGGGCTCCCTGCCCCTCTCTGCCTGTTCTGGACTGTGTTCTGG
GCCTGCTGAGGATGGCAGAGCTGGTGTCCATCCAGCACTGACCAGCCCTGATTCCCCGAC
CACCGCCCAGGGTGGAGAAGGAGGCCCTTGCTTGGCGTGGGGGATGGCTTAACTGTACCT
GTTTGGATGCTTCTGAATAGAAATAAAGTGGGTTTTCCCTGGAGGT

*FIG. 17G*

MAIAP
MGPKDSAKCLHRGPQPSHWAAGDGPTQERCGPRSLGSPVLGLDTCRAWDHVDGQILGQLRPLTEE
EEEEGAGATLSRGPAFPGMGSEELRLASFYDWPLTAEVPPELLAAAGFFHTGHQDKVRCFFCYGG
LQSWKRGDDPWTEHAKWFPSCQFLLRSKGRDFVHSVQETHSQLLGSWDPWEEPEDAAPVAPSVPA
SGYPELPTPRREVQSESAQEPGARDVEAQLRRLQEERTCKVCLDRAVSIVFVPCGHLVCAECAPG
LQLCPICRAPVRSRVRTFLSZARCHGRPGGLQSGLPAPLCLFWTVFWAC

Nor-90 (originally identified as an autoantigen in scleroderma pigmentosum patients)
GAACTGAGGAGCTTGTGGAGAAAAGCTATACACCAACAAATCTTGTTACTTCGAATGGAA
AAAGAAAACCAGAAACTTGAAGCAAGCAGAGATGAACTCCAGTCCAGAAAAGTTAAATTA
GACTATGAAGAAGTTGGTGCATGTCAGAAAGAGGTCTTAATAACTTGGGATAAGAAGTTG
TTAAACTGCAGAGCTAAAATCAGATGTGATATGGAAGATATTCATACTCTTCTTAAAGAA
GGAGTTCCCAAAAGTCGACGAGGAGAAATTTGGCAGTTTCTGGCTTTACAGTACCGACTC
AGACACAGATTGCCTAATAAACAACAGCCTCCTGACATATCCTATAAGGAACTTTTGAAG
CAGCTCACTGCTCAGCAGCATGCGATTCTTGTGGATTTAGGAAGGACGTTTCCTACTCAC
CCTTACTTTTCAGTACAGCTTGGGCCAGGACAGCTGTCACTGTTTAACCTCCTGAAAGCC
TATTCATTCTTTGCTGGACAAAGAATGGGATACTGTCAGGGGATCAGCTTTGTGGCTGGA
GTCCTGCTTCTGCACATGAGTGAAGAGCAAGCCTTTGAAATGCTGAAATTCCTCATGTAT
GACCTCGGCTTCCGCAAGCAGTACAGACCTGACATGATGTCGCTGCAGATTCAAATGTAC
CAGCTGTCCAGGCTCCTTCATGACTATCACAGAGATCTCTACAATCACCTTGAAGAAAAT
GAAATCAGCCCCAGTCTTTATGCTGCCCCCTGGTTCCTCACATTGTTTGCCTCTCAGTTT
TCATTAGGATTTGTAGCCAGAGTTTTTGATATTATTTTTCTTCAGGGAACTGAAGTTATA
TTCAAGGTTGCACTCAGCCTACTGAGCAGCCAAGAGACACTTATAATGGGAATGTGAGAG
CTTTGAAAATATTGTTGAGTTTCTTAAAAACACGCTACCTGATATGAATACCTCTGAAAT
GGAAAAAATTATTACCCAGGTTTTTGAGATGGATATTTCTAAGCAGTTGCATGCCTATGA
GGTGGAATATCATGTGCTACAGGATGAGCTTCAGGAATCTTCATATTCCTGTGAGGATAG
TGAAACTTTGGAGAAGCTGGAGAGGGCCAATAGCCAACTGAAAAGACAAAACATGGACCT
CCTAGAAAAATTACAGGTAGCTCATACTAAAATCCAGGCCTTGGAATCAAACCTGGAAAA
TCTTTTGACGAGAGAGACCAAAATGAAGTCTTTAATCCGGACCCTGGAACAAGAAAAAAT
GGCTTATCAAAAGACAGTGGAGCAACTCCGGAAGCTGCTGCCCGCGGATGCTCTAGTCAA
TTGTGACCTGTTGCTGAGAGACCTAAACTGCAACCCTAACAACAAAGCCAGATAGGAAAT
AAGCCATAATTGAAGAGCACGGCTCAGCAGAAAGTGCTCCTTAGAATACTACAGAGAGGA
AGAGCCTGCATGTCGCTGGCCCAAGGCTGGACCCTGAAGCTGATGGAACCACCTAATACT
GGTGCTGAGCTCCTAGTCACAGCAGGTGGACCTCGTGCTCATCAGAGCATGCCAATCTAA
GCCCATTGGACATAGTAGACTGGTTTTTGTTGTTGCTATGACATATAAATATATATATAA
AATGAACATAGTTCATGCTTTCAGATAAAATGAGTAGATGTATATTTAGATTAATTTTTT
TAGTCAGAACTTCATGAAATCCACACCAAAGGAAAGGTAAACTGAAATTTCCCTTGGACA
TATGTGAAATCTTTTTGTCTTTATAGTGAAACAAAGCCAGAGCATCTTTGTATATTGCAA
TATACTTGAAAAAAATGAATGTATTTTTTTCTCCAAAGAACAGCATGTTTCACTCAATGG
TGAAAAGGTGGAAACATTTATGTTAACTTTATGTGTTCTGTCTTGATATCTACTGACATT
GTCTATATGAGGAAAATGATTACTGGTCATGCTCCTGTGATTTTTGGGAAGGTAGGGTC
ATTTCTCCCTGCCTGCTTTGTGCCAACTAGCATGTTGCATCTACTGCATTATGAATCTGG
TGGCTTACTTTTAAACATACTAAAAACAGTAGGACTTGGCTGAATCTACCCCCAGGTAAA
GGAGAATGTTGCTTATTTTTTAGCAAACTAACAGCCTTATTCTCAACTAAAATATCACAC
CTGAAAAATTTAATTTAGGACCTAAAATGTCTAGATTAGCTTTCTGCTTTTTTATTTGA
ATAACTCATTCAGTTGTGAATGAATTCCTCTTTATTTGGTGCCACAGTCACCAAATGACA
AGGATTTGCCACTTTCCCACCAAATTGTGAGTGCTTGTAATTTAGGTCTCTCTACCTTAA

FIG. 17H

```
ATTCAGTATAAGGAAACGTAATTATGATTGATTTTTTCCAAAGATGACAAGCTGTGTTGA
AATACATTTTTCTTTTGACCAATTGACAGAATCTAATAAGCTTTAATAATCTTCCCCTTT
TATGTGAAAAGTTTTGAGAACTGTGAAATGTTTAGGAACAAACTGTTGAAATCCATTGGA
AGGGAAAAAAGAAAGTGGTACCAGTGTTACCAGCTCAACTAAAACCTGCAATTGTGCATT
TCAACTTTTCACTTCCTCAGCATACAAATAGCTCATTAGAAGACATTCACGCATGGTGGG
TATAGGCAAGGAAAGTAATTTTCAAAGTACATTTGCAGTTCTCTTTTTCAGAGATGATTC
TATGATAGCGCCTCTGAAAGTTGATGCAGCATTTTCGCCTTTCCAAAAAGTATTTATCCT
CACTGCTTTTTGCAGTACTTGTATTTTCACAGATGGATTATCTGGGGTAATTTTCTTCAA
AGGGAGTTTGTTATACACAGTGAAAATGTATTATAGAGTAGAATAGTAAAGCTCTAGGGG
TTTCAGAAAGCTTTGATGAACAGATGACAAACATCTGAAACCCCTCCGCACTGTTACCC
AGTGTGTATATAATGACTTGTTATAGCTCAGTGTGCCCTTGAATCCATACAGTTTCTTAA
AAGACAATAAAATCTTATTAATAAAGTTAATGTAACTTCTAAGTTCTAGAAAATGCTGAT
TCTGTCTGCCCCATTCAATTGGGGCTACTAATTGATTTGTTGCTTGGATTTCCTGAGAA
TTTCTCTATTTGTAGGAGGGGTTTTTTCTTTTTACGGTCTGTTGATGACAATTACTTTAT
GGGTGTGATGCACCGATGGTAGCCAAGGAATCTGTTGGGGAAGTTCGGAAAGAAACCTTT
TCTTTCTTTTATTCAGTTTAAAGTAAACTTTATCCTGGATGTTTAGAATCAACATTAAGA
GTTATATTATGGTGTTCAGAGATTAAGCTGACTTGGATACAATATTTTCTTTTGAAAATG
AATTTTCTTTTTCATTTGTGATTTTTAAAAAATGTTGCACCAGTTATGCTTCATGCATCG
TTACATCTTCATCAGGTTAATGTAATGTCTAGTTCCTTTGCAATAAATATATTGCTGC
```

BR-1 (a novel gene; likely an alternatively spliced form of BR-2)

```
GCTGACTGGCTAGCACAAAACAACCCTCCTCAAATGCTATGGGAAAGAACAGAAGAGGAT
TCTAAAAGCATTAAAAGTGATGTTCCAGTGTACTTGAAAAGGTTGAAAGGAAATAAACAT
GATGATGGTACGCAAAGTGATTCAGAGAACGCTGGGGCTCACAGGCGCTGTAGCAAACGT
GCAACTCTTGAGGAACACTTAAGACGCCACCATTCAGAACACAAAAAGCTACAGAAGGTC
CAGGCTACTGAAAAGCATCAAGACCAAGCTGTTACTAGCTCTGCGCATCACAGAGGGGGG
CATGGTGTTCCACATGGGAAATTGTTAAAACAGAAATCAGAGGAGCCATCGGTGTCAATA
CCCTTCCTACAAACTGCATTATTAAGAAGTTCAGGGAGTCTTGGGCACAGACCAAGCCAG
GAGATGGATAAAATGTTAAAAAATCAAGCAACTTCTGCTACTTCTGAAAAGGATAATGAT
GATGACCAAAGTGACAAGGGTACTTATACCATTGAGTTAGAGAATCCCAACAGTGAGGAA
GTGGAAGCAAGAAAAATGATTGACAAGGTGTTTGGAGTAGATGACAATCAGGATTATAAT
AGGCCTGTTATCAACGAAAAACATAAAGATCTAATAAAAGATTGGGCTCTCAGTTCTGCT
GCAGCAGTAATGGAAGAAAGAAAACCACTGACTACATCTGGATTTCACCACTCAGAGGAA
GGCACATCTTCATCTGGAAGCAAACGTTGGGTTTCACAGTGGGCTAGTTTGGCTGCCAAT
CATACAAGGCATATCAAGAAGAAAGGATAATGGAATTTTCTGCACCTCTTCCTTTAGAGA
ATGAGACAGAGATCAGTGAGTCTGGCATGACAGTGAGAAGTACTGGCTCTGCAACTTCCT
TGGCTAGCCAGGGAGAGAGAAGGAGACGAACTCTTCCCCAGCTTCCAAATGAAGAAAAGT
CTCTTGAGAGCCACAGAGCAAAGGTTGTAACACAGAGGTCAGAGATAGGAGAAAAACAAG
ACACAGAACTTCAGGAGAAAGAAACACCTACACAGGTATACCAGAAAGATAAACAAGATG
CTGACAGACCCTTGAGTAAAATGAACAGGGCAGTAAATGGAGAGACTCTCAAAACTGGTG
GAGATAATAAAACCCTACTTCACTTAGGCAGCTCTGCTCCTGGAAAAGAGAAAAGTGAAA
CTGATAAGGAAACTTCTTTGGTAAAGCAAACATTAGCAAAACTTCAACAACAAGAACAAA
GGGAGGAGGCTCAGTGGACACCTACTAAATTGTCTTCCAAAAATGTTTCAGGTCAGACAG
ATAAATGTAGGGAGGAAACTTTTAAACAAGAATCACAACCTCCAGAAAAAAATTCAGGAC
ATTCTACAAGCAAAGGAGACAGAGTGGCACAAAGTGAGAGCAAGAGAAGAAAAGCTGAGG
AAATTCTGAAAAGTCAGACTCCAAAGGGAGGAGACAAGAAGGAATCCTCCAAGTCATTAG
TGCGACAAGGGAGCTTCACTATAGAAAAACCCAGCCCAAACATACCCATAGAACTTATTC
CCCATATAAATAAACAGACTTCCTCTACTCCTTCTTCTTTAGCATTAACATCTGCAAGTA
GAATACGAGAAAGAAGTGAGTCTTTGGATCCTGATTCTAGTATGGACACAACCCTTATTC
TAAAAGACACAGAAGCAGTAATGGCTTTTCTAGAAGCTAAACTACGTGAAGATAATAAAA
CTGATGAAGGACCAGATACTCCCAGTTATAATAGAGACAATTCTATTTCACCAGAATCTG
ATGTAGATACAGCTAGTACAATCAGTCTGGTTACTGGAGAAACTGAAAGAAAGTCAACCC
AAAAGCGAAAGAGTTTCACTAGCCTCTATAAAGATAGGTGTTCCACAGGTTCTCCTTCCA
AAGATGTTACAAAATCATCATCTTCAGGTGCTAGGG
```

*FIG. 17I*

BR-2 (a novel gene; 5' end; likely an alternatively spliced form of BR-1)

```
GGATGACGTAGCTTTGCCAAAGACTTAGAAGCTAAGCAGAAAATGAGCTTAACATCCTGG
TTTTTGGTGAGCAGTGGAGGCACTCGCCACAGGCTGCCACGAGAAATGATTTTTGTTGGA
AGAGATGACTGTGAGCTCATGTTGCAGTCTCGTAGTGTGGATAAGCAACACGCTGTCATC
AACTATGATGCGTCTACGGATGAGCATTTAGTGAAGGATTTGGGCAGCCTCAATGGGACT
TTTGTGAATGATGTAAGGATTCCGGAACAGACTTATATCACCTTGAAACTTGAAGATAAG
CTGAGATTTGGATATGATACAAATCTTTTCACTGTAGTACAAGGAGAAATGAGGGTCCCT
GAAGAAGCTCTTAAGCATGAGAAGTTTACCATTCAGCTTCAGTTGTCCCAAAAATCTTCA
GAATCAGAATTATCCAAATCTGCAAGTGCCAAAAGCATAGATTCAAAGGTAGCAGACGCT
GCTACTGAAGTGCAGCACAAAACTACTGAAGCACTGAAATCCGAGGAAAAAGCCATGGAT
ATTTCTGCTATGCCCCGTGGTACTCCATTATATGGGCAGCCGTCATGGTGGGGGGATGAT
GAGGTGGATGAAAAAAGAGCTTTCAAGACAAATGGCAAACCTGAAAAAAAAAACCATGAA
GCTGGAACATCAGGGTGCAGCATAGATGCCAAGCAAGTTGAGGAACAATCTGCAGCTGCA
AATGAAGAAGTACTTTTTCCTTTCTGTAGGGAACCAAGTTATTTTGAAATCCCTACAAAA
GAATTCCAGCAACCATCACAAATAACAGAAAGCACTATTCATGAAATCCCAACAAAAGAC
ACGCCAAGTTCCCATATAACAGGTGCAGGGCATGCTTCATTTACCATTGAATTTGATGAC
AGTACCCCAGGGAAGGTAACTATTAGAGACCATGTGACAAAGTTTACTTCTGATCAGCGC
CACAAGTCCAAGAAGTCTTCTCCTGGAACTCAAGACTTGCTGGGGATTCAAACAGGAATG
ATGGCACCCGAAAACAAAGTTGCTGACTGGCTAGCACAAAACAACCCTCCTCAAATGCTA
TGGGAAAGAACAGAAGAGGATTCTAAAAGCATTAAAAGTGATGTTCCAGTGTACTTGAAA
AGGTTGAAAGGAAATAAACATGATGATGGTACGCAAAGTGATTCAGAGAACGCTGGGGCT
CACAGGCGCTGTAGCAAACGTGCAACTCTTGAGGAACACTTAAGACGCCACCATTCAGAA
CACAAAAAGCTACAGAAGGTCCAGGCTACTGAAAAGCATCAAGACCAAGCTGTTGTGTTT
GGAGTAGATGACAATCAGGATTATAATAGGCCTGTTATCAACGAAAAACATAAAGATCTA
ATAAAAGATTGGGCTCTCAGTTCTGCTGCAGCAGTAATGGAAGAAAGAAAACCACTGACT
ACATCTGGATTTCACCACTCAGAGGAAGGCACATCTTCATCTGGAAGCAAACGTTGGGTT
TCACAGTGGGCTAGTTTGGCTGCCAATCATACAAGGCATGATCAAGAAGAAAGGATAATG
GAATTTTCTGCACCTCTTCCTTTAGAGAATGAGACAGAGATCAGTGAGTCTGGCATGACA
GTGAGAAGTACTGGCTCTGCAACTTCCTTGGCTAGCCAGGGAGAGAGAAGGAGACGAACT
CTTCCCCAGCTTCCAAATGAAGAAAAGTCTCTTGAGAGCCACAGAGCAAAGGTTGTAACA
CAGAGGTCAGAGATAGGAGAAAAACAAGACACAGAACTTCAGGAGAAAGAAACACCTACA
CAGGTATACCAGAAAGATAAACAAGATGCTGACAGACCCTTGAGTAAAATGAACAGGGCA
GTAAATGGAGAGACTCTCAAAACTGGTGGAGATAATAAAACCCTACTTCACTTAGGCAGC
TCTGCTCCTGGAAAAGAGAAAAGTGAAACTGATAAGGAAACTTCTTTGGTAAAGCAAACA
TTAGCAAAACTTCAACAACAAGAACAAAGGGAGGAGGCTCAGTGGACACCTACTAAATTG
TCTTCCAAAAATGTTTCAGGTCAGACAGATAAATGTAGGGAGGAAACTTTTAAACAAGAA
TCACAACCTCCAGAAAAAAATTCAGGACATTCTACAAGCAAAGGAGACAGAGTGGCACAA
AGTGAGAGCAAGAGAAGAAAAGCTGAGGAAATTCTGAAAAGTCAGACTCCAAAGGGAGGA
GACAAGAAGGAATCCTCCAAGTCATTAGTGCGACAAGGGAGCTTCACTATAGAAAACCC
AGCCCAAACATACCCATAGAACTTATTCCCCATATAAATAAACAGACTTCCTCTACTCCT
TCTTCTTTAGCATTAACATCTGCAAGTAGAATACGAGAAAGAAGTGAGTCTTTGGATCCT
GATTCTAGTATGGACAC
```

*FIG. 17J*

Gene AS (encodes a novel gene product; may be anti-sense of tyrosinase-replated protein-2)

```
AAAAGGAGGAGGCTTAATCAATATTGGGGGGGGGGTTATTATTAGATATCACAAATTGTC
AGGTCTATCTTTATTTGAAGGTAGAGGTAGCCTCAAGCACTTTAGTTGGGTTTGTTAAAC
AAGCAAGCAAAGCGGAAACTACAGCTAAGCATCTTCTGAATGAGATCATCATCACTATAG
AAGAACCTATGTCAAAGATCTTCAACTCAAGAAGGAACAGTGAGGATTAGTTCCTTTATT
GTCAGCGTCAGAACTGTGGCTTGGCCAGCCTCTTCTCTTAGGTAAGGCATGAGCACCCTA
GGCTTCTTCTGTGTATCTCTTGCTGCTTAAATGTGTCTCCATTAGGGGTGTATATCCTTT
TCGAAGTCTTCTATATTGAAGAAAAGCCAACAGCACAAAAAGACCAACCAAAGCCACCAG
TGTTCCCATGACTACTAAGAGAGTTGTGGGCCAACCTGGAGTTTCTTCAACTGAAACTGG
CAGATCGATGGCATAGCTGTAGCCAAGTTGGTCTGAGGTTAAAAAGAGTTCTTCATTAGT
CACTGGAGGGAAGAAAGGAACCATGTTGTACATCCGATTGTGACCAATAGGGGCCAGCTC
CTGAGGCCAGGCATCTGCAGGAGGATTAAATCTTTTCATCCACTCATCAAAGATGGCATC
AGTAAAGGAATGAAGAACCACAAAAATGGGATCATTGGCGGCTGAATGTGGCAAAGCGTT
TGTCCCGTTCAGGAAGGAATGAACCAAATTATGAAGGCTCATCACTTGAGAATCCAGAGT
CCCATCTGCTTTATCAAACCCTTCCAAAGCATTCCTGAAACTGAAGGTAGAGTTCTGGAA
GAAGGGAGGATTGTCAAACTTCTGGAGAGACAGGCAATCTCGTATGTCTTTTAAGGTTGG
CAATTTCATGCTGTTTCTTCCCATTTGATTTCTTCTCAGCAAACCTTCATAGGTTCCATT
GCACAAGGTGACCAGGTGGTTGTAGTCATCCAAGCTATCACAGACAGTTTCCCAGCTGGA
GAATCTTGAGTTCCGACTAATCAGAGTCGGATCGTCTGGTCTCGCTGCCCCAAACAGCTG
GTCTGTACACACATCACACTCGTTCCTCCCAGTGGCAAAGTTCCAGTAGGGCAAAGCAAA
AGACTCATTGCCAATGAGTCGCTGGAGATCTCTTTCCAGACACAACAAATGGTACCGGTG
CCAGGTAACAAATGCAGGTCCTTGATGTGAGAAATCTATGGCCCTGTAGGGGCGTCCTGG
TCCTAATAATGTATCTCTAACAGAATAATAATGGAGCCACACAAAAAAATCATAAACACT
GCAGTTGGCAAACTGCGGCTGGGTTCCATTGGGCCCAAGCAGGCCCAGCCAGTGTTGTGT
GGTGATCACGTAGTCGGGGTGTACTCTCTTCTTCGCGAGATCTAAGGCGCCCAAGAACTG
CTCTCTTTCCTGAGGACTCAAGGAATGGATGTTCTGCCGAATCACTGGTGGTTTCTTCCG
CTCGCAGTTGGGACCGGTCCAGCCAAACTTGCAGTCTCCACAATTATAGCCGGCAAAGTT
TCCTGTGCACTTGCAGGTCCGGTGGAAGAATTTTCTTGGCCACAGCTCACGGTCATCCTG
GTTTCGTAGGATGTAGGGACCACTCCAGGGCCTTGTGTCGGCTCGCACCTCTGTGCACTG
CCCCCGGCCTTGCTGAGAGCCACAGACATTGGCCGACTCTGCACCCAGGCGTGGGCAGCA
CTCCTTGTTCACTAGGCTGTCCACCGTCATGCAGACTCGGGGGAACTGACCCTGGGCTCC
TGGCAGGATTTTGCAGCCCAAGCAACTGAGCAGAAACCCCCACCAAAGGGGGCTCATGGC
TTTATAATTGGGAGAGCTCTCTCTCTCTTACTTTCCTTGTCTCTGTCGTACTTTTCTC
CTTATCTTCTACTCTTTCAGTCTTTTCTTTTCAGTATTTTTTATTTTTCTTTGCTTTCTA
TTCCTTTCTTCTTAAAAAAATACCCACAAGAATCACAGAGGTTACATGTGTGCACGGTTA
CATGTGTGCACATGTGTACATGAACGTGCACACACAATTTTATGTGATTCAAACAACTAA
CAGACTTAATTTCCTTAGAAGCGCCTCTAACAACCAAATTTAATGAGGGTAGCGCTTCTC
ACCATCTTCCCCCGTTAAGTCAGGCTTTGTCTAATTGAGTTAATTTACAGAGCACCCAGT
CATACTACTTATTATGCTGGTATTTCTAAACCCTCTCCCTCCCTCCTTAGCTCTTGACTT
TAATCTCGTGCCGAATTCGGCACGAGAATTGTTAAAACAGAAATCAGAGGAGCCATCGGT
GTCAATACCCTTCCTACAAACTGCATTATTAAGAAGTTCAGGGAGTCTTGGGCACAGACC
AAGCCAGGAGATGGATAAAATGTTAAAAAATCAAGCAACTTCTGCTACTTCTGAAAAGGA
TAATGATGATGACCAAAGTGACAAGGGTACTTATACCATTGAGTTAGAGAATCCCAACAG
TGAGGAAGTGGAAGCAAGAAAAATGATTGACAAGGTGTTTGGAGTAGATGACAATCAGGA
TTATAATAGGCCTGTTATCAACGAAAAACATAAAGATCTAATAAAAGATTGGGCTCTCAG
TTCTGCTGCAGCAGTAATGGAAGAAAGAAAACCACTGACTACATCTGGATTTCACCACTC
AGAGGAAGGCACATCTTCATCTGGAAGCAAACGTTAGGTTTCACAGTGGGCTAGTTTGGC
TGCCAATCATACAAGGCATGATCAAGAAGAAAGGATAATGGAATTTTCTGCACCTCTTCC
TTTAGAGAATGAGACAGAGATCAGTGAGTCTGGCATGACAGTGAGAAGTACTGGCTCTGC
AACTTCCTTGGCTAGCCAGGGAGAGAGAAGGAGACGAACTCTTCCCCAGCTTCCAAATGA
AGAAAAGTCTCTTGAGAGCCACAGAGCAAAGGTTGTAACACAGAGGTCAGAGATAGGAGA
AAAACAAGACACAGAACTTCAGGAGAAAGAAACACCTACACAGGTATACCAGAAAGATAA
ACAAGATGCTGACAGACCCTTGAGTAAAATGAACAGGGCAGTAAATGGAGAGACTCTCAA
AACTGGTGGAGATAATAAAACCCTACTTCACTTAGGCAGCTCTGCTCCTGGAAAAGAGAA
AAGTGAAACTGATAAGGAAACTTCTTTGGTAAAGCAAACATTAGCAAAACTTCAACAACA
AGAACAAAGGGAGGAGGCTCAGTGGACACCTACTAAATTGTCTTCCAAAAATGTTTCAGG
TCAGACAGATAAATGTAGGGAGGAAACTTTTAAACAAGAATCACAACCTCCAGAAAAAAA
TTCAGGACATTCTACAAGCAAAGGAGACAGAGTGGCACAAAGTGAGAGCAAGAGAAGAAA
AGCTGAGGAAATTCTGAAAAGTCAGACTCCAAAGGGAGGAGACAAGAAGGAATCCTCCAA
GTCATTAGTGCGACAAGGGAGCTTCACTATAGAAAAACCCAGCCCAAACATACCCATAGA
ACTTATTCCCCATATAAATAAACAGACTTCCTCTACTCCTTCTTCTTTAGCATTAACATC
TGCAAGTAGAATACGAG
```

*FIG. 17K*

SEQUENCE LISTING

<160> NUMBER OF SEQ ID NOS: 68

<210> SEQ ID NO 1
<211> LENGTH: 1433
<212> TYPE: DNA
<213> ORGANISM: homo sapiens

<400> SEQUENCE: 1

```
ttcggtttcg cttccgcctc cagcgcgagc cccgccgccg ccgagcatgg acgaccccga      60
ctgcgactcc acctgggagg aggacgagga ggatgcggag gacgcggagg acgaggactg     120
cgaggacggc gaggccgccg cgcgaggga cgcggacgca ggggacgagg acgaggagtc     180
ggaggagccg cgggcggcgc ggcccagctc gttccagtcc agaatgacag ggtccagaaa     240
ctggcgagcc acgagggaca tgtgtaggta tcggcacaac tatccggatc tggtggaacg     300
agactgcaat ggggacacgc caaacctgag tttctacaga aatgagatcc gcttcctgcc     360
caacggctgt ttcattgagg acattcttca gaactggacg gacaactatg acctccttga     420
ggacaatcac tcctacatcc agtggctgtt tcctctgcga gaaccaggag tgaactggca     480
tgccaagccc ctcacgctca gggaggtcga ggtgtttaaa agctcccagg agatccagga     540
gcggcttgtc cgggcctacg agctcatgct gggcttctac gggatccggc tggaggaccg     600
aggcacgggc acggtgggcc gagcacagaa ctaccagaag cgcttccaga acctgaactg     660
gcgcagccac aacaacctcc gcatcacacg catcctcaag tcgctgggtg agctgggcct     720
cgagcacttc caggcgccgc tggtccgctt cttcctggag gagacgctgg tgcggcggga     780
gctgccgggg gtgcggcaga gtgccctgga ctacttcatg ttcgccgtgc gctgccgaca     840
ccagcgccgc cagctggtgc acttcgcctg ggagcacttc cggccccgct gcaagttcgt     900
ctgggggccc caagacaagc tgcggaggtt caagcccagc tctctgcccc atccgctcga     960
gggctccagg aagtggagg aggaaggaag ccccgggac cccgaccacg aggccagcac    1020
ccagggtcgg acctgtgggc cagagcatag caagggtggg ggcagggtgg acgaggggcc    1080
ccagccacgg agcgtggagc cccaggatgc gggaccccctg gagaggagcc aggggatga    1140
ggcaggggggc cacgggggaag ataggccgga gcccttaagc cccaaagaga gcaagaagag    1200
gaagctggag ctgagccggc gggagcagcc gcccacagag ccaggccctc agagtgcctc    1260
agaggtggag aagatcgctc tgaatttgga ggggtgtgcc ctcagccagg gcagcctcag    1320
gacggggacc caggaagtgg gcggtcagga ccctggggag gcagtgcaac cctgccggca    1380
acccctggga gccagggtgg ccgacaaggt gaggaaaccg gaggaaggtg gat            1433
```

<210> SEQ ID NO 2
<211> LENGTH: 477
<212> TYPE: PRT
<213> ORGANISM: homo sapiens

<400> SEQUENCE: 2

```
Ser Val Ser Leu Pro Pro Pro Ala Arg Ala Pro Pro Pro Ser Met
 1               5                  10                  15
Asp Asp Pro Asp Cys Asp Ser Thr Trp Glu Glu Asp Glu Glu Asp Ala
            20                  25                  30
```

-continued

```
Glu Asp Ala Glu Asp Asp Cys Glu Asp Gly Glu Ala Ala Gly Ala
         35                  40                  45
Arg Asp Ala Asp Ala Gly Asp Glu Asp Glu Glu Ser Glu Glu Pro Arg
 50                  55                  60
Ala Ala Arg Pro Ser Ser Phe Gln Ser Arg Met Thr Gly Ser Arg Asn
 65                  70                  75                  80
Trp Arg Ala Thr Arg Asp Met Cys Arg Tyr Arg His Asn Tyr Pro Asp
                 85                  90                  95
Leu Val Glu Arg Asp Cys Asn Gly Asp Thr Pro Asn Leu Ser Phe Tyr
                100                 105                 110
Arg Asn Glu Ile Arg Phe Leu Pro Asn Gly Cys Phe Ile Glu Asp Ile
            115                 120                 125
Leu Gln Asn Trp Thr Asp Asn Tyr Asp Leu Leu Glu Asp Asn His Ser
    130                 135                 140
Tyr Ile Gln Trp Leu Phe Pro Leu Arg Glu Pro Gly Val Asn Trp His
145                 150                 155                 160
Ala Lys Pro Leu Thr Leu Arg Glu Val Glu Val Phe Lys Ser Ser Gln
                165                 170                 175
Glu Ile Gln Glu Arg Leu Val Arg Ala Tyr Glu Leu Met Leu Gly Phe
            180                 185                 190
Tyr Gly Ile Arg Leu Glu Asp Arg Gly Thr Gly Thr Val Gly Arg Ala
        195                 200                 205
Gln Asn Tyr Gln Lys Arg Phe Gln Asn Leu Asn Trp Arg Ser His Asn
    210                 215                 220
Asn Leu Arg Ile Thr Arg Ile Leu Lys Ser Leu Gly Glu Leu Gly Leu
225                 230                 235                 240
Glu His Phe Gln Ala Pro Leu Val Arg Phe Phe Leu Glu Glu Thr Leu
                245                 250                 255
Val Arg Arg Glu Leu Pro Gly Val Arg Gln Ser Ala Leu Asp Tyr Phe
            260                 265                 270
Met Phe Ala Val Arg Cys Arg His Gln Arg Gln Leu Val His Phe
        275                 280                 285
Ala Trp Glu His Phe Arg Pro Arg Cys Lys Phe Val Trp Gly Pro Gln
    290                 295                 300
Asp Lys Leu Arg Arg Phe Lys Pro Ser Ser Leu Pro His Pro Leu Glu
305                 310                 315                 320
Gly Ser Arg Lys Val Glu Glu Glu Gly Ser Pro Gly Asp Pro Asp His
                325                 330                 335
Glu Ala Ser Thr Gln Gly Arg Thr Cys Gly Pro Glu His Ser Lys Gly
            340                 345                 350
Gly Gly Arg Val Asp Glu Gly Pro Gln Pro Arg Ser Val Glu Pro Gln
        355                 360                 365
Asp Ala Gly Pro Leu Glu Arg Ser Gln Gly Asp Glu Ala Gly Gly His
    370                 375                 380
Gly Glu Asp Arg Pro Glu Pro Leu Ser Pro Lys Glu Ser Lys Lys Arg
385                 390                 395                 400
Lys Leu Glu Leu Ser Arg Arg Glu Gln Pro Thr Glu Pro Gly Pro
                405                 410                 415
Gln Ser Ala Ser Glu Val Glu Lys Ile Ala Leu Asn Leu Glu Gly Cys
            420                 425                 430
Ala Leu Ser Gln Gly Ser Leu Arg Thr Gly Thr Gln Glu Val Gly Gly
        435                 440                 445
Gln Asp Pro Gly Glu Ala Val Gln Pro Cys Arg Gln Pro Leu Gly Ala
```

```
                450             455             460
Arg Val Ala Asp Lys Val Arg Lys Pro Glu Glu Gly Gly
465                 470                 475

<210> SEQ ID NO 3
<211> LENGTH: 978
<212> TYPE: DNA
<213> ORGANISM: homo sapiens

<400> SEQUENCE: 3
cgcggtggct agtggtggtg cccagacctt ggcccttgcc gggtcccctg ccccatcggg      60
gcaccccaag gctggacaca gtgagaacgg ggttgaggag gacacagaag gtcgaacggg     120
gcccaaagaa ggtaccccctg ggagcccatc ggagacccca ggccccagcc cagcaggacc    180
tgcaggggac gagccagccg agagcccatc ggagacccca ggccccgcc cagcaggacc      240 tgcaggggac gagccggccg agagcccatc ggagacccca ggccccgcc cagcaggacc      300 tgcaggggac gagccagcca gacccatc ggagacccca ggcccagcc cggcaggacc        360 tacaagggat gagccagccg agagcccatc ggagacccca ggccccgcc cggcaggacc      420 tgcaggggac gagccagccg agagcccatc ggagacccca ggccccgcc cggcaggacc      480 tgcaggggac gagccagccg agagcccatc ggagacccca ggcccagcc cggcaggacc      540 tacaagggat gagccagcca aggcggggga ggcagcagag ttgcaggacg cagaggtgga     600
gtcttctgcc aagtctggga agccttaagg aaaggagtgc ccgtcggcgt cttggtcctc    660
ctgtccctgc tgcaggggct ggggcctccg gagctgctgc gggctcccct caggctctgc    720
ttcgtgaccc gtgacccatg acccacagtg ctggcctcct gtgggccac tatagcagcc     780 accagaagcc gcgaggccct cagggaagcc caaggcctgc agaagcctcc tggcctggct    840
gtgtcttccc cacccagctc tccctgcgc ccctgtcttt gtaaattgac ccttctggag     900 tgggggggcgg cgggcagggc tgcttttctt agtctgatgc caagcaaggc cttttctgaa   960
taaattcatt tgactttg                                                  978

<210> SEQ ID NO 4
<211> LENGTH: 243
<212> TYPE: PRT
<213> ORGANISM: homo sapiens

<400> SEQUENCE: 4

Arg Trp Leu Val Val Pro Arg Pro Trp Pro Leu Pro Gly Pro Leu
  1               5                  10                  15

Pro His Arg Gly Thr Pro Arg Leu Asp Thr Val Arg Thr Gly Leu Arg
                 20                  25                  30

Arg Thr Gln Lys Val Glu Arg Gly Pro Lys Lys Val Pro Leu Gly Ala
             35                  40                  45

His Arg Arg Pro Gln Ala Pro Ala Gln Gln Asp Leu Gln Gly Thr Ser
         50                  55                  60

Gln Pro Arg Ala His Arg Pro Gln Ala Pro Ala Gln Gln Asp Leu
 65                  70                  75                  80

Gln Gly Thr Ser Arg Pro Arg Ala His Arg Pro Gln Ala Pro Ala
                 85                  90                  95

Gln Gln Asp Leu Gln Gly Thr Ser Gln Pro Arg Pro His Arg Arg Pro
                100                 105                 110

Gln Ala Pro Ala Arg Gln Asp Leu Gln Gly Met Ser Gln Pro Arg Ala
            115                 120                 125
```

```
His Arg Arg Pro Gln Ala Pro Ala Arg Gln Asp Leu Gln Gly Thr Ser
    130                 135                 140

Gln Pro Arg Ala His Arg Pro Gln Ala Pro Ala Arg Gln Asp Leu
145                 150                 155                 160

Gln Gly Thr Ser Gln Pro Arg Ala His Arg Pro Gln Ala Pro Ala
                165                 170                 175

Arg Gln Asp Leu Gln Gly Met Ser Gln Pro Arg Gly Arg Gln Gln
                180                 185                 190

Ser Cys Arg Thr Gln Arg Trp Ser Leu Leu Pro Ser Leu Gly Ser Leu
    195                 200                 205

Lys Glu Arg Ser Ala Arg Arg Leu Gly Pro Pro Val Pro Ala Ala
    210                 215                 220

Gly Ala Gly Ala Ser Gly Ala Ala Ala Gly Ser Pro Gln Ala Leu Leu
225                 230                 235                 240

Arg Asp Pro
```

<210> SEQ ID NO 5
<211> LENGTH: 3400
<212> TYPE: DNA
<213> ORGANISM: homo sapiens

<400> SEQUENCE: 5

```
gaactgagga gcttgtggag aaaagctata caccaacaaa tcttgttact tcgaatggaa      60
aaagaaaacc agaaacttga agcaagcaga gatgaactcc agtccagaaa agttaaatta     120
gactatgaag aagttggtgc atgtcagaaa gaggtcttaa taacttggga taagaagttg     180
ttaaactgca gagctaaaat cagatgtgat atggaagata ttcatactct tcttaaagaa     240
ggagttccca aaagtcgacg aggagaaatt tggcagtttc tggctttaca gtaccgactc     300
agacacagat tgcctaataa caacagcct cctgacatat cctataagga acttttgaag     360
cagctcactg ctcagcagca tgcgattctt gtggatttag aaggacgtt tcctactcac     420
ccttactttt cagtacagct tgggccagga cagctgtcac tgtttaacct cctgaaagcc     480
tattcattct ttgctggaca agaatgggga tactgtcagg gatcagctt tgtggctgga     540
gtcctgcttc tgcacatgag tgaagagcaa gcctttgaaa tgctgaaatt cctcatgtat     600
gacctcggct ccgcaagca gtacagacct gacatgatgt cgctgcagat tcaaatgtac     660
cagctgtcca ggctccttca tgactatcac agagatctct acaatcacct tgaagaaaat     720
gaaatcagcc ccagtcttta tgctgccccc tggttcctca cattgtttgc ctctcagttt     780
tcattaggat ttgtagccag agttttgat attattttc ttcagggaac tgaagttata     840
ttcaaggttg cactcagcct actgagcagc caagagacac ttataatggg aatgtgagag     900
ctttgaaaat attgttgagt ttcttaaaaa cacgctacct gatatgaata cctctgaaat     960
ggaaaaaatt attcccagg tttttgagat ggatatttct aagcagttgc atgcctatga    1020
ggtggaatat catgtgctac aggatgagct tcaggaatct tcatattcct gtgaggatag    1080
tgaaactttg gagaagctgg agagggccaa tagccaactg aaaagacaaa acatggacct    1140
cctagaaaaa ttacaggtag ctcatactaa aatccaggcc ttggaatcaa acctggaaaa    1200
tcttttgacg agagagacca aaatgaagtc tttaatccgg accctggaac aagaaaaaat    1260
ggcttatcaa aagacagtgg agcaactccg gaagctgctg cccgcggatg ctctagtcaa    1320
ttgtgacctg ttgctgagag acctaaactg caacccctaac aacaaagcca gataggaaat    1380
aagccataat tgaagagcac ggctcagcag aaagtgctcc ttagaatact acagagagga    1440
```

-continued

```
agagcctgca tgtcgctggc ccaaggctgg accctgaagc tgatggaacc acctaatact    1500
ggtgctgagc tcctagtcac agcaggtgga cctcgtgctc atcagagcat gccaatctaa    1560
gcccattgga catagtagac tggttttgt tgttgctatg acatataaat atatatataa     1620
aatgaacata gttcatgctt tcagataaaa tgagtagatg tatatttaga ttaatttttt    1680
tagtcagaac ttcatgaaat ccacaccaaa ggaaaggtaa actgaaattt cccttggaca    1740
tatgtgaaat cttttgtct ttatagtgaa acaaagccag agcatctttg tatattgcaa     1800
tatacttgaa aaaatgaat gtatttttt ctccaaagaa cagcatgttt cactcaatgg      1860
tgaaaggtg gaaacattta tgttaacttt atgtgttctg tcttgatatc tactgacatt     1920
gtctatatga ggaaaatgat tactggtcat gctcctgtga ttttttggga aggtagggtc    1980
atttctccct gcctgctttg tgccaactag catgttgcat ctactgcatt atgaatctgg    2040
tggcttactt ttaaacatac taaaaacagt aggacttggc tgaatctacc cccaggtaaa    2100
ggagaatgtt gcttatttt tagcaaacta acagccttat tctcaactaa aatatcacac     2160
ctgaaaaatt taatttttg gtgccacagt caccaaatga caaggatttg ccactttccc     2220
accaaattgt gagtgcttgt aatttaggtc tctctacctt aaattcagta taaggaaacg    2280
taattatgat tgatttttc caaagatgac aagctgtgtt gaaatacatt tttcttttga     2340
ccaattgaca gaatctaata agctttaata atcttcccct tttatgtgaa aagttttgag    2400
aactgtgaaa tgtttaggaa caaactgttg aaatccattg aagggaaaa aagaaagtgg     2460
taccagtgtt accagctcaa ctaaaacctg caattgtgca tttcaacttt tcacttcctc    2520
agcatacaaa tagctcatta gaagacattc acgcatggtg ggtataggca aggaaagtaa    2580
ttttcaaagt acatttgcag ttctcttttt cagagatgat tctatgatag cgcctctgaa    2640
agttgatgca gcattttcgc cttccaaaa agtatttatc ctcactgctt tttgcagtac     2700
ttgtattttc acagatggat tatctggggt aattttcttc aaagggagtt tgttatacac    2760
agtgaaaatg tattatagag tagaatagta aagctctagg ggtttcagaa agctttgatg    2820
aacagatgac aaacatctga aaccccctcc gcactgttac ccagtgtgta tataatgact    2880
tgttatagct cagtgtgccc ttgaatccat acagtttctt aaaagacaat aaaatcttat    2940
taataaagtt aatgtaactt ctaagttcta gaaaatgctg attctgtctg ccccattcaa    3000
ttgggggcta ctaattgatt tgttgcttgg atttcctgag aatttctcta tttgtaggag    3060
gggtttttc ttttacggt ctgttgatga caattacttt atgggtgtga tgcaccgatg      3120
gtagccaagg aatctgttgg ggaagttcgg aaagaaacct tttctttctt ttattcagtt    3180
taaagtaaac tttatcctgg atgtttagaa tcaacattaa gagttatatt atggtgttca    3240
gagattaagc tgacttggat acaatatttt cttttgaaaa tgaattttct ttttcatttg    3300
tgatttttaa aaaatgttgc accagttatg cttcatgcat cgttacatct tcatcaggtt    3360
aatgtaatgt ctagttcctt tgcaataaat atattgctgc                          3400
```

<210> SEQ ID NO 6
<211> LENGTH: 366
<212> TYPE: PRT
<213> ORGANISM: homo sapiens

<400> SEQUENCE: 6

Met Thr Val Arg Asn Ile Ala Ser Ile Cys Asn Met Gly Thr Asn Ala
1               5                   10                  15

Ser Ala Leu Glu Lys Asp Ile Gly Pro Glu Gln Phe Pro Ile Asn Glu
            20                  25                  30

```
His Tyr Phe Gly Leu Val Asn Phe Gly Asn Thr Cys Tyr Cys Asn Ser
         35                  40                  45
Val Leu Gln Ala Leu Tyr Phe Cys Arg Pro Phe Arg Glu Asn Val Leu
 50                  55                  60
Ala Tyr Lys Ala Gln Gln Lys Lys Glu Asn Leu Leu Thr Cys Leu
 65                  70                  75                  80
Ala Asp Leu Phe His Ser Ile Ala Thr Gln Lys Lys Val Gly Val
                 85                  90                  95
Ile Pro Pro Lys Lys Phe Ile Ser Arg Leu Arg Lys Glu Asn Asp Leu
                100                 105                 110
Phe Asp Asn Tyr Met Gln Gln Asp Ala His Glu Phe Leu Asn Tyr Leu
                115                 120                 125
Leu Asn Thr Ile Ala Asp Ile Leu Gln Glu Glu Lys Lys Gln Glu Lys
            130                 135                 140
Gln Asn Gly Lys Leu Lys Asn Gly Asn Met Asn Glu Pro Ala Glu Asn
145                 150                 155                 160
Asn Lys Pro Glu Leu Thr Trp Val His Glu Ile Phe Gln Gly Thr Leu
                165                 170                 175
Thr Asn Glu Thr Arg Cys Leu Asn Cys Glu Thr Val Ser Ser Lys Asp
                180                 185                 190
Glu Asp Phe Leu Asp Leu Ser Val Asp Val Glu Gln Asn Thr Ser Ile
            195                 200                 205
Thr His Cys Leu Arg Asp Phe Ser Asn Thr Glu Thr Leu Cys Ser Glu
        210                 215                 220
Gln Lys Tyr Tyr Cys Glu Thr Cys Cys Ser Lys Gln Glu Ala Gln Lys
225                 230                 235                 240
Arg Met Arg Val Lys Lys Leu Pro Met Ile Leu Ala Leu His Leu Lys
                245                 250                 255
Arg Phe Lys Tyr Met Glu Gln Leu His Arg Tyr Thr Lys Leu Ser Tyr
                260                 265                 270
Arg Val Val Phe Pro Leu Glu Leu Arg Leu Phe Asn Thr Ser Ser Asp
            275                 280                 285
Ala Val Asn Leu Asp Arg Met Tyr Asp Leu Val Ala Val Val His
        290                 295                 300
Cys Gly Ser Gly Pro Asn Arg Gly His Tyr Ile Thr Ile Val Lys Ser
305                 310                 315                 320
His Gly Phe Trp Leu Leu Phe Asp Asp Ile Val Glu Lys Ile Asp
                325                 330                 335
Ala Gln Ala Ile Glu Glu Phe Tyr Gly Leu Thr Ser Asp Ile Ser Lys
                340                 345                 350
Asn Ser Glu Ser Gly Tyr Ile Leu Phe Tyr Gln Ser Arg Glu
            355                 360                 365

<210> SEQ ID NO 7
<211> LENGTH: 3207
<212> TYPE: DNA
<213> ORGANISM: homo sapiens

<400> SEQUENCE: 7
gagaactaca aaaagaaaa agcagaaaat gaaaaaatac aaaatgagca gcttgagaaa      60
cttcaagaac aagttacaga tttgcgatca caaaatacca aaatttctac ccagctagat    120
tttgcttcta acgttatga aatgctgcca gataatgttg aaggatatcg tcgagaaata     180
acatcacttc ctgagagaaa tcagaaactc actgccacaa ctccaaagcc agaacagatt    240
```

-continued

```
atccatacga tgactccgat ttgagaggag ccaatgagaa gctagctgtc gccgaagttt      300
gagccgaaaa tttgaagaag gaaaaggaaa tgcttaaatt gtctgaagtt cgtctttctc      360
agcaaagaga gtctttgtta gctgaacaaa ggggcaaaa cttactgcta actaatctgc       420
aaacaattca gggaatactg gagcgatctg aaacagaaac caaacaaagg cttagtagcc      480
agatagaaaa actggaacat gagatctctc atctaaagaa gaagttggaa atgaggtgg       540
aacaaaggca tacacttact agaaatctag atgttcaact tttagataca aagagacaac      600
tggatacaga gacaaatctt catcttaaca caaagaact attaaaaaat gctcaaaaag       660
aaattgccac attgaaacag cacctcagta atatggaagt ccaagttgct tctcagtctt     720
cacagagaac tggtaaaggt cggcctagca caaagaaga tgtggatgat cttgtgagtc      780
tgctaagaca gacagaagag caggtgaatg acttaaagga gagactcaaa aaaacaagt      840
acgagcaatg tggaacaata tcaagcaatg gttactagtt tagaagaatc cctgaacaag     900
gaaaacagg tgacagaaga agtgcgtaag aatattgaag ttcgtttaaa agagtcagct      960
gaatttcaga cacagttgga aaagaagttg atggaagtag agaaggaaaa acaagaactt   1020
caggatgata aagaagagc catagagagc atggaacaac agttatctga attgaagaaa    1080
acactttcct agtgttcaga atgaagtaca agaagctctt cagagagcaa gcacagcttt    1140
aagtaatgag cagcaagcca gacgtgactg tcaggaacaa gctaaaatag ctgtggaagc   1200
tcagaataag tatgagagag aattgatgct gcatgctgct gatgttgaag ctctacaagc   1260
tgcgaaggag caggtttcaa aaatggcatc agtccgtcag catttggaag aaacaacaca   1320
gaaagcagaa tcacagttgt tggagtgtaa agcatcttgg gaggaaagag agaatgtt    1380
aaaggatgaa gtttccaaat gtgtatgtcg ctgtgaagat ctggagaaac aaaacagatt   1440
acttcatgat cagatcgaaa aattaagtga caaggtcgtt gcctctgtga aggaaggtgt   1500
acaagtcccc actgaatgta tctctcagtg aagaaggaaa atctcaagaa caaattttgg   1560
aaattctcag atttatacga cgagaaaaag aaattgctga aactaggttt gaggtggctc    1620
aggttgagag tctgcgttat cgacaaaggg ttgaacttt agaaagagag ctgcaggaac   1680
tgcaagatag tctaaatgct gaaagggaga agtccaggt aactgcaaaa acaatggctc    1740
agcatgaaga actgatgaag aaaactgaaa caatgaatgt agttatggag accaataaaa    1800
tgctaagaga agagaaggag agactagaac aggatctaca gcaaatgcaa gcaaaggtga   1860
ggaaactgga gttagatatt ttacccttac aagaagcaaa tgctgagctg agtgagaaaa   1920
gcggtatgtt gcaggcagag aagaagctct tagaagagga tgtcaaacgt tggaaagcac   1980
gtaaccagca tctagtaagt caacagaaag atccagatac agaagaatat cggaagctcc   2040
tttctgaaaa ggaagttcat actaagcgta ttcaacaatt gacagaagaa attggtagac   2100
ttaaagctga aattgcaaga tcaaatgcat ctttgactaa caaccagaac ttaattcaga   2160
gtctgaagga agatctaaat aaagtaagaa ctgaaaagga aaccatccag aaggacttag   2220
atgccaaaat aattgatatc caagaaaaag tcaaaactat tactcaagtt aagaaaattg   2280
gacgtaggta caagactcaa tatgaagaac ttaaagcaca acaggataag gttatggaga   2340
catcggctca gtcttctgga gaccatcagg agcagcatgt ttcagtccag gaaatgcagg   2400
aactcaaaga aacgctcaac caagctgaaa caaaatcaaa atcacttgaa agtcaagtag   2460
agaatttgca gaagacatta tttgaaaaag agacagaagc aagaaatctc caggaacaga   2520
ctgtgcaact tcagtctgaa ctttcacgac tttgtcagga ttttcaagat agaaccacac   2580
```

-continued

| | |
|---|---|
| aggagggagca gctccgacaa cagataacta aaaaaaaaaa actcgtgccg aattcggcac | 2640 |
| gagctcccag ccaaattgaa agccggaccc caggccgccg cgttgccgcc cggcctcccc | 2700 |
| gccagcgcgc caccatgggc agtcccggtt tccccttgta agatggcgg tgagggatcg | 2760 |
| ctgcaacctt tagattaatg actctccgaa acatcgcctc ccatctgtaa tatgggcacc | 2820 |
| caatgctttt gttttggaaa aagacattgg tccagagcag tttccaatca atgaacacta | 2880 |
| tttcggattg gtcaattttg gaaacacatg ctactgtaac tccgtgcttc aggcattgta | 2940 |
| cttctgccgt ccattccggg agaatgtgtt ggcatacaag gcccagcaaa gaagaagga | 3000 |
| aaacttgctg acgtgcctgg cggacctttt ccacagcatt gccacacaga gaagaaggt | 3060 |
| tggcgtcatc ccaccaaaga agttcatttc aaggctgaga aaagagaatg atctctttga | 3120 |
| taactacatg cagcaggatg ctcatgaatt tttaaattat ttgctaaaca ctattgcgga | 3180 |
| catccttcag gaggagaaga aacaggg | 3207 |

<210> SEQ ID NO 8
<211> LENGTH: 3683
<212> TYPE: DNA
<213> ORGANISM: homo sapiens

<400> SEQUENCE: 8

| | |
|---|---|
| aacagatgga aaatagtac agtatgaatg tgagggggat acttgccagg aagagaaaat | 60 |
| agatgcctta cagttagagt attcatattt actaacaagc cagctggaat ctcagcgaat | 120 |
| ctactgggaa acaagatag ttcggataga aaggacaca gcagaggaaa ttaacaacat | 180 |
| gaagaccaag tttaaagaaa caattgagaa gtgtgataat ctagagcaca aactaaatga | 240 |
| tctcctaaaa gaaaagcagt ctgtggaaag aaagtgcact cagctaaaca caaaagtggc | 300 |
| caaactcacc aacgagctca agaggagca ggaaatgaac aagtgtttgc gagccaacca | 360 |
| agtcctcctg cagaacaagc taaagagga ggagagggtg ctgaaggaga cctgtgacca | 420 |
| aaaagatctg cagatcaccg agatccagga gcagctgcgt gacgtcatgt ctacctgga | 480 |
| gacacagcag aagatcaacc atctgcctgc cgagacccgg caggaaatcc aggaggggaca | 540 |
| gatcaacatc gccatggcct cggcctcgag ccctgcctct tcgggggca gtgggaagtt | 600 |
| gccctccagg aagggccgca gcaagagggg caagtgacct tcagagcaac agacatccct | 660 |
| gagactgttc tccctgacac tgtgagagtg tgctgggacc ttcagctaaa tgtgagggtg | 720 |
| ggccctaata agtacaagtg aggatcaagc cacagttgtt tggctctttc atttgctagt | 780 |
| gtgtgatgta gtgaatgtaa agggtgctga ctggagagct gatagaaagg cgctgcgttc | 840 |
| gaaaaggtct taagagttca ctaacctcac attctaatga ccattttgcc ttcctgcttg | 900 |
| gtagaagccc caactctgct gtgcattttt ccattgtatt tatggagttg gcgtatttga | 960 |
| cattcagttc tggggtaggt ttaagatgtt aagttatttc ttgtaacctc aaaggtaagg | 1020 |
| ttatctagca ctaaagcacc aaacctctct gagggcataa cagctgcttt aaagagaggt | 1080 |
| ttccattggc tattaaggag ttatgaaaac tccctagcaa tagtgtcata tcattatcat | 1140 |
| ctccccttc ctctggggag tggaagaatt gcttgaatgt tatctgaaaa gaggcctggt | 1200 |
| agtaaaccag gccctggctc tttaccagca gtcatctctt cttgctctgg ggccagccag | 1260 |
| gaaaaacaaa caacccgggg cacattgggt agactcagtg taggaaaaat ggtggcagct | 1320 |
| ccactgttta ttttttggtga cttcgtacgt cattatgaac cgcaattaag gaggaggctt | 1380 |
| aatggctgtt cccaaactca aatctcagag tgggtatcct agcatctagc aagactgagt | 1440 |
| ggggagattt ctcatccgtg tgaaaatgta gagtgaggcc tctgactagc taattgtgta | 1500 |

-continued

```
ttttgttggg tttagtatttt tctaaatgtt tacaaaatat tgggctgcat gttcaggttg      1560
cagctagagg gagcttgggc agattttcaa ttacgctttc aagatataac caaaagctgt      1620
ttctaaatcc taaaattaga atttcaacag agccccttt agaacagtca tataacgctt       1680
gtgtgggcca acagaggggc tgtgtactct ctctggaacc ataaatgtca ataaatttat      1740
aacctgcagt aattgagcaa acttaaaata agacctgtgt tggaatttag tttcttgaag      1800
aggtagaggg ataggttagt aagatgtatt gttaaacaac aggttttagt ttttgcttta      1860
taattagcca caggttttca aatgatcaca tttcagaata ggttttagc ctgtaattag       1920 gcctcatccc ctttgaccta aatgtcttac atgttacttg ttagcacatc aactgtatca      1980
ctaatcacca tctgtttttg tgggatgtgc tgcagcattt cccaaaaaac tttacgtgta      2040
atgttgcaaa atgaatgtac tcagacattc ttaattttta cttagggcag accaactctt      2100
tgagtctctc ttggacttat atatacagat atcttaagag tgggaatgta aagcataacc      2160
taattctctt tcctatagag attctatttt atttaaaatc tatttttaca ctagttagaa      2220
tcctgctgtt ttggatcaag tacttgtctt gcatgtctga ccttgcagaa gctggggtgg      2280
atcatagcat actaatgaag agaattagaa gtagtttaca aagctcgctc actcctcatt      2340
tctctgtgat ccttctatc cagtggcccc accaccacct gggaaaacag attttcagt        2400 acaggtggga taaatgctct gaaaggctgt gcccagagga atgagcaaat aggcaagtgt      2460
ttccaaacta cttggaggtt tacaaaaaat atgtcccaga aaaaaaaaa ctcgtgccga       2520 attcggcacg agggaggacc tgactcccct cacctttggg gtgcaggaac tcaacctgac      2580
tggctccttc tggaatgact cctttgccag gctctcactg acctatgaac gactcttttgg    2640 taccacagtg acattcaagt tcattctggc caaccgcctc tacccagtgt ctgcccggca     2700
ctggtttacc atggagcgcc tcgaagtcca cagcaatggc tccgtcgcct acttcaatgc      2760
ttcccaggtc acagggccca gcatctactc cttccactgc gagtatgtca gcagcctgag      2820
caagaagggt agtctcctcg tggcccgcac gcagccctct ccctggcaga tgatgcttca      2880
ggacttccag atccaggctt tcaacgtaat ggggagcag ttctcctacg ccagcgactg       2940
tgccagcttc ttctcccccg gcatctggat ggggctgctc acctccctgt tcatgctctt      3000
catcttcacc tatggcctgc acatgatcct cagcctcaag accatggatc gctttgatga     3060
ccacaagggc cccactattt ctttgaccca gattgtgtga ccctgtgcca gtggggggt      3120 tgagggtggg acggtgtccg tgttgttgct ttcccaccct gcagcgcact ggactgaaga     3180
gcttccctct tcctactgca gcatgaactg caagctcccc tcagcccatc ttgctccctc     3240
ttcagcccgc tgaggagctt tcttgggctg ccccatctc tcccaacaag gtgtacatat       3300
tctgcgtaga tgctagacca accagcttcc cagggttcgt cgctgtgagg cgtaagggac     3360
atgaattcta gggtctccctt tctccttatt tattcttgtg gctacatcat ccctggctgt    3420
ggatagtgct tttgtgtagc aaatgctccc tccttaaggt tatagggctc cctgagtttg    3480
ggagtgtgga agtactactt aactgtctgt cctgcttggc tgtcgttatc gttttctggt     3540
gatgttgtgc taacaataag aagtacacgg gtttatttct gtggcctgag aaggaaggga    3600
cctccacgac aggtgggctg ggtgcgatcg ccggctgttt ggcatgttcc caccgggagt     3660
gccgggcagg agcatggggt gct                                             3683
```

<210> SEQ ID NO 9
<211> LENGTH: 3505
<212> TYPE: DNA

<213> ORGANISM: homo sapiens

<400> SEQUENCE: 9

| | | | | | |
|---|---|---|---|---|---|
| aaatatagat | ctcgacctcg | aaattgtaca | gtctttgcag | catggtcatg | gaggatggac | 60 |
| tgatggaatg | tttgagactt | taactacaac | tggaactgtt | tgtggcattg | atgaagatca | 120 |
| tgacattgta | gtacagtatc | caagtggcaa | taggtggacc | ttcaatcctg | ctgttctcac | 180 |
| taaagcgaac | attgtccgaa | gtggagatgc | tgctcagggt | gcagaaggag | gcacctcgca | 240 |
| gtttcaagtg | ggtgatcttg | tacaagtttg | ttatgacctg | gaacgaatta | aacttctaca | 300 |
| aagaggacat | ggagaatggg | ctgaagcgat | gcttccaact | ttaggtaaag | ttggccgagt | 360 |
| acaacagatt | tattcagaca | gtgatttaaa | ggtggaagtt | tgtggaacat | cttggacata | 420 |
| caatccagca | gcagtttcca | aggtggcatc | tgcaggatca | gccattagca | atgcatctgg | 480 |
| tgaaagactc | tcacaactcc | tgaagaaatt | atttgaaacc | caagaatctg | gtgacctcaa | 540 |
| tgaagaatta | gttaaggctg | ctgccaatgg | agatgttgct | aaagtggaag | atttgcttaa | 600 |
| aagaccagat | gtggatgtaa | atgggcaatg | tgctggccac | acagctatgc | aagctgctag | 660 |
| tcagaatgga | catgttgaca | ttttgaagtt | acttttgaag | caaaacgtgg | atgtcgaagc | 720 |
| agaggataaa | gatggtgata | gagcagttca | ccatgcagct | tttggagatg | aaggcgctgt | 780 |
| tatagaagta | ctacatcgag | gtagtgctga | tttgaatgct | cgaaacaagc | gccgacagac | 840 |
| accacttcat | attgctgtca | ataaaggtca | tcttcaagtt | gtgaagactt | tattggactt | 900 |
| tggctgtcat | cccagtctcc | aggattctga | aggtgatacc | cctcttcatg | atgcaataag | 960 |
| taagaaacgt | gatgatatcc | tagcagttct | tttggaagct | ggagcagatg | ttaccatcac | 1020 |
| aaacaataat | ggatttaatg | ctctgcatca | tgctgcacta | aggggaaatc | ccagtgcaat | 1080 |
| gcgtgtttta | ctatctaaat | taccaagacc | atggattgtg | gatgagaaga | agatgatgg | 1140 |
| ttatactgcc | ttcacatctg | gctgcccttaa | taatcacgta | gaagtggctg | aactgttggt | 1200 |
| acatcagggt | aatgcaaacc | tggatatcca | gaatgtgaac | caacaaactg | ccctacacct | 1260 |
| tgctgttgaa | cgacagcata | cccagattgt | taggcttttg | gtccgtgcag | gtgccaagct | 1320 |
| tgatattcag | gataaggatg | gggatactcc | tttgcatgaa | gctctaaggc | atcacacttt | 1380 |
| gtctcagcta | cgtcagctcc | aagatatgca | agatgtgggg | aaggtggatg | ctgcctggga | 1440 |
| gccatccaaa | aacacgttaa | taatgggact | tggtacccag | ggggcagaga | agaagagtgc | 1500 |
| agcatctatt | gcctgtttct | tggcagccaa | tggtgctgac | ctgagcattc | gaaataagaa | 1560 |
| gggtcaatcg | ccacttgatc | tctgtcctga | tccgaatctc | tgcaaagcac | tggcaaagtg | 1620 |
| tcataaggaa | aaagtcagtg | gtcaagtggg | ttctcggagt | ccttctatga | ttagtaatga | 1680 |
| ttctgaaacc | ttagaagagt | gtatggtgtg | ctcagatatg | aagagagata | ctcttttggg | 1740 |
| tccatgtgga | catattgcta | cctgttcttt | atgttctcca | cgtgtcaaga | aatgcctcat | 1800 |
| ctgtaaagaa | caggttcaat | ccaggacaaa | gattgaagaa | tgtgtggtat | gctctgacaa | 1860 |
| gaaagcagct | gttcttttttc | aaccctgtgg | ccacatgtgt | gcttgtgaga | actgtgctaa | 1920 |
| cctgatgaaa | aagtgtgtgc | agtgtcgagc | agtagttgaa | cgaagagtgc | ctttcattat | 1980 |
| gtgctgtgga | gggaaaagtt | cagaagatgc | cactgatgat | atctcaagtg | gaatattcc | 2040 |
| agtattacaa | aaggacaagg | ataataccaa | tgtcaatgca | gatgtgcaaa | agttgcagca | 2100 |
| acagttacaa | gacattaaag | agcagacaat | gtgccctgtg | tgtctagatc | gtctgaagaa | 2160 |
| tatgatttc | ctttgtggtc | acggaacctg | tcaactctgt | ggagaccgca | tgagtgaatg | 2220 |
| tcctatctgt | cgcaaggcta | ttgaacgaag | gattcttttg | tattaactaa | gacacatggt | 2280 |

-continued

```
gtattttgtt agctaatgta tctagtcatg agatcttaat aggcttttga tctagttgga      2340
agttctgatg agttaatttc taatatcata gtttctttac tagagtataa ttgggctgta      2400
aatgtaccag aacaaaaaac cctacaaaat ggtgttggaa attgtgtttt ttgttttttgt    2460 tttaaatttg aaacatcaaa ttcatgtaac tcataggata atttaccttt ggcttctaag     2520
aggaaagtcc tttaaggata tcctttttta aaaaattgca ttttttctctt ataatttgta    2580 aatttgttgg atctcaaaag acataattct ttgtgatcag ttatccttca tttcatcgtg     2640
gttttacaca gtgagttgat aacaggttct ctgagaagtc atgcatcaaa taaaagaggc     2700
aggtcaaaca attatgtcac atggtaaatt ataaaatgac agtacaagtt ccagatagtt     2760
aagggaatac cgaagggatg attctttttt taagataaca ggaagttacc cacatgtttg     2820
tttctgaatt cttagagtaa atggaagcat agaatgaggg aataatgact ttgcatttct     2880
cttgttttct agattcaaaa ggaacattgt ttaacttgaa tcagattacc agtttcaagg     2940
tgactgatag acaagaaaag gaaaaataag caataatagt gggcaactga agagaaaaaa     3000
aaaacgagta tctattaact ggccactaac agttgccttt cttacattaa tttatacact     3060
attttgttca gccagtgttt ttaaaaaaaa tctatgaaaa gtgtacttcc ggttttctgt     3120
gattacttat ctgggcttga tctgaccagt gaaatgacat tgccctattt ggacctctga     3180
ggttctattt agctttgcag atgtacatag tatcccagtg atctgcaaaa ttaatgcctt     3240
ttccaagaaa aaatcttttc ttctctgtat cagttaattc tgacagtgtt agtgattctg     3300
tcttcattat aggccttatt tccattatct ctttctttat agtatttttt gttataaaga    3360
aaacagtctt tctgtgtata cctacggatg agggtattat ttaaactgcc aacaatatcc     3420
aagacatggt caataaccta attataaata ctttagaaag agtgaccagg acatgtatag     3480
aaatgtctgc ttacctgtag acttt                                           3505
```

<210> SEQ ID NO 10
<211> LENGTH: 1168
<212> TYPE: PRT
<213> ORGANISM: homo sapiens

<400> SEQUENCE: 10

```
Asn Ile Asp Leu Asp Leu Glu Ile Val Gln Ser Leu Gln His Gly His
  1               5                  10                  15

Gly Gly Trp Thr Asp Gly Met Phe Glu Thr Leu Thr Thr Thr Gly Thr
             20                  25                  30

Val Cys Gly Ile Asp Glu Asp His Asp Ile Val Val Gln Tyr Pro Ser
         35                  40                  45

Gly Asn Arg Trp Thr Phe Asn Pro Ala Val Leu Thr Lys Ala Asn Ile
     50                  55                  60

Val Arg Ser Gly Asp Ala Ala Gln Gly Ala Glu Gly Gly Thr Ser Gln
 65                  70                  75                  80

Phe Gln Val Gly Asp Leu Val Gln Val Cys Tyr Asp Leu Glu Arg Ile
                 85                  90                  95

Lys Leu Leu Gln Arg Gly His Gly Glu Trp Ala Glu Ala Met Leu Pro
            100                 105                 110

Thr Leu Gly Lys Val Gly Arg Val Gln Gln Ile Tyr Ser Asp Ser Asp
        115                 120                 125

Leu Lys Val Glu Val Cys Gly Thr Ser Trp Thr Tyr Asn Pro Ala Ala
    130                 135                 140

Val Ser Lys Val Ala Ser Ala Gly Ser Ala Ile Ser Asn Ala Ser Gly
```

-continued

```
            145                 150                 155                 160
Glu Arg Leu Ser Gln Leu Leu Lys Lys Leu Phe Glu Thr Gln Glu Ser
                165                 170                 175
Gly Asp Leu Asn Glu Glu Leu Val Lys Ala Ala Asn Gly Asp Val
                180                 185                 190
Ala Lys Val Glu Asp Leu Leu Lys Arg Pro Asp Val Asp Val Asn Gly
                195                 200                 205
Gln Cys Ala Gly His Thr Ala Met Gln Ala Ala Ser Gln Asn Gly His
        210                 215                 220
Val Asp Ile Leu Lys Leu Leu Lys Gln Asn Val Asp Val Glu Ala
225                 230                 235                 240
Glu Asp Lys Asp Gly Asp Arg Ala Val His His Ala Ala Phe Gly Asp
                245                 250                 255
Glu Gly Ala Val Ile Glu Val Leu His Arg Gly Ser Ala Asp Leu Asn
                260                 265                 270
Ala Arg Asn Lys Arg Arg Gln Thr Pro Leu His Ile Ala Val Asn Lys
        275                 280                 285
Gly His Leu Gln Val Val Lys Thr Leu Leu Asp Phe Gly Cys His Pro
        290                 295                 300
Ser Leu Gln Asp Ser Glu Gly Asp Thr Pro Leu His Asp Ala Ile Ser
305                 310                 315                 320
Lys Lys Arg Asp Asp Ile Leu Ala Val Leu Leu Glu Ala Gly Ala Asp
                325                 330                 335
Val Thr Ile Thr Asn Asn Asn Gly Phe Asn Ala Leu His His Ala Ala
                340                 345                 350
Leu Arg Gly Asn Pro Ser Ala Met Arg Val Leu Leu Ser Lys Leu Pro
                355                 360                 365
Arg Pro Trp Ile Val Asp Glu Lys Lys Asp Asp Gly Tyr Thr Ala Leu
        370                 375                 380
His Leu Ala Ala Leu Asn Asn His Val Glu Val Ala Glu Leu Leu Val
385                 390                 395                 400
His Gln Gly Asn Ala Asn Leu Asp Ile Gln Asn Val Asn Gln Gln Thr
                405                 410                 415
Ala Leu His Leu Ala Val Glu Arg Gln His Thr Gln Ile Val Arg Leu
        420                 425                 430
Leu Val Arg Ala Gly Ala Lys Leu Asp Ile Gln Asp Lys Asp Gly Asp
        435                 440                 445
Thr Pro Leu His Glu Ala Leu Arg His His Thr Leu Ser Gln Leu Arg
        450                 455                 460
Gln Leu Gln Asp Met Gln Asp Val Gly Lys Val Asp Ala Ala Trp Glu
465                 470                 475                 480
Pro Ser Lys Asn Thr Leu Ile Met Gly Leu Gly Thr Gln Gly Ala Glu
                485                 490                 495
Lys Lys Ser Ala Ala Ser Ile Ala Cys Phe Leu Ala Ala Asn Gly Ala
        500                 505                 510
Asp Leu Ser Ile Arg Asn Lys Lys Gly Gln Ser Pro Leu Asp Leu Cys
        515                 520                 525
Pro Asp Pro Asn Leu Cys Lys Ala Leu Ala Lys Cys His Lys Glu Lys
        530                 535                 540
Val Ser Gly Gln Val Gly Ser Arg Ser Pro Ser Met Ile Ser Asn Asp
545                 550                 555                 560
Ser Glu Thr Leu Glu Glu Cys Met Val Cys Ser Asp Met Lys Arg Asp
                565                 570                 575
```

```
Thr Leu Phe Gly Pro Cys Gly His Ile Ala Thr Cys Ser Leu Cys Ser
            580                 585                 590

Pro Arg Val Lys Lys Cys Leu Ile Cys Lys Glu Gln Val Gln Ser Arg
        595                 600                 605

Thr Lys Ile Glu Glu Cys Val Val Cys Ser Asp Lys Lys Ala Ala Val
    610                 615                 620

Leu Phe Gln Pro Cys Gly His Met Cys Ala Cys Glu Asn Cys Ala Asn
625                 630                 635                 640

Leu Met Lys Lys Cys Val Gln Cys Arg Ala Val Val Glu Arg Arg Val
                645                 650                 655

Pro Phe Ile Met Cys Cys Gly Lys Ser Ser Glu Asp Ala Thr Asp
            660                 665                 670

Asp Ile Ser Ser Gly Asn Ile Pro Val Leu Gln Lys Asp Lys Asp Asn
        675                 680                 685

Thr Asn Val Asn Ala Asp Val Gln Lys Leu Gln Gln Leu Gln Asp
    690                 695                 700

Ile Lys Glu Gln Thr Met Cys Pro Val Cys Leu Asp Arg Leu Lys Asn
705                 710                 715                 720

Met Ile Phe Leu Cys Gly His Gly Thr Cys Gln Leu Cys Gly Asp Arg
                725                 730                 735

Met Ser Glu Cys Pro Ile Cys Arg Lys Ala Ile Glu Arg Arg Ile Leu
            740                 745                 750

Leu Tyr Glx Leu Arg His Met Val Tyr Phe Val Ser Glx Cys Ile Glx
        755                 760                 765

Ser Glx Asp Leu Asn Arg Leu Leu Ile Glx Leu Glu Val Leu Met Ser
    770                 775                 780

Glx Phe Leu Ile Ser Glx Phe Leu Tyr Glx Ser Ile Ile Gly Leu Glx
785                 790                 795                 800

Met Tyr Gln Asn Lys Lys Pro Tyr Lys Met Val Leu Glu Ile Val Phe
                805                 810                 815

Phe Val Phe Val Leu Asn Leu Lys His Gln Ile His Val Thr His Arg
            820                 825                 830

Ile Ile Tyr Leu Trp Leu Leu Arg Gly Lys Ser Phe Lys Asp Ile Leu
        835                 840                 845

Phe Glx Lys Ile Ala Phe Phe Ser Tyr Asn Leu Glx Ile Cys Trp Ile
    850                 855                 860

Ser Lys Asp Ile Ile Leu Cys Asp Gln Leu Ser Phe Ile Ser Ser Trp
865                 870                 875                 880

Phe Tyr Thr Val Ser Glx Glx Gln Val Leu Glx Glu Val Met His Gln
                885                 890                 895

Ile Lys Glu Ala Gly Gln Thr Ile Met Ser His Gly Lys Leu Glx Asn
            900                 905                 910

Asp Ser Thr Ser Ser Arg Glx Leu Arg Glu Tyr Arg Arg Asp Asp Ser
        915                 920                 925

Phe Phe Lys Ile Thr Gly Ser Tyr Pro His Val Cys Phe Glx Ile Leu
    930                 935                 940

Arg Val Asn Gly Ser Ile Glu Glx Gly Asn Asn Asp Phe Ala Phe Leu
945                 950                 955                 960

Leu Phe Ser Arg Phe Lys Arg Asn Ile Val Glx Leu Glu Ser Asp Tyr
                965                 970                 975

Gln Phe Gln Gly Asp Glx Glx Thr Arg Lys Gly Lys Ile Ser Asn Asn
            980                 985                 990
```

```
Ser Gly Gln Leu Lys Arg Lys Lys Arg Val Ser Ile Asn Trp Pro
        995                 1000                1005
Leu Thr Val Ala Phe Leu Thr Leu Ile Tyr Thr Leu Phe Cys Ser Ala
    1010                1015                1020
Ser Val Phe Lys Lys Asn Leu Glx Lys Val Tyr Phe Arg Phe Ser Val
1025                1030                1035                1040
Ile Thr Tyr Leu Gly Leu Ile Glx Pro Val Lys Glx His Cys Pro Ile
                1045                1050                1055
Trp Thr Ser Glu Val Leu Phe Ser Phe Ala Asp Val His Ser Ile Pro
            1060                1065                1070
Val Ile Cys Lys Ile Asn Ala Phe Ser Lys Lys Ser Phe Leu Leu
                1075                1080            1085
Cys Ile Ser Glx Phe Glx Gln Cys Glx Glx Phe Cys Leu His Tyr Arg
        1090                1095                1100
Pro Tyr Phe His Tyr Leu Phe Leu Tyr Ser Ile Phe Cys Tyr Lys Glu
1105                1110                1115                1120
Asn Ser Leu Ser Val Tyr Thr Tyr Gly Glx Gly Tyr Tyr Leu Asn Cys
                1125                1130                1135
Gln Gln Tyr Pro Arg His Gly Gln Glx Pro Asn Tyr Lys Tyr Phe Arg
            1140                1145                1150
Lys Ser Asp Gln Asp Met Tyr Arg Asn Val Cys Leu Pro Val Asp Phe
                1155                1160                1165

<210> SEQ ID NO 11
<211> LENGTH: 1246
<212> TYPE: DNA
<213> ORGANISM: homo sapiens

<400> SEQUENCE: 11
cggcacgagc tcgtgccggg caggcctgtg cctatccctg ctgtcccag gtgggcccc      60 gggggtcagg agctccagaa gggccagctg ggcatattct gagattggcc atcagccccc   120
atttctgctg caaacctggt cagagccagt gttccctcca tgggacctaa agacagtgcc   180
aagtgcctgc accgtggacc acagccgagc cactgggcag ccgtgatgg tcccacgcag    240 gagcgctgtg gaccccgctc tctgggcagc cctgtcctag gcctggacac ctgcagagcc   300
tgggaccacg tggatgggca gatcctgggc cagctgcggc ccctgacaga ggaggaagag   360
gaggagggcg ccggggccac cttgtccagg gggcctgcct tccccggcat gggctctgag   420
gagttgcgtc tggcctcctt ctatgactgg ccgctgactg ctgaggtgcc acccgagctg   480
ctggctgctg ccggcttctt ccacacaggc atcaggaca aggtgaggtg cttcttctgc   540
tatgggggcc tgcagagctg gaagcgcggg gacgacccct ggacggagca tgccaagtgg  600
ttccccagct gtcagttcct gctccggtca aaaggaagag actttgtcca cagtgtgcag   660
gagactcact cccagctgct gggctcctgg gaccgtgggg aagaaccgga agacgcagcc   720
cctgtggccc cctccgtccc tgcctctggg taccctgagc tgcccacacc caggagagag   780
gtccagtctg aaagtgccca ggagccagga gccaggatg tggaggcgca gctgcggcgg    840
ctgcaggagg agaggacgtg caaggtgtgc ctggaccgcg ccgtgtccat cgtctttgtg    900
ccgtgcggcc acctggtctg tgctgagtgt gcccccggcc tgcagctgtg ccccatctgc   960 agagccccg tccgcagccg cgtgcgcacc ttcctgtcct aggccaggtg ccatggccgg    1020
ccaggtgggc tgcagagtgg gctccctgcc cctctctgcc tgttctggac tgtgttctgg  1080
gcctgctgag gatggcagag ctggtgtcca tccagcactg accagccctg attccccgac  1140
```

```
caccgcccag ggtggagaag gaggcccttg cttggcgtgg gggatggctt aactgtacct    1200
gtttggatgc ttctgaatag aaataaagtg ggttttccct ggaggt                  1246

<210> SEQ ID NO 12
<211> LENGTH: 309
<212> TYPE: PRT
<213> ORGANISM: homo sapiens

<400> SEQUENCE: 12

Met Gly Pro Lys Asp Ser Ala Lys Cys Leu His Arg Gly Pro Gln Pro
 1               5                  10                  15

Ser His Trp Ala Ala Gly Asp Gly Pro Thr Gln Glu Arg Cys Gly Pro
                20                  25                  30

Arg Ser Leu Gly Ser Pro Val Leu Gly Leu Asp Thr Cys Arg Ala Trp
            35                  40                  45

Asp His Val Asp Gly Gln Ile Leu Gly Gln Leu Arg Pro Leu Thr Glu
        50                  55                  60

Glu Glu Glu Glu Glu Gly Ala Gly Ala Thr Leu Ser Arg Gly Pro Ala
 65                  70                  75                  80

Phe Pro Gly Met Gly Ser Glu Glu Leu Arg Leu Ala Ser Phe Tyr Asp
                85                  90                  95

Trp Pro Leu Thr Ala Glu Val Pro Pro Glu Leu Leu Ala Ala Ala Gly
               100                 105                 110

Phe Phe His Thr Gly His Gln Asp Lys Val Arg Cys Phe Phe Cys Tyr
           115                 120                 125

Gly Gly Leu Gln Ser Trp Lys Arg Gly Asp Asp Pro Trp Thr Glu His
       130                 135                 140

Ala Lys Trp Phe Pro Ser Cys Gln Phe Leu Leu Arg Ser Lys Gly Arg
145                 150                 155                 160

Asp Phe Val His Ser Val Gln Glu Thr His Ser Gln Leu Leu Gly Ser
                165                 170                 175

Trp Asp Pro Trp Glu Glu Pro Glu Asp Ala Ala Pro Val Ala Pro Ser
            180                 185                 190

Val Pro Ala Ser Gly Tyr Pro Glu Leu Pro Thr Pro Arg Arg Glu Val
        195                 200                 205

Gln Ser Glu Ser Ala Gln Glu Pro Gly Ala Arg Asp Val Glu Ala Gln
    210                 215                 220

Leu Arg Arg Leu Gln Glu Glu Arg Thr Cys Lys Val Cys Leu Asp Arg
225                 230                 235                 240

Ala Val Ser Ile Val Phe Val Pro Cys Gly His Leu Val Cys Ala Glu
                245                 250                 255

Cys Ala Pro Gly Leu Gln Leu Cys Pro Ile Cys Arg Ala Pro Val Arg
            260                 265                 270

Ser Arg Val Arg Thr Phe Leu Ser Glx Ala Arg Cys His Gly Arg Pro
        275                 280                 285

Gly Gly Leu Gln Ser Gly Leu Pro Ala Pro Leu Cys Leu Phe Trp Thr
    290                 295                 300

Val Phe Trp Ala Cys
305

<210> SEQ ID NO 13
<211> LENGTH: 3478
<212> TYPE: DNA
<213> ORGANISM: homo sapiens

<400> SEQUENCE: 13
```

-continued

```
gaactgagga gcttgtggag aaaagctata caccaacaaa tcttgttact tcgaatggaa      60
aaagaaaacc agaaacttga agcaagcaga gatgaactcc agtccagaaa agttaaatta     120
gactatgaag aagttggtgc atgtcagaaa gaggtcttaa taacttggga taagaagttg     180
ttaaactgca gagctaaaat cagatgtgat atggaagata ttcatactct tcttaaagaa     240
ggagttccca aaagtcgacg aggagaaatt tggcagtttc tggctttaca gtaccgactc     300
agacacagat tgcctaataa acaacagcct cctgacatat cctataagga acttttgaag     360
cagctcactg ctcagcagca tgcgattctt gtggatttag gaaggacgtt tcctactcac     420
ccttactttt cagtacagct tgggccagga cagctgtcac tgtttaacct cctgaaagcc     480
tattcattct ttgctggaca aagaatggga tactgtcagg ggatcagctt tgtggctgga     540
gtcctgcttc tgcacatgag tgaagagcaa gcctttgaaa tgctgaaatt cctcatgtat     600
gacctcggct tccgcaagca gtacagacct gacatgatgt cgctgcagat tcaaatgtac     660
cagctgtcca ggctccttca tgactatcac agagatctct acaatcacct tgaagaaaat     720
gaaatcagcc ccagtcttta tgctgccccc tggttcctca cattgtttgc ctctcagttt     780
tcattaggat ttgtagccag agttttttgat attatttttc ttcagggaac tgaagttata     840
ttcaaggttg cactcagcct actgagcagc aagagacac ttataatggg aatgtgagag     900
ctttgaaaat attgttgagt ttcttaaaaa cacgctacct gatatgaata cctctgaaat     960
ggaaaaaatt attacccagg tttttgagat ggatatttct aagcagttgc atgcctatga    1020
ggtggaatat catgtgctac aggatgagct tcaggaatct tcatattcct gtgaggatag    1080
tgaaactttg gagaagctgg agagggccaa tagccaactg aaaagacaaa acatggacct    1140
cctagaaaaa ttcaggtag ctcatactaa aatccaggcc ttggaatcaa acctggaaaa    1200
tcttttgacg agagagacca aaatgaagtc tttaatccgg accctggaac aagaaaaaat    1260
ggcttatcaa aagacagtgg agcaactccg gaagctgctg cccgcggatg ctctagtcaa    1320

ttgtgacctg ttgctgagag acctaaactg caaccctaac aacaaagcca gataggaaat    1380
aagccataat tgaagagcac ggctcagcag aaagtgctcc ttagaatact acagagagga    1440
agagcctgca tgtcgctggc ccaaggctgg accctgaagc tgatggaacc acctaatact    1500
ggtgctgagc tcctagtcac agcaggtgga cctcgtgctc atcagagcat gccaatctaa    1560
gcccattgga catagtagac tggtttttgt tgttgctatg acatataaat atatatataa    1620
aatgaacata gttcatgctt tcagataaaa tgagtagatg tatattt aga ttaatttttt    1680

tagtcagaac ttcatgaaat ccacaccaaa ggaaaggtaa actgaaattt cccttggaca    1740

tatgtgaaat cттттттgтcт ttatagtgaa acaaagccag agcatctttg tatattgcaa    1800

tatacttgaa aaaatgaat gtatttttt ctccaaagaa cagcatgttt cactcaatgg    1860

tgaaaaggtg aaacattta tgttaacttt atgtgttctg tcttgatatc tactgacatt    1920
gtctatatga ggaaaatgat tactggtcat gctcctgtga тттттттggga aggtagggtc    1980 atttctccct gcctgcttt  gccaactag catgttgcat ctactgcatt atgaatctgg    2040

tggcttactt ttaaacatac taaaaacagt aggacttggc tgaatctacc cccaggtaaa    2100
ggagaatgtt gcttatttt  tagcaaacta acagccttat tctcaactaa atatcacac    2160 ctgaaaaatt тaaттттagga cctaaaatgt ctagattagc tttctgctt тттттaтттga    2220 ataactcatt cagttgtgaa tgaattcctc tttatttggt gccacagtca ccaaatgaca    2280
aggatttgcc actttcccac caaattgtga gtgcttgtaa tttaggtctc tctaccttaa    2340
```

| | |
|---|---|
| attcagtata aggaaacgta attatgattg attttttcca aagatgacaa gctgtgttga | 2400 |
| aatacatttt tcttttgacc aattgacaga atctaataag ctttaataat cttccccttt | 2460 |
| tatgtgaaaa gttttgagaa ctgtgaaatg tttaggaaca aactgttgaa atccattgga | 2520 |
| agggaaaaaa gaaagtggta ccagtgttac cagctcaact aaaacctgca attgtgcatt | 2580 |
| tcaactttc acttcctcag catacaaata gctcattaga agacattcac gcatggtggg | 2640 |
| tataggcaag gaaagtaatt ttcaaagtac atttgcagtt ctcttttca gagatgattc | 2700 |
| tatgatagcg cctctgaaag ttgatgcagc attttcgcct ttccaaaaag tatttatcct | 2760 |
| cactgctttt tgcagtactt gtattttcac agatggatta tctggggtaa ttttcttcaa | 2820 |
| agggagtttg ttatacacag tgaaaatgta ttatagagta gaatagtaaa gctctagggg | 2880 |
| tttcagaaag ctttgatgaa cagatgacaa acatctgaaa cccctccgc actgttaccc | 2940 |
| agtgtgtata taatgacttg ttatagctca gtgtgccctt gaatccatac agtttcttaa | 3000 |
| aagacaataa aatcttatta ataaagttaa tgtaacttct aagttctaga aaatgctgat | 3060 |
| tctgtctgcc ccattcaatt gggggctact aattgatttg ttgcttggat ttcctgagaa | 3120 |
| tttctctatt tgtaggaggg gtttttctt tttacggtct gttgatgaca attactttat | 3180 |
| gggtgtgatg caccgatggt agccaaggaa tctgttgggg aagttcggaa agaaaccttt | 3240 |
| tctttctttt attcagttta aagtaaactt tatcctggat gtttagaatc aacattaaga | 3300 |
| gttatattat ggtgttcaga gattaagctg acttggatac aatattttct tttgaaaatg | 3360 |
| aattttcttt ttcatttgtg attttttaaaa aatgttgcac cagttatgct tcatgcatcg | 3420 |
| ttacatcttc atcaggttaa tgtaatgtct agttcctttg caataaatat attgctgc | 3478 |

<210> SEQ ID NO 14
<211> LENGTH: 1956
<212> TYPE: DNA
<213> ORGANISM: homo sapiens

<400> SEQUENCE: 14

| | |
|---|---|
| gctgactggc tagcacaaaa caaccctcct caaatgctat gggaaagaac agaagaggat | 60 |
| tctaaaagca ttaaaagtga tgttccagtg tacttgaaaa ggttgaaagg aaataaacat | 120 |
| gatgatggta cgcaaagtga ttcagagaac gctggggctc acaggcgctg tagcaaacgt | 180 |
| gcaactcttg aggaacactt aagacgccac cattcagaac acaaaaagct acagaaggtc | 240 |
| caggctactg aaaagcatca agaccaagct gttactagct ctgcgcatca cagagggggg | 300 |
| catggtgttc cacatgggaa attgttaaaa cagaaatcag aggagccatc ggtgtcaata | 360 |
| cccttcctac aaactgcatt attaagaagt tcagggagtc ttgggcacag accaagccag | 420 |
| gagatggata aaatgttaaa aaatcaagca acttctgcta cttctgaaaa ggataatgat | 480 |
| gatgaccaaa gtgacaaggg tacttatacc attgagttag agaatcccaa cagtgaggaa | 540 |
| gtggaagcaa gaaaaatgat tgacaaggtg tttggagtag atgacaatca ggattataat | 600 |
| aggcctgtta tcaacgaaaa acataaagat ctaataaaag attgggctct cagttctgct | 660 |
| gcagcagtaa tggaagaaag aaaaccactg actacatctg gatttcacca ctcagaggaa | 720 |
| ggcacatctt catctggaag caaacgttgg gtttcacagt gggctagttt ggctgccaat | 780 |
| catacaaggc atatcaagaa gaaaggataa tggaattttc tgcacctctt cctttagaga | 840 |
| atgagacaga gatcagtgag tctggcatga cagtgagaag tactggctct gcaacttcct | 900 |
| tggctagcca gggagagaga aggagacgaa ctccttccca gcttccaaat gaagaaaagt | 960 |
| ctcttgagag ccacagagca aaggttgtaa cacagaggtc agagatagga gaaaaacaag | 1020 |

-continued

```
acacagaact tcaggagaaa gaaacaccta cacaggtata ccagaaagat aaacaagatg    1080
ctgacagacc cttgagtaaa atgaacaggg cagtaaatgg agagactctc aaaactggtg    1140
gagataataa aaccctactt cacttaggca gctctgctcc tggaaaagag aaaagtgaaa    1200
ctgataagga aacttctttg gtaaagcaaa cattagcaaa acttcaacaa caagaacaaa    1260
gggaggaggc tcagtggaca cctactaaat tgtcttccaa aaatgtttca ggtcagacag    1320
ataaatgtag ggaggaaact tttaaacaag aatcacaacc tccagaaaaa aattcaggac    1380
attctacaag caaaggagac agagtggcac aaagtgagag caagagaaga aaagctgagg    1440
aaattctgaa aagtcagact ccaaagggag gagacaagaa ggaatcctcc aagtcattag    1500
tgcgacaagg gagcttcact atagaaaaac ccagcccaaa catacccata gaacttattc    1560
cccatataaa taaacagact tcctctactc cttcttcttt agcattaaca tctgcaagta    1620
gaatacgaga agaagtgag tctttggatc ctgattctag tatggacaca acccttattc    1680
taaaagacac agaagcagta atggctttc tagaagctaa actacgtgaa gataataaaa    1740
ctgatgaagg accagatact cccagttata atagagacaa ttctatttca ccagaatctg    1800
atgtagatac agctagtaca atcagtctgg ttactggaga aactgaaaga aagtcaaccc    1860
aaaagcgaaa gagtttcact agcctctata agataggtg ttccacaggt tctccttcca    1920
aagatgttac aaaatcatca tcttcaggtg ctaggg                              1956
```

<210> SEQ ID NO 15
<211> LENGTH: 2417
<212> TYPE: DNA
<213> ORGANISM: homo sapiens

<400> SEQUENCE: 15

```
ggatgacgta gctttgccaa agacttagaa gctaagcaga aaatgagctt aacatcctgg     60
tttttggtga gcagtggagg cactcgccac aggctgccac gagaaatgat ttttgttgga    120
agagatgact gtgagctcat gttgcagtct cgtagtgtgg ataagcaaca cgctgtcatc    180
aactatgatg cgtctacgga tgagcattta gtgaaggatt tgggcagcct caatgggact    240
tttgtgaatg atgtaaggat tccggaacag acttatatca ccttgaaact tgaagataag    300
ctgagatttg gatatgatac aaatcttttc actgtagtac aaggagaaat gagggtccct    360
gaagaagctc ttaagcatga gaagtttacc attcagcttc agttgtccca aaaatcttca    420
gaatcagaat tatccaaatc tgcaagtgcc aaaagcatag attcaaaggt agcagacgct    480
gctactgaag tgcagcacaa aactactgaa gcactgaaat ccgaggaaaa agccatggat    540
atttctgcta tgccccgtgg tactccatta tatgggcagc cgtcatggtg ggggatgat    600
gaggtggatg aaaaaagagc tttcaagaca aatggcaaac ctgaaaaaaa aaaccatgaa    660
gctggaacat cagggtgcag catagatgcc aagcaagttg aggaacaatc tgcagctgca    720
aatgaagaag tactttttcc tttctgtagg gaaccaagtt attttgaaat ccctacaaaa    780
gaattccagc aaccatcaca aataacagaa agcactattc atgaaatccc aacaaaagac    840
acgccaagtt cccatataac aggtgcaggg catgcttcat ttaccattga atttgatgac    900
agtaccccag ggaaggtaac tattagagac catgtgacaa agtttacttc tgatcagcgc    960
cacaagtcca agaagtcttc tcctggaact caagacttgc tggggattca acaggaatg    1020
atggcacccg aaaacaaagt tgctgactgg ctagcacaaa acaaccctcc tcaaatgcta   1080
tgggaaagaa cagaagagga ttctaaaagc attaaaagtg atgttccagt gtacttgaaa   1140
```

-continued

```
aggttgaaag gaaataaaca tgatgatggt acgcaaagtg attcagagaa cgctggggct    1200
cacaggcgct gtagcaaacg tgcaactctt gaggaacact taagacgcca ccattcagaa    1260
cacaaaaagc tacagaaggt ccaggctact gaaaagcatc aagaccaagc tgttgtgttt    1320
ggagtagatg acaatcagga ttataatagg cctgttatca acgaaaaaca taaagatcta    1380
ataaaagatt gggctctcag ttctgctgca gcagtaatgg aagaaagaaa accactgact    1440
acatctggat ttcaccactc agaggaaggc acatcttcat ctggaagcaa acgttgggtt    1500
tcacagtggg ctagtttggc tgccaatcat acaaggcatg atcaagaaga aggataatg     1560 gaattttctg caccctcttcc tttagagaat gagacagaga tcagtgagtc tggcatgaca    1620
gtgagaagta ctggctctgc aacttccttg gctagccagg gagagagaag gagacgaact    1680
cttccccagc ttccaaatga agaaaagtct cttgagagcc acagagcaaa ggttgtaaca    1740
cagaggtcag atataggaga aaaacaagac acagaacttc aggagaaaga aacacctaca    1800
caggtatacc agaaagataa acaagatgct gacagaccct tgagtaaaat gaacagggca    1860
gtaaatggag agactctcaa aactggtgga gataataaaa ccctacttca cttaggcagc    1920
tctgctcctg gaaagagaaa aagtgaaact gataaggaaa cttctttggt aaagcaaaca    1980
ttagcaaaac ttcaacaaca agaacaaagg gaggaggctc agtggacacc tactaaattg    2040
tcttccaaaa atgtttcagg tcagacagat aaatgtaggg aggaaacttt taaacaagaa    2100
tcacaacctc cagaaaaaaa ttcaggacat tctacaagca aaggagacag agtggcacaa    2160
agtgagagca agaagaaaa agctgaggaa attctgaaaa gtcagactcc aaagggagga    2220
gacaagaagg aatcctccaa gtcattagtg cgacaaggga gcttcactat agaaaaaccc    2280
agcccaaaca tacccataga acttattccc catataaata aacagacttc ctctactcct    2340
tcttctttag cattaacatc tgcaagtaga atacgagaaa gaagtgagtc tttggatcct    2400
gattctagta tggacac                                                   2417
```

<210> SEQ ID NO 16
<211> LENGTH: 3617
<212> TYPE: DNA
<213> ORGANISM: homo sapiens

<400> SEQUENCE: 16

```
aaaaggagga ggcttaatca atattggggg ggggttatt attagatatc acaaattgtc     60
aggtctatct ttatttgaag gtagaggtag cctcaagcac tttagttggg tttgttaaac    120
aagcaagcaa agcggaaact acagctaagc atcttctgaa tgagatcatc atcactatag    180
aagaacctat gtcaaagatc ttcaactcaa gaaggaacag tgaggattag ttcctttatt    240
gtcagcgtca gaactgtggc ttggccagcc tcttctctta ggtaaggcat gagcacccta    300
ggcttcttct gtgtatctct tgctgcttaa atgtgtctcc attaggggtg tatatccttt    360
tcgaagtctt ctatattgaa gaaaagccaa cagcacaaaa agaccaacca agccaccag     420 tgttcccatg actactaaga gagttgtggg ccaacctgga gtttcttcaa ctgaaactgg    480
cagatcgatg gcatagctgt agccaagttg gtctgaggtt aaaagagtt cttcattagt     540 cactggaggg aagaaaggaa ccatgttgta catccgattg tgaccaatag gggccagctc    600
ctgaggccag gcatctgcag gaggattaaa tcttttcatc cactcatcaa agatggcatc    660
agtaaaggaa tgaagaacca caaaatggg atcattggcg gctgaatgtg caaagcgtt      720 tgtcccgttc aggaaggaat gaaccaaatt atgaaggctc atcacttgag aatccagagt    780
cccatctgct ttatcaaacc cttccaaagc attcctgaaa ctgaaggtag agttctggaa    840
```

-continued

```
gaagggagga ttgtcaaact tctggagaga caggcaatct cgtatgtctt ttaaggttgg      900
caatttcatg ctgtttcttc ccatttgatt tcttctcagc aaaccttcat aggttccatt      960
gcacaaggtg accaggtggt tgtagtcatc caagctatca cagacagttt cccagctgga     1020
gaatcttgag ttccgactaa tcagagtcgg atcgtctggt ctcgctgccc caaacagctg     1080
gtctgtacac acatcacact cgttcctccc agtggcaaag ttccagtagg gcaaagcaaa     1140
agactcattg ccaatgagtc gctggagatc tctttccaga cacaacaaat ggtaccggtg     1200
ccaggtaaca aatgcaggtc cttgatgtga gaaatctatg ccctgtaggg gcgtcctgg      1260 tcctaataat gtatctctaa cagaataata atggagccac acaaaaaaat cataaacact     1320
gcagttggca aactgcggct gggttccatt gggcccaagc aggcccagcc agtgttgtgt     1380
ggtgatcacg tagtcggggt gtactctctt cttcgcgaga tctaaggcgc ccaagaactg     1440
ctctctttcc tgaggactca aggaatggat gttctgccga atcactggtg gtttcttccg     1500
ctcgcagttg ggaccggtcc agccaaactt gcagtctcca caattatagc cggcaaagtt     1560
tcctgtgcac ttgcaggtcc ggtggaagaa ttttcttggc cacagctcac ggtcatcctg     1620
gtttcgtagg atgtagggac cactccaggg ccttgtgtcg gctcgcacct ctgtgcactg     1680
cccccggcct tgctgagagc cacagacatt ggccgactct gcacccaggc gtgggcagca     1740
ctccttgttc actaggctgt ccaccgtcat gcagactcgg gggaactgac cctgggctcc     1800
tggcaggatt ttgcagccca agcaactgag cagaaacccc caccaaaggg ggctcatggc     1860
tttataattg ggagagctct ctctctctct tactttcctt gtctctgtcg tacttttctc     1920
cttatcttct actctttcag tcttttcttt tcagtatttt ttatttttct ttgctttcta     1980
ttcctttctt cttaaaaaaa tacccacaag aatcacagag gttacatgtg tgcacggtta     2040
catgtgtgca catgtgtaca tgaacgtgca cacacaattt tatgtgattc aaacaactaa     2100
cagacttaat ttccttagaa gcgcctctaa caaccaaatt taatgagggt agcgcttctc     2160
accatcttcc cccgttaagt caggctttgt ctaattgagt taatttacag agcacccagt     2220
catactactt attatgctgg tatttctaaa ccctctccct ccctccttag ctcttgactt     2280
taatctcgtg ccgaattcgg cacgagaatt gttaaaacag aaatcagagg agccatcggt     2340
gtcaataccc ttcctacaaa ctgcattatt aagaagttca gggagtcttg ggcacagacc     2400
aagccaggag atggataaaa tgttaaaaaa tcaagcaact tctgctactt ctgaaaagga     2460
taatgatgat gaccaaagtg acaagggtac ttataccatt gagttagaga atcccaacag     2520
tgaggaagtg gaagcaagaa aaatgattga caaggtgttt ggagtagatg acaatcagga     2580
ttataatagg cctgttatca acgaaaaaca taaagatcta ataaaagatt gggctctcag     2640
ttctgctgca gcagtaatgg aagaaagaaa accactgact acatctggat tcaccactc      2700 agaggaaggc acatcttcat ctggaagcaa acgttaggtt tcacagtggg ctagtttggc     2760
tgccaatcat acaaggcatg atcaagaaga aggataatg gaattttctg cacctcttcc      2820
tttagagaat gagacagaga tcagtgagtc tggcatgaca gtgagaagta ctggctctgc     2880
aacttccttg gctagccagg gagagagaag gagacgaact cttccccagc ttccaaatga     2940
agaaaagtct cttgagagcc acagagcaaa ggttgtaaca cagaggtcag agataggaga     3000 aaacaagac acagaacttc aggagaaaga aacacctaca caggtatacc agaaagataa      3060
acaagatgct gacagaccct tgagtaaaat gaacagggca gtaaatggag agactctcaa     3120
aactggtgga gataataaaa ccctacttca cttaggcagc tctgctcctg gaaaagagaa     3180
```

-continued

```
aagtgaaact gataaggaaa cttctttggt aaagcaaaca ttagcaaaac ttcaacaaca      3240
agaacaaagg gaggaggctc agtggacacc tactaaattg tcttccaaaa atgtttcagg      3300
tcagacagat aaatgtaggg aggaaacttt taaacaagaa tcacaacctc cagaaaaaaa      3360
ttcaggacat tctacaagca aaggagacag agtggcacaa agtgagagca agagaagaaa      3420
agctgaggaa attctgaaaa gtcagactcc aaagggagga gacaagaagg aatcctccaa      3480
gtcattagtg cgacaaggga gcttcactat agaaaaaccc agcccaaaca tacccataga      3540
acttattccc catataaata aacagacttc ctctactcct tcttctttag cattaacatc      3600
tgcaagtaga atacgag                                                    3617
```

<210> SEQ ID NO 17
<211> LENGTH: 1737
<212> TYPE: DNA
<213> ORGANISM: homo sapiens

<400> SEQUENCE: 17

```
atgacagggt ccagaaactg gcgagccacg agggacatgt gtaggtatcg gcacaactat        60
ccggatctgg tggaacgaga ctgcaatggg gacacgccaa acctgagttt ctacagaaat       120
gagatccgct tcctgcccaa cggctgtttc attgaggaca ttcttcagaa ctggacggac       180
aactatgacc tccttgagga caatcactcc tacatccagt ggctgtttcc tctgcgagaa       240
ccaggagtga actggcatgc caagcccctc acgctcaggg aggtcgaggt gtttaaaagc       300
tcccaggaga tccaggagcg gcttgtccgg gcctacgagc tcatgctggg cttctacggg       360
atccggctgg aggaccgagg cacgggcacg gtgggccgag cacagaacta ccagaagcgc       420
ttccagaacc tgaactggcg cagccacaac aacctccgca tcacacgcat cctcaagtcg       480
ctgggtgagc tgggcctcga gcacttccag gcgccgctgg tccgcttctt cctggaggag       540
acgctggtgc ggcgggagct gccggggggtg cggcagagtg ccctggacta cttcatgttc       600
gccgtgcgct gccgacacca gcgccgccag ctggtgcact tcgcctggga gcacttccgg       660
ccccgctgca agttcgtctg ggggcccccaa gacaagctgc ggaggttcaa gcccagctct       720
ctgccccatc cgctcgaggg ctccaggaag gtggaggagg aaggaagccc cggggacccc       780
gaccacgagg ccagcacccca gggtcggacc tgtgggccag agcatagcaa gggtgggggc       840
agggtggacg aggggcccca gccacggagc gtggagcccc aggatgcggg acccctggag       900
aggagccagg gggatgaggc aggggggccac ggggaagata ggccggagcc cttaagcccc       960
aaagagagca agaagaggaa gctggagctg agccggcggg agcagccgcc cacagagcca      1020
ggccctcaga gtgcctcaga ggtggagaag atcgctctga atttggaggg gtgtgccctc      1080
agccagggca gcctcaggac ggggacccag gaagtgggcg tcaggaccc tggggaggca      1140 gtgcagccct gccgccaacc cctgggagcc agggtggccg acaaggtgag gaagcggagg      1200
aaggtggatg agggtgctgg ggacagtgct gcggtgccca gtggtggtgc ccagaccttg      1260
gcccttgccg ggtcccctgc cccatcgggg caccccaagg ctggacacag tgagaacggg      1320
gttgaggagg acacagaagg tcgaacgggg cccaaagaag gtaccctgg gagcccatcg      1380 gagacccag gccccgccc agcaggacct gcaggggacg agccagccga gagcccatcg      1440 gagacccag gccccagccc ggcaggacct acaagggatg agccagccga gagcccatcg      1500 gagacccag gccccagccc ggcaggacct gcaggggacg agccagccga gagcccatcg      1560 gagacccag gccccagccc ggcaggacct gcaggggacg agccagccga gagcccatcg      1620 gagacccag gccccagccc ggcaggacct acaagggatg agccagccaa ggcggggggag      1680
```
gcagcagagt tgcaggacgc agaggtggag tcttctgcca agtctgggaa gccttaa    1737

<210> SEQ ID NO 18
<211> LENGTH: 578
<212> TYPE: PRT
<213> ORGANISM: homo sapiens

<400> SEQUENCE: 18

Met Thr Gly Ser Arg Asn Trp Arg Ala Thr Arg Asp Met Cys Arg Tyr
1               5                   10                  15

Arg His Asn Tyr Pro Asp Leu Val Glu Arg Asp Cys Asn Gly Asp Thr
            20                  25                  30

Pro Asn Leu Ser Phe Tyr Arg Asn Glu Ile Arg Phe Leu Pro Asn Gly
        35                  40                  45

Cys Phe Ile Glu Asp Ile Leu Gln Asn Trp Thr Asp Asn Tyr Asp Leu
    50                  55                  60

Leu Glu Asp Asn His Ser Tyr Ile Gln Trp Leu Phe Pro Leu Arg Glu
65                  70                  75                  80

Pro Gly Val Asn Trp His Ala Lys Pro Leu Thr Leu Arg Glu Val Glu
                85                  90                  95

Val Phe Lys Ser Ser Gln Glu Ile Gln Glu Arg Leu Val Arg Ala Tyr
            100                 105                 110

Glu Leu Met Leu Gly Phe Tyr Gly Ile Arg Leu Glu Asp Arg Gly Thr
        115                 120                 125

Gly Thr Val Gly Arg Ala Gln Asn Tyr Gln Lys Arg Phe Gln Asn Leu
    130                 135                 140

Asn Trp Arg Ser His Asn Asn Leu Arg Ile Thr Arg Ile Leu Lys Ser
145                 150                 155                 160

Leu Gly Glu Leu Gly Leu Glu His Phe Gln Ala Pro Leu Val Arg Phe
                165                 170                 175

Phe Leu Glu Glu Thr Leu Val Arg Arg Glu Leu Pro Gly Val Arg Gln
            180                 185                 190

Ser Ala Leu Asp Tyr Phe Met Phe Ala Val Arg Cys Arg His Gln Arg
        195                 200                 205

Arg Gln Leu Val His Phe Ala Trp Glu His Phe Arg Pro Arg Cys Lys
    210                 215                 220

Phe Val Trp Gly Pro Gln Asp Lys Leu Arg Arg Phe Lys Pro Ser Ser
225                 230                 235                 240

Leu Pro His Pro Leu Glu Gly Ser Arg Lys Val Glu Glu Glu Gly Ser
                245                 250                 255

Pro Gly Asp Pro Asp His Glu Ala Ser Thr Gln Gly Arg Thr Cys Gly
            260                 265                 270

Pro Glu His Ser Lys Gly Gly Arg Val Asp Glu Gly Pro Gln Pro
        275                 280                 285

Arg Ser Val Glu Pro Gln Asp Ala Gly Pro Leu Glu Arg Ser Gln Gly
    290                 295                 300

Asp Glu Ala Gly Gly His Gly Glu Asp Arg Pro Glu Pro Leu Ser Pro
305                 310                 315                 320

Lys Glu Ser Lys Lys Arg Lys Leu Glu Leu Ser Arg Arg Glu Gln Pro
                325                 330                 335

Pro Thr Glu Pro Gly Pro Gln Ser Ala Ser Glu Val Glu Lys Ile Ala
            340                 345                 350

Leu Asn Leu Glu Gly Cys Ala Leu Ser Gln Gly Ser Leu Arg Thr Gly
        355                 360                 365

```
Thr Gln Glu Val Gly Gly Gln Asp Pro Gly Glu Ala Val Gln Pro Cys
    370                 375                 380

Arg Gln Pro Leu Gly Ala Arg Val Ala Asp Lys Val Arg Lys Arg Arg
385                 390                 395                 400

Lys Val Asp Glu Gly Ala Gly Asp Ser Ala Val Ala Ser Gly Gly
                405                 410                 415

Ala Gln Thr Leu Ala Leu Ala Gly Ser Pro Ala Pro Ser Gly His Pro
                420                 425                 430

Lys Ala Gly His Ser Glu Asn Gly Val Glu Glu Asp Thr Glu Gly Arg
                435                 440                 445

Thr Gly Pro Lys Glu Gly Thr Pro Gly Ser Pro Ser Glu Thr Pro Gly
    450                 455                 460

Pro Arg Pro Ala Gly Pro Ala Gly Asp Glu Pro Ala Glu Ser Pro Ser
465                 470                 475                 480

Glu Thr Pro Gly Pro Ser Pro Ala Gly Pro Thr Arg Asp Glu Pro Ala
                485                 490                 495

Glu Ser Pro Ser Glu Thr Pro Gly Pro Arg Pro Ala Gly Pro Ala Gly
                500                 505                 510

Asp Glu Pro Ala Glu Ser Pro Ser Glu Thr Pro Gly Pro Arg Pro Ala
                515                 520                 525

Gly Pro Ala Gly Asp Glu Pro Ala Glu Ser Pro Ser Glu Thr Pro Gly
                530                 535                 540

Pro Ser Pro Ala Gly Pro Thr Arg Asp Glu Pro Ala Lys Ala Gly Glu
545                 550                 555                 560

Ala Ala Glu Leu Gln Asp Ala Glu Val Glu Ser Ser Ala Lys Ser Gly
                565                 570                 575

Lys Pro

<210> SEQ ID NO 19
<211> LENGTH: 176
<212> TYPE: PRT
<213> ORGANISM: homo sapiens

<400> SEQUENCE: 19

Met Arg Val Leu Gly Thr Val Leu Arg Trp Pro Val Val Pro Arg
1               5                   10                  15

Pro Trp Pro Leu Pro Gly Pro Leu Pro His Arg Gly Thr Pro Arg Leu
                20                  25                  30

Asp Thr Val Arg Thr Gly Leu Arg Arg Thr Gln Lys Val Glu Arg Gly
                35                  40                  45

Pro Lys Lys Val Pro Leu Gly Ala His Arg Arg Pro Gln Ala Pro Ala
50                  55                  60

Gln Gln Asp Leu Gln Gly Thr Ser Gln Pro Arg Ala His Arg Arg Pro
65                  70                  75                  80

Gln Ala Pro Ala Arg Gln Asp Leu Gln Gly Met Ser Gln Pro Arg Ala
                85                  90                  95

His Arg Arg Pro Gln Ala Pro Ala Arg Gln Asp Leu Gln Gly Thr Ser
                100                 105                 110

Gln Pro Arg Ala His Arg Arg Pro Gln Ala Pro Ala Arg Gln Asp Leu
                115                 120                 125

Gln Gly Thr Ser Gln Pro Arg Ala His Arg Arg Pro Gln Ala Pro Ala
                130                 135                 140

Arg Gln Asp Leu Gln Gly Met Ser Gln Pro Arg Arg Gly Arg Gln Gln
145                 150                 155                 160
```

```
Ser Cys Arg Thr Gln Arg Trp Ser Leu Leu Pro Ser Leu Gly Ser Leu
            165                 170                 175
```

<210> SEQ ID NO 20
<211> LENGTH: 49
<212> TYPE: PRT
<213> ORGANISM: homo sapiens

<400> SEQUENCE: 20

```
Ser Pro Ser Glu Thr Pro Gly Pro Arg Pro Ala Gly Pro Ala Gly Asp
  1               5                  10                  15

Glu Pro Ala Glu Ser Pro Ser Glu Thr Pro Gly Pro Arg Pro Ala Gly
             20                  25                  30

Pro Ala Gly Asp Glu Pro Ala Lys Thr Pro Ser Glu Thr Pro Gly Pro
             35                  40                  45

Ser
```

<210> SEQ ID NO 21
<211> LENGTH: 50
<212> TYPE: PRT
<213> ORGANISM: homo sapiens

<400> SEQUENCE: 21

```
Ala His Arg Arg Pro Gln Ala Pro Ala Gln Gln Asp Leu Gln Gly Thr
  1               5                  10                  15

Ser Gln Pro Arg Ala His Arg Arg Pro Gln Ala Pro Ala Gln Gln Asp
             20                  25                  30

Leu Gln Gly Thr Ser Gln Pro Arg Ala His Arg Arg Pro Gln Ala Pro
             35                  40                  45

Ala Gln
     50
```

<210> SEQ ID NO 22
<211> LENGTH: 9
<212> TYPE: PRT
<213> ORGANISM: homo sapiens

<400> SEQUENCE: 22

```
Ser Leu Gly Ser Pro Val Leu Gly Leu
  1               5
```

<210> SEQ ID NO 23
<211> LENGTH: 10
<212> TYPE: PRT
<213> ORGANISM: homo sapiens

<400> SEQUENCE: 23

```
Arg Leu Ala Ser Phe Tyr Asp Trp Pro Leu
  1               5                  10
```

<210> SEQ ID NO 24
<211> LENGTH: 20
<212> TYPE: PRT
<213> ORGANISM: homo sapiens
<220> FEATURE:
<221> NAME/KEY: VARIANT
<222> LOCATION: (2)...(17)
<223> OTHER INFORMATION: Xaa at 2 is Thr or Met;
      Xaa at 4 is Gln or Arg;
      Xaa at 7 is Ala or Pro;
      Xaa at 16 is Arg or Gln.
<220> FEATURE:
<221> NAME/KEY: VARIANT

```
<222> LOCATION: 2, 4, 7, 16
<223> OTHER INFORMATION: Xaa = Any Amino Acid

<400> SEQUENCE: 24

Gly Xaa Ser Xaa Pro Arg Xaa His Arg Pro Gln Ala Pro Ala Xaa
 1               5                  10                  15

Gln Asp Leu Gln
            20

<210> SEQ ID NO 25
<211> LENGTH: 14
<212> TYPE: PRT
<213> ORGANISM: homo sapiens

<400> SEQUENCE: 25

Ala His Arg Arg Pro Gln Ala Pro Ala Gln Gln Asp Leu Gln
 1               5                  10

<210> SEQ ID NO 26
<211> LENGTH: 20
<212> TYPE: PRT
<213> ORGANISM: homo sapiens

<400> SEQUENCE: 26

Gly Thr Ser Gln Pro Arg Ala His Arg Pro Gln Ala Pro Ala Arg
 1               5                  10                  15

Gln Asp Leu Gln
            20

<210> SEQ ID NO 27
<211> LENGTH: 20
<212> TYPE: PRT
<213> ORGANISM: homo sapiens

<400> SEQUENCE: 27

Gly Met Ser Gln Pro Arg Ala His Arg Pro Gln Ala Pro Ala Arg
 1               5                  10                  15

Gln Asp Leu Gln
            20

<210> SEQ ID NO 28
<211> LENGTH: 20
<212> TYPE: PRT
<213> ORGANISM: homo sapiens

<400> SEQUENCE: 28

Gly Thr Ser Gln Pro Arg Ala His Arg Pro Gln Ala Pro Ala Gln
 1               5                  10                  15

Gln Asp Leu Gln
            20

<210> SEQ ID NO 29
<211> LENGTH: 20
<212> TYPE: PRT
<213> ORGANISM: homo sapiens

<400> SEQUENCE: 29

Gly Thr Ser Gln Pro Arg Pro His Arg Pro Gln Ala Pro Ala Arg
 1               5                  10                  15

Gln Asp Leu Gln
            20
```

```
<210> SEQ ID NO 30
<211> LENGTH: 20
<212> TYPE: PRT
<213> ORGANISM: homo sapiens
<220> FEATURE:
<221> NAME/KEY: VARIANT
<222> LOCATION: (1)...(20)
<223> OTHER INFORMATION: Xaa at 9 is Arg or Ser;
      Xaa at 14 is Ala or Thr;
      Xaa at 15 is Gly or Arg;
      Xaa at 20 is Glu or Lys
<220> FEATURE:
<221> NAME/KEY: VARIANT
<222> LOCATION: 9, 14, 15, 20
<223> OTHER INFORMATION: Xaa = Any Amino Acid

<400> SEQUENCE: 30

Ser Pro Ser Glu Thr Pro Gly Pro Xaa Pro Ala Gly Pro Xaa Xaa Asp
 1               5                  10                  15

Glu Pro Ala Xaa
            20

<210> SEQ ID NO 31
<211> LENGTH: 20
<212> TYPE: PRT
<213> ORGANISM: homo sapiens

<400> SEQUENCE: 31

Ser Pro Ser Glu Thr Pro Gly Pro Arg Pro Ala Gly Pro Ala Gly Asp
 1               5                  10                  15

Glu Pro Ala Glu
            20

<210> SEQ ID NO 32
<211> LENGTH: 20
<212> TYPE: PRT
<213> ORGANISM: homo sapiens

<400> SEQUENCE: 32

Ser Pro Ser Glu Thr Pro Gly Pro Ser Pro Ala Gly Pro Thr Arg Asp
 1               5                  10                  15

Glu Pro Ala Glu
            20

<210> SEQ ID NO 33
<211> LENGTH: 20
<212> TYPE: PRT
<213> ORGANISM: homo sapiens

<400> SEQUENCE: 33

Ser Pro Ser Glu Thr Pro Gly Pro Ser Pro Ala Gly Pro Thr Arg Asp
 1               5                  10                  15

Glu Pro Ala Lys
            20

<210> SEQ ID NO 34
<211> LENGTH: 6670
<212> TYPE: DNA
<213> ORGANISM: homo sapiens

<400> SEQUENCE: 34
ccggcccggt cgacccgccg ccgccgagca tggacgaccc cgactgcgac tccacctggg      60
aggaggacga ggaggatgcg gaggacgcgg aggacgagga ctgcgaggag gccgaggccg     120
ccggcgcgag ggacgcggac gcaggggacg aggacgagga gtcggaggag ccgcgggggc     180
```

```
cgtgcccagc tcgttccagt ccagaatgac agggtccaga aactggcgag ccacgaggga    240
catgtgtagg tatcggcaca actatccggt acgtacctgc ccctgccccg ggacacagaa    300
ccctcccgcc agctgctctt ctcaggcaga atgtcccagg ttctactgga aggctggcct    360
ggcttgctgt gccagggcca cagttctggg caggaccctg cctgggcac aacctggtat     420
agattcagag ccctgccctt ccctctcgc gggagaccgg gggcatcccc tactttctg      480
agcttcagca caccgtcgcc ttgcaaacat ggccatagtg ccagcctcgt gatgcacacg    540
tgtgggtcc gtgataccgc ccacacagca ccccacccc atgccagccc tgtctcctgc      600
aggttgtcct cagccattac cctccacacc cctgaatcac ggaaacccct gtgctgcctt    660
cagggtgctg aggaggggac cctaggcctg gcctggctgg cgaaatgggg aaggggtcc     720
ctggggcttg gaggcagctg ctgtcctctg aatggccccc acctgcagag tgaggagcca    780
ggcgggctct tggggtattg ggccagcctg gaggtttgca gatgcgcctc cccgaaagac    840
acggagggcc ccagggcagc ttgtgtctga tggatccctg ctgtcccctt tctctggccc    900
ttcaggatct ggtggaacga gactgcaatg ggacacgcc aaacctgagt ttctacagaa      960
atgagatccg cttcctgccc aacggtaggt gcctcacaac cactggcagc cggcgcttcc   1020
atccttgcct ggcaggggtg gtccactggg ccctggtttg ggatgtaccc ggcgattacc   1080
agggccacgg ctttcaaata gccccacagt gcccctgga ggcggccaga gggcatccag     1140
gatccccggc ttggaatctc cgcagtggtg tttgggtcgg ggtgggctat ctctgtaaag   1200
agccagagac tgaatatctg cagcttttca ggccacacag tctctatcaa aactactgaa   1260
ctcctgcacg acctcatgaa agccacatgt aaaccaacag gctaaggata gcttttatat   1320
ttttaaatgg ttgcaaaaaa ttaaaagtag aggccgggcc tggtggctca cgcttgtaat   1380
cccagcactt tgggaggcca aggcgggtgg atcacaaagt catgagttcg agaccagcct   1440
ggccaatatg gtgaaaccct gtctctacta aaaatacaaa aaaattagc caggtgtggt    1500
agcgtgcgcc tgtagtccca gctactcagg aggctgaggc aggagaatcg cttgaacttg   1560
ggaggtggag gttgcgtgag ccgagatctc gccactgccc tccagcctgg caacagaat    1620
gagactctgt ctcaaaaaaa aaaaaaaaa aaaaagaac agtgttctat tactttgata    1680
ttataagaaa ttaaaatttc agtgtcaata agcttcacg gcacgtgccc acacctgttt    1740
atgcacgtgc cgggctgcaa cgtgaaacag agactgggtg gctgcacgaa acactgtcag   1800
gcccccatct caggagactg tgcctgccac atcatgggac tgggttcagc tgggggctgt   1860
gtttgaggac agatttctgt ggctgacggg ccacgctttt gcaggaggca ctgaggcccc   1920
ctcctgtaca gacaggtcct ggtcgaggac cagtggttcc cccagaggga cttccgggct   1980
ctcagtgggg tttgccgcca ccagcaaca agggtccagg tcacagatgg cagcagggca    2040
agggctgtgc atcggaggag ggatgggcag aaccactgag cctagcaccc tgaagagcct   2100
caggagatga gggcgaggaa tagcttgggg aagctgctgg cagcactctc tccttatgtc   2160
ccccacccac acccgtcct cctgagcacg gcagggtgg ctgccacagc tgacttgtcc     2220
catgggctc ccaggctgtt tcattgagga cattcttcag aactggacag acaactatga    2280
cctccttgag gacaatcact cctacatcca gtggtgagtt gggaggatg ggaggatggg    2340
gggttggcga ggccacaggg ggagggccct cccaggcagg agccctcccg acgctgcttc   2400
ctggcacgga ctgagcactc cctgcccttc ctggaagctg gtgtccacat tacacgatg    2460
gacattactg gacatgcaag ggccgctgag ggaaggctca ggtctgtccc caatctgtgg   2520
```

```
gctcttggtg accagggaga caggaagggc tgcacacaag ctccctgaaa caggagaggg    2580
ggcaggcact gctcgagagg ggcagcctta gtgccaggag gcctcagtga gcctcaaggg    2640 gcggccccg tctcggactc agctgggca gggtcctggc gtagtgctgg gatgagactt     2700
gtggcaggcg tcttggggac ccacaatgtc cccggaaaca tagcatgccc tgctttgggg    2760
acagctcgct gggcgtccac agggagcctc tcgtggtgtg tgacgtgtca tgagtgacaa    2820
cacaagagag ggaagagtga ggagtagaaa ggaaggccct gtccgcccgg gctggatggc    2880
tgcagggccc ctcgctgcct gagtcacctc cccagtcctg ctgagcatgc aggctgtgac    2940
ttacgcacca cacacctcct gtcctgggcc cttgcacgct cacctgagct ctcccaccct    3000
cgctcctcca cctagccact ccctcctaga gttgagcctg gaacccaga ggggattgga     3060 actgccccgg gctacacagc gagcacctgc ccgaggtctg gaagcggctc tcctaatccc    3120
ttgcctgagc atctcttctc ctgcaggctg tttcctctgc gagaaccagg agtgaactgg    3180
catgccaagc ccctcacgct cagggaggtc gaggtgagcc aggccttggg gctgtgactg    3240
gaggggaaga tggggaggcc tgggcaagcc acgcgcagag acgggtcgc ctctggcagt     3300 aggcatttgg tgcccctca gggtcccttg aaggcagaa gggccgaaag agcctccagt      3360
atgatgacct tccctcccca gtggtcctca ccccaccagg catctagaga aactcaattt    3420
ccgaggctgt ttgtccccat gcgggagtct gggctgagc ctgagagacc cggaatggcg     3480
ggacctgcct ttctcaccac tggtttaggc tggagtgggg tcacccaagt gtggaagctg    3540
cccctgaggg atgcagggac ttagagagcc gaggggcccc tcctggcact ttcccatggc    3600
cagcgacttc ctctcagggg agggcggcca tgcaggccct ggtgagagct cggagcagct    3660
cagaggagag atggaggcat gagtgtgtct cttgtcactt taccctaaaa gtctgagtcc    3720
aggctaggtg ccgtggctca cgtttgtaat cccagcactt tgagaggctg aggcgggtgg    3780
atcacctgag gtcaggagtt tgagaccagc tggccaacgt gacaaaaccc cgtttctact    3840
taaaaataga aaaaaattag ccaggtgtgg tggcaggcaa ctgtaatccc agctactcgg    3900
gaggcagagg ttgcagtgac ttgaggattg cagtgaccct tgaggctaca ccattgcact    3960
ccagcctggg caacagagca agactctgtc tctaaataaa tgtctgtctg tctgtctgtc    4020
tagtccccag gcctctgagt gagctgggac ccacggcctc ccccacactc aggaaccggg    4080
gcttcaggga tggtgcctga gctctccaag ggggtctttt ccaggtgttt aaaagctccc    4140
aggagatcca ggagcggctt gtccgggcct acgcagctca tgctgggctt ctacgggatc    4200
cggctggagg accgaggcac gggcacgtg ggccgagcac agaactacca gaagcgcttc     4260
cagaacctga actggtgagg cccggctgct cccgcccacc cccacccggg cgcagaacag    4320
ggccacgtca ggtttcgggc aggtcacaga gcgctgctgc agacgagaa ctccagggct     4380 gtttgggcaa tcgaccaagg ccctgagtcc cctccttgct gcctgtagag ccgggcggtc    4440
cctccccgat aggttggtga aaggtaaag aatgctcttc ctgcacccag gaggtggcag     4500
tccacataga gaagcaggca ggggtgatgg agaacctgca ggcggtacag ccagttctca    4560
cagggtgttc gaggcgcctg taccctgcgg ggcccttgt ggctctcatc cagccagctc     4620
ctccccacca gggggactcg gggtacagcc accctctagg tgatgcgtca gcatccccct    4680 aaccccgtg tgtgtaggcc cacaggccat tttcacaggg atggcatgag tcctcccctg     4740
ggcccagaga ggtaaatggg gagagagact gaatcgtggg ccagggtggg gagacctcgt    4800
ggagccgggt ggagggcag gccagggcgg ggtgcggccc agcaggaggg gccccggcca     4860
ttgacctctc ctgacccgga tctctcgcag cgcagccaca acaacctccg catcacacgc    4920
```

-continued

```
atcctcaagt cgctgggtga gctgggcctc gagcacttcc aggcgccgct ggtccgcttc      4980
ttcctggagg agagcctggt gcggcgggag ctgccggggg tgcggcagag tgccctggac      5040
tacttcatgt tcgccgtcgg ctgccgacac cagcgccgcc agctggtgca cttcgcctgg      5100
gagcacttcc ggccccgctg caagttcgtc tgggggcccc aagacaagct gcggaggttc      5160
aagcccagct ctctgccgca tccgctcgag ggctccagga aggtggagga ggaaggaagc      5220
cccggggacc ccgaccacga ggccagcacc caggqtcgga cctgtgggcc agagcatagc      5280
aagggtgggg gcagggtgga cgaggggccc cagccacgga gcgtggagcc ccaggatgcg      5340
ggacccctgg agaggagcca gggggatgag gcaggggqcc acggggaaga taggccggag      5400
cccttaagcc ccaaagagag caagaagagg aagctggagc tgagccggcg ggagcagccg      5460
cccacagagc caggccctca gagtgcctca gaggtggaga agatcgctct gaatttggag      5520
gggtgtgccc tcagccaggg cagcctcagg acggggaccc aggaagtggg cggtcaggac      5580
cctggggagg cagtgcagcc ctgccgccaa cccctgggag ccagggtggc cgacaaggtg      5640
aggaagcgga ggaaggtgga tgagggtgct ggggacagtg ctgcggtggc cagtggtggt      5700
gcccagacct tggcccttgc cgggtcccct gccccatcgg ggcaccccaa ggctggacac      5760
agtgagaacg gggttgagga ggacacagaa ggtcgaacgg ggcccaaaga aggtacccct      5820
gggagcccat cggagacccc aggccccagc ccagcaggac ctgcagggga cgagccggcc      5880
gagagcccat cggagacccc aggcccccgc ccagcaggac ctgcagggga cgagccagcc      5940
gagagcccat cggagacccc aggcccccgc ccggcaggac ctgcagggga cgagccagcc      6000
aagaccccat cggagacccc aggccccagc ccggcaggac ctacaaggga tgagccagcc      6060
gagagcccat cggagacccc aggcccccgc ccggcaggac ctgcagggga cgagccagcc      6120
gagagcccat cggagacccc aggcccccgc ccggcaggac ctgcagggga cgagccagcc      6180
gagagcccat cggagacccc aggccccagc ccggcaggac ctacaaggga tgagccagcc      6240
aaggcggggg aggcagcaga gttgcaggac gcagaggtgg agtcttctgc caagtctggg      6300
aagccttaag gaaaggagtg cccgtcggcg tcttggtcct cctgtccctg ctgcaggggc      6360
tggggcctcc ggagctgctg cgggctcccc tcaggctctg cttcgtgacc cgtgacccat      6420
gacccacagt gctggcctcc tgtggggcca ctatagcagc caccagaagc cgcgaggccc      6480
tcagggaagc ccaaggcctg cagaagcctc ctggcctggc tgtgtcttcc ccacccagct      6540
ctcccctgcg cccctgtctt tgtaaattga cccttctgga gtgggggcg gcgggcaggg      6600 ctgcttttct tagtctgatg ccaagcaagg ccttttctga ataaattcat ttgactttga      6660
aaaaaaaaa                                                              6670
```

<210> SEQ ID NO 35
<211> LENGTH: 618
<212> TYPE: PRT
<213> ORGANISM: homo sapiens

<400> SEQUENCE: 35

```
Met Thr Gly Ser Arg Asn Trp Arg Ala Thr Arg Asp Met Cys Arg Tyr
 1               5                  10                  15

Arg His Asn Tyr Pro Asp Leu Val Glu Arg Asp Cys Asn Gly Asp Thr
            20                  25                  30

Pro Asn Leu Ser Phe Tyr Arg Asn Glu Ile Arg Phe Leu Pro Asn Gly
        35                  40                  45

Cys Phe Ile Glu Asp Ile Leu Gln Asn Trp Thr Asp Asn Tyr Asp Leu
```

-continued

```
            50                  55                  60
Leu Glu Asp Asn His Ser Tyr Ile Gln Trp Leu Phe Pro Leu Arg Glu
 65                  70                  75                  80

Pro Gly Val Asn Trp His Ala Lys Pro Leu Thr Leu Arg Glu Val Glu
                 85                  90                  95

Val Phe Lys Ser Ser Gln Glu Ile Gln Glu Arg Leu Val Arg Ala Tyr
                100                 105                 110

Ala Ala His Ala Gly Leu Leu Arg Asp Pro Ala Gly Gly Pro Arg His
                115                 120                 125

Gly His Gly Gly Pro Ser Thr Glu Leu Pro Glu Ala Leu Pro Glu Pro
130                 135                 140

Glu Leu Arg Ser His Asn Asn Leu Arg Ile Thr Arg Ile Leu Lys Ser
145                 150                 155                 160

Leu Gly Glu Leu Gly Leu Glu His Phe Gln Ala Pro Leu Val Arg Phe
                165                 170                 175

Phe Leu Glu Glu Ser Leu Val Arg Arg Glu Leu Pro Gly Val Arg Gln
                180                 185                 190

Ser Ala Leu Asp Tyr Phe Met Phe Ala Val Gly Cys Arg His Gln Arg
                195                 200                 205

Arg Gln Leu Val His Phe Ala Trp Glu His Phe Arg Pro Arg Cys Lys
                210                 215                 220

Phe Val Trp Gly Pro Gln Asp Lys Leu Arg Arg Phe Lys Pro Ser Ser
225                 230                 235                 240

Leu Pro His Pro Leu Glu Gly Ser Arg Lys Val Glu Glu Glu Gly Ser
                245                 250                 255

Pro Gly Asp Pro Asp His Glu Ala Ser Thr Gln Gly Arg Thr Cys Gly
                260                 265                 270

Pro Glu His Ser Lys Gly Gly Arg Val Asp Glu Gly Pro Gln Pro
                275                 280                 285

Arg Ser Val Glu Pro Gln Asp Ala Gly Pro Leu Glu Arg Ser Gln Gly
                290                 295                 300

Asp Glu Ala Gly Gly His Gly Glu Asp Arg Pro Glu Pro Leu Ser Pro
305                 310                 315                 320

Lys Glu Ser Lys Lys Arg Lys Leu Glu Leu Ser Arg Arg Glu Gln Pro
                325                 330                 335

Pro Thr Glu Pro Gly Pro Gln Ser Ala Ser Glu Val Glu Lys Ile Ala
                340                 345                 350

Leu Asn Leu Glu Gly Cys Ala Leu Ser Gln Gly Ser Leu Arg Thr Gly
                355                 360                 365

Thr Gln Glu Val Gly Gly Gln Asp Pro Gly Glu Ala Val Gln Pro Cys
370                 375                 380

Arg Gln Pro Leu Gly Ala Arg Val Ala Asp Lys Val Arg Lys Arg Arg
385                 390                 395                 400

Lys Val Asp Glu Gly Ala Gly Asp Ser Ala Val Ala Ser Gly Gly
                405                 410                 415

Ala Gln Thr Leu Ala Leu Ala Gly Ser Pro Ala Pro Ser Gly His Pro
                420                 425                 430

Lys Ala Gly His Ser Glu Asn Gly Val Glu Glu Asp Thr Glu Gly Arg
                435                 440                 445

Thr Gly Pro Lys Glu Gly Thr Pro Gly Ser Pro Ser Glu Thr Pro Gly
                450                 455                 460

Pro Ser Pro Ala Gly Pro Ala Gly Asp Glu Pro Ala Glu Ser Pro Ser
465                 470                 475                 480
```

```
Glu Thr Pro Gly Pro Arg Pro Ala Gly Pro Ala Gly Asp Glu Pro Ala
            485                 490                 495

Glu Ser Pro Ser Glu Thr Pro Gly Pro Arg Pro Ala Gly Pro Ala Gly
            500                 505                 510

Asp Glu Pro Ala Lys Thr Pro Ser Glu Thr Pro Gly Pro Ser Pro Ala
            515                 520                 525

Gly Pro Thr Arg Asp Glu Pro Ala Glu Ser Pro Ser Glu Thr Pro Gly
            530                 535                 540

Pro Arg Pro Ala Gly Pro Ala Gly Asp Glu Pro Ala Glu Ser Pro Ser
545                 550                 555                 560

Glu Thr Pro Gly Pro Arg Pro Ala Gly Pro Ala Gly Asp Glu Pro Ala
            565                 570                 575

Glu Ser Pro Ser Glu Thr Pro Gly Pro Ser Pro Ala Gly Pro Thr Arg
            580                 585                 590

Asp Glu Pro Ala Lys Ala Gly Glu Ala Ala Glu Leu Gln Asp Ala Glu
            595                 600                 605

Val Glu Ser Ser Ala Lys Ser Gly Lys Pro
            610                 615

<210> SEQ ID NO 36
<211> LENGTH: 355
<212> TYPE: DNA
<213> ORGANISM: homo sapiens

<400> SEQUENCE: 36
caaagtcaaa tgaatttatt cagaaaaggc cttgcttggt atcagactaa gaaaagcagc      60
cctgcccgcc gccccccact ccagaagggt caatttacaa agacaggggc caggggagaa     120
gctgggtggg aagacacag ccaggccagg aggcttctgc aggccttggc tatccctgag      180
ggcctcgcgg cttctggtgg ctgctatagt ggccccacag gaggcacgca ctgtgggtca     240
tgggtcacgg gtcacgaagc agagcctgag gggagcccgc agcagctccg agccccagg     300 ccctgcagca gggacaggag gaccaagacg ccgacggcac tcctttcctt aaggc         355

<210> SEQ ID NO 37
<211> LENGTH: 270
<212> TYPE: DNA
<213> ORGANISM: homo sapiens

<400> SEQUENCE: 37
gaagggtcaa tttacaaaga caggggcgca ggggagagct gggtggggaa gacacagcca     60
ggccaggagg cttctgcagg ccttgggttc cctgagggcc tcgcggcttc tggtggctgc    120
tatagtggcc ccacaggagg cagcactgtg gtcatgggt cacgggtcac gaagcagagc     180
ctgaggggag cccgcagcag ctccggagcc ccagccctgc agcagggaca ggaggaccaa    240
gacgccgacg ggactccttt ccttaaggct                                     270

<210> SEQ ID NO 38
<211> LENGTH: 141
<212> TYPE: DNA
<213> ORGANISM: homo sapiens

<400> SEQUENCE: 38
aaagtcaaat gaattattc agaaaaggcc ttgcttggta tcagactaag aaaagcagcc      60
ctgcccgccg cccccactc cagaagggtc aatttacaaa gacaggggcg caggggagag     120
ctgggtgggg aagacacagc c                                              141
```

<210> SEQ ID NO 39
<211> LENGTH: 192
<212> TYPE: DNA
<213> ORGANISM: homo sapiens

<400> SEQUENCE: 39
caaggcgggg gaggcagcag agttgcagga cgcagaggtg gagtcttctg ccaagtctgg      60
gaagccttaa ggaaaggagt gcccgtcggc gtcttggtcc tcctgtccct gctgcagggg    120
ctggggctcc ggagctgctg cgggctccct caggctctgc ttcgtgaccc gtgacccatg    180
acccacagtg ct                                                        192

<210> SEQ ID NO 40
<211> LENGTH: 309
<212> TYPE: DNA
<213> ORGANISM: homo sapiens
<220> FEATURE:
<221> NAME/KEY: misc_feature
<222> LOCATION: 1, 80, 254, 265, 275, 282, 290, 304
<223> OTHER INFORMATION: n = A,T,C or G

<400> SEQUENCE: 40
ncaaagtcaa atgaatttat tcagaaaagg ccttgcttgg tatcagacta agaaaagcag      60
ccctgcccgc cgcccccccan tccagaaggg tcaatttaca aagacagggg cgcaggggag    120
agctgggtgg ggaagacaca gccaggccag gagcttctgc aggccttggg cttccctgag    180
ggcctcgcgg cttctgggtg gctgctatag tggccccaca ggaggccatg cactgtgggg    240
gtcattgggt cacngggtca cgaangcata gcctnagggg gnagcccgtn agcagctccg    300 ggangggccc                                                            309

<210> SEQ ID NO 41
<211> LENGTH: 178
<212> TYPE: DNA
<213> ORGANISM: homo sapiens

<400> SEQUENCE: 41
gggaagccca aggcctgcag aagcctccgt ggcctggcat gtgtcttccc cacccagctc      60 tccctgcgc ccctgtcttt gtaaattgac ccttctggag tgggggcgg cgggcagggc     120 tgcttttctt agtctgatac caagcaaggc cttttctgaa taaattcatt tgactttg      178

<210> SEQ ID NO 42
<211> LENGTH: 166
<212> TYPE: DNA
<213> ORGANISM: homo sapiens
<220> FEATURE:
<221> NAME/KEY: misc_feature
<222> LOCATION: 15, 22, 24, 76, 77, 119, 153, 163
<223> OTHER INFORMATION: n = A,T,C or G

<400> SEQUENCE: 42
cggcctgcag aagcntcctg gncntggttg ttttttcccc acccagctct ccctgcgcc       60 ccttttttt taaatnnacc cttctggagt gggggcggc gggcagggct gcttttttna     120
gtctgatgcc aagcaaggcc tttttgaat aanttcattt ganttt                    166

<210> SEQ ID NO 43
<211> LENGTH: 209
<212> TYPE: DNA
<213> ORGANISM: homo sapiens
<220> FEATURE:

```
<221> NAME/KEY: misc_feature
<222> LOCATION: 11, 90, 138, 166, 185, 190, 200
<223> OTHER INFORMATION: n = A,T,C or G

<400> SEQUENCE: 43
gaaggtggat nagggtgctg tggacagtgc tacggtggcc agtggtggtg cccagacctt      60 ggccttgcc gggtcccctg ccccatcgcn cggccaaggc tggacacagt gagaacgggg     120
ttgaggagga cacagaangt caaacggggc ccaaagaagg tacccntggg gagcccatca    180
gagancccan gccccagccn ggcagggac                                       209

<210> SEQ ID NO 44
<211> LENGTH: 241
<212> TYPE: DNA
<213> ORGANISM: homo sapiens

<400> SEQUENCE: 44
tttttttttt tttttttttt ttttcaaagt caaatgaatt tattcagaaa aggccttgct     60
tggcatcaga ctaagaaaag cagccctgcc cgccgccccc cactccagaa gggtcaattt    120
acaaagacag gggcgcttgg gagagctggg tggggaagac acagccaggc caggaggctt    180
ctgcaggcct tgggcttccc tgagggcctc gcggcttctg gtggctgcta tagtggcccc    240
a                                                                     241

<210> SEQ ID NO 45
<211> LENGTH: 5922
<212> TYPE: DNA
<213> ORGANISM: homo sapiens

<400> SEQUENCE: 45
gcggccgcgg ggaccctcgg cgtggtcctc tgaccctgca aacccgcgac ggaggaaggg     60
gaggtcctgc ccgaggcgcc agcccgagga ggaggatgcc catttaaccc gccctcgcct    120
gccgggcgct tgcctcggtg cccgccgccg gagcctccga gccgcgcccg tggaagtgct    180
gcatggggca gggctgctga agcgcggagt tcggggtcgc gccgctccca ggcaggcgcg    240
ggagcccggt gcggcagttg gcacagtttc ggcggcgcct tctgcgcggg agtgggggc     300 gcggtgcgcc cggccggcct ccgcggtgcc ctggtgaggc gagagttatg gagccgccca    360
gctgcattca ggatgagccg ttcccgcacc ccctggagcc cgagccgggc gtctcagctc    420
agcccggccc cggaagcca agcgataagc ggttccggct gtggtacgtt ggggggtcgt     480
gcctggacca caggaccacg ctgcctatgc tgccctggct catggccgag atccgcaggc    540
gcagccagaa gcccgaggcg ggcggctgcg gggcgccggc ggcccgagag gtgatcctgg    600
tgctcagcgc gccttcctg cgttgcgtcc ccgcgccggg cgctgggcc tcgggggcca      660 ctagtccgtc ggccacgcag cccaacccgg cggtattcat cttcgagcac aaggcgcagc    720
atatctcgcg cttcatccac aacagccacg acctcaccta ctttgcctac ctgatcaagg    780
cgcagcccga cgaccccgag tcgcagatgg cctgccacgt tttccgcgcc acagacccca    840
gccaggttcc tgatgttatt agcagcataa ggcaattatc taaagcggcc atgaaagagg    900
atgccaaacc cagcaaagat aatgaggacg ccttttacaa ctctcagaag ttcgaagtcc    960
tgtactgtgg aaaggtgacc gtgacccaca gaaggcccc ctcaagcctc atcgatgact    1020
gcatggagaa gttcagcctg cacgaacagc agcgcctgaa gatccaaggc gagcagcgcg    1080
gtccggaccc aggagaggac ctggctgact tggaggtggt ggtgcccggg tccccggag     1140 actgcctgcc ggaggaggct gacggcaccg acacccacct tggcttacct gccggggcca    1200
```

-continued

```
gccagcctgc cctgaccagc tctcgggtct gcttccctga gcggattttg gaagattctg    1260
gctttgatga gcagcaggag tttcggtctc ggtgcagcag tgtcaccggc gtgcaacgga    1320
gagttcacga gggcagccag aaatcccagc cgcgacggag acacgcgagc gcacccagtc    1380
acgtccagcc ctcggactcg gagaagaaca ggaccatgct cttccaggtt gggcgatttg    1440
agattaacct tatcagtcca gacactaaat cagttgtgct agaaaagaat tttaaagata    1500
tctcctcttg ttctcagggt ataaagcatg tggatcactt tggctttatc tgccgggagt    1560
ctccagagcc tggacttagc cagtatattt gttatgtatt ccagtgtgcc agcgaatctc    1620
tggttgatga ggtaatgctg actctgaaac aggccttcag tacggcggct gccctgcaga    1680
gtgccaagac gcagattaaa ctgtgtgagg cctgcccgat gcactctttg cataagctct    1740
gtgaaaggat tgaaggtctc tacccaccaa gagccaagct ggtgatacag aggcatctct    1800
catcactgac agataatgag caagctgaca tctttgaaag agttcagaaa atgaagccag    1860
tcagtgacca ggaagaaaat gaacttgtga ttttacacct gaggcagctg tgtgaagcca    1920
agcagaagac acacgtgcac atcggggaag gcccttctac tatttcaaat agtacaatcc    1980
cagaaaatgc aacaagcagt ggaaggttca aacttgacat tctgaaaaat aaagctaaga    2040
gatccttaac tagctccctg gaaaatatct tctcaagggg agctaacaga atgagaggtc    2100
ggcttggaag tgtggacagt tttgaacggt ccaacagtct tgcttcagag aaggactact    2160
caccagggga ttctccacca gggacaccgc cagcgtcccc accgtcctca gcttggcaaa    2220
cgtttcccga gaggattcc gactcccgc agtttcgaag acgggcacac acgttcagcc    2280
acccaccttc aagcacaaag agaaagctga atttgcagga tgggagggct cagggtgtgc    2340 gttccctct gctgaggcag agctccagtg aacagtgcag caatctttcg tcagttcgac    2400
gcatgtacaa ggagagtaat tcttcctcca gtcttccaag tcttcacact tccttctctg    2460 cccccttcctt cactgccccc tctttcctga aaagcttta ccagaattca ggtagactgt    2520
ccccacagta tgaaaatgaa atcagacaag acactgcttc agaatcaagt gatggagaag    2580
ggagaaaaag gacctcatct acctgcagca atgagtccct aagtgtggga ggaacctctg    2640
tcactcctcg ccggatctcc tggcggcagc gcattttcct cagggttgct ctcccatga    2700 acaaatctcc ctcagcaatg caacagcaag atggattgga caggaacgag ctgctgccac    2760 tgtccccct ctctccaacc atggaggagg aaccgctggt tatattcctg tctggggagg    2820
atgacccaga aaagattgaa gaaagaaaga atcaaaaga actgaggagc ttgtggagaa    2880
aagctataca ccaacaaatc ttgttacttc gaatggaaaa agaaaccag aaacttgaag    2940 gagcaagcag agatgaactc cagtccagaa agtttaaatt agactatgaa gaagttggtg    3000
catgtcagaa agaggtctta ataacttggg ataagaagtt gttaaactgc agagctaaaa    3060
tcagatgtga tatggaagat attcatactc ttcttaaaga aggagttccc aaaagtcgac    3120
gaggagaaat ttggcagttt ctggctttac agtaccgact cagacacaga ttgcctaata    3180
aacaacagcc tcctgacata tcctataagg aactttgaa gcagctcact gctcagcagc    3240
atgcgattct cgtggattta ggaaggacgt ttcctactca cccttacttt tcagtacagc    3300
ttgggccagg acagctgtca ctgtttaacc tcctgaaagc ctattctttg ctggacaaag    3360
aagtgggata ctgtcagggg atcagctttg tggctggagt cctgcttctg cacatgagtg    3420
aagagcaagc ctttgaaatg ctgaaattcc tcatgtatga cctcggcttc cgcaagcagt    3480
acagacctga catgatgtcg ctgcagattc aaatgtacca gctgtccagg ctccttcatg    3540
```

```
actatcacag agatctctac aatcaccttg aagaaaatga aatcagcccc agtctttatg   3600
ctgcccctg gttcctcaca ttgtttgcct ctcagttttc attaggattt gtagccagag   3660
tttttgatat tattttttctt cagggaactg aagttatatt caaggttgca ctcagcctac   3720
tgagcagcca agagacactt ataatggaat gtgagagctt tgaaaatatt gttgagtttc   3780
ttaaaaacac gctacctgat atgaatacct ctgaaatgga aaaaattatt acccaggttt   3840
ttgagatgga tatttctaag cagttgcatg cctatgaggt ggaatatcat gtgctacagg   3900
atgagcttca ggaatcttca tattcctgtg aggatagtga aactttggag aagctggaga   3960
gggccaatag ccaactgaaa agacaaaaca tggacctcct agaaaaatta caggtagctc   4020
atactaaaat ccaggccttg gaatcaaacc tggaaaatct tttgacgaga gagaccaaaa   4080
tgaagtcttt aatccggacc ctggaacaag aaaaaatggc ttatcaaaag acagtggagc   4140
aactccggaa gctgctgccc gcggatgctc tagccaattg tgacctgttg ctgagagacc   4200
taaactgcaa ccctaacaac aaagccaaga taggaaataa gccataattg aagaggcacg   4260
gcctcagcag aaagtgctcc ttagaatact acagagagga gagcctgca tgtcgctggc    4320
ccaaggctgg accctgaagc tgatggaacc acctaatact ggtgctgagc tcctagtcac   4380
agcaggtgga cctcgtgctc atcagagcat gccaatccta agccattgga catatgtaga   4440
ctggtttttg ttgttgctat gtacatataa atatatatat aaaatgaaca tagttcatgc   4500
tttcagataa aatgagtaga tgtatattta gattaatttt tttagtcaga acttcatgaa   4560
atccacacca aaggaaaggt aaactgaaat ttcccttgga catatgtgaa atcttttttgt   4620
ctttatagtg aaacaaagcc agagcatctt tgtatattgc aatatacttg aaaaaaatga   4680
atgtattttt ttctccaaag aacagcatgt ttcactcaat ggtgaaaagg tggaaacatt   4740
tatgtaactt tatgtgtatc tgtcttgata tctactgaca ttgtctatat gaggaaaatg   4800
attactggtc atgctcctgt gagtttttttg ggaaggtagg gtcatttctc cctgcctgct   4860
ttgtgccaac tagcatgttg catctacatg cattatgagt ctggttaggc attactttaa   4920
acatacataa agagacagta ggacattgtg gctgagtcta cccagctcaa ggtaaaggag   4980
aatgttgcta atttttttagc aaactagacc agcattatta ctcaaactaa aaatatcaca   5040
cctgaaaaat ttaatttagg acctaaaatg tctagattag cttttctgctt tttttatttg   5100
aataactcat tcagttgtga atgaattcct ctttatttgg tgccacagtc accaaatgac   5160
aaggatttgc cactttccca ccaaattgtg agtgcttgta atttaggtct ctctacctta   5220
aattcagtat aaggaaacgt aattatgatt gattttttcc aaagatgaca agctgtgttg   5280
aaatacattt tttctttttga ccaattgaca gaatctaata agctttaata atcttcccct   5340
tttatgtgaa aagttttgag aactgtgaaa tgtttaggaa caaactgttg aaatccattg   5400
gaagggaaaa aagaaagtgg taccagtgtt accagctcaa ctaaaacctg caattctgca   5460
tttcaactct tcacttcctc agcctacaaa tagctcatta gatgacattc acgcatgctg   5520
ggtataggca aggaaagtaa ttttcaaagt acatttgcag ttctcttttt cagagatgat   5580
tctatgatag tgcctctgaa agttgatgca gcattttttgc ctttccaaaa agtatttatc   5640
ctcactgctt tttgcagtac ttgtatttttc acagatggat tatctggggt aattttcttc   5700
aaagggagtt tgttatacac agtgaaaatg tattatagag tagaatagta aagctctagg   5760
ggtttcagaa agctttgatg aacagatgac aaacatctga aacccctcc gcactgttac    5820
ccagtgtgta tataatgact tgttatagct cagtgtgccc ttgaatccat acagtttctt   5880
aaaagacaat aaaatcttat taataaagtt aatgtaactt ct                      5922
```

-continued

```
<210> SEQ ID NO 46
<211> LENGTH: 1299
<212> TYPE: PRT
<213> ORGANISM: homo sapiens

<400> SEQUENCE: 46
```

| | | | | | | | | | | | | | | | |
|---|---|---|---|---|---|---|---|---|---|---|---|---|---|---|---|
| Met | Glu | Pro | Pro | Ser | Cys | Ile | Gln | Asp | Glu | Pro | Phe | Pro | His | Pro | Leu |
| 1 | | | | 5 | | | | | 10 | | | | | 15 | |
| Glu | Pro | Glu | Pro | Gly | Val | Ser | Ala | Gln | Pro | Gly | Pro | Gly | Lys | Pro | Ser |
| | | | 20 | | | | | 25 | | | | | 30 | | |
| Asp | Lys | Arg | Phe | Arg | Leu | Trp | Tyr | Val | Gly | Gly | Ser | Cys | Leu | Asp | His |
| | | 35 | | | | | 40 | | | | | 45 | | | |
| Arg | Thr | Thr | Leu | Pro | Met | Leu | Pro | Trp | Leu | Met | Ala | Glu | Ile | Arg | Arg |
| | 50 | | | | | 55 | | | | | 60 | | | | |
| Arg | Ser | Gln | Lys | Pro | Glu | Ala | Gly | Cys | Gly | Ala | Pro | Ala | Ala | Arg | |
| 65 | | | | | 70 | | | | 75 | | | | | 80 | |
| Glu | Val | Ile | Leu | Val | Leu | Ser | Ala | Pro | Phe | Leu | Arg | Cys | Val | Pro | Ala |
| | | | | 85 | | | | | 90 | | | | | 95 | |
| Pro | Gly | Ala | Gly | Ala | Ser | Gly | Gly | Thr | Ser | Pro | Ser | Ala | Thr | Gln | Pro |
| | | | 100 | | | | | 105 | | | | | 110 | | |
| Asn | Pro | Ala | Val | Phe | Ile | Phe | Glu | His | Lys | Ala | Gln | His | Ile | Ser | Arg |
| | | 115 | | | | | 120 | | | | | 125 | | | |
| Phe | Ile | His | Asn | Ser | His | Asp | Leu | Thr | Tyr | Phe | Ala | Tyr | Leu | Ile | Lys |
| | 130 | | | | | 135 | | | | | 140 | | | | |
| Ala | Gln | Pro | Asp | Asp | Pro | Glu | Ser | Gln | Met | Ala | Cys | His | Val | Phe | Arg |
| 145 | | | | | 150 | | | | 155 | | | | | 160 | |
| Ala | Thr | Asp | Pro | Ser | Gln | Val | Pro | Asp | Val | Ile | Ser | Ser | Ile | Arg | Gln |
| | | | | 165 | | | | | 170 | | | | | 175 | |
| Leu | Ser | Lys | Ala | Ala | Met | Lys | Glu | Asp | Ala | Lys | Pro | Ser | Lys | Asp | Asn |
| | | | 180 | | | | | 185 | | | | | 190 | | |
| Glu | Asp | Ala | Phe | Tyr | Asn | Ser | Gln | Lys | Phe | Glu | Val | Leu | Tyr | Cys | Gly |
| | | 195 | | | | | 200 | | | | | 205 | | | |
| Lys | Val | Thr | Val | Thr | His | Lys | Lys | Ala | Pro | Ser | Ser | Leu | Ile | Asp | Asp |
| | 210 | | | | | 215 | | | | | 220 | | | | |
| Cys | Met | Glu | Lys | Phe | Ser | Leu | His | Glu | Gln | Gln | Arg | Leu | Lys | Ile | Gln |
| 225 | | | | | 230 | | | | 235 | | | | | 240 | |
| Gly | Glu | Gln | Arg | Gly | Pro | Asp | Pro | Gly | Glu | Asp | Leu | Ala | Asp | Leu | Glu |
| | | | | 245 | | | | | 250 | | | | | 255 | |
| Val | Val | Val | Pro | Gly | Ser | Pro | Gly | Asp | Cys | Leu | Pro | Glu | Glu | Ala | Asp |
| | | | 260 | | | | | 265 | | | | | 270 | | |
| Gly | Thr | Asp | Thr | His | Leu | Gly | Leu | Pro | Ala | Gly | Ala | Ser | Gln | Pro | Ala |
| | | 275 | | | | | 280 | | | | | 285 | | | |
| Leu | Thr | Ser | Ser | Arg | Val | Cys | Phe | Pro | Glu | Arg | Ile | Leu | Glu | Asp | Ser |
| | 290 | | | | | 295 | | | | | 300 | | | | |
| Gly | Phe | Asp | Glu | Gln | Gln | Glu | Phe | Arg | Ser | Arg | Cys | Ser | Ser | Val | Thr |
| 305 | | | | | 310 | | | | 315 | | | | | 320 | |
| Gly | Val | Gln | Arg | Arg | Val | His | Glu | Gly | Ser | Gln | Lys | Ser | Gln | Pro | Arg |
| | | | | 325 | | | | | 330 | | | | | 335 | |
| Arg | Arg | His | Ala | Ser | Ala | Pro | Ser | His | Val | Gln | Pro | Ser | Asp | Ser | Glu |
| | | | 340 | | | | | 345 | | | | | 350 | | |
| Lys | Asn | Arg | Thr | Met | Leu | Phe | Gln | Val | Gly | Arg | Phe | Glu | Ile | Asn | Leu |
| | | 355 | | | | | 360 | | | | | 365 | | | |
| Ile | Ser | Pro | Asp | Thr | Lys | Ser | Val | Val | Leu | Glu | Lys | Asn | Phe | Lys | Asp |

-continued

```
        370             375             380
Ile Ser Ser Cys Ser Gln Gly Ile Lys His Val Asp His Phe Gly Phe
385                 390                 395                 400

Ile Cys Arg Glu Ser Pro Glu Pro Gly Leu Ser Gln Tyr Ile Cys Tyr
                405                 410                 415

Val Phe Gln Cys Ala Ser Glu Ser Leu Val Asp Glu Val Met Leu Thr
            420                 425                 430

Leu Lys Gln Ala Phe Ser Thr Ala Ala Leu Gln Ser Ala Lys Thr
            435                 440                 445

Gln Ile Lys Leu Cys Glu Ala Cys Pro Met His Ser Leu His Lys Leu
450                 455                 460

Cys Glu Arg Ile Glu Gly Leu Tyr Pro Pro Arg Ala Lys Leu Val Ile
465                 470                 475                 480

Gln Arg His Leu Ser Ser Leu Thr Asp Asn Glu Gln Ala Asp Ile Phe
                485                 490                 495

Glu Arg Val Gln Lys Met Lys Pro Val Ser Asp Gln Glu Glu Asn Glu
            500                 505                 510

Leu Val Ile Leu His Leu Arg Gln Leu Cys Glu Ala Lys Gln Lys Thr
            515                 520                 525

His Val His Ile Gly Glu Gly Pro Ser Thr Ile Ser Asn Ser Thr Ile
530                 535                 540

Pro Glu Asn Ala Thr Ser Ser Gly Arg Phe Lys Leu Asp Ile Leu Lys
545                 550                 555                 560

Asn Lys Ala Lys Arg Ser Leu Thr Ser Ser Leu Glu Asn Ile Phe Ser
                565                 570                 575

Arg Gly Ala Asn Arg Met Arg Gly Arg Leu Gly Ser Val Asp Ser Phe
            580                 585                 590

Glu Arg Ser Asn Ser Leu Ala Ser Glu Lys Asp Tyr Ser Pro Gly Asp
            595                 600                 605

Ser Pro Gly Thr Pro Pro Ala Ser Pro Pro Ser Ser Ala Trp Gln
    610                 615                 620

Thr Phe Pro Glu Glu Asp Ser Asp Ser Pro Gln Phe Arg Arg Arg Ala
625                 630                 635                 640

His Thr Phe Ser His Pro Pro Ser Ser Thr Lys Arg Lys Leu Asn Leu
                645                 650                 655

Gln Asp Gly Arg Ala Gln Gly Val Arg Ser Pro Leu Leu Arg Gln Ser
            660                 665                 670

Ser Ser Glu Gln Cys Ser Asn Leu Ser Ser Val Arg Arg Met Tyr Lys
            675                 680                 685

Glu Ser Asn Ser Ser Ser Leu Pro Ser Leu His Thr Ser Phe Ser
690                 695                 700

Ala Pro Ser Phe Thr Ala Pro Ser Phe Leu Lys Ser Phe Tyr Gln Asn
705                 710                 715                 720

Ser Gly Arg Leu Ser Pro Gln Tyr Glu Asn Glu Ile Arg Gln Asp Thr
                725                 730                 735

Ala Ser Glu Ser Ser Asp Gly Glu Gly Arg Lys Arg Thr Ser Ser Thr
            740                 745                 750

Cys Ser Asn Glu Ser Leu Ser Val Gly Thr Ser Val Thr Pro Arg
            755                 760                 765

Arg Ile Ser Trp Arg Gln Arg Ile Phe Leu Arg Val Ala Ser Pro Met
    770                 775                 780

Asn Lys Ser Pro Ser Ala Met Gln Gln Gln Asp Gly Leu Asp Arg Asn
785                 790                 795                 800
```

-continued

Glu Leu Leu Pro Leu Ser Pro Leu Ser Pro Thr Met Glu Glu Pro
                805                 810                 815

Leu Val Ile Phe Leu Ser Gly Glu Asp Pro Glu Lys Ile Glu Glu
                820                 825                 830

Arg Lys Lys Ser Lys Glu Leu Arg Ser Leu Trp Arg Lys Ala Ile His
                835                 840                 845

Gln Gln Ile Leu Leu Arg Met Glu Lys Asn Gln Lys Leu Glu
                850                 855                 860

Gly Ala Ser Arg Asp Glu Leu Gln Ser Arg Lys Val Lys Leu Asp Tyr
865                 870                 875                 880

Glu Glu Val Gly Ala Cys Gln Lys Glu Val Leu Ile Thr Trp Asp Lys
                885                 890                 895

Lys Leu Leu Asn Cys Arg Ala Lys Ile Arg Cys Asp Met Glu Asp Ile
                900                 905                 910

His Thr Leu Leu Lys Glu Gly Val Pro Lys Ser Arg Arg Gly Glu Ile
                915                 920                 925

Trp Gln Phe Leu Ala Leu Gln Tyr Arg Leu Arg His Arg Leu Pro Asn
    930                 935                 940

Lys Gln Gln Pro Pro Asp Ile Ser Tyr Lys Glu Leu Leu Lys Gln Leu
945                 950                 955                 960

Thr Ala Gln Gln His Ala Ile Leu Val Asp Leu Gly Arg Thr Phe Pro
                965                 970                 975

Thr His Pro Tyr Phe Ser Val Gln Leu Gly Pro Gly Gln Leu Ser Leu
                980                 985                 990

Phe Asn Leu Leu Lys Ala Tyr Ser Leu Leu Asp Lys Glu Val Gly Tyr
                995                1000                1005

Cys Gln Gly Ile Ser Phe Val Ala Gly Val Leu Leu Leu His Met Ser
    1010                1015                1020

Glu Glu Gln Ala Phe Glu Met Leu Lys Phe Leu Met Tyr Asp Leu Gly
1025                1030                1035                1040

Phe Arg Lys Gln Tyr Arg Pro Asp Met Met Ser Leu Gln Ile Gln Met
                1045                1050                1055

Tyr Gln Leu Ser Arg Leu Leu His Asp Tyr His Arg Asp Leu Tyr Asn
                1060                1065                1070

His Leu Glu Glu Asn Glu Ile Ser Pro Ser Leu Tyr Ala Ala Pro Trp
                1075                1080                1085

Phe Leu Thr Leu Phe Ala Ser Gln Phe Ser Leu Gly Phe Val Ala Arg
    1090                1095                1100

Val Phe Asp Ile Ile Phe Leu Gln Gly Thr Glu Val Ile Phe Lys Val
1105                1110                1115                1120

Ala Leu Ser Leu Leu Ser Ser Gln Glu Thr Leu Ile Met Glu Cys Glu
                1125                1130                1135

Ser Phe Glu Asn Ile Val Glu Phe Leu Lys Asn Thr Leu Pro Asp Met
                1140                1145                1150

Asn Thr Ser Glu Met Glu Lys Ile Ile Thr Gln Val Phe Glu Met Asp
                1155                1160                1165

Ile Ser Lys Gln Leu His Ala Tyr Glu Val Glu Tyr His Val Leu Gln
    1170                1175                1180

Asp Glu Leu Gln Glu Ser Ser Tyr Ser Cys Glu Asp Ser Glu Thr Leu
1185                1190                1195                1200

Glu Lys Leu Glu Arg Ala Asn Ser Gln Leu Lys Arg Gln Asn Met Asp
                1205                1210                1215

-continued

```
Leu Leu Glu Lys Leu Gln Val Ala His Thr Lys Ile Gln Ala Leu Glu
        1220                1225                1230

Ser Asn Leu Glu Asn Leu Leu Thr Arg Glu Thr Lys Met Lys Ser Leu
    1235                1240                1245

Ile Arg Thr Leu Glu Gln Glu Lys Met Ala Tyr Gln Lys Thr Val Glu
    1250                1255                1260

Gln Leu Arg Lys Leu Leu Pro Ala Asp Ala Leu Ala Asn Cys Asp Leu
1265                1270                1275                1280

Leu Leu Arg Asp Leu Asn Cys Asn Pro Asn Asn Lys Ala Lys Ile Gly
                1285                1290                1295

Asn Lys Pro

<210> SEQ ID NO 47
<211> LENGTH: 2020
<212> TYPE: DNA
<213> ORGANISM: homo sapiens

<400> SEQUENCE: 47
```

| | | | | | |
|---|---|---|---|---|---|
| gttcgaggag | ctgctgctgc | tgaggcggcg | gcaactgcat | tgaggtggtg | gcggcgctgc | 60 |
| cggccccggc | cgctcgctct | cggctcgcct | tccagcctcg | cctgagcccg | ccgggcccgc | 120 |
| gccggccagc | gcctgcccta | tgagtgtgtc | actggttgtt | atccgattgg | agctcgcgga | 180 |
| acactcgcct | gtccccgccg | gcttcggctt | cagcgccgcg | gccggggaaa | tgtctgatga | 240 |
| ggagataaaa | aagacgacac | tagcctcagc | tgtagcctgt | ttagaaggca | agtcaccagg | 300 |
| agagaaagta | gcgattatcc | atcagcatct | cggccgtcga | gaaatgacag | atgtgatcat | 360 |
| tgagaccatg | aagtccaacc | cagatgaact | aaaaactaca | gtggaagaaa | ggaagtcttc | 420 |
| agaagcctcc | cccactgcgc | aaagaagtaa | agatcacagt | aaggaatgca | taaacgctgc | 480 |
| cccagattct | ccgtccaaac | agcttccaga | ccagatttca | ttcttcagtg | aaatccatc | 540 |
| agttgaaata | gttcatggta | ttatgcacct | atataagaca | aataagatga | cctccttaaa | 600 |
| agaagatgtg | cggcgcagtg | ccatgctgtg | tattctcaca | gtccctgctg | caatgaccag | 660 |
| tcatgacctt | atgaagtttg | ttgccccatt | taacgacgta | attgaacaaa | tgaaaattat | 720 |
| cagagactct | actcccaacc | aatatatggt | gctgataaag | tttcgtgcac | aggctgatgc | 780 |
| ggatagtttt | tatatgacat | gcaatggccg | ccagttcaac | tcaatagaag | atgacgtttg | 840 |
| ccagctagtg | tatgtggaaa | gagctgaagt | gctcaaatct | gaagatggcg | ccagcctccc | 900 |
| agtgatggac | ctgactgaac | tccccaagtg | cacggtgtgt | ctggagcgca | tggacgagtc | 960 |
| tgtgaatggc | atcctcacaa | cgttatgtaa | ccacagcttc | acagccagt | gtctacagcg | 1020 |
| ctgggacgat | accacgtgtc | ctgtttgccg | gtactgtcaa | acgcccgagc | cagtagaaga | 1080 |
| aaataagtgt | tttgagtgtg | gtgttcagga | aaatctttgg | atttgtttaa | tatgcggcca | 1140 |
| cataggatgt | ggacggtatg | tcagtcgaca | tgcttataag | cactttgagg | aaacgcagca | 1200 |
| cacgtatgcc | atgcagctta | ccaaccatcg | agtctgggac | tatgctggag | ataactatgt | 1260 |
| tcatcgactg | gttgcaagta | aaacagatgg | aaaaatagta | cagtatgaat | gtgaggggga | 1320 |
| tacttgccag | gaagagaaaa | tagatgcctt | acagttagag | tattcatatt | tactaacaag | 1380 |
| ccagctggaa | tctcagcgaa | tctactggga | aacaagata | gttcggatag | agaaggacac | 1440 |
| agcagaggaa | attaacaaca | tgaagaccaa | gtttaaagaa | acaattgaga | agtgtgataa | 1500 |
| tctagagcac | aaactaaatg | atctcctaaa | agaaaagcag | tctgtggaaa | gaaagtgcac | 1560 |
| tcagctaaac | acaaaagtgg | ccaaactcac | caacgagctc | aaagaggagc | aggaaatgaa | 1620 |

```
caagtgtttg cgagccaacc aagtcctcct gcagaacaag ctaaaagagg aggagagggt    1680
gctgaaggag acctgtgacc aaaaagatct gcagatcacc gagatccagg agcagctgcg    1740
tgacgtcatg ttctacctgg agacacagca gaagatcaac catctgcctg ccgagacccg    1800
gcagaaatcc aggagggaca gatcaacatc gccatggcct cggcctcgag ccctgcctct    1860 tcgggggca gtgggaagtt gccctccagg aagggccgca gcaagagggg caagtgacct     1920
tcagagcaac agacatccct gagactgttc tccctgacac tgtgagagtg tgctgggacc    1980
ttcagctaaa tgtgagggtg ggccctaata agtacaagtg                          2020
```

<210> SEQ ID NO 48
<211> LENGTH: 600
<212> TYPE: PRT
<213> ORGANISM: homo sapiens

<400> SEQUENCE: 48

```
Met Ser Val Ser Leu Val Val Ile Arg Leu Glu Leu Ala Glu His Ser
 1               5                  10                  15

Pro Val Pro Ala Gly Phe Gly Phe Ser Ala Ala Gly Glu Met Ser
                20                  25                  30

Asp Glu Glu Ile Lys Lys Thr Thr Leu Ala Ser Ala Val Ala Cys Leu
             35                  40                  45

Glu Gly Lys Ser Pro Gly Glu Lys Val Ala Ile His Gln His Leu
 50                  55                  60

Gly Arg Arg Glu Met Thr Asp Val Ile Ile Glu Thr Met Lys Ser Asn
 65                  70                  75                  80

Pro Asp Glu Leu Lys Thr Thr Val Glu Glu Arg Lys Ser Ser Glu Ala
                 85                  90                  95

Ser Pro Thr Ala Gln Arg Ser Lys Asp His Ser Lys Glu Cys Ile Asn
                100                 105                 110

Ala Ala Pro Asp Ser Pro Ser Lys Gln Leu Pro Asp Gln Ile Ser Phe
            115                 120                 125

Phe Ser Gly Asn Pro Ser Val Glu Ile Val His Gly Ile Met His Leu
        130                 135                 140

Tyr Lys Thr Asn Lys Met Thr Ser Leu Lys Glu Asp Val Arg Arg Ser
145                 150                 155                 160

Ala Met Leu Cys Ile Leu Thr Val Pro Ala Ala Met Thr Ser His Asp
                165                 170                 175

Leu Met Lys Phe Val Ala Pro Phe Asn Asp Val Ile Glu Gln Met Lys
            180                 185                 190

Ile Ile Arg Asp Ser Thr Pro Asn Gln Tyr Met Val Leu Ile Lys Phe
        195                 200                 205

Arg Ala Gln Ala Asp Ala Asp Ser Phe Tyr Met Thr Cys Asn Gly Arg
    210                 215                 220

Gln Phe Asn Ser Ile Glu Asp Val Cys Gln Leu Val Tyr Val Glu
225                 230                 235                 240

Arg Ala Glu Val Leu Lys Ser Glu Asp Gly Ala Ser Leu Pro Val Met
                245                 250                 255

Asp Leu Thr Glu Leu Pro Lys Cys Thr Val Cys Leu Glu Arg Met Asp
            260                 265                 270

Glu Ser Val Asn Gly Ile Leu Thr Thr Leu Cys Asn His Ser Phe His
        275                 280                 285

Ser Gln Cys Leu Gln Arg Trp Asp Asp Thr Thr Cys Pro Val Cys Arg
    290                 295                 300
```

-continued

```
Tyr Cys Gln Thr Pro Glu Pro Val Glu Glu Asn Lys Cys Phe Glu Cys
305                 310                 315                 320

Gly Val Gln Glu Asn Leu Trp Ile Cys Leu Ile Cys Gly His Ile Gly
            325                 330                 335

Cys Gly Arg Tyr Val Ser Arg His Ala Tyr Lys His Phe Glu Thr
        340                 345                 350

Gln His Thr Tyr Ala Met Gln Leu Thr Asn His Arg Val Trp Asp Tyr
    355                 360                 365

Ala Gly Asp Asn Tyr Val His Arg Leu Val Ala Ser Lys Thr Asp Gly
370                 375                 380

Lys Ile Val Gln Tyr Glu Cys Glu Gly Asp Thr Cys Gln Glu Glu Lys
385                 390                 395                 400

Ile Asp Ala Leu Gln Leu Glu Tyr Ser Tyr Leu Leu Thr Ser Gln Leu
                405                 410                 415

Glu Ser Gln Arg Ile Tyr Trp Glu Asn Lys Ile Val Arg Ile Glu Lys
            420                 425                 430

Asp Thr Ala Glu Glu Ile Asn Asn Met Lys Thr Lys Phe Lys Glu Thr
        435                 440                 445

Ile Glu Lys Cys Asp Asn Leu Glu His Lys Leu Asn Asp Leu Leu Lys
    450                 455                 460

Glu Lys Gln Ser Val Glu Arg Lys Cys Thr Gln Leu Asn Thr Lys Val
465                 470                 475                 480

Ala Lys Leu Thr Asn Glu Leu Lys Glu Glu Gln Met Asn Lys Cys
                485                 490                 495

Leu Arg Ala Asn Gln Val Leu Leu Gln Asn Lys Leu Lys Glu Glu
            500                 505                 510

Arg Val Leu Lys Glu Thr Cys Asp Gln Lys Asp Leu Gln Ile Thr Glu
        515                 520                 525

Ile Gln Glu Gln Leu Arg Asp Val Met Phe Tyr Leu Glu Thr Gln Gln
    530                 535                 540

Lys Ile Asn His Leu Pro Ala Glu Thr Arg Gln Lys Ser Arg Arg Asp
545                 550                 555                 560

Arg Ser Thr Ser Pro Trp Pro Arg Pro Arg Ala Leu Pro Leu Arg Gly
                565                 570                 575

Ala Val Gly Ser Cys Pro Pro Gly Arg Ala Ala Arg Gly Ala Ser
            580                 585                 590

Asp Leu Gln Ser Asn Arg His Pro
        595                 600

<210> SEQ ID NO 49
<211> LENGTH: 226
<212> TYPE: DNA
<213> ORGANISM: homo sapiens
<220> FEATURE:
<221> NAME/KEY: misc_feature
<222> LOCATION: 163, 168
<223> OTHER INFORMATION: n = A,T,C or G

<400> SEQUENCE: 49
ctgggatact cccctcccag ggtgtctggt ggcaggcctg tgcctatccc tgctgtcccc      60
agggtgggcc ccgggggtca ggagctccag aagggccagc tggcatatt ctgagattgg     120 ccatcagccc ccatttctgc tgcaaacctg gtcagagcca gtnttccntc catgggacct    180
aaagacagtg ccaagtgcct gcaccgtgga ccacagccga gccact                   226

<210> SEQ ID NO 50
```

<211> LENGTH: 441
<212> TYPE: DNA
<213> ORGANISM: homo sapiens

<400> SEQUENCE: 50

| | | | | | | |
|---|---|---|---|---|---|---|
| gaaaaaaaaa | acgagtatct | attaactggc | cactaacagt | tgcctttctt | acattaattt | 60 |
| atacactatt | ttgttcagcc | agtgttttta | aaaaaatct | atgaaaagtg | tacttccggt | 120 |
| tttctgtgat | tacttatctg | ggcttgatct | gaccagtgaa | atgacattgc | cctatttgga | 180 |
| cctctgaggt | tctatttagc | tttgcagatg | tacatagtat | cccagtgatc | tgcaaaatta | 240 |
| atgccttttc | caagaaaaaa | tcttttcttc | tctgtatcag | ttaattctga | cagtgttagt | 300 |
| gattctgtct | tcattatagg | cctatttcc | attatctctt | tctttatagt | attttttgtt | 360 |
| ataaagaaaa | cagtctttct | gtgtatacct | acggatgagg | gtattattta | aactgccaac | 420 |
| aatatccaag | acatggtcaa | t | | | | 441 |

<210> SEQ ID NO 51
<211> LENGTH: 393
<212> TYPE: DNA
<213> ORGANISM: homo sapiens

<400> SEQUENCE: 51

| | | | | | | |
|---|---|---|---|---|---|---|
| aagtctacag | gtaagcagac | atttctatac | atgtcctggt | cactctttct | aaagtattta | 60 |
| taattaggtt | attgaccatg | tcttggatat | tgttggcagt | ttaaataata | ccctcatccg | 120 |
| taggtataca | cagaaagact | gttttcttta | taacaaaaaa | tactataaag | aaagagataa | 180 |
| tggaaataag | gcctataatg | aagacagaat | cactaacact | gtcagaatta | actgatacag | 240 |
| agaagaaaag | attttttctt | ggaaaaggca | ttaattttgc | agatcactgg | gatactatgt | 300 |
| acatctgcaa | agctaaatag | aacctcagag | gtccaaatag | ggcaatgtca | tttcactggt | 360 |
| cagatcaagc | ccagataagt | aatcacagaa | aac | | | 393 |

<210> SEQ ID NO 52
<211> LENGTH: 427
<212> TYPE: DNA
<213> ORGANISM: homo sapiens

<400> SEQUENCE: 52

| | | | | | | |
|---|---|---|---|---|---|---|
| ttttttttttg | tctatcagtc | accttgaaac | tggtaatctg | attcaagtta | aacaatgttc | 60 |
| cttttgaatc | tagaaaacaa | gagaaatgca | aagtcattat | tccctcattc | tatgcttcca | 120 |
| tttactctaa | gaattcagaa | acaaacatgt | gggtaacttc | ctgttatctt | aaaaaaagaa | 180 |
| tcatcccttc | ggtattccct | taactatctg | gaacttgtac | tgtcatttta | taatttacca | 240 |
| tgtgacataa | ttgtttgacc | tgcctctttt | atttgatgca | tgacttctca | gagaacctgt | 300 |
| tatcaactca | ctgtgtaaaa | ccacgatgaa | atgaaggata | actgatcaca | agaattatg | 360 |
| tcttttgata | tccaacaaat | ttacaaatta | taagagaaaa | atgcaatttt | ttaaaaaagg | 420 |
| atatcct | | | | | | 427 |

<210> SEQ ID NO 53
<211> LENGTH: 417
<212> TYPE: DNA
<213> ORGANISM: homo sapiens

<400> SEQUENCE: 53

| | | | | | | |
|---|---|---|---|---|---|---|
| aaaaacactg | gctgaacaaa | atagtgtata | aattaatgta | agaaaggcaa | ctgttagtgg | 60 |
| ccagttaata | gatactcgtt | ttttttttttc | tcttcagttg | cccactatta | ttgcttattt | 120 |

```
ttccttttct tgtctatcag tcaccttgaa actggtaatc tgattcaagt taaacaatgt      180
tccttttgaa tctagaaaac aagagaaatg caaagtcatt attccctcat tctatgcttc      240
catttactct aagaattcag aaacaaacat gtgggtaact tcctgttatc ttaaaaaaag      300
aatcatccct tcggtattcc cttaactatc tggaacttgt actgtcattt tataatttac      360
catgtgacat aattgtttga cctgcctctt ttatttgatg catgacttct cagagaa         417

<210> SEQ ID NO 54
<211> LENGTH: 362
<212> TYPE: DNA
<213> ORGANISM: homo sapiens

<400> SEQUENCE: 54
ctcttcagtt gcccactatt attgcttatt tttccttttc ttgtctatca gtcaccttga       60
aactggtaat ctgattcaag ttaaacaatg ttccttttga atctagaaaa caagagaaat      120
gcaaagtcat tattccctca ttctatgctt ccatttactc taagaattca gaaacaaaca      180
tgtgggtaac ttcctgttat cttaaaaaaa gaatcatccc ttcggtattc ccttaactat      240
ctggaacttg tactgtcatt ttataattta ccatgtgaca taattgtttg acctgcctct      300
tttatttgat gcatgacttc tcagagaacc tgttatcaac tcactgtgta aaaccacgat      360
ga                                                                    362

<210> SEQ ID NO 55
<211> LENGTH: 236
<212> TYPE: DNA
<213> ORGANISM: homo sapiens

<400> SEQUENCE: 55
tttttctctt cagttgcccg ctattattgc ttatttttcc ttttcttgtc tatcagtcac       60
cttgaaactg gtaatctgat tcaagttaaa caatgttcct tttgaatcta gaaaacaaga      120
gaaatgcaaa gtcattattc cctcattcta tgcttccatt tactctaaga attcagaaac      180
aaacatgtgg gtaacttcct gttatcttaa aaaagaatc atcccttcgg tcgacg           236

<210> SEQ ID NO 56
<211> LENGTH: 368
<212> TYPE: DNA
<213> ORGANISM: homo sapiens

<400> SEQUENCE: 56
agaaacagtc tttctgtgta tacctacgga tgagggtatt atttaaactg ccaacaatat       60
ccaagacatg gtcaataacc taattataaa tactttagaa agagtgacca ggacatgtat      120
agaaatgtct gcttacctgt agactttaaa acaaacaaa aaaacaaac aaaattttg        180 gagcatttaa tcattttttt tctccttta tctcctttgt aatcttattg tctcctgagt       240
aaatatacac ataaatgttt ggggattcat tgctgctaga ttatatcagg tgtttacata      300
gtgtctacta tatgctgttg ataagctttt tcctaaaaat agttatcctc ttttgtagtg      360
tttttccc                                                              368

<210> SEQ ID NO 57
<211> LENGTH: 153
<212> TYPE: DNA
<213> ORGANISM: homo sapiens

<400> SEQUENCE: 57
```

| | |
|---|---|
| ttttttttttg tctatcagtc accttgaaac tggtaatctg attcaagtta aacaatgttc | 60 |
| cttttgaatc tagaaaacaa gagaaatgca aagtcattat tccctcattc tatgcttcca | 120 |
| tttactctaa gaattcagaa acaaacatgt ggg | 153 |

<210> SEQ ID NO 58
<211> LENGTH: 324
<212> TYPE: DNA
<213> ORGANISM: homo sapiens

<400> SEQUENCE: 58

| | |
|---|---|
| agaaaacagt ctttctgygt atacctacgg atsagggtat tatttaaact gccamcaata | 60 |
| tccaagvcat ggtcaataac ctaadcataa mtactttaga aagagtgacc aggccatgta | 120 |
| tagaaatgtc tgcttactgt agactttaaa acaaacaaa aaaacaaaca aatthttgga | 180 |
| gcatttaatc attthttttc tccttttatc tccthtgta atcttattgt ctcctgagta | 240 |
| aatatacaca taaatstttk gggattcatt gctgbhagat tatatcaggt gtttacatag | 300 |
| tgtctactat atgctgttga taag | 324 |

<210> SEQ ID NO 59
<211> LENGTH: 416
<212> TYPE: DNA
<213> ORGANISM: homo sapiens

<400> SEQUENCE: 59

| | |
|---|---|
| gtctatcagt caccttgaaa ctggtaatct gattcaagtt aaacaatgtt cctttgaat | 60 |
| ctagaaaaca agagaaatgc aaagtcatta ttccctcatt ctatgcttcc atttactcta | 120 |
| agaattcaga acaaacatg tgggtaactt cctgttatct taaaaaaga atcatcccctt | 180 |
| cggtattccc ttaactatct ggaacttgta ctgtcatttt ataatttacc atgtgacata | 240 |
| attgtttgac ctgcctcttt tatttgatgc atgacttctc agagaacctg ttatcaactc | 300 |
| actgtgtaaa accacgatga aatgaaggat aactgatcac aaagaattat gtcttttgag | 360 |
| atccaacaaa tttacaaatt ataagagaaa aatgcaattt tttaaaaag gatatc | 416 |

<210> SEQ ID NO 60
<211> LENGTH: 2489
<212> TYPE: DNA
<213> ORGANISM: homo sapiens

<400> SEQUENCE: 60

| | |
|---|---|
| ctccgccgcg ggagggagct gcggctgtgc cggccgagcg ggggagggcg ccgccactca | 60 |
| gagccaggga gggagccgct ggagcggaag cccggaggcc gcgctgcgcc ggggtgaggt | 120 |
| ggctttgacc ccgggttgcc cggccagcac gaccgaggag gtggctggac agctggagga | 180 |
| tgaacggaga agccgactgc cccacagacc tggaaatggc cgcccccaaa ggccaagacc | 240 |
| gttggtccca ggaagacatg ctgactttgc tggaatgcat gaagaacaac cttccatcca | 300 |
| atgacagctc caagttcaaa accaccgaat cacacatgga ctgggaaaaa gtagcattta | 360 |
| aagacttttc tggagacatg tgcaagctca aatgggtgga gatttctaat gaggtgagga | 420 |
| agttccgtac attgacagaa ttgatcctcg atgctcagga acatgttaaa aatccttaca | 480 |
| aaggcaaaaa actcaagaaa cacccagact tcccaaagaa gccccctgacc ccttatttcc | 540 |
| gcttcttcat ggagaagcgg gccaagtatg cgaaactcca ccctgagatg agcaacctgg | 600 |
| acctaaccaa gattctgtcc aagaaataca aggagcttcc ggagaagaag aagatgaaat | 660 |
| atattcagga cttccagaga gagaaacagg agttcgagcg aaacctggcc cgattcaggg | 720 |

-continued

```
aggatcaccc cgacctaatc cagaatgcca agaaatcgga catcccagag aagcccaaaa      780
cccccagca gctgtggtac acccacgaga agaaggtgta tctcaaagtg cggccagatg      840
agatcatgag agactatatc cagaagcacc cagagctgaa catcagtgag agggtatca      900
ccaagtccac cctcaccaag gccgaacgcc agctcaagga caagtttgac gggcgaccca      960
ccaagccacc tccgaacagc tactcgctgt actgcgcaga gctcatggcc aacatgaagg     1020
acgtgcccag cacagagcgc atggtgctgt gcagccagca gtggaagctg ctgtcccaga     1080
aggagaagga cgcctatcac aagaagtgtg atcagaaaaa gaaagattac gaggtggagc     1140
tgctccgttt cctcgagagc ctgcctgagg aggagcagca gcgggtcttg ggggaagaga     1200
agatgctgaa catcaacaag aagcaggcca ccagccccgc ctccaagaag ccagcccagg     1260
aagggggcaa gggcggctcc gagaagccca agcggcccgt gtcggccatg ttcatcttct     1320
cggaggagaa acggcggcag ctgcaggagg agcggcctga gctctccgag agcgagctga     1380
cccgcctgct ggcccgaatg tggaacgacc tgtctgagaa gaagaaggcc aagtacaagg     1440
cccgagaggc ggcgctcaag gctcagtcgg agaggaagcc cggcggggag cgcgaggaac     1500
ggggcaagct gcccgagtcc cccaaaagag ctgaggagat ctggcaacag agcgttatcg     1560
gcgactacct ggcccgcttc aagaatgacc gggtgaaggc cttgaaagcc atggaaatga     1620
cctggaataa catggaaaag aaggagaaac tgatgtggat taagaaggca gccgaagacc     1680
aaaagcgata tgagagagag ctgagtgaga tgcgggcacc tccagctgct acaaattctt     1740
ccaagaagat gaaattccag ggagaaccca agaagcctcc catgaacggt taccagaagt     1800
tctcccagga gctgctgtcc aatggggagc tgaaccacct gccgctgaag gagcgcatgg     1860
tggagatcgg cagtcgctgg cagcgcatct cccagagcca gaggagcac tacaaaaagc     1920
tggccgagga gcagcaaaag cagtacaagg tgcacctgga cctctgggtt aagagcctgt     1980
ctccccagga ccgtgcagca tataaagagt acatctccaa taaacgtaag agcatgacca     2040
agctgcgagg cccaaacccc aaatccagcc ggactactct gcagtccaag tcggagtccg     2100
aggaggatga tgaagaggat gaggatgacg aggacgagga tgaagaagag aaagatgatg     2160
agaatgggga ctcctctgaa gatggcggcg actcctctga gtccagcagc gaggacgaga     2220
gcgaggatgg ggatgagaat gaagaggatg acgaggacga agacgacgac gaggatgacg     2280
atgaggatga agataatgag tccgagggca gcagctccag ctcctcctcc tcagggggact     2340
cctcagactc tgactccaac tgaggctcag ccccacccca gggcagccag ggagagccca     2400
ggagctcccc tccccaactg accacctttg tttctccccc atgttctgtc ccttgccccc     2460
ctggcctccc ccactttctt tctttctttt                                      2489
```

<210> SEQ ID NO 61
<211> LENGTH: 727
<212> TYPE: PRT
<213> ORGANISM: homo sapiens

<400> SEQUENCE: 61

```
Met Asn Gly Glu Ala Asp Cys Pro Thr Asp Leu Glu Met Ala Ala Pro
  1               5                  10                  15

Lys Gly Gln Asp Arg Trp Ser Gln Glu Asp Met Leu Thr Leu Leu Glu
             20                  25                  30

Cys Met Lys Asn Asn Leu Pro Ser Asn Asp Ser Ser Lys Phe Lys Thr
         35                  40                  45

Thr Glu Ser His Met Asp Trp Glu Lys Val Ala Phe Lys Asp Phe Ser
```

-continued

```
                50                  55                  60
Gly Asp Met Cys Lys Leu Lys Trp Val Glu Ile Ser Asn Glu Val Arg
 65                  70                  75                  80

Lys Phe Arg Thr Leu Thr Glu Leu Ile Leu Asp Ala Gln Glu His Val
                     85                  90                  95

Lys Asn Pro Tyr Lys Gly Lys Lys Leu Lys Lys His Pro Asp Phe Pro
                    100                 105                 110

Lys Lys Pro Leu Thr Pro Tyr Phe Arg Phe Met Glu Lys Arg Ala
                115                 120                 125

Lys Tyr Ala Lys Leu His Pro Glu Met Ser Asn Leu Asp Leu Thr Lys
130                 135                 140

Ile Leu Ser Lys Lys Tyr Lys Glu Leu Pro Glu Lys Lys Met Lys
145                 150                 155                 160

Tyr Ile Gln Asp Phe Gln Arg Glu Lys Gln Glu Phe Glu Arg Asn Leu
                    165                 170                 175

Ala Arg Phe Arg Glu Asp His Pro Asp Leu Ile Gln Asn Ala Lys Lys
                180                 185                 190

Ser Asp Ile Pro Glu Lys Pro Lys Thr Pro Gln Gln Leu Trp Tyr Thr
                195                 200                 205

His Glu Lys Lys Val Tyr Leu Lys Val Arg Pro Asp Glu Ile Met Arg
210                 215                 220

Asp Tyr Ile Gln Lys His Pro Glu Leu Asn Ile Ser Glu Glu Gly Ile
225                 230                 235                 240

Thr Lys Ser Thr Leu Thr Lys Ala Glu Arg Gln Leu Lys Asp Lys Phe
                    245                 250                 255

Asp Gly Arg Pro Thr Lys Pro Pro Asn Ser Tyr Ser Leu Tyr Cys
                260                 265                 270

Ala Glu Leu Met Ala Asn Met Lys Asp Val Pro Ser Thr Glu Arg Met
                275                 280                 285

Val Leu Cys Ser Gln Gln Trp Lys Leu Leu Ser Gln Lys Glu Lys Asp
                290                 295                 300

Ala Tyr His Lys Lys Cys Asp Gln Lys Lys Lys Asp Tyr Glu Val Glu
305                 310                 315                 320

Leu Leu Arg Phe Leu Glu Ser Leu Pro Glu Glu Gln Gln Arg Val
                    325                 330                 335

Leu Gly Glu Glu Lys Met Leu Asn Ile Asn Lys Lys Gln Ala Thr Ser
                340                 345                 350

Pro Ala Ser Lys Lys Pro Ala Gln Glu Gly Gly Lys Gly Gly Ser Glu
                355                 360                 365

Lys Pro Lys Arg Pro Val Ser Ala Met Phe Ile Phe Ser Glu Glu Lys
                370                 375                 380

Arg Arg Gln Leu Gln Glu Glu Arg Pro Glu Leu Ser Glu Ser Glu Leu
385                 390                 395                 400

Thr Arg Leu Leu Ala Arg Met Trp Asn Asp Leu Ser Glu Lys Lys Lys
                    405                 410                 415

Ala Lys Tyr Lys Ala Arg Glu Ala Ala Leu Lys Ala Gln Ser Glu Arg
                420                 425                 430

Lys Pro Gly Gly Glu Arg Glu Glu Arg Gly Lys Leu Pro Glu Ser Pro
                435                 440                 445

Lys Arg Ala Glu Glu Ile Trp Gln Gln Ser Val Ile Gly Asp Tyr Leu
                450                 455                 460

Ala Arg Phe Lys Asn Asp Arg Val Lys Ala Leu Lys Ala Met Glu Met
465                 470                 475                 480
```

```
Thr Trp Asn Asn Met Glu Lys Lys Glu Lys Leu Met Trp Ile Lys Lys
                485                 490                 495
Ala Ala Glu Asp Gln Lys Arg Tyr Glu Arg Glu Leu Ser Glu Met Arg
            500                 505                 510
Ala Pro Pro Ala Ala Thr Asn Ser Ser Lys Lys Met Lys Phe Gln Gly
        515                 520                 525
Glu Pro Lys Lys Pro Pro Met Asn Gly Tyr Gln Lys Phe Ser Gln Glu
    530                 535                 540
Leu Leu Ser Asn Gly Glu Leu Asn His Leu Pro Leu Lys Glu Arg Met
545                 550                 555                 560
Val Glu Ile Gly Ser Arg Trp Gln Arg Ile Ser Gln Ser Gln Lys Glu
                565                 570                 575
His Tyr Lys Lys Leu Ala Glu Glu Gln Lys Gln Tyr Lys Val His
            580                 585                 590
Leu Asp Leu Trp Val Lys Ser Leu Ser Pro Gln Asp Arg Ala Ala Tyr
        595                 600                 605
Lys Glu Tyr Ile Ser Asn Lys Arg Lys Ser Met Thr Lys Leu Arg Gly
    610                 615                 620
Pro Asn Pro Lys Ser Ser Arg Thr Thr Leu Gln Ser Lys Ser Glu Ser
625                 630                 635                 640
Glu Glu Asp Asp Glu Asp Glu Asp Glu Asp Glu Glu
                645                 650                 655
Glu Glu Asp Asp Glu Asn Gly Asp Ser Ser Asp Gly Gly Asp Ser
            660                 665                 670
Ser Glu Ser Ser Ser Glu Asp Glu Ser Glu Asp Gly Asp Glu Asn Glu
        675                 680                 685
Glu Asp Asp Glu Asp Glu Asp Asp Glu Asp Glu Asp Glu
    690                 695                 700
Asp Asn Glu Ser Glu Gly Ser Ser Ser Ser Ser Ser Gly Asp
705                 710                 715                 720
Ser Ser Asp Ser Asp Ser Asn
                725

<210> SEQ ID NO 62
<211> LENGTH: 607
<212> TYPE: DNA
<213> ORGANISM: homo sapiens
<220> FEATURE:
<221> NAME/KEY: misc_feature
<222> LOCATION: 602
<223> OTHER INFORMATION: n = A,T,C or G

<400> SEQUENCE: 62
ttttcagcat gagaatatgt gaatatgttt atttaggttt aacttacttc ttactatata      60
gatttggctt gttttttata ataacaactg atatatgatt cacaaaaaag cagagaagag     120
taagagaaag agagagaaat ggagaaagag aagaaaaaag ggataaagaa tgaaagagag     180
aaagagaata ccattctcta aggaagagg tgcagaaaat tccattatcc tttcttcttg     240
atcatgcctt gtatgattgg cagccaaact agcccactgt gaaacccaac gtttgcttcc     300
agatgaagat gtgccttcct ctgagtggtg aaatccagat gtagtcagtg gttttctttc     360
ttccattact gctgcagcag aactgagagc ccaatctttt attagatctt tatgtttttc     420
gttgataaca ggcctattat aatccgattg tcatctactc caaacacaac agctggtctg     480
atgctttcag tagccggacc tctgtagctt ttgtgttcga atggtggcgt ctaagtgttc     540
```

```
ctcaagagtt gcacgtttgc tacagcgccg tgagccccag cgttctctga atcacttgcg    600 tncatca                                                              607
```

<210> SEQ ID NO 63
<211> LENGTH: 402
<212> TYPE: DNA
<213> ORGANISM: homo sapiens
<220> FEATURE:
<221> NAME/KEY: misc_feature
<222> LOCATION: 35
<223> OTHER INFORMATION: n = A,T,C or G

<400> SEQUENCE: 63

```
ggcagagcac agaccaagcc aggagatgga taaangttaa aaaatcaagc aacttctgct    60
acttctgaaa aggataatga tgatgaccaa agtgacaagg gtacttatac cattgagtta    120
gagaatccca acagtgagga agtggaagca agaaaaatga ttcacaaggt aaataattga    180
aatttgagtg tgatcttagt tgttgtgtgg tgtatttgac tggtggaaat tattggagag    240
tcagcatgag atgttgtcat gcagtcagtg gtatgtgaat tttagggttt tattagggaa    300
ctgcaagact aacagtaaga ccaacatgct ttgtgatttt atttgctgat attctgaatt    360
tacctgagtt tcatacataa agctctgtac atttaaaagg tt                      402
```

<210> SEQ ID NO 64
<211> LENGTH: 607
<212> TYPE: DNA
<213> ORGANISM: homo sapiens
<220> FEATURE:
<221> NAME/KEY: misc_feature
<222> LOCATION: 602
<223> OTHER INFORMATION: n = A,T,C or G

<400> SEQUENCE: 64

```
ttttcagcat gagaatatgt gaatatgttt atttaggttt aacttacttc ttactatata    60
gatttggctt gttttttata ataacaactg atatatgatt cacaaaaaag cagagaagag    120
taagagaaag agagagaaat ggagaaagag aagaaaaaag ggataaagaa tgaaagagag    180
aaagagaata ccattctcta aggaagagg tgcagaaaat tccattatcc tttcttcttg    240
atcatgcctt gtatgattgg cagccaaact agcccactgt gaaacccaac gtttgcttcc    300
agatgaagat gtgccttcct ctgagtggtg aaatccagat gtagtcagtg gttttctttc    360
ttccattact gctgcagcag aactgagagc ccaatctttt attagatctt tatgttttc     420 gttgataaca ggcctattat aatccgattg tcatctactc caaacacaac agctggtctg    480
atgctttcag tagccggacc tctgtagctt ttgtgttcga atggtggcgt ctaagtgttc    540
ctcaagagtt gcacgtttgc tacagcgccg tgagccccag cgttctctga atcacttgcg    600 tncatca                                                              607
```

<210> SEQ ID NO 65
<211> LENGTH: 317
<212> TYPE: DNA
<213> ORGANISM: homo sapiens
<220> FEATURE:
<221> NAME/KEY: misc_feature
<222> LOCATION: 17, 25, 37, 41, 53, 68, 70, 144
<223> OTHER INFORMATION: n = A,T,C or G

<400> SEQUENCE: 65

```
tggggcgtgt gtggaanaac gttantgccc agcggantag nggccccgga gcncgaccgc    60
agcggcanan cgacaacagc ggcgacgacg acgacgacga ggtgggggga ggacggcgtg    120
```

```
cgagagactc acgggacgcg acgnccccgc ctcccccgtc cggtccctct ctccacggta      180 agggatgac  gtagctttgc caaagactta gaagctaagc agaaaatgag cttaacatcc      240
tggtttttgg tgagcagtgg aggcactcgc cacaggctgc cacgagaaat gatttttgtt      300
ggaaaaaatg actgtga                                                    317
```

<210> SEQ ID NO 66
<211> LENGTH: 420
<212> TYPE: DNA
<213> ORGANISM: homo sapiens

<400> SEQUENCE: 66

```
gtccctgaag aagctcttaa ggtaacagtt tttacttaac ttcttttgca aatctactct      60
tcactatggt tgattttact tcttgatgtt tcacttccat tttttaaatgt tttatagcat     120 gagaagttta ccattcagct tcagttgtcc caaaaatctt cagaatcaga attatccaaa     180
tctgcaagtg ccaaaagcat agattcaaag gtagcagacg ctgctactga agtgcagcac     240
aaaactactg aagcactgaa atccgaggaa aaagccatgg gtaagctggc tctctcgaaa     300
gacatcttta tactgatctt cgaagacact gcatgcttgt ctcagaaagt gctatgtcca     360
ttaaaatatt atatagtgat atcagagtgt gtttatgcta ccagtgcttc atagacatat     420
```

<210> SEQ ID NO 67
<211> LENGTH: 7497
<212> TYPE: DNA
<213> ORGANISM: homo sapiens

<400> SEQUENCE: 67

```
gcgcaagagg atcagggata gcctctgagc tcgggttccc agggttcgta gcttccaacg      60
gctgcgcgcg cacttcggtc gcgggcggtg aggtgctgtt gctgaaacgc tgccgctgag     120
ggtggactcg atttcccagg gtcccgccgc gggagtctcc ggcgggcggg cgcgcgcgag     180
ccaccgagcg aggtgataga ggcggcggcc caggcgtctg ggtcctgctg gtcttcgcct     240
ttcttctccg cttctacccc gtcggccgct gccactgggg tccctggccc caccgacatg     300
gcggcggtgt tgcagcaagt cctggagcgc acggagctga acaagctgcc caagtctgtc     360
cagaacaaac ttgaaaagtt ccttgctgat cagcaatccg agatcgatgg cctgaagggg     420
cggcatgaga aatttaaggt ggagagcgaa caacagtatt ttgaaataga aaagaggttg     480
tcccacagtc aggagagact tgtgaatgaa acccgagagt gtcaaagctt gcggcttgag     540
ctagagaaac tcaacaatca actgaaggca ctaactgaga aaacaaaga acttgaaatt     600 gctcaggatc gcaatattgc cattcagagc caatttacaa gaacaaagga agaattagaa     660
gctgagaaaa gagacttaat tagaaccaat gagagactat ctcaagaact tgaatactta     720
acagaggatg ttaaacgtct gaatgaaaaa cttaaagaaa gcaatacaac aaagggtgaa     780
cttcagttaa aattggatga acttcaagct tctgatgttt ctgttaagta tcgagaaaaa     840
cgcttggagc aagaaaagga attgctacat agtcagaata catggctgaa tacagagttg     900
aaaaccaaaa ctgatgaact tctggctctt ggaagagaaa aagggaatga gattctagag     960
cttaaatgta atcttgaaaa taaaaagaa gaggtttcta gactggaaga acaaatgaat     1020
ggcttaaaaa catcaaatga acatcttcaa aagcatgtgg aggatctgtt gaccaaatta     1080
aaagaggcca aggaacaaca ggccagtatg aagagaaat tccacaatga attaaatgcc     1140
cacataaaac tttctaattt gtacaagagt gccgctgatg actcagaagc aaagagcaat     1200
```

-continued

```
gaactaaccc gggcagtaga ggaactacac aaacttttga aagaagctgg tgaagccaac    1260
aaagcaatac aagatcatct tctagaggtg gagcaatcca aagatcaaat ggaaaaagaa    1320
atgcttgaga aaatagggag attggagaag gaattagaga atgcaaatga ccttcttttct   1380 gccacaaaac gtaaaggagc catattgtct gaagaagagc ttgccgccat gtctcctact    1440
gcagcagctg tagctaagat agtgaaacct gggatgaaac taactgagct ctataatgct    1500
tatgtggaaa ctcaggatca gttgcttttg gagaaactag agaacaaaag aattaataag    1560
tacctagatg aaatagtgaa agaagtggaa gccaaagcac caattttgaa acgccagcgt    1620
gaggaatatg aacgtgcaca gaaagctgta gcaagtttat ctgttaagct tgaacaagct    1680
atgaaggaga ttcagcgatt gcaggaggac actgataaag ccaacaagca atcatctgta    1740
cttgagagag ataatcgaag aatggaaata caagtaaaag atctttcaca acagattaga    1800
gtgcttttga tggaacttga agaagcaagg ggtaaccacg taattcgtga tgaggaagta    1860
agctctgctg atataagtag ttcatctgag gtaatatcac agcatctagt atcttacaga    1920
aatattgaag agcttcaaca acaaaatcaa cgtctcttag tggcccttag agagcttggg    1980
gaaaccagag aaagagaaga acaagaaaca acttcatcca aaatcactga gcttcagctc    2040
aaacttgaga gtgcccttac tgaactagaa caactccgca aatcacgaca gcatcaaatg    2100
cagcttgttg attccatagt tcgtcagcgt gatatgtacc gtattttatt gtcacaaaca    2160
acaggagttg ccattccatt acatgcttca agcttagatg atgtttctct tgcatcaact    2220
ccaaaacgtc caagtacatc acagactgtt tccactcctg ctccagtacc tgttattgaa    2280
tcaacagagg ctatagaggc taaggctgcc cttaaacagt tgcaggaaat ttttgagaac    2340
tacaaaaaag aaaaagcaga aaatgaaaaa atacaaaatg agcagcttga gaaacttcaa    2400
gaacaagtta cagatttgcg atcacaaaat accaaaattt ctacccagct agattttgct    2460
tctaaacgtt atgaaatgct gcaagataat gttgaaggat atcgtcgaga aataacatca    2520
cttcatgaga gaaatcagaa actcactgcc acaactcaaa agcaagaaca gattatcaat    2580
acgatgactc aagatttgag aggagcaaat gagaagctag ctgtcgcaga agtaagagca    2640
gaaaatttga agaaggaaaa ggaaatgctt aaattgtctg aagttcgtct ttctcagcaa    2700
agagagtctt tgttagctga acaaaggggg caaaacttac tgctaactaa tctgcaaaca    2760
attcagggaa tactggagcg atctgaaaca gaaaccaaac aaaggcttag tagccagata    2820
gaaaaactgg aacatgagat ctctcatcta aagaagaagt tggaaaatga ggtggaacaa    2880
aggcatacac ttactagaaa tctagatgtt caacttttag atacaaagag acaactggat    2940
acagagacaa atcttcatct taacacaaaa gaactattaa aaaatgctca aaaagaaatt    3000
gccacattga aacagcacct cagtaatatg gaagtccaag ttgcttctca gtcttcacag    3060
agaactggta aaggtcagcc tagcaacaaa gaagatgtgg atgatcttgt gagtcagcta    3120
agacagacag aagagcaggt gaatgactta aaggagagac tcaaaacaag tacgagcaat    3180
gtggaacaat atcaagcaat ggttactagt ttagaagaat ccctgaacaa ggaaaaacag    3240
gtgacagaag aagtgcgtaa gaatattgaa gttcgtttaa aagagtcagc tgaatttcag    3300
acacagttgg aaaagaagtt gatggaagta gagaaggaaa acaagaact tcaggatgat    3360 aaaagaagag cctagagag catggaacaa cagttatctg aattgaagaa acacttttct    3420
agtgttcaga atgaagtaca agaagctctt cagagagcaa gcacagcttt aagtaatgag    3480
cagcaagcca gacgtgactg tcaggaacaa gctaaaatag ctgtggaagc tcagaataag    3540
tatgagagag aattgatgct gcatgctgct gatgttgaag ctctacaagc tgcgaaggag    3600
```

```
caggtttcaa aaatggcatc agtccgtcag catttggaag aaacaacaca gaaagcagaa    3660
tcacagttgt tggagtgtaa agcatcttgg gaggaaagag agagaatgtt aaaggatgaa    3720
gtttccaaat gtgtatgtcg ctgtgaagat ctggagaaac aaaacagatt acttcatgat    3780
cagatcgaaa aattaagtga caaggtcgtt gcctctgtga aggaaggtgt acaaggtcca    3840
ctgaatgtat ctctcagtga agaaggaaaa tctcaagaac aaattttgga aattctcaga    3900
tttatacgac gagaaaaaga aattgctgaa actaggtttg aggtggctca ggttgagagt    3960
ctgcgttatc gacaaagggt tgaactttta gaaagagagc tgcaggaact cgaagatagt    4020
ctaaatgctg aaagggagaa agtccaggta actgcaaaaa caatggctca gcatgaagaa    4080
ctgatgaaga aaactgaaac aatgaatgta gttatggaga ccaataaaat gctaagagaa    4140
gagaaggaga gactagaaca ggatctacag caaatgcaag caaggtgag gaaactggag    4200 ttagatattt tacccttaca agaagcaaat gctgagctga gtgagaaaag cggtatgttg    4260
caggcagaga agaagctctt agaagaggat gtcaaacgtt ggaaagcacg taaccagcat    4320
ctagtaagtc aacagaaaga tccagataca gaagaatatc ggaagctcct ttctgaaaag    4380
gaagttcata ctaagcgtat tcaacaattg acagaagaaa ttggtagact taaagctgaa    4440
attgcaagat caaatgcatc tttgactaac aaccagaact taattcagag tctgaaggaa    4500
gatctaaata agtaagaac tgaaaaggaa accatccaga aggacttaga tgccaaaata    4560
attgatatcc aagaaaaagt caaaactatt actcaagtta agaaaattgg acgtaggtac    4620
aagactcaat atgaagaact taaagcacaa caggataagg ttatggagac atcggctcag    4680
tcctctggag accatcagga gcagcatgtt tcagtccagg aaatgcagga actcaaagaa    4740
acgctcaacc aagctgaaac aaaatcaaaa tcacttgaaa gtcaagtaga gaatctgcag    4800
aagacattat ctgaaaaaga gacagaagca agaaatctcc aggaacagac tgtgcaactt    4860
cagtctgaac tttcacgact tcgtcaggat cttcaagata gaaccacaca ggaggagcag    4920
ctccgacaac agataactga aaaggaagaa aaaccagaa aggctattgt agcagcaaag    4980
tcaaaaattg cacacttagc tggtgtaaaa gatcagctaa ctaaagaaaa tgaggagctt    5040
aaacaaagga atggagcctt agatcagcag aaagatgaat tggatgttcg cattactgcg    5100
ctaaagtccc aatatgaagg tcgaattagt cgcttggaaa gagaactcag ggagcatcaa    5160
gagagacacc ttgagcagag agatgagcct caagaaccttt ctaataaggt ccctgaacag    5220
cagagacaga tcacattgaa aacaactcca gcttctggtg aaagaggaat tgccagcaca    5280
tcagacccac caacagccaa tatcaagcca actcctgttg tgtctactcc aagtaaagtg    5340
acagctgcag ctatggctgg aaataagtca acacccaggg ctagtatccg cccaatggtt    5400
acacctgcaa ctgttacaaa tcccactact accccaacag ctacagtgat gcccactaca    5460
caagtggaat cacaggaagc tatgcagtca gaagggcctg tggaacatgt tccagttttt    5520
ggaagcacaa gtggatccgt tcgttctact agtcctaatg tccagccttc tatctctcaa    5580
cctattttaa ctgttcagca acaaacacag gctacagctt ttgtgcaacc cactcaacag    5640
agtcatcctc agattgagcc tgccaatcaa gagttatctt caaacatagt agaggttgtt    5700
cagagttcac cagttgagcg gccttctact tccacagcag tatttggcac agtttcggct    5760
acccccagtt cttctttgcc aaagcgtaca cgtgaagagg aagaggatag caccatgaaa    5820
gcatcagacc aagtctctga tgatacagtg gaaatgcctc ttccaaagaa gttgaaaagt    5880
gtcacacctg taggaactga ggaagaagtt atggcagaag aaagtactga tggagaggta    5940
```

-continued

```
gagactcagg tatacaacca ggattctcaa gattccattg agaaggagt tacccaggga    6000 gattatacac ctatggaaga cagtgaagaa acctctcagt ctctacaaat agatcttggg    6060
ccacttcaat cagatcagca gacgacaact tcatcccagg atggtcaagg caaaggagat    6120
gatgtcattg taattgacag tgatgatgaa gaagaggatg aggaagatga tgatgatgat    6180
gaagatgaca cagggatggg agatgagggt gaagatagta atgaaggaac tggtagtgcc    6240
gatggcaatg atggttatga agctgatgat gctgagggtg gtgatgggac tgatccaggt    6300
acagaaacag aagaaagtat gggtggaggt gaaggtaatc acagagctgc tgattctcaa    6360
aacagtggtg aaggaaatac aggtgctgca gaatcttctt tttctcagga ggtttctaga    6420
gaacaacagc catcatcagc atctgaaaga caggcccctc gagcacctca gtcaccgaga    6480
cgcccaccac atccacttcc cccaagactg accattcatg ccccacctca ggagttggga    6540
ccaccagttc agagaattca gatgacccga aggcagtctg taggacgtgg ccttcagttg    6600
actccaggaa taggtggcat gcaacagcat tttttttgatg atgaagacag aacagttcca    6660
agtactccaa ctcttgtggt gccacatcgt actgatggat ttgctgaagc aattcattcg    6720
ccgcaggttg ctggtgtccc tagattccgg tttgggccac tgaagatat gccacaaaca    6780 agttctagtc actctgatct tggccagctt gcttctcaag gaggtttagg aatgtatgaa    6840
acacccctgt tcctagctca tgaagaagag tcaggtggcc gaagtgttcc cactactcca    6900
ctacaagtag cagccccagt gactgtattt actgagagca ccacctctga tgcttcggaa    6960
catgcctctc aatctgttcc aatggtgact acatccactg gcactttatc tacaacaat    7020 gaaacagcaa caggtgatga tggagatgaa gtatttgtgg aggcagaatc tgaaggtatt    7080
agttcagaag caggcctaga aattgatagc cagcaggaag aagagccggt tcaagcatct    7140
gatgagtcag atctcccctc caccagccag gatcctcctt ctagctcatc tgtagatact    7200
agtagtagtc aaccaaagcc tttcagacga gtaagacttc agacaacatt gagacaaggt    7260
gtccgtggtc gtcagtttaa cagacagaga ggtgtgagcc atgcaatggg agggagagga    7320
ggaataaaca gaggaaatat taattaaatg gtctgtaaac aataacaact gtgaataaga    7380
ttatcaaatc tgtttagtg taatgattgt caagttaaa aacattttta tatataaact    7440
ggtatactca tgtcaatatt ctttattaat aaaatgtttt tcagtgtcaa aaaaaaa    7497
```

<210> SEQ ID NO 68
<211> LENGTH: 2349
<212> TYPE: PRT
<213> ORGANISM: homo sapiens

<400> SEQUENCE: 68

```
Met Ala Ala Val Leu Gln Gln Val Leu Glu Arg Thr Glu Leu Asn Lys
 1               5                  10                  15

Leu Pro Lys Ser Val Gln Asn Lys Leu Glu Lys Phe Leu Ala Asp Gln
            20                  25                  30

Gln Ser Glu Ile Asp Gly Leu Lys Gly Arg His Glu Lys Phe Lys Val
        35                  40                  45

Glu Ser Glu Gln Gln Tyr Phe Glu Ile Glu Lys Arg Leu Ser His Ser
    50                  55                  60

Gln Glu Arg Leu Val Asn Glu Thr Arg Glu Cys Gln Ser Leu Arg Leu
65                  70                  75                  80

Glu Leu Glu Lys Leu Asn Asn Gln Leu Lys Ala Leu Thr Glu Lys Asn
                85                  90                  95

Lys Glu Leu Glu Ile Ala Gln Asp Arg Asn Ile Ala Ile Gln Ser Gln
```

-continued

```
                  100                 105                 110
Phe Thr Arg Thr Lys Glu Glu Leu Glu Ala Glu Lys Arg Asp Leu Ile
            115                 120                 125
Arg Thr Asn Glu Arg Leu Ser Gln Glu Leu Tyr Leu Thr Glu Asp
130                 135                 140
Val Lys Arg Leu Asn Glu Lys Leu Lys Glu Ser Asn Thr Thr Lys Gly
145                 150                 155                 160
Glu Leu Gln Leu Lys Leu Asp Glu Leu Gln Ala Ser Asp Val Ser Val
                165                 170                 175
Lys Tyr Arg Glu Lys Arg Leu Glu Gln Glu Lys Glu Leu Leu His Ser
            180                 185                 190
Gln Asn Thr Trp Leu Asn Thr Glu Leu Lys Thr Lys Thr Asp Glu Leu
        195                 200                 205
Leu Ala Leu Gly Arg Glu Lys Gly Asn Glu Ile Leu Glu Leu Lys Cys
    210                 215                 220
Asn Leu Glu Asn Lys Lys Glu Glu Val Ser Arg Leu Glu Glu Gln Met
225                 230                 235                 240
Asn Gly Leu Lys Thr Ser Asn Glu His Leu Gln Lys His Val Glu Asp
                245                 250                 255
Leu Leu Thr Lys Leu Lys Glu Ala Lys Glu Gln Gln Ala Ser Met Glu
            260                 265                 270
Glu Lys Phe His Asn Glu Leu Asn Ala His Ile Lys Leu Ser Asn Leu
        275                 280                 285
Tyr Lys Ser Ala Ala Asp Asp Ser Glu Ala Lys Ser Asn Glu Leu Thr
    290                 295                 300
Arg Ala Val Glu Glu Leu His Lys Leu Leu Lys Glu Ala Gly Glu Ala
305                 310                 315                 320
Asn Lys Ala Ile Gln Asp His Leu Leu Glu Val Glu Gln Ser Lys Asp
                325                 330                 335
Gln Met Glu Lys Glu Met Leu Glu Lys Ile Gly Arg Leu Glu Lys Glu
            340                 345                 350
Leu Glu Asn Ala Asn Asp Leu Leu Ser Ala Thr Lys Arg Lys Gly Ala
        355                 360                 365
Ile Leu Ser Glu Glu Glu Leu Ala Ala Met Ser Pro Thr Ala Ala Ala
    370                 375                 380
Val Ala Lys Ile Val Lys Pro Gly Met Lys Leu Thr Glu Leu Tyr Asn
385                 390                 395                 400
Ala Tyr Val Glu Thr Gln Asp Gln Leu Leu Glu Lys Leu Glu Asn
                405                 410                 415
Lys Arg Ile Asn Lys Tyr Leu Asp Glu Ile Val Lys Glu Val Glu Ala
                420                 425                 430
Lys Ala Pro Ile Leu Lys Arg Gln Arg Glu Glu Tyr Glu Arg Ala Gln
            435                 440                 445
Lys Ala Val Ala Ser Leu Ser Val Lys Leu Glu Gln Ala Met Lys Glu
        450                 455                 460
Ile Gln Arg Leu Gln Glu Asp Thr Asp Lys Ala Asn Lys Gln Ser Ser
465                 470                 475                 480
Val Leu Glu Arg Asp Asn Arg Met Glu Ile Gln Val Lys Asp Leu
                485                 490                 495
Ser Gln Gln Ile Arg Val Leu Met Glu Leu Glu Glu Ala Arg Gly
            500                 505                 510
Asn His Val Ile Arg Asp Glu Glu Val Ser Ser Ala Asp Ile Ser Ser
        515                 520                 525
```

-continued

```
Ser Ser Glu Val Ile Ser Gln His Leu Val Ser Tyr Arg Asn Ile Glu
    530                 535                 540
Glu Leu Gln Gln Gln Asn Gln Arg Leu Leu Val Ala Leu Arg Glu Leu
545                 550                 555                 560
Gly Glu Thr Arg Glu Arg Glu Gln Glu Thr Thr Ser Ser Lys Ile
                565                 570                 575
Thr Glu Leu Gln Leu Lys Leu Glu Ser Ala Leu Thr Glu Leu Glu Gln
                580                 585                 590
Leu Arg Lys Ser Arg Gln His Gln Met Gln Leu Val Asp Ser Ile Val
        595                 600                 605
Arg Gln Arg Asp Met Tyr Arg Ile Leu Leu Ser Gln Thr Thr Gly Val
        610                 615                 620
Ala Ile Pro Leu His Ala Ser Ser Leu Asp Asp Val Ser Leu Ala Ser
625                 630                 635                 640
Thr Pro Lys Arg Pro Ser Thr Ser Gln Thr Val Ser Thr Pro Ala Pro
                645                 650                 655
Val Pro Val Ile Glu Ser Thr Glu Ala Ile Glu Ala Lys Ala Ala Leu
                660                 665                 670
Lys Gln Leu Gln Glu Ile Phe Glu Asn Tyr Lys Lys Glu Lys Ala Glu
        675                 680                 685
Asn Glu Lys Ile Gln Asn Glu Gln Leu Glu Lys Leu Gln Glu Gln Val
        690                 695                 700
Thr Asp Leu Arg Ser Gln Asn Thr Lys Ile Ser Thr Gln Leu Asp Phe
705                 710                 715                 720
Ala Ser Lys Arg Tyr Glu Met Leu Gln Asp Asn Val Glu Gly Tyr Arg
                725                 730                 735
Arg Glu Ile Thr Ser Leu His Glu Arg Asn Gln Lys Leu Thr Ala Thr
                740                 745                 750
Thr Gln Lys Gln Glu Gln Ile Ile Asn Thr Met Thr Gln Asp Leu Arg
        755                 760                 765
Gly Ala Asn Glu Lys Leu Ala Val Ala Glu Val Arg Ala Glu Asn Leu
        770                 775                 780
Lys Lys Glu Lys Glu Met Leu Lys Leu Ser Glu Val Arg Leu Ser Gln
785                 790                 795                 800
Gln Arg Glu Ser Leu Leu Ala Glu Gln Arg Gly Gln Asn Leu Leu Leu
                805                 810                 815
Thr Asn Leu Gln Thr Ile Gln Gly Ile Leu Glu Arg Ser Glu Thr Glu
                820                 825                 830
Thr Lys Gln Arg Leu Ser Ser Gln Ile Glu Lys Leu Glu His Glu Ile
        835                 840                 845
Ser His Leu Lys Lys Leu Glu Asn Glu Val Glu Gln Arg His Thr
        850                 855                 860
Leu Thr Arg Asn Leu Asp Val Gln Leu Leu Asp Thr Lys Arg Gln Leu
865                 870                 875                 880
Asp Thr Glu Thr Asn Leu His Leu Asn Thr Lys Glu Leu Leu Lys Asn
                885                 890                 895
Ala Gln Lys Glu Ile Ala Thr Leu Lys Gln His Leu Ser Asn Met Glu
                900                 905                 910
Val Gln Val Ala Ser Gln Ser Ser Gln Arg Thr Gly Lys Gly Gln Pro
        915                 920                 925
Ser Asn Lys Glu Asp Val Asp Asp Leu Val Ser Gln Leu Arg Gln Thr
930                 935                 940
```

-continued

```
Glu Glu Gln Val Asn Asp Leu Lys Glu Arg Leu Lys Thr Ser Thr Ser
945                 950                 955                 960

Asn Val Glu Gln Tyr Gln Ala Met Val Thr Ser Leu Glu Glu Ser Leu
                965                 970                 975

Asn Lys Glu Lys Gln Val Thr Glu Glu Val Arg Lys Asn Ile Glu Val
            980                 985                 990

Arg Leu Lys Glu Ser Ala Glu Phe Gln Thr Gln Leu Glu Lys Lys Leu
        995                 1000                1005

Met Glu Val Glu Lys Glu Lys Gln Glu Leu Gln Asp Asp Lys Arg Arg
    1010                1015                1020

Ala Ile Glu Ser Met Glu Gln Gln Leu Ser Glu Leu Lys Lys Thr Leu
1025                1030                1035                1040

Ser Ser Val Gln Asn Glu Val Gln Glu Ala Leu Gln Arg Ala Ser Thr
                1045                1050                1055

Ala Leu Ser Asn Glu Gln Gln Ala Arg Arg Asp Cys Gln Glu Gln Ala
            1060                1065                1070

Lys Ile Ala Val Glu Ala Gln Asn Lys Tyr Glu Arg Glu Leu Met Leu
        1075                1080                1085

His Ala Ala Asp Val Glu Ala Leu Gln Ala Ala Lys Glu Gln Val Ser
    1090                1095                1100

Lys Met Ala Ser Val Arg Gln His Leu Glu Glu Thr Thr Gln Lys Ala
1105                1110                1115                1120

Glu Ser Gln Leu Leu Glu Cys Lys Ala Ser Trp Glu Arg Glu Arg
                1125                1130                1135

Met Leu Lys Asp Glu Val Ser Lys Cys Val Cys Arg Cys Glu Asp Leu
            1140                1145                1150

Glu Lys Gln Asn Arg Leu Leu His Asp Gln Ile Glu Lys Leu Ser Asp
        1155                1160                1165

Lys Val Val Ala Ser Val Lys Glu Gly Val Gln Gly Pro Leu Asn Val
    1170                1175                1180

Ser Leu Ser Glu Glu Gly Lys Ser Gln Glu Gln Ile Leu Glu Ile Leu
1185                1190                1195                1200

Arg Phe Ile Arg Arg Glu Lys Glu Ile Ala Glu Thr Arg Phe Glu Val
                1205                1210                1215

Ala Gln Val Glu Ser Leu Arg Tyr Arg Gln Arg Val Glu Leu Leu Glu
            1220                1225                1230

Arg Glu Leu Gln Glu Leu Glu Asp Ser Leu Asn Ala Glu Arg Glu Lys
        1235                1240                1245

Val Gln Val Thr Ala Lys Thr Met Ala Gln His Glu Glu Leu Met Lys
    1250                1255                1260

Lys Thr Glu Thr Met Asn Val Val Met Glu Thr Asn Lys Met Leu Arg
1265                1270                1275                1280

Glu Glu Lys Glu Arg Leu Glu Gln Asp Leu Gln Gln Met Gln Ala Lys
                1285                1290                1295

Val Arg Lys Leu Glu Leu Asp Ile Leu Pro Leu Gln Glu Ala Asn Ala
            1300                1305                1310

Glu Leu Ser Glu Lys Ser Gly Met Leu Gln Ala Glu Lys Lys Leu Leu
        1315                1320                1325

Glu Glu Asp Val Lys Arg Trp Lys Ala Arg Asn Gln His Leu Val Ser
    1330                1335                1340

Gln Gln Lys Asp Pro Asp Thr Glu Glu Tyr Arg Lys Leu Leu Ser Glu
1345                1350                1355                1360

Lys Glu Val His Thr Lys Arg Ile Gln Gln Leu Thr Glu Glu Ile Gly
```

-continued

```
                    1365                1370                1375
Arg Leu Lys Ala Glu Ile Ala Arg Ser Asn Ala Ser Leu Thr Asn Asn
                1380                1385                1390
Gln Asn Leu Ile Gln Ser Leu Lys Glu Asp Leu Asn Lys Val Arg Thr
            1395                1400                1405
Glu Lys Glu Thr Ile Gln Lys Asp Leu Asp Ala Lys Ile Ile Asp Ile
        1410                1415                1420
Gln Glu Lys Val Lys Thr Ile Thr Gln Val Lys Lys Ile Gly Arg Arg
1425                1430                1435                1440
Tyr Lys Thr Gln Tyr Glu Glu Leu Lys Ala Gln Gln Asp Lys Val Met
                1445                1450                1455
Glu Thr Ser Ala Gln Ser Ser Gly Asp His Gln Glu Gln His Val Ser
                1460                1465                1470
Val Gln Glu Met Gln Glu Leu Lys Glu Thr Leu Asn Gln Ala Glu Thr
            1475                1480                1485
Lys Ser Lys Ser Leu Glu Ser Gln Val Glu Asn Leu Gln Lys Thr Leu
            1490                1495                1500
Ser Glu Lys Glu Thr Glu Ala Arg Asn Leu Gln Glu Gln Thr Val Gln
1505                1510                1515                1520
Leu Gln Ser Glu Leu Ser Arg Leu Arg Gln Asp Leu Gln Asp Arg Thr
                1525                1530                1535
Thr Gln Glu Glu Gln Leu Arg Gln Gln Ile Thr Glu Lys Glu Lys
                1540                1545                1550
Thr Arg Lys Ala Ile Val Ala Ala Lys Ser Lys Ile Ala His Leu Ala
            1555                1560                1565
Gly Val Lys Asp Gln Leu Thr Lys Glu Asn Glu Glu Leu Lys Gln Arg
            1570                1575                1580
Asn Gly Ala Leu Asp Gln Gln Lys Asp Glu Leu Asp Val Arg Ile Thr
1585                1590                1595                1600
Ala Leu Lys Ser Gln Tyr Glu Gly Arg Ile Ser Arg Leu Glu Arg Glu
                1605                1610                1615
Leu Arg Glu His Gln Glu Arg His Leu Glu Gln Arg Asp Glu Pro Gln
                1620                1625                1630
Glu Pro Ser Asn Lys Val Pro Glu Gln Gln Arg Gln Ile Thr Leu Lys
            1635                1640                1645
Thr Thr Pro Ala Ser Gly Glu Arg Gly Ile Ala Ser Thr Ser Asp Pro
            1650                1655                1660
Pro Thr Ala Asn Ile Lys Pro Thr Pro Val Val Ser Thr Pro Ser Lys
1665                1670                1675                1680
Val Thr Ala Ala Ala Met Ala Gly Asn Lys Ser Thr Pro Arg Ala Ser
                1685                1690                1695
Ile Arg Pro Met Val Thr Pro Ala Thr Val Thr Asn Pro Thr Thr Thr
                1700                1705                1710
Pro Thr Ala Thr Val Met Pro Thr Thr Gln Val Glu Ser Gln Glu Ala
            1715                1720                1725
Met Gln Ser Glu Gly Pro Val Glu His Val Pro Val Phe Gly Ser Thr
            1730                1735                1740
Ser Gly Ser Val Arg Ser Thr Ser Pro Asn Val Gln Pro Ser Ile Ser
1745                1750                1755                1760
Gln Pro Ile Leu Thr Val Gln Gln Thr Gln Ala Thr Ala Phe Val
            1765                1770                1775
Gln Pro Thr Gln Gln Ser His Pro Gln Ile Glu Pro Ala Asn Gln Glu
            1780                1785                1790
```

-continued

```
Leu Ser Ser Asn Ile Val Glu Val Gln Ser Ser Pro Val Glu Arg
    1795                1800                1805

Pro Ser Thr Ser Thr Ala Val Phe Gly Thr Val Ser Ala Thr Pro Ser
    1810                1815                1820

Ser Ser Leu Pro Lys Arg Thr Arg Glu Glu Glu Asp Ser Thr Ile
1825                1830                1835                1840

Glu Ala Ser Asp Gln Val Ser Asp Thr Val Glu Met Pro Leu Pro
                1845                1850                1855

Lys Lys Leu Lys Ser Val Thr Pro Val Gly Thr Glu Glu Val Met
                1860                1865                1870

Ala Glu Glu Ser Thr Asp Gly Glu Val Glu Thr Gln Val Tyr Asn Gln
    1875                1880                1885

Asp Ser Gln Asp Ser Ile Gly Glu Gly Val Thr Gln Gly Asp Tyr Thr
    1890                1895                1900

Pro Met Glu Asp Ser Glu Glu Thr Ser Gln Ser Leu Gln Ile Asp Leu
1905                1910                1915                1920

Gly Pro Leu Gln Ser Asp Gln Gln Thr Thr Thr Ser Ser Gln Asp Gly
                1925                1930                1935

Gln Gly Lys Gly Asp Asp Val Ile Val Ile Asp Ser Asp Asp Glu Glu
                1940                1945                1950

Glu Asp Glu Glu Asp Asp Asp Asp Glu Asp Asp Thr Gly Met Gly
                1955                1960                1965

Asp Glu Gly Glu Asp Ser Asn Glu Gly Thr Gly Ser Ala Asp Gly Asn
    1970                1975                1980

Asp Gly Tyr Glu Ala Asp Asp Ala Glu Gly Gly Asp Gly Thr Asp Pro
1985                1990                1995                2000

Gly Thr Glu Thr Glu Glu Ser Met Gly Gly Gly Glu Gly Asn His Arg
                2005                2010                2015

Ala Ala Asp Ser Gln Asn Ser Gly Glu Gly Asn Thr Gly Ala Ala Glu
                2020                2025                2030

Ser Ser Phe Ser Gln Glu Val Ser Arg Glu Gln Gln Pro Ser Ser Ala
                2035                2040                2045

Ser Glu Arg Gln Ala Pro Arg Ala Pro Gln Ser Pro Arg Arg Pro Pro
    2050                2055                2060

His Pro Leu Pro Pro Arg Leu Thr Ile His Ala Pro Pro Gln Glu Leu
2065                2070                2075                2080

Gly Pro Pro Val Gln Arg Ile Gln Met Thr Arg Arg Gln Ser Val Gly
                2085                2090                2095

Arg Gly Leu Gln Leu Thr Pro Gly Ile Gly Gly Met Gln Gln His Phe
    2100                2105                2110

Phe Asp Asp Glu Asp Arg Thr Val Pro Ser Thr Pro Thr Leu Val Val
    2115                2120                2125

Pro His Arg Thr Asp Gly Phe Ala Glu Ala Ile His Ser Pro Gln Val
    2130                2135                2140

Ala Gly Val Pro Arg Phe Arg Phe Gly Pro Pro Glu Asp Met Pro Gln
2145                2150                2155                2160

Thr Ser Ser Ser His Ser Asp Leu Gly Gln Leu Ala Ser Gln Gly Gly
                2165                2170                2175

Leu Gly Met Tyr Glu Thr Pro Leu Phe Leu Ala His Glu Glu Glu Ser
                2180                2185                2190

Gly Gly Arg Ser Val Pro Thr Thr Pro Leu Gln Val Ala Ala Pro Val
    2195                2200                2205
```

-continued

```
Thr Val Phe Thr Glu Ser Thr Thr Ser Asp Ala Ser Glu His Ala Ser
    2210                2215                2220
Gln Ser Val Pro Met Val Thr Thr Ser Thr Gly Thr Leu Ser Thr Thr
2225                2230                2235                2240
Asn Glu Thr Ala Thr Gly Asp Asp Gly Asp Glu Val Phe Val Glu Ala
                2245                2250                2255
Glu Ser Glu Gly Ile Ser Ser Glu Ala Gly Leu Glu Ile Asp Ser Gln
                2260                2265                2270
Gln Glu Glu Glu Pro Val Gln Ala Ser Asp Glu Ser Asp Leu Pro Ser
            2275                2280                2285
Thr Ser Gln Asp Pro Pro Ser Ser Ser Ser Val Asp Thr Ser Ser Ser
    2290                2295                2300
Gln Pro Lys Pro Phe Arg Arg Val Arg Leu Gln Thr Thr Leu Arg Gln
2305                2310                2315                2320
Gly Val Arg Gly Arg Gln Phe Asn Arg Gln Arg Gly Val Ser His Ala
                2325                2330                2335
Met Gly Gly Arg Gly Gly Ile Asn Arg Gly Asn Ile Asn
                2340                2345
```

TUMOR ANTIGENS AND USES THEREOF

CROSS REFERENCE TO RELATED APPLICATIONS

This application is a U.S. National Stage application, filed under 35. U.S.C. §371(f), of International Application No. PCT/US99/17738 filed Aug. 6, 1999, which claims priority from U.S. Provisional Application Ser. No. 60/095,766 filed Aug. 7, 1998.

BACKGROUND OF THE INVENTION

There is compelling evidence that malignant melanoma cells evoke specific humoral and cellular anti-tumor immune responses in some patients. For example, the radial growth phase of primary melanoma is regularly associated with a significant dermal lymphocytic reaction that often results in partial tumor destruction. Moreover, clonal expansion of T cells occurs in primary regressing melanoma; lymphocytes explanted from such lesions demonstrate cytotoxicity towards autologous melanoma cells in vitro.

Although a brisk lymphocytic infiltrate in the vertical growth phase of primary melanoma occurs infrequently, this response is tightly correlated with prolonged survival and a reduced incidence of metastatic disease. Melanoma that has spread to regional lymph nodes may occasionally elicit a striking lymphocytic reaction which is also highly associated with improved survival. In rare cases, widely disseminated melanoma may undergo spontaneous regression accompanied by a diffuse infiltrate of lymphocytes, plasma cells, and macrophages. Notwithstanding these provocative findings, however, it is clear that most patients fail to develop anti-melanoma immune responses that are sufficiently potent to prevent lethal tumor progression.

The application of gene transfer technologies to investigative efforts in tumor immunology has led to the development of several novel strategies to enhance the frequency and intensity of anti-tumor immune responses. A large number of pre-clinical studies have convincingly demonstrated that engineering murine tumor cells to express a variety of immunostimulatory molecules can lead to enhanced tumor immunogenicity. Among the approaches utilizing ex vivo modification of tumor cells, we have shown that vaccination with irradiated tumor cells engineered to secrete granulocyte-macrophage colony stimulating factor (GM-CSF) stimulates potent, specific, and long-lasting anti-tumor immunity in multiple murine tumor model systems, including malignant melanoma (Dranoff et al., *Proc. Natl. Acad. Sci., U.S.A.*, 90:3539-3543, 1993). Immunization requires the participation of both CD4- and CD8-positive T lymphocytes and likely involves improved tumor antigen presentation by dendritic cells and macrophages recruited to the vaccination site. Identification of individual tumor antigens is likely to contribute to improved cancer diagnosis and treatment.

SUMMARY OF THE INVENTION

Vaccination with irradiated, autologous melanoma cells engineered to secrete GM-CSF stimulates potent anti-tumor immunity in humans with metastatic melanoma. We established a melanoma cell line from a metastatic tumor removed from a vaccinated patient, and constructed a cDNA expression library from mRNA isolated from the melanoma cells. The library was screened with serum from vaccinated patients, and several tumor antigen clones were isolated.

In a first aspect, the invention features a method of identifying a nucleic acid encoding a tumor antigen or a fragment thereof, comprising: a) identifying a patient with a tumor;

b) obtaining tumor cells from the patient; c) vaccinating the patient with a vaccine preparation comprising the tumor cells together with a GM-CSF sustained delivery system to generate an immune response in the patient; and d) isolating, either from an autologous post-vaccination tumor sample obtained from the patient, or from allogeneic tumor cells, nucleic acid that encodes a tumor antigen or a fragment thereof, wherein the nucleic acid encoding the tumor antigen or fragment is detected by an antibody in serum obtained from the patient, wherein the antibody specifically binds the tumor antigen.

In a second aspect, the invention features a method of identifying a nucleic acid encoding a tumor antigen or a fragment thereof, comprising: a) identifying a patient with a tumor; b) obtaining tumor cells from the patient; c) vaccinating the patient with a vaccine preparation comprising the tumor cells together with a GM-CSF sustained delivery system to generate an immune response in the patient; and d) isolating, either from an autologous post-vaccination tumor sample obtained from the patent, or from allogeneic tumor cells, nucleic acid that encodes the tumor antigen or the fragment thereof, wherein the nucleic acid encoding the tumor antigen or fragment is detected by a cytotoxic T lymphocyte obtained from the patent, wherein the cytotoxic T lymphocyte specifically binds the tumor antigen.

In a third aspect, the invention features a method of identifying a tumor antigen or a fragment thereof, comprising: a) identifying a patient with a tumor; b) obtaining tumor cells from the patient; c) vaccinating the patient with a vaccine preparation comprising the tumor cells together with a GM-CSF sustained delivery system to generate an immune response in the patient; and d) isolating the tumor antigen or the fragment thereof either from an autologous post-vaccination tumor sample obtained from the patient or from allogeneic tumor cells, wherein the tumor antigen or fragment is detected by an antibody in serum obtained from the patient, wherein the antibody specifically binds the tumor antigen.

In a fourth aspect, the invention features a method of identifying a tumor antigen or a fragment thereof, comprising: a) identifying a patient with a tumor; b) obtaining tumor cells from the patient; c) vaccinating the patient with a vaccine preparation comprising the tumor cells together with a GM-CSF sustained delivery system to generate an immune response in the patient; and d) isolating the tumor antigen or the fragment thereof from either an autologous post-vaccination tumor sample obtained from the patient or from allogeneic tumor cells, wherein the tumor antigen or the fragment is detected by a cytotoxic T lymphocyte obtained from the patient, wherein the cytotoxic T lymphocyte specifically binds the tumor antigen.

In preferred embodiments of the first, second, third, and fourth aspects of the invention, the GM-CSF sustained delivery system comprises a plasmid or viral expression vector encoding GM-CSF that is transfected or transduced into the tumor cells prior to vaccination, or the GM-CSF sustained delivery system comprises cells expressing GM-CSF that are mixed with the tumor cells prior to vaccination (for example, allogeneic cells or other cultured cells) or the GM-CSF sustained delivery system comprises microspheres releasing GM-CSF that are mixed with the tumor cells prior to vaccination.

In other embodiments of the first four aspects of the invention, the serum may be pre-vaccination serum, or post-vaccination serum, and detection by post-vaccination serum may be more sensitive than detection by pre-vaccination serum.

In still other embodiments of the first four aspects of the invention, the cells are irradiated prior to vaccination, the tumor may be a leukemia, a lymphoma, a brain tumor (e.g., a glioblastoma or a neuroblastoma), a melanoma, a sarcoma, or a carcinoma such as a uterine, cervical, testicular, liver, ovarian, lung (e.g., non-small cell lung), renal cell, colon, breast, prostate, or bladder carcinoma, and vaccination increases the number of T lymphocytes and/or plasma cells in the patient's tumor, relative to the number of T lymphocytes and/or plasma cells in the patient's tumor prior to the vaccination.

In yet other embodiments of the first four aspects of the invention the tumor antigen fragment contains at least 10 amino acids, preferably at least 15, 20, 25, or 30 amino acids, more preferably at least 50 amino acids. Most preferably, the entire tumor antigen is identified.

In a fifth aspect, the invention features a method of monitoring or diagnosing a tumor in a patient, comprising detecting or measuring, in a sample from the patient, a tumor antigen, a nucleic acid encoding a tumor antigen, an antibody that specifically binds a tumor antigen, or a cytotoxic T lymphocyte that specifically binds a tumor antigen. The tumor antigen is identified by the method of the first four aspects of the invention.

In preferred embodiments of the fifth aspect of the invention, the sample is selected from: a tumor or tissue biopsy, a lymph node, bone marrow, cells, blood, urine, stool, sputum, saliva, cerebrospinal fluid, or uterine tissue.

In a sixth aspect, the invention features a substantially pure polypeptide or fragment thereof, wherein the fragment is at least ten amino acids long, and wherein the polypeptide comprises a polypeptide substantially identical to a polypeptide encoded by a nucleic acid sequence selected from TRAAM (SEQ ID NOs: 1, 3, and 17); TPR/UBP3 (SEQ ID NO: 7); UBP3 (SEQ ID NO: 7); BRAP-2/H$^+$-ATPase (SEQ ID NO: 8); KOO8-1 (SEQ ID NO: 9); MAIAP (SEQ ID NO: 11); Gene AS (SEQ ID NO: 16); BR-1 (SEQ ID NO: 14); and BR-2 (SEQ ID NO: 15). In a preferred embodiment, the polypeptide is a human polypeptide.

In a seventh aspect, the invention features a purified nucleic acid comprising a sequence encoding a polypeptide or a fragment thereof, wherein the fragment is at least ten amino acids long, and wherein the polypeptide comprises a polypeptide substantially identical to a polypeptide encoded by a nucleic acid sequence selected from TRAAM (SEQ ID NOs: 1, 3, and 17); TPR/UBP3 (SEQ ID NO: 7); UBP3 (SEQ ID NO: 7); BRAP-2/H$^+$-ATPase (SEQ ID NO: 8); KOO8-1 (SEQ ID NO: 9); MAIAP (SEQ ID NO: 11); Gene AS (SEQ ID NO: 16); BR-1 (SEQ ID NO: 14); and BR-2 (SEQ ID NO: 15). In a preferred embodiment, the nucleic acid comprises a nucleotide sequence set forth in the seventh aspect of the invention.

In an eighth aspect, the invention features a purified nucleic acid having a nucleotide sequence that hybridizes under high stringency conditions to a probe comprising at least fourteen consecutive nucleotides that are complementary to: TRAAM; TPR/UBP3; UBP3; BRAP-2/H$^+$-ATPase; KOO8-1; MAIAP; Gene AS; BR-1; and BR-2. In a ninth aspect, the invention features a purified nucleic acid comprising a probe, wherein the probe hybridizes under high stringency conditions to TRAAM; TPR/UBP3; UBP3; BRAP-2/H$^+$-ATPase; KOO8-1; MAIAP; Gene AS; BR-1; or BR-2, wherein the probe has a nucleotide sequence complementary to at least 14 consecutive nucleotides of TRAAM; TPR/UBP3; UBP3; BRAP-2/H$^+$-ATPase; KOO8-1; MAIAP; Gene AS; BR-1; or BR-2.

In preferred embodiments of the eighth and ninth aspects of the invention, the nucleic acid is DNA or RNA.

In a tenth aspect, the invention features a vector comprising a tumor antigen nucleic acid according to the ninth aspect of the invention.

In an eleventh aspect, the invention features a cell containing nucleic acid according to the seventh, eighth, ninth, and tenth aspects of the invention.

In a twelfth aspect, the invention features a substantially pure antibody that specifically binds a polypeptide or a fragment thereof, wherein the polypeptide comprises a polypeptide encoded by a nucleic acid sequence chosen from: TRAAM; TPR/UBP3; UBP3; BRAP-2/H$^+$-ATPase; H$^+$-ATPase; KOO8-1; MAIAP; Gene AS, BR-1; and BR-2.

In a thirteenth aspect, the invention features a method of generating an antibody that specifically binds a polypeptide or a fragment thereof, wherein the polypeptide comprises a polypeptide substantially identical to a polypeptide encoded by a nucleic acid sequence selected from the group consisting of TRAAM; TPR/UBP3; UBP3; BRAP-2/H$^+$-ATPase; H$^+$-ATPase; KOO8-1; MAIAP; Gene AS; BR-1; and BR-2, the method comprising administering the polypeptide, or fragment thereof, to an animal capable of generating an immune response, and isolating the antibody from the animal.

In a fourteenth aspect, the invention features a method of detecting the presence of a polypeptide or a fragment thereof in a biological sample, wherein the polypeptide comprises a polypeptide substantially identical to a polypeptide encoded by a nucleic acid selected from the group consisting of TRAAM; TPR/UBP3; UBP3; BRAP-2/H-ATPase; H$^+$-ATPase; KOO8-1; MAIAP; Gene AS; BR-1; and BR-2, the method comprising contacting the sample with an antibody that specifically binds the polypeptide or a fragment thereof, and assaying for binding of the antibody to the polypeptide.

In a fifteenth aspect, the invention features a method of testing a patient for the presence of a tumor or an increased likelihood of developing a tumor, comprising: a) obtaining a sample from the patient, b) measuring the level of an antibody in the sample, wherein the antibody specifically binds a tumor antigen, wherein the tumor antigen comprises a polypeptide encoded by a nucleic acid selected from the group consisting of: TRAAM; TPR/UBP3; UBP3; BRAP-2/H$^+$-ATPase; KOO8-1; MAIAP; Gene AS; BR-1; BR-2; KIAA0603; TPR; NOR-90; and BRAP-2, c) comparing the antibody level in the patient sample to the antibody level in a reference sample, wherein an increase in the antibody level in the patient sample, relative to the antibody level in the reference sample, indicates that the patient has a tumor or the increased likelihood of developing a tumor.

In a sixteenth aspect, the invention features a method of testing a patient for the presence of a tumor or an increased likelihood of developing a tumor, comprising: a) obtaining a sample from the patient, b) measuring the level of cytotoxic T lymphocytes in the sample, wherein the cytotoxic T lymphocytes specifically bind a tumor antigen, wherein the tumor antigen comprises a polypeptide encoded by a nucleic acid selected from the group consisting of: TRAAM; TPR/UBP3; UBP3; BRAP-2/H$^+$-ATPase; KOO8-1; MAIAP; Gene AS; BR-1; BR-2; KIAA0603; TPR; NOR-90; and BRAP-2, c) comparing the cytotoxic T lymphocyte level in the patient sample to the cytotoxic T lymphocyte level in a reference sample, wherein an increase in the cytotoxic T lymphocyte level in the patient sample, relative to the cytotoxic T lymphocyte level in the reference sample, indicates the patient has a tumor or the increased likelihood of developing a tumor.

In preferred embodiments of the fifteenth and sixteenth aspects of the invention, the tumor may be a leukemia, a lymphoma, a brain tumor (e.g., a glioblastoma or a neuroblastoma), a melanoma, a sarcoma, or a carcinoma such as a uterine, cervical, testicular, liver, ovarian, lung (e.g., non-small cell lung), renal cell, colon, breast, prostate, or bladder carcinoma.

In a seventeenth aspect, the invention features a method of testing a patient for the presence of a tumor or the increased likelihood of developing a tumor, comprising: a) obtaining a sample from the patient, b) measuring the level of a tumor antigen in the sample, wherein the tumor antigen comprises a polypeptide substantially identical to a polypeptide encoded by a nucleic acid selected from the group consisting of: TRAAM; TPR/UBP3; UBP3; BRAP-2/H$^+$-ATPase; H$^+$-ATPase; KOO8-1; MAIAP; Gene AS; BR-1; BR-2; KIAA0603; TPR; NOR-90; and BRAP-2, c) comparing the tumor antigen level in the patient sample to the tumor antigen level in a reference sample, wherein an increase in the tumor antigen level in the patient sample, relative to the tumor antigen level in the reference sample, indicates that the patient has a tumor or the increased likelihood of developing a tumor.

In preferred embodiments of the seventeenth aspect of the invention, the tumor antigen level may be measured by measuring the level of tumor antigen polypeptide, or by measuring the level of nucleic acid encoding the tumor antigen. The nucleic acid may be genomic DNA, mRNA, or cDNA.

In other embodiments of the seventeenth aspect, the sample may be selected from: a tumor or tissue biopsy, a lymph node, bone marrow, cells, blood, urine, stool, sputum, saliva, cerebrospinal fluid, or uterine tissue.

In still other embodiments of the seventeenth aspect, the tumor may be a leukemia, a lymphoma, a brain tumor (e.g., a glioblastoma or a neuroblastoma), a melanoma, a sarcoma, or a carcinoma such as a uterine, cervical, testicular, liver, ovarian, lung (e.g., non-small cell lung), renal cell, colon, breast, prostate, or bladder carcinoma.

In an eighteenth aspect, the invention features a method of determining the level of an antibody in a patient, wherein the antibody specifically binds a tumor antigen polypeptide comprising a polypeptide encoded by a nucleic acid selected from the group consisting of: TRAAM; TPR/UBP3; UBP3; BRAP-2/H$^+$-ATPase; H$^+$-ATPase; KOO8-1; MAIAP; Gene AS; BR-1; BR-2; KIAA0603; TPR; NOR-90; and BRAP-2, comprising: a) obtaining a sample containing the antibody from the patient, and b) measuring the level of the antibody in the patient sample, compared to a reference sample.

In a nineteenth aspect, the invention features a method of determining the level of cytotoxic T lymphocytes in a patient, wherein the cytotoxic T lymphocytes specifically bind a tumor antigen polypeptide comprising a polypeptide encoded by a nucleic acid selected from the group consisting of: TRAAM; TPR/UBP3; UBP3; BRAP-2/H$^+$-ATPase; H$^+$-ATPase; KOO8-1; MAIAP; Gene AS; BR-1; BR-2; KIAA0603; TPR; NOR-90; and BRAP-2, comprising: a) obtaining a sample containing the cytotoxic T lymphocytes from the patient, and b) measuring the level of cytotoxic T lymphocytes in the patient sample, compared to a reference sample.

In a twentieth aspect, the invention features a method of treatment or prophylaxis for a patient that has a tumor or is at risk for developing a tumor, comprising vaccinating the patient with a tumor antigen encoded by a nucleic acid selected from: TRAAM; TPR/UBP3; UBP3; BRAP-2/H$^+$-ATPase; H$^+$-ATPase; KOO8-1; MAIAP; Gene AS; BR-1; BR-2; KIAA0603; TPR; NOR-90; and BRAP-2.

In preferred embodiments of the twentieth aspect of the invention, the vaccinating may be with a tumor antigen polypeptide, or with a nucleic acid encoding the tumor antigen polypeptide, and the nucleic acid may be within an expression vector. In another embodiment of the twentieth aspect, the nucleic acid is within a cell capable of expressing the nucleic acid. The nucleic acid may be introduced into the cell in vivo or ex vivo.

In a twenty-first aspect, the invention features a method for treating a tumor in a patient, comprising administering to the patient, an antibody that specifically binds a tumor antigen encoded by a nucleic acid selected from TRAAM; TPR/UBP3; UBP3; BRAP-2/H$^+$-ATPase; H$^+$-ATPase; KOO8-1; MAIAP; Gene AS; BR-1; BR-2; KIAA0603; TPR; NOR-90; and BRAP-2. In a preferred embodiment, the antibody is coupled to a toxic or radioactive moiety.

In a twenty-second aspect, the invention features a method for treating a tumor in a patient, comprising administering to the patient, cytotoxic T lymphocytes that specifically bind a tumor antigen encoded by a nucleic acid selected from TRAAM; TPR/UBP3; UBP3; BRAP-2/H$^+$-ATPase; H$^+$-ATPase; KOO8-1; MAIAP; Gene AS; BR-1; BR-2; KIAA0603; TPR; NOR-90; and BRAP-2.

In a twenty-third aspect, the invention features a method for detecting a tumor in a patient, comprising: a) introducing, into the patient, an antibody coupled to an imaging compound, wherein the antibody specifically binds a tumor antigen encoded by a nucleic acid selected from TRAAM; TPR/UBP3; UBP3; BRAP-2/H$^+$-ATPase; H$^+$-ATPase; KOO8-1; MAIAP; Gene AS; BR-1; BR-2; KIAA0603; TPR; NOR-90; and BRAP-2, and b) detecting immune complexes formed between the antibody and the tumor antigen in the patient.

In a twenty-fourth aspect, the invention features a vaccine for treatment of a tumor or prophylaxis against developing a tumor, the vaccine comprising a tumor antigen polypeptide or a fragment thereof, wherein the tumor antigen polypeptide comprises a polypeptide substantially identical to a polypeptide encoded by a nucleic acid selected from TRAAM; TPR/UBP3; UBP3; BRAP-2/H$^+$-ATPase; H$^+$-ATPase; KOO8-1; MAIAP; Gene AS; BR-1; BR-2; KIAA0603; TPR; NOR-90; and BRAP-2.

In a twenty-fifth aspect, the invention features a vaccine for treatment of a tumor or prophylaxis against developing a tumor, the vaccine comprising a nucleic acid encoding a tumor antigen, or a fragment thereof, wherein said tumor antigen is substantially identical to a tumor antigen encoded by a nucleic acid selected from TRAAM; TPR/UBP3; UBP3; BRAP-2/H-ATPase; H$^+$-ATPase; KOO8-1; MAIAP; Gene AS; BR-1; BR-2; KIAA0603; TPR; NOR-90; and BRAP-2.

In preferred embodiments of the twenty-fifth aspect, the nucleic acid may be within a cell capable of expressing the nucleic acid, and the nucleic acid may be within a vector.

In a preferred embodiment of the first through fifth, fifteenth through seventeenth, and twenty through twenty-fifth aspects of the invention, the tumor is metastatic.

In a twenty-sixth aspect, the invention features a method of identifying a nucleic acid encoding a tumor antigen or a fragment thereof, comprising: a) identifying a patient with a tumor; b) vaccinating the patient with a vaccine preparation comprising allogeneic tumor cells together with a GM-CSF sustained delivery system to generate an immune response in the patient; and c) isolating, either from an autologous post-vaccination tumor sample obtained from the patient, or from allogeneic tumor cells, nucleic acid that encodes a tumor antigen or a fragment thereof, wherein the nucleic acid encoding the tumor antigen or fragment is detected by an antibody in serum obtained from the patient, wherein the antibody specifically binds the tumor antigen.

In a twenty-seventh aspect, the invention features a method of identifying a nucleic acid encoding a tumor antigen or a fragment thereof, comprising: a) identifying a patient with a tumor;

b) vaccinating the patient with a vaccine preparation comprising allogeneic tumor cells together with a GM-CSF sustained delivery system to generate an immune response in the patient; and c) isolating, either from an autologous post-vaccination tumor sample obtained from the patient, or from allogeneic tumor cells, nucleic acid that encodes a tumor antigen or tumor antigen fragment, wherein the nucleic acid encoding the tumor antigen or fragment is detected by a cytotoxic T lymphocyte obtained from the patient, wherein the cytotoxic T lymphocyte specifically binds the tumor antigen.

In a twenty-eighth aspect, the invention features a method of identifying a tumor antigen or a fragment thereof, comprising: a) identifying a patient with a tumor; b) vaccinating the patient with a vaccine preparation comprising allogeneic tumor cells together with a GM-CSF sustained delivery system to generate an immune response in the patient; and c) isolating the tumor antigen or tumor antigen fragment either from an autologous post-vaccination tumor sample obtained from the patient, or from allogeneic tumor cells, wherein the tumor antigen or tumor antigen fragment is detected by an antibody in serum obtained from the patient, wherein the antibody specifically binds the tumor antigen.

In a twenty-ninth aspect, the invention features a method of identifying a tumor antigen or a fragment thereof, comprising: a) identifying a patient with a tumor; b) vaccinating the patient with a vaccine preparation comprising allogeneic tumor cells together with a GM-CSF sustained delivery system to generate an immune response in the patient; and c) isolating the tumor antigen or tumor antigen fragment either from an autologous post-vaccination tumor sample obtained from the patient, or from allogeneic tumor cells, wherein the nucleic acid encoding the tumor antigen or tumor antigen fragment is detected by a cytotoxic T lymphocyte obtained from the patient, wherein the cytotoxic T lymphocyte specifically binds the tumor antigen.

In preferred embodiments of the twenty-sixth through twenty-ninth aspects of the invention, the GM-CSF sustained delivery system comprises a plasmid or viral expression vector encoding GM-CSF that is transfected or transduced into the allogeneic tumor cells prior to vaccination, or the GM-CSF sustained delivery system comprises cells expressing GM-CSF that are mixed with the allogeneic tumor cells prior to vaccination, or the GM-CSF sustained delivery system comprises microspheres releasing GM-CSF that are mixed with the allogeneic tumor cells prior to vaccination.

In other embodiments of the twenty-sixth through twenty-ninth aspects of the invention, the serum may be pre-vaccination serum, or post-vaccination serum, and detection by post-vaccination serum may be more sensitive than detection by pre-vaccination serum.

In still other embodiments of the twenty-sixth through twenty-ninth aspects of the invention, the cells are irradiated prior to vaccination, the allogeneic tumor cells may originate from a leukemia, a lymphoma, a brain tumor (e.g., a glioblastoma or a neuroblastoma), a melanoma, a sarcoma, or a carcinoma such as a uterine, cervical, testicular, liver, ovarian, lung (e.g., non-small cell lung), renal cell, colon, breast, prostate, or bladder carcinoma, and vaccination increases the number of T lymphocytes and/or plasma cells in the patient's tumor, relative to the number of T lymphocytes and/or plasma cells in the patient's tumor prior to the vaccination.

In a thirtieth aspect, the invention features a substantially pure MAIAP polypeptide, wherein the polypeptide includes an amino acid sequence substantially identical to the amino acid sequence set forth in SEQ ID NO: 12. In a preferred embodiment of the thirtieth aspect of the invention, the MAIAP polypeptide includes the amino acid sequence set forth in SEQ ID NO: 12.

In a thirty-first aspect, the invention features a substantially pure MAIAP nucleic acid, wherein the nucleic acid encodes the MAIAP polypeptide set forth in SEQ ID NO: 12. In a preferred embodiment of the thirty-first aspect of the invention, the nucleic acid includes the nucleotide sequence set forth in SEQ ID NO: 11.

In a thirty-second aspect, the invention features a substantially pure nucleic acid that includes at least 14 consecutive nucleotides that display at least 85%, 90%, 92%, 95%, or 98% sequence identity to a nucleotide sequence that is complementary to a nucleic acid that encodes MAIAP. In preferred embodiments of the thirty-second aspect of the invention, the nucleic acid includes at least 16, 18, 22, 25, 50, 75, or 100 consecutive nucleotides that display at least 85%, 90%, 92%, 95%, or 98% sequence identity to a nucleotide sequence that is complementary to a nucleic acid that encodes MAIAP, and the nucleic acid hybridizes under high stringency conditions to a MAIAP nucleic acid.

In a thirty-third aspect, the invention features a substantially pure nucleic acid including at least 14 nucleotides, wherein the nucleic acid hybridizes under high stringency conditions to a nucleic acid that encodes MAIAP. In a preferred embodiment of the thirty-third aspect of the invention, the nucleic acid includes at least 16, 18, 22, 25, 50, 75, or 100 nucleotides.

In further embodiments of the thirty-second and thirty-third aspects of the invention, the substantially pure nucleic acid is an antisense nucleic acid.

In a thirty-fourth aspect, the invention features a method for stimulating apoptosis in a population of cells. The method includes introducing into the cells a MAIAP antisense nucleic acid, wherein the MAIAP antisense nucleic acid decreases the level of MAIAP in the cells, wherein the decrease stimulates apoptosis in the population of cells.

In various preferred embodiments of the thirty-fourth aspect of the invention, the cells are tumor cells, the cells are exposed to an apoptotic stimulus before or after the MAIAP antisense nucleic acid is introduced into the cells, and the apoptotic stimulus is gamma irradiation or a chemotherapeutic agent.

In a thirty-fifth aspect, the invention features a method for inhibiting apoptosis in a population of cells having an increased risk for undergoing apoptosis. The method includes introducing into the cells a substantially pure MAIAP polypeptide, wherein the substantially pure MAIAP polypeptide inhibits apoptosis in the cells, compared to cells not containing the substantially pure MAIAP polypeptide.

In one preferred embodiment of the thirty-fifth aspect of the invention, the MAIAP polypeptide is encoded by a substantially pure MAIAP nucleic acid, wherein the nucleic acid is introduced into the cells. The MAIAP nucleic acid may be introduced into the cells ex vivo or in vivo.

In another preferred embodiment of the thirty-fifth aspect of the invention, the increased risk for undergoing apoptosis is caused by: exposure to gamma irradiation, exposure to a chemotherapeutic agent, exposure to a toxin, exposure to hypoxia, an injury, a degenerative disease, or an attack by cells of the immune system.

In a thirty-sixth aspect, the invention features a method of identifying a compound that modulates apoptosis or radiation sensitivity. The method includes the steps of: (a) exposing a sample to a test compound, wherein the sample comprises a MAIAP nucleic acid, a MAIAP reporter gene, or a MAIAP polypeptide; and (b) assaying for a change in the level of MAIAP biological activity in the sample, relative to a sample not exposed to the test compound, wherein an increase in the level of said MAIAP biological activity in the sample, relative to a sample not exposed to the compound, indicates a compound that inhibits apoptosis or decreases radiation sensitivity, and a decrease in the level of the MAIAP biological activity in the sample, relative to a sample not exposed to the compound, indicates a compound that stimulates apoptosis or increases radiation sensitivity.

In various preferred embodiments of the thirty-sixth aspect of the invention, the MAIAP nucleic acid is genomic DNA, cDNA, mRNA, cRNA, or a substantially pure genomic DNA fragment. In other preferred embodiments of the thirty-sixth aspect of the invention, the MAIAP nucleic acid, MAIAP reporter gene, or MAIAP polypeptide is within a cell, wherein the cell is exposed to the test compound.

In a thirty-seventh aspect, the invention features a substantially pure TRAAM polypeptide or a fragment thereof, wherein the fragment includes at least 10 amino acids, wherein the polypeptide includes an amino acid sequence substantially identical to the amino acid sequence set forth in SEQ ID NO: 18, or SEQ ID NO: 19.

In preferred embodiments of the thirty-seventh aspect of the invention, the TRAAM polypeptide or fragment includes the partial TRAM repeat sequence set forth in SEQ ID NO: 25, the full TRAM repeat sequence set forth in SEQ ID NO: 24, or the PSET repeat sequence set forth in SEQ ID NO: 30.

In a thirty-eighth aspect, the invention features a substantially pure TRAAM nucleic acid, wherein the nucleic acid encodes a TRAAM polypeptide substantially identical to the polypeptide set forth in SEQ ID NO: 18 or SEQ ID NO: 19. In a preferred embodiment of the thirty-eighth aspect of the invention, the TRAAM nucleic acid includes the nucleotide sequence set forth in SEQ ID NO: 17.

In a thirty-ninth aspect, the invention features a substantially pure nucleic acid that includes at least 14 consecutive nucleotides that display at least 85%, 90%, 92%, 95%, or 98% sequence identity to a nucleotide sequence that is complementary to a nucleic acid that encodes a TRAAM polypeptide (SEQ ID NO: 18 or 19). In preferred embodiments of the thirty-ninth aspect of the invention, the substantially pure nucleic acid includes 16, 18, 22, 25, 50, 75, or 100 consecutive nucleotides that display at least 85%, 90%, 92%, 95%, or 98% sequence identity to a nucleotide sequence that is complementary to a nucleic acid that encodes a TRAAM polypeptide (SEQ ID NO: 18 or 19), and the nucleic acid hybridizes under high stringency conditions to a TRAAM nucleic acid.

In a fortieth aspect, the invention features a substantially pure nucleic acid including at least 14 nucleotides, wherein the nucleic acid hybridizes under high stringency conditions to a nucleic acid that encodes a TRAAM polypeptide (SEQ ID NO: 18 or 19). In a preferred embodiment of the fortieth aspect of the invention, the substantially pure nucleic acid includes at least 16, 18, 22, 25, 50, 75, or 100 nucleotides.

In preferred embodiments of the thirty-ninth and fortieth aspects of the invention, the substantially pure nucleic acid is an antisense nucleic acid.

By "tumor antigen" is meant an immunogenic polypeptide expressed by tumor cells, or a nucleic acid that encodes a such a polypeptide. A tumor antigen may be broadly expressed in various types of normal and tumor cells, expressed only in tumor cells of a particular type (e.g., melanoma), or expressed only in some tumor cells of a particular type (e.g., in the melanoma cells of a first patient, but not in the melanoma cells second patient). Tumor antigens or nucleic acids that encode tumor antigens may be present at higher levels in patient samples than in reference samples. Moreover, antibodies against tumor antigens may be present in patient serum, saliva, or tears at higher levels than those found in reference samples. Patients that mount a sufficient immune response against a tumor antigen expressed by their tumor cells experience tumor regression. Examples of tumor antigens are described below. They include: TRAAM; TPR/UBP3; UBP3; BRAP-2/$H^+$-ATPase; $H^+$-ATPase; KOO8-1; MAIAP; Gene AS; BR-1; BR-2; KIAA0603; TPR; NOR-90; and BRAP-2 (see FIGS. 6 through 8 and 17; SEQ ID NOs: 1-19 and 45-48).

By "tumor antigen nucleic acid" is meant DNA or RNA that encodes a tumor antigen of the invention. The tumor antigen nucleic acid may also be complementary to the coding strand of a tumor antigen nucleic acid; hence, this definition includes primers, probes, and antisense nucleic acids.

By "vaccination" is meant administration of an immunogenic preparation comprising either tumor cells, tumor antigen, nucleic acid that encodes tumor antigen, cells expressing tumor antigen, or a mixture thereof, to a patient who has a tumor or is likely to develop a tumor. A vaccination may employ only one tumor antigen, or more than one tumor antigen. The vaccination stimulates an immune response within the patient, which may result in partial or complete inhibition of tumor growth or partial or complete tumor regression, if the patient's tumor bears a tumor antigen similar to a tumor antigen used for vaccination. In addition, vaccination may provide prophylaxis against the development of a new tumor that bears a tumor antigen similar to a tumor antigen used for vaccination.

By "GM-CSF sustained delivery system" is meant a means for ensuring that GM-CSF is released from a vaccination site for at least 24 hours after vaccination, such that the GM-CSF secretion rate is approximately 84 to 965 ng/$10^6$ GM-CSF-secreting cells/24 hours, or, sufficient to induce an immune response. A GM-CSF sustained delivery system may employ an expression vector encoding GM-CSF, which is transfected or transduced into autologous tumor cells obtained from the patient prior to using the cells for vaccination; hence, the transfected autologous tumor cells used for vaccination secrete GM-CSF. Alternatively, a GM-CSF sustained delivery system may employ an expression vector transfected or transduced into non-autologous cells, such as allogeneic tumor cells, or other cultured cells, which would, as a result, secrete GM-CSF. A GM-CSF sustained delivery system may encompass any cells that secrete sufficient GM-CSF as defined below. GM-CSFsecreting cells may be mixed with the autologous tumor cells, and the cell mixture is then used for vaccination. In addition, allogeneic tumor cells that secrete GM-CSF may be used alone for vaccination. A GM-CSF sustained delivery system may also employ microspheres that slowly release GM-CSF, such as those that may be obtained from Immunex or Novartis. The microspheres are mixed with autologous tumor cells or allogeneic tumor cells, and the tumor cell/ microsphere mixture is used for vaccination. For vaccinations containing autologous or allogeneic tumor cells mixed with either GM-CSF-secreting cells or microspheres, sufficient GM-CSF-secreting cells or microspheres must be mixed with the tumor cells such that GM-CSF equivalent to that released by GM-CSF-secreting autologous tumor cells (e.g., 84 to 965 ng/106 GM-CSF-secreting autologous tumor cells/24 hours), sufficient to obtain an immune response to the vaccination, is released. Similar approaches may also be used to achieve a GM-CSF sustained delivery system that is combined in a vaccine preparation either with autologous tumor cells, allogenic tumor cells, or with one or more tumor antigens.

By "pre-vaccination serum" is meant serum derived from the blood of an individual who has not been vaccinated with tumor cells or a tumor antigen.

By "post-Vaccination serum" is meant serum derived from the blood of an individual after the individual has been vaccinated with tumor cells or a tumor antigen and has mounted an immune response against the vaccination material.

By "treatment" or "amelioration" of a tumor is meant that a therapy (e.g., chemotherapy, radiation therapy, or vaccination with a tumor antigen in order to enhance an anti-tumor immune response), administered either alone or in combination with other therapies, alleviates disease in at least some patients to which the therapy is administered. For example, treatment of a patient's cancer might reduce or inhibit tumor growth, or might even induce partial or complete tumor regression. Furthermore, the treatment may be prophylactic in that it prevents the development of new tumors in a patient in remission from cancer or in a patient who has metastatic cancer.

By "prophylaxis" against a tumor is meant that protective therapy (such as vaccination with one or more tumor antigens) is administered to a subject adjudged to have a higher than average risk of developing a tumor. Subjects with a relatively high risk of developing a tumor include those having a family history of cancer, those having one or more genetic mutations that are associated with a high risk for cancer (e.g., a mutation that inactivates a tumor suppressor gene), those expressing relatively high levels of tumor antigen or antibodies against tumor antigen, and those who have cancer or are in remission from cancer.

By "sample" is meant a tumor or tissue biopsy, a lymph node, bone marrow, cells, blood, serum, urine, stool, sputum, saliva, or other specimen obtained from a patient. The sample is analyzed in order to determine the level of one or more tumor antigens, or the level of antibodies or cytotoxic T lymphocytes that specifically bind a tumor antigen, by methods that are known in the art. For example, ELISA is used to measure levels of tumor antigen or antibodies against tumor antigen, and the polymerase chain reaction is used to measure levels of tumor antigen nucleic acid.

By "reference sample" is meant a sample in which one or more tumor antigens or antibodies or cytotoxic T lymphocytes that specifically bind a tumor antigen have been measured, and to which levels of tumor antigen or antibodies or cytotoxic T lymphocytes that specifically bind a tumor antigen in a patient sample are compared. Reference levels may be higher, lower, or the same as patient sample levels. Comparison of patient sample levels and reference sample levels allows a diagnosis of cancer and/or a prognosis of a cancer, for patients whose cancer cells express the tumor antigen being measured.

By "high stringency conditions" is meant conditions that allow hybridization comparable with the hybridization that occurs using a DNA probe of at least 500 nucleotides in length, in a buffer containing 0.5 M $NaHPO_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1× Denhardt's solution, 10% dextran sulfate, and 0.1% SDS, at a temperature of 42° C. (these are typical conditions for high stringency Northern or Southern hybridizations). High stringency hybridization is relied upon for the success of numerous techniques routinely performed by molecular biologists, such as high stringency PCR, DNA sequencing, single strand conformational polymorphism analysis, and in situ hybridization. In contrast to Northern and Southern hybridizations, these techniques are usually performed with relatively short probes (e.g., usually 16 nucleotides or longer for PCR or sequencing, and 40 nucleotides or longer for in situ hybridization). The high stringency conditions used in these techniques are well known to those skilled in the art of molecular biology, and may be found, for example, in F. Ausubel et al., *Current Protocols in Molecular Biology*, John Wiley & Sons, New York, N.Y., 1997, hereby incorporated by reference.

By "probe" or "primer" is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules, and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for nucleic acid encoding a tumor antigen preferably have at least 35% sequence identity, more preferably at least 45-55% sequence identity, even more preferably at least 60-75% sequence identity, still more preferably at least 80-90% sequence identity, and most preferably 100% sequence identity. Probes may be detectably-labelled, either radioactively, or non-radioactively, by methods well-known to those skilled in the art. Probes are used for methods involving nucleic acid hybridization, such as: nucleic acid sequencing, nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

By "pharmaceutically acceptable carrier" means a carrier that is physiologically acceptable to the treated mammal while retaining the therapeutic properties of the compound with which it is administered. One exemplary pharmaceutically acceptable carrier is physiological saline. Other physiologically acceptable carriers and their formulations are known to one skilled in the art and described, for example, in *Remington's Pharmaceutical Sciences* (18th edition), ed. A. Gennaro, 1990, Mack Publishing Company, Easton, Pa.

By "substantially identical" is meant a polypeptide or nucleic acid exhibiting at least 80%, preferably at least 85%, more preferably at least 90%, and most preferably at least 95% identity to a reference amino acid or nucleic acid sequence. For polypeptides, the length of comparison sequences is at least 16 amino acids, preferably at least 20 amino acids, more preferably at least 25 amino acids, and most preferably 35 amino acids. For nucleic acids, the length of comparison sequences is at least 50 nucleotides, preferably at least 60 nucleotides, more preferably at least 75 nucleotides, and most preferably at least 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705).

By "substantially pure polypeptide" is meant a polypeptide (or a fragment thereof) that has been separated from the components that naturally accompany it. Typically, the polypeptide is substantially pure when it is at least 60%, by weight, free from the proteins and naturally-occurring organic molecules with which it is naturally associated. Preferably, the polypeptide is a tumor antigen polypeptide that is at least 75%, more preferably at least 90%, and most preferably at least 99%, by weight, pure. A substantially pure tumor antigen polypeptide may be obtained, for example, by extraction from a natural source (e.g., a tumor cell), by expression of a recombinant nucleic acid encoding a tumor antigen polypeptide, or by chemically synthesizing the polypeptide. Purity can be measured by any appropriate method, e.g., by column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides not only includes those derived from eukaryotic organisms but also those synthesized in *E. coli* or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformation" is meant any method for introducing foreign molecules into a cell, e.g., a bacterial, yeast, fungal, algal, plant, insect, or animal cell. Lipofection, DEAE-dextran-mediated transfection, microinjection, protoplast fusion, calcium phosphate precipitation, transduction (e.g., bacteriophage, adenoviral or retroviral delivery), electroporation, and biolistic transformation are just a few of the methods known to those skilled in the art which may be used.

By "transformed cell," "transfected cell," or "transduced cell," means a cell (or a descendent of a cell) into which a DNA molecule encoding a polypeptide of the invention has been introduced, by means of recombinant DNA techniques.

By "promoter" is meant a minimal sequence sufficient to direct transcription. Also included in the invention are those promoter elements which are sufficient to render promoter-dependent gene expression controllable for cell type-specific, tissue-specific, temporal-specific, or inducible by external signals or agents; such elements may be located in the 5' or 3' or intron sequence regions of the native gene.

By "operably linked" is meant that a gene and one or more regulatory sequences are connected in such a way as to permit gene expression when the appropriate molecules (e.g., transcriptional activator proteins) are bound to the regulatory sequences.

By "detectably-labeled" is meant any means for marking and identifying the presence of a molecule, e.g., an oligonucleotide probe or primer, a gene or fragment thereof, a cDNA molecule, or an antibody. Methods for detectably-labeling a molecule are well known in the art and include, without limitation, radioactive labeling (e.g., with an isotope such as $^{32}P$ or $^{35}S$) and nonradioactive labeling (e.g., chemiluminescent labeling, e.g., fluorescein labeling).

By "purified antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody, e.g., an antibody that binds a polypeptide or fragment of a polypeptide disclosed herein. A purified antibody may be obtained, for example, by affinity chromatography using recombinantly-produced protein or conserved motif peptides and standard techniques.

By "specifically binds" is meant an antibody that recognizes and binds a given tumor antigen polypeptide but that does not substantially recognize and bind other molecules in a sample, e.g., a biological sample, that naturally includes protein.

By "antisense nucleic acid" is meant a nucleic acid complementary to (i.e., that base-pairs with) a tumor antigen-encoding nucleic acid of the invention, e.g., a MAIAP nucleic acid. Preferably, the antisense nucleic acid decreases expression (i.e., transcription and/or translation) of the tumor antigen-encoding nucleic acid (e.g., MAIAP) by at least 5%, more preferably by at least 10%, still more preferably by at least 20% to 30%, and most preferably by at least 50% to 70%.

By "MAIAP polypeptide" is meant a polypeptide comprising an amino acid sequence that is substantially identical, as defined above, to the MAIAP polypeptide sequence shown in FIG. 17 and set forth in SEQ ID NO: 12.

By "MAIAP biological activity" is meant the ability of a MAIAP polypeptide to inhibit apoptosis or decrease radiation sensitivity in cells containing the MAIAP polypeptide; relative to cells not containing the MAIAP polypeptide. The level of MAIAP biological activity may be directly measured using any of the many known assays for measuring apoptosis or assessing relative radiation sensitivity. The relative level of MAIAP biological activity may also be assessed by measuring the level of MAIAP mRNA (e.g., by reverse transcription-polymerase chain reaction (RT-PCR) amplification or Northern hybridization), the level of MAIAP protein (e.g., by ELISA or Western hybridization), the activity of a reporter gene under the transcriptional regulation of a MAIAP transcriptional regulatory region (by reporter gene assay, as described below), or the specific interaction of MAIAP with another molecule (e.g., by the two-hybrid assay).

By "apoptosis" is meant a cell death pathway wherein a dying cell displays a set of well-characterized biochemical hallmarks that include cytolemmal membrane blebbing, cell soma shrinkage, chromatin condensation, nuclear disintegration, and DNA laddering. There are many well-known assays for determining the apoptotic state of a cell, including, and not limited to: reduction of MTT tetrazolium dye, TUNEL staining, Annexin V staining, propidium iodide staining, DNA laddering, PARP cleavage, caspase activation, and assessment of cellular and nuclear morphology. Any of these or other known assays may be used in the methods of the invention to determine whether cells are undergoing apoptosis.

By "increased risk for undergoing apoptosis" is meant a population of cells that is exposed to an apoptotic stimulus, e.g., gamma irradiation, a chemotherapeutic agent, a toxin, an injury, an attack by cells of the immune system, hypoxia, or a degenerative disease. Apoptosis is stimulated in such a cell population by at least 5%, preferably by at least 10%, more preferably by at least 25%, still more preferably by at least 50%, and most preferably by at least 75%.

By "stimulating apoptosis" is meant increasing the number of apoptotic cells in a population of cells by at least 5%, preferably by at least 10%, more preferably by at least 25%, still more preferably by at least 50%, and most preferably by at least 75%.

By "inhibiting apoptosis" is meant decreasing the number of apoptotic cells in a population of cells by at least 1% to 5%, preferably by at least 10%, more preferably by at least 25%, still more preferably by at least 50%, and most preferably by at least 75%.

By "test compound" is meant a chemical, be it naturally-occurring or artificially-derived, that is surveyed for its ability, when applied to cells, cell lysates, or fractions thereof, to modulate radiation sensitivity, susceptibility for undergoing apoptosis, or tumor antigen (e.g., MAIAP) biological activity, in one of the assay methods described herein. Test compounds may include, for example, peptides, polypeptides, synthesized organic molecules, naturally occurring organic molecules, and nucleic acid molecules.

By "expose" is meant to allow contact between an animal, cell, lysate or extract derived from a cell, or molecule derived from a cell, and a test compound or apoptotic stimulus (e.g., radiation or a chemotherapeutic agent).

By "assaying" is meant analyzing the effect of a treatment, be it chemical or physical, administered to whole animals, cells, or molecules derived therefrom. The material being analyzed may be an animal, a cell, a lysate or extract derived from a cell, or a molecule derived from a cell. The analysis may be, for example, for the purpose of detecting altered gene expression, altered RNA stability, altered protein stability, altered protein levels, or altered protein biological activity. The means for analyzing may include, for example, antibody labeling, immunoprecipitation, phosphorylation assays, and methods known to those skilled in the art for detecting nucleic acids.

By "sample" is meant an animal, a cell, a lysate or extract derived from a cell, or a molecule derived from a cell or cellular material, which is assayed as described above.

By "modulating" is meant changing, either by decrease or increase.

By "a decrease" is meant a lowering in the level of: a) protein (e.g., as measured by ELISA); b) reporter gene activity (e.g., as measured by reporter gene assay, for example, lacZ/β-galactosidase, green fluorescent protein, or luciferase activity); c) mRNA (e.g., as measured by RT-PCR relative to an internal control, for example, a "housekeeping" gene product such as β-actin or glyceraldehyde 3-phosphate dehydrogenase (GAPDH)); or d) the number of apoptotic cells in a test sample. In all cases, the lowering is preferably by at least 30%, more preferably by at least 40% to 60%, and even more preferably by at least 70%.

By "an increase" is meant a rise in the level of: a) protein (e.g., as measured by ELISA); b) reporter gene activity (e.g., as measured by reporter gene assay, for example, lacZ/β-galactosidase, green fluorescent protein, or luciferase activity); c) mRNA (e.g., as measured by RT-PCR relative to an internal control, for example, a "housekeeping" gene product such as β-actin or glyceraldehyde 3-phosphate dehydrogenase (GAPDH)) or d) the number of apoptotic cells in a test sample. Preferably, the increase is by at least 1.5-fold to 2-fold, more preferably by at least 3-fold, and most preferably by at least 5-fold.

By "alteration in the level of gene expression" is meant a change transcription, translation, or mRNA or protein stability such that the overall amount of a product of the gene, i.e., mRNA or polypeptide, is increased or decreased.

By "reporter gene" is meant any gene that encodes a product whose expression is detectable and/or quantitatable by immunological, chemical, biochemical or biological assays. A reporter gene product may, for example, have one of the following attributes, without restriction: fluorescence (e.g., green fluorescent protein), enzymatic activity (e.g., lacZ/β-galactosidase, luciferase, chloramphenicol acetyltransferase), toxicity (e.g., ricin A), or an ability to be specifically bound by a second molecule (e.g., biotin or a detectably labelled antibody). It is understood that any engineered variants of reporter genes, which are readily available to one skilled in the art, are also included, without restriction, in the foregoing definition.

By "tumor antigen fragment" is meant a protein fragment comprising at least 10 amino acids, preferably at least 15, 20, 25, or 30 amino acids, and most preferably at least 50 amino acids, which correspond to an amino acid sequence of a tumor antigen as defined above.

BRIEF DESCRIPTION OF THE DRAWINGS

FIG. 5 is a diagram of cell cycle analyses showing that transfection of MAIAP into A293 cells increases their resistance to radiation.

FIG. 6 is a diagram showing the full-length sequence of the $TRAAM_{U937}$ cDNA clone (SEQ ID NO: 17).

FIG. 7 is a diagram showing the long open reading frame of the $TRAAM_{U937}$ cDNA clone ($TRAAM_{U937}$-ORF 1; SEQ ID NO: 18), which contains the PSET peptide.

FIG. 8 is a diagram showing the short open reading frame of the $TRAAM_{U937}$ cDNA clone ($TRAAM_{U937}$-ORF$^2$; SEQ ID NO: 19), which contains the TRAM peptide.

FIG. 17 is a set of DNA sequences that encode tumor antigens and tumor antigen polypeptide fragments of the invention, and their encoded polypeptides (SEQ ID NOs: 1-16).

DETAILED DESCRIPTION OF THE INVENTION

Figure 1:
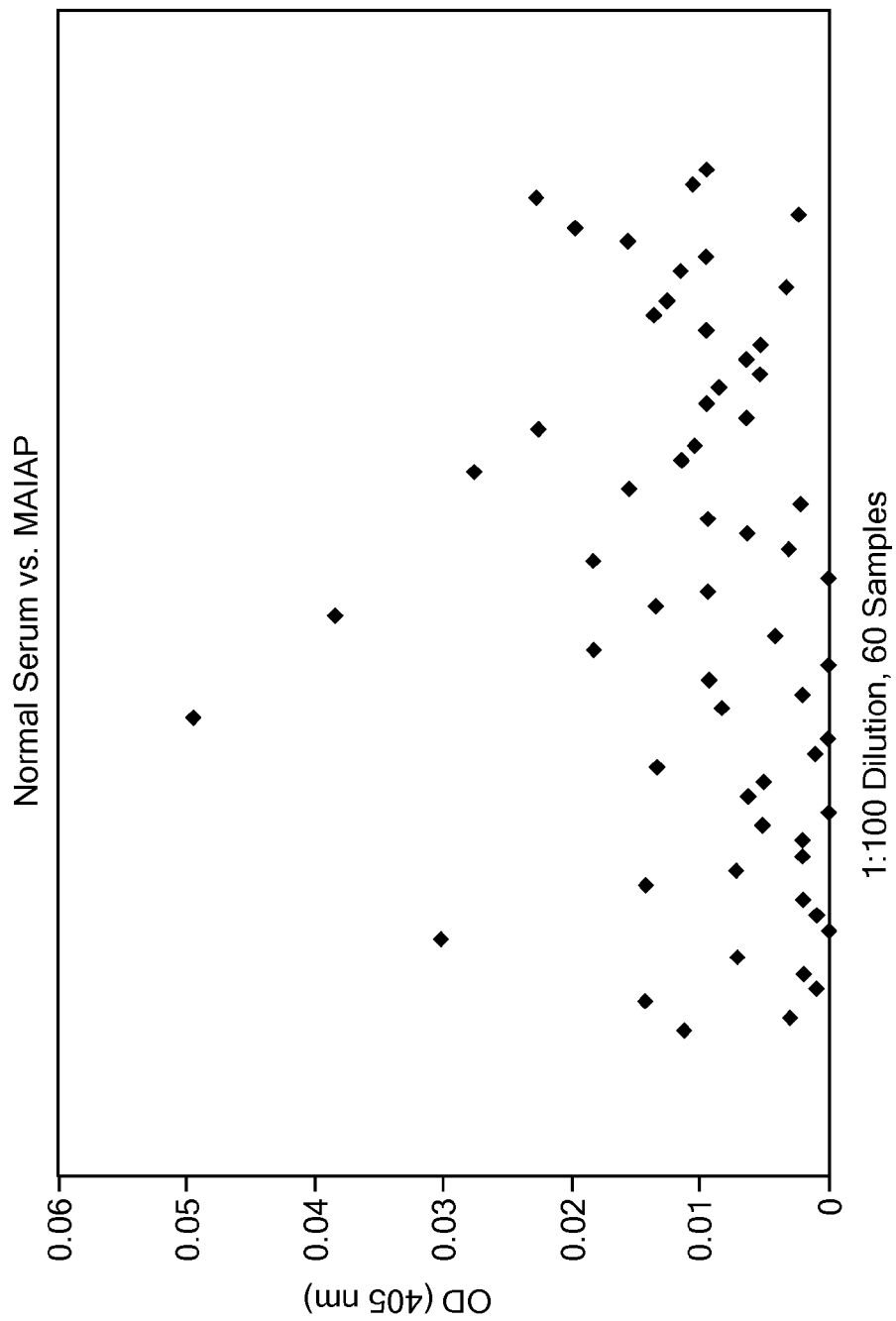
FIG. 1 is a graph showing the relative reactivity of sixty normal serum samples against a MAIAP-GST fusion protein.

The clinical study described herein demonstrates that vaccination with irradiated, autologous melanoma cells engineered to secrete granulocyte-macrophage colony stimulating factor (GM-CSF) consistently augments anti-tumor cellular and humoral immunity in patients with metastatic melanoma. The most convincing evidence that this immunization scheme (previously published in Soiffer et al., *Hum. Gene Ther.*, 8:111-123, 1997) enhances anti-melanoma immunity is the finding that distant metastases were frequently infiltrated by large numbers of T lymphocytes and plasma cells following, but not before, vaccination. Anti-melanoma immune reactions were found in metastases, including bulky lesions, derived from a variety of sites, and were documented pathologically in one patient to be persistent five months after the completion of therapy in all eight sites of metastatic disease. Immunohistochemical analysis demonstrated that both CD4 and CD8 positive T cells were in direct contact with dying melanoma cells. Analysis of the infiltrating T lymphocytes and plasma cells suggested several potential anti-tumor effector mechanisms including lymphocyte-mediated cytotoxicity, cytokine production, and antibody formation. Anti-melanoma immune responses were more intense at dose levels 2 and 3 than at dose level 1 (dose levels are described below), though no clear relationship to the level of GM-CSF secretion could be delineated.

Histopathologic assessment revealed that the coordinated activation of T lymphocytes and plasma cells resulted in destruction of at least 80% of the tumor cells in the infiltrated metastases. In most cases, however, these anti-tumor immune responses failed to induce clinical regressions; rather, the necrotic tumor masses were largely replaced by inflammatory cells, edema, and extensive fibrosis. These findings underscore the limitations of relying exclusively upon traditional measurements of tumor shrinkage in assessing the anti-tumor activity of this vaccination scheme. Additional studies are required to clarify the mechanisms underlying the resistance of the residual tumor cells.

Other strategies to enhance the frequency and intensity of anti-melanoma immune responses are under clinical investigation. These include vaccination with autologous, hapten-modified tumor cells in conjunction with Bacille Calmette Guerin (BCG) and cyclophosphamide (Berd et al., *Cancer Res.*, 51:2731-2734, 1991); immunization with allogeneic melanoma cells in a variety of forms, including intact cells or shed antigens with BCG, viral-modified cell lysates, and cell lysates admixed with complex adjuvants (Oratz et al., *J. Biol. Resp. Modif.*, 8:355-358, 1989; Mitchell et al., *J. Clin, Oncol.*, 8:856-869, 1990; Hersey et al., *Cancer Immunol. Immunother*, 25:257-265, 1987; Morton et al., *Ann. Surg.*, 216:463-482, 1992; Singhuff et al., *J. Surg. Oncol.*, 39:139-147); and vaccination with defined melanoma antigens such as the ganglioside GM2 or peptides derived from the MAGE and melanocyte differentiation protein families (Livingston et al., *J. Clin. Oncol.*, 12: 1036-1044, 1994; Marchand et al., *Int. J. Cancer*, 63:883-885 1995; Jager et al., *Int. J. Cancer*, 67:54-62, 1996). However, the prominent plasma cell infiltration, IgG antibody response, extensive fibrosis, and vasculopathy observed in the work described herein have not been described with hapten-modified tumor cell vaccines. Further investigations are required to characterize these differences more thoroughly and to determine whether the mechanisms underlying the two vaccination strategies involve distinct or overlapping pathways.

Several additional features of the anti-tumor immune responses elicited here underscore distinctive properties of this immunization scheme. First, all patients developed impressive admixtures of dendritic cells, macrophages, eosinophils, and T lymphocytes at vaccination sites. The dramatic influx of dendritic cells and macrophages supports the hypothesis, derived from studies in experimental murine model systems, that GM-CSF functions to improve tumor antigen presentation by increasing the numbers and activities of host-derived antigen-presenting cells (Dranoff et al., *Proc. Natl. Acad. Sci., U.S.A.*, 90:3539-3543, 1993). All patients also developed, as a function of vaccination, intense infiltrates of T lymphocytes and eosinophils in response to injections of irradiated, non-transfected melanoma cells. While the antigens stimulating these delayed-type hypersensitivity reactions remain to be determined (and in particular to delineate whether they represent previously reported or novel melanoma targets and/or components of the culture media), the prominent eosinophil component distinguishes these infiltrates from the classical tuberculin-type reactions generated by other vaccination schemes (Barth et al., *Cancer. Res.*, 54:3342-3345, 1994). This histopathology, moreover, bears a remarkable resemblance to that observed in allergic disease and parasitic infection, suggesting intriguing connections among these forms of immunity (Hus et al., *J. Allergy Clin. Immunol.*, 54:339-349, 1974).

Histopathologic examination of metastases resected following vaccination delineated the context in which eosinophils mediate anti-tumor activity. Degranulating eosinophils (along with neutrophils and lymphocytes) were found in association with damaged endothelium within the tumor vasculature; this vasculopathy resulted in significant zonal necrosis within the tumor mass.

Further clinical development of this cancer immunization strategy will require simpler methods of vaccine production that are more amenable to widespread application. For example, adenoviral vectors may be used to transfer genes to freshly dissociated, non-replicating tumor cells from patients who have, e.g., metastatic melanoma or non-small cell lung carcinoma.

Tumor Antigens

In order to identify individual tumor antigens involved in inducing anti-melanoma immunity, we established a melanoma cell line from a post-vaccination metastatic tumor that demonstrated striking T cell and plasma cell infiltration upon removal, and constructed a cDNA expression library from mRNA isolated from the melanoma cell line. The library was screened with post-vaccination serum, and the following clones were isolated: MAIAP (SEQ ID NOs: 11 and 12); TRAAM (SEQ ID NOs: 1-4; also SEQ ID NOs: 17-19); KIAA0603 (SEQ ID NOs: 45 and 46); TPR/UBP-3 (SEQ ID NO: 7); BRAP-2/H$^+$-ATPase (SEQ ID NO: 8); KOO8-1 (SEQ ID NOs: 9 and 10); NOR-90 (SEQ ID NO: 13); BR-1 (SEQ ID NO: 14); BR-2 (SEQ ID NO: 15); and Gene AS (SEQ ID NO: 16).

1. MAIAP

MAIAP (melanoma-associated inhibitor of apoptosis protein; SEQ ID NOs: 11 and 12), which we originally designated "IAP-M," is a novel member of the "inhibitor of apoptosis" protein family. There is a single EST match in the database (AA379765; SEQ ID NO: 49; from a human skin tumor).

Northern analysis demonstrated highest expression in spinal cord, with lower expression in testis, placenta, and lymph node. We observed transcripts of various sizes, including a major species of approximately 1.5 kilobases (kb) and minor species of about 4.0, 2.0, and 0.8 kb. MAIAP expression in a melanoma cell line derived from the patient whose sera was used to clone MAIAP was approximately 30- to 50-fold higher than in spinal cord. We have also observed expression in a second melanoma cell line (derived from a different patient in our clinical trial), two lung cancer cell line (A549 and H125), and a transformed kidney cell line (A293).

Figure 2:
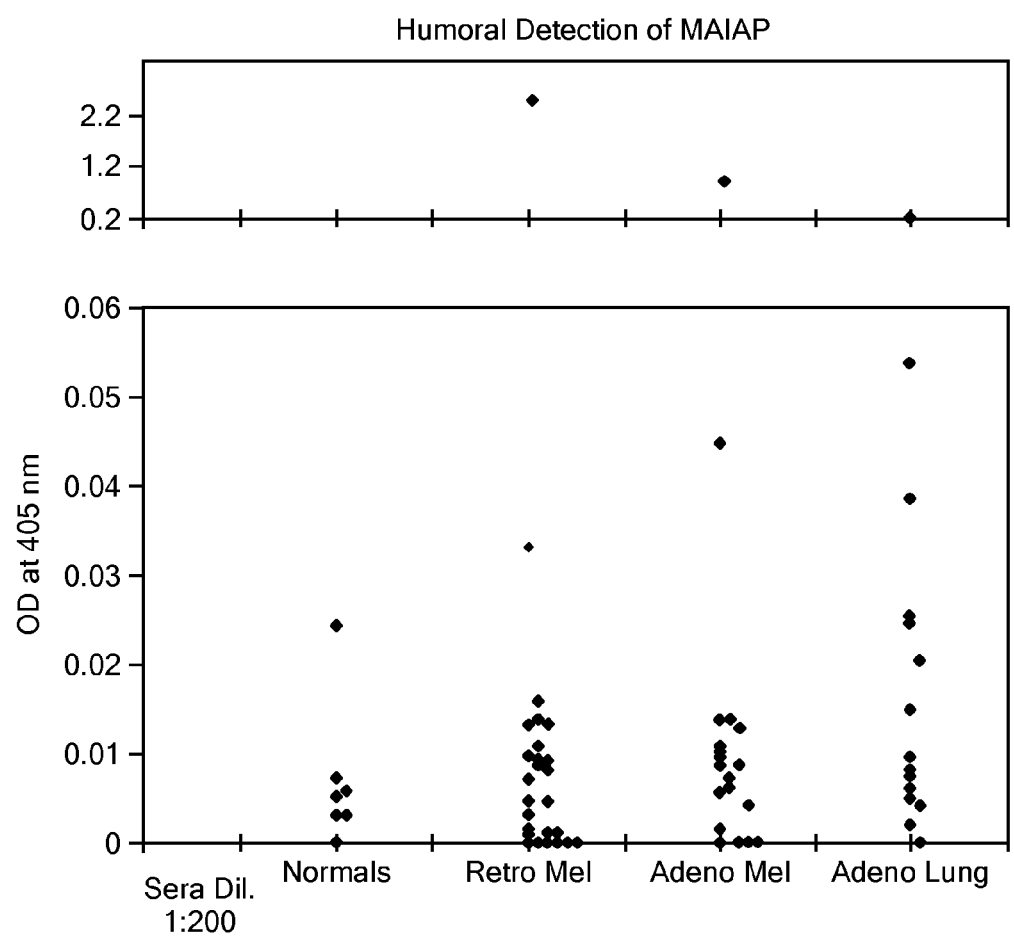
FIG. 2 is a graph showing that sera from 4 out of 48 vaccinated melanoma patients and 5 out of 15 vaccinated lung cancer patients show relatively high reactivity against MAIAP.
Figure 3:
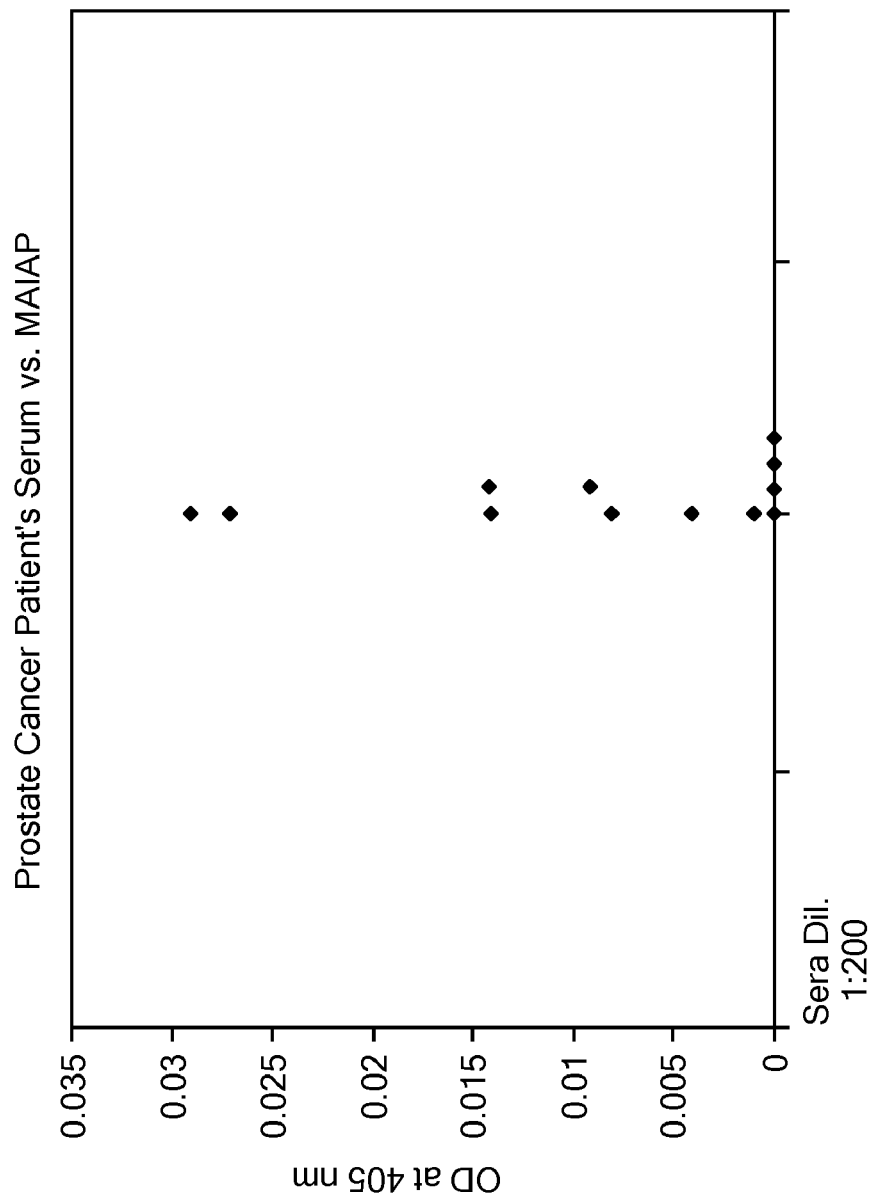
FIG. 3 is a graph showing that sera from 0 out of 15 prostate cancer patients show higher than average reactivity against MAIAP.

We have produced recombinant MAIAP in bacteria as a GST fusion protein. This protein product is recognized by Western analysis using patient sera. We have set up an ELISA assay to test reactivity of patient sera against MAIAP. Sixty normal blood bank donors (30 male and 30 female) showed minimal levels (FIG. 1) of IgG MAIAP-specific antibodies at either 1:100 or 1:200 sera dilutions. In contrast, when tested at sera dilutions of 1:200, 4 out of 48 melanoma patients (treated on one of two GM-CSF-secreting, autologous melanoma cell protocols; either a retroviral vector encoding GM-CSF or an adenoviral vector encoding GM-CSF were used to genetically modify the tumor cells in the respective trials) demonstrated significant reactivity against MAIAP (FIG. 2; "Retro Mel" and "Adeno Mel" respectively). Moreover, the sera of 5 out of 15 lung cancer patients (treated with a GM-CSF-secreting autologous tumor cell vaccine in a vaccine trial for lung cancer) demonstrated reactivity against MAIAP (FIG. 2; "Adeno Lung"). By contrast, 0 out of 15 prostate cancer patients tested to date showed reactivity against MAIAP (FIG. 3; compare with normal serum samples in FIG. 1).

Figure 4:
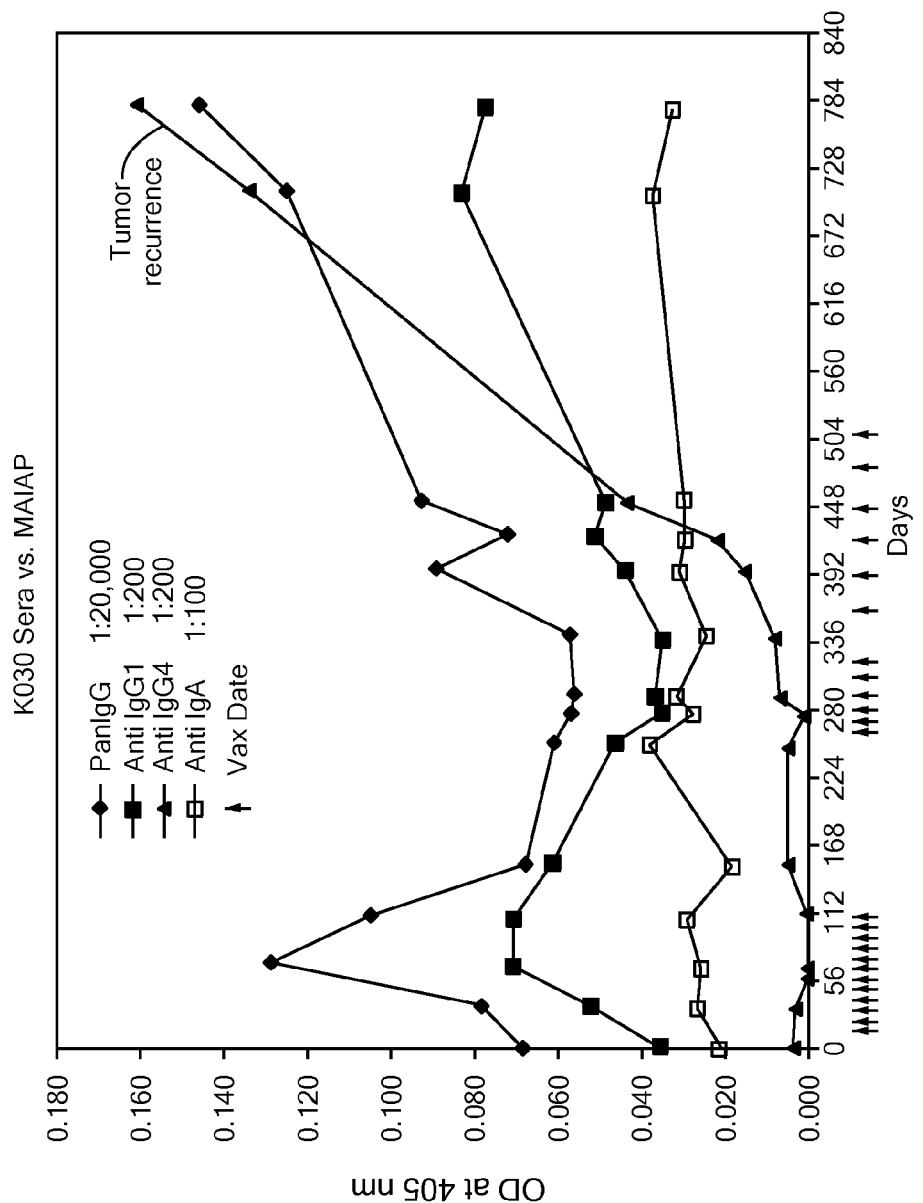
FIG. 4 is a graph showing a time course of the relative levels of anti-MAIAP antibodies in the serum of a melanoma patient (K030) before, during, and after vaccination with GM-CSF-secreting autologous tumor cells.

A detailed analysis of reactivity against MAIAP has been conducted in patient K030, who participated in the trial testing the efficacy of vaccination with autologous tumor cells expressing retrovirally-encoded GM-CSF. This patient demonstrated very high reactivity against MAIAP at the time of entering the study (i.e., prior to receiving the vaccination). Nonetheless, vaccination induced an increase in anti-MAIAP antibody titers (FIG. 4; the abscissa refers to the number of days after entering the study, and the arrows on the abscissa represent the dates on which the patient was vaccinated). The vaccination induced the development of IgG4 antibodies against MAIAP, which were not present upon the patient's entry into the study. In contrast to reactivity against MAIAP, reactivity against control antigens (from candida yeast and mumps virus) was not affected by vaccination. Significantly, the increased anti-MAIAP antibody titers were temporally associated with tumor destruction in this patient.

We identified two peptides derived from MAIAP which bind to HLA-A2 class I molecules. These are: JS34 (SLG-SPVLGL; SEQ ID NO: 22) AND JS90 (RLASFYDWPL; SEQ ID NO: 23). They were identified using the peptide motif scoring system "HLA Peptide Binding Predictions" (K. C. Parker et al., *J. Immunol.*, 152:163, 1994), which is available through the World Wide Web at: http://bimas.dcrt.nih.gov:80/cgi-bin/molbio/ken_parker_comboform. One of skill in the art will recognize that other MAIAP peptides that bind HLA molecules may be identified using analogous programs. We have produced HLA-A2 soluble tetramers folded with these peptides, and will use them to assess the presence of anti-MAIAP cytotoxic T lymphocytes in the blood of HLA-2-positive patients that show antibody reactivity to MAIAP.

We have constructed a high-titer retroviral vector encoding MAIAP. This vector was used to transfect A293 cells in order to generate a partner cell line expressing high levels of MAIAP. Preliminary studies have shown that MAIAP-transfected cells demonstrate superior resistance to radiation, compared to untransfected A293 cells. Briefly, we irradiated untransfected and MAIAP-transfected A293 cells with 15,000 rads, harvested cells 1 hour, 24 hours, and 48 hours after irradiation, stained the harvested cells with propidium iodide, and subjected them to cell cycle analysis using a fluorescence-activated cell sorter (FACS). The cell cycle profiles shown in FIG. 5 indicate a markedly increased proportion of transfected cells accumulating in the G2/M phase, compared to untransfected cells. Accumulation in the G2/M phase allows for repair of radiation-induced DNA damage. This finding suggests that high-level expression of MAIAP is associated with the development of radiation-resistant cancer cells and that MAIAP increases cellular resistance to apoptotic stimuli. Therefore, methods for targeting cells that overexpress MAIAP, as well as methods for inhibiting MAIAP expression or MAIAP biological activity, may prove to be valuable anti-cancer strategies. Various anti-MAIAP strategies could be combined for maximum efficacy. For example, a drug that inhibits MAIAP activity, such as a MAIAP antisense nucleic acid, dominant-negative protein, or small-molecule inhibitor, could be used in combination with a vaccine containing tumor cells that naturally overexpress or are genetically engineered to overexpress MAIAP. Such combination therapies might be more effective than either therapy alone.

MAIAP Therapy for Inhibition of Apoptosis

Because MAIAP, a member of the IAP (inhibitor of apoptosis) family, is highly expressed in the spinal cord, it is possible that altered expression of MAIAP or mutations in the MAIAP gene may be associated with diseases that affect the spinal cord. For example, NAIP, another member of the IAP family that is highly expressed in the nervous system, has been shown to be mutated in spinal muscular atrophy, a neurodegenerative disease.

Given the relationship of MAIAP to other IAPs, it is likely that therapies for increasing the intracellular level of MAIAP in cells that are at increased risk for undergoing apoptosis will prove useful for treating diseases or conditions that involve higher-than-normal levels of cell death. Examples of cells and diseases, conditions, or situations in which it would be desirable to inhibit apoptosis include, but are not limited to: neurons (e.g., in degenerative and autoimmune diseases of the central or peripheral nervous system, such as stroke, Alzheimer's disease, Parkinson's disease, multiple sclerosis, and amyotrophic lateral sclerosis) cardiomyocytes (e.g., in heart disease or post-myocardial infarction), skeletal myocytes (e.g., in muscular degenerative disease, such as Duchenne's muscular dystrophy), kidney and liver cells (e.g., in early stages of progressive organ failure from disease or exposure to toxins), hair follicle cells (e.g., in hair loss), ovarian follicle cells, ova, sperm cells (e.g., in infertility), pancreatic islet cells, e.g., beta cells (e.g., in autoimmune diabetes) or retinal photoreceptor cells (e.g., in retinal degenerative conditions such as those resulting from retinitis pigmentosa, chemical toxicity, retinal detachment, glaucoma, diabetes, and axotomy).

Expression vectors encoding MAIAP may also be introduced into cells ex vivo in order to enhance the survival of cell or organ transplants. For example, the vectors may be introduced into pancreatic beta cells prior to transplantation into diabetic patients or into dopaminergic neurons prior to transplantation into Parkinson's patients. Transplanted cells containing MAIAP expression vectors are more likely to survive in the patient after transplantation than cells not containing such vectors.

MAIAP Antisense Therapy

We have shown that MAIAP, a member of the IAP family, increases cellular resistance to radiation exposure. Accordingly, decreasing the intracellular level of MAIAP polypeptide by antisense therapy should be a useful therapeutic approach for sensitizing tumor cells to apoptotic stimuli, such as gamma-radiation therapy and chemotherapeutic agents.

Antisense therapy is based on the well-known principle of suppressing gene expression by intracellular hybridization of endogenous nucleic acid (genomic DNA or mRNA) molecules encoding a protein of interest with a complementary antisense nucleic acid, such as an antisense oligonucleotide or antisense RNA. Antisense nucleic acids may inhibit protein expression at the transcriptional level, at the translational level, or at both levels. Antisense oligonucleotides or antisense RNA, generated by well-known methods, may be administered to patients by conventional drug delivery techniques. The antisense nucleic acids enter the appropriate cell type and hybridize with the endogenous target nucleic acid to inhibit transcription or translation of the target protein. Antisense mRNA may also be provided intracellularly to a patient by administration of a gene therapy vector encoding an antisense RNA of interest. Expression of the antisense RNA may limited to a particular cell type, for example, by placing a DNA molecule encoding the antisense RNA under the transcriptional regulation of a tissue-specific promoter. Inhibition of MAIAP transcription or translation using MAIAP antisense RNA decreases a cell's resistance to various apoptotic stimuli, e.g., exposure to radiation or toxins such as cancer chemotherapeutic agents.

Numerous examples of therapeutic benefit derived from antisense therapy are known in the art. Just a few representative examples are described in: Gokhale et al., *Gene Ther.* 4:1289-1299, 1997; Martens et al., *Proc. Natl. Acad. Sci. USA* 95:2664-2669, 1998; Offensperger et al., *Mol. Biotechnol.* 9:161-170, 1998; Kondo et al., *Oncogene* 16:3323-3330, 1998; and Higgens et al., *Proc. Natl. Acad. Sci. USA* 90:9901-9905, 1993.

MAIAP antisense nucleic acids contain at least 10 consecutive nucleotides that are complementary to (i.e., base-pair with) a MAIAP mRNA or DNA sequence, and preferably contain 14-18 consecutive nucleotides that are complementary to a MAIAP mRNA or DNA. MAIAP antisense nucleic acids may contain 25, 40, 60, 85, 120, or more consecutive nucleotides that are complementary to a mRNA or DNA, and may be as long as a full-length MAIAP gene or mRNA.

Any region of the human coding or non-coding MAIAP sequence may be used as a target for antisense inhibition of transcription or translation, and particular sequences for antisense nucleic acids may be selected by well-known approaches. For example, if desired, computer algorithms may be used to identify sequences that form the most stable hybridization duplexes. Computer algorithms may also be used to identify regions of the that are relatively accessible within a folded mRNA molecule; antisense nucleic acids against such regions are more likely to effectively inhibit translation of mRNA. Computer algorithms that may be used to identify optimal sequences for generating antisense nucleic acids include, but are not limited to, OLIGO 5.0 from National Biosciences Inc. (http://www.sxst.it/nbi_olg.htm) and MFOLD (http://mfold2.wust1.edu/~mfold/rna/form1.cgi). References describing algorithms for predicting secondary structure are described in M. Zuker et al. "Algorithms and Thermodynamics for RNA Secondary Structure Prediction: A Practical Guide." in: *RNA Biochemistry and Biotechnology*, J. Barciszewski & B.F.C. Clark, eds., NATO ASI Series, Kluwer Academic Publishers (1999) and in Mathews et al. *J. Mol. Biol.* 288:911-940 (1999).

Test Compounds

In general, novel drugs for modulation of MAIAP expression or activity (or mimicry of MAIAP activity) may be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their cell death-modulatory or radiation sensitivity-modulatory activities should be employed whenever possible.

When a crude extract is found to modulate (i.e., stimulate or inhibit) or mimic MAIAP expression or activity, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits MAIAP expression or activity (or mimics the same). The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art.

Compounds identified as being of therapeutic value may be subsequently analyzed using animal models for diseases in which it is desirable to increase MAIAP expression or activity, or to mimic MAIAP activity (for example, to increase levels in cells that are susceptible to apoptosis, such as cardiomyocytes in an animal prone to myocardial infarctions), or to decrease or MAIAP expression or activity (for example, in cancer cells in an animal tumor model, thereby rendering the tumor cells more susceptible to apoptosis).

Below are examples of high-throughput systems useful for evaluating the efficacy of a molecule or compound for increasing or decreasing MAIAP expression or activity, or for mimicking its activity.

Assays for Identifying Compounds that Modulate Apoptotic Cell Death

We have shown that MAIAP, a member of the IAP (inhibitor of apoptosis) family, increases cellular resistance to radiation exposure. Since radiation induces apoptosis in normal cells, measurements of MAIAP levels may be used to determine the apoptotic status of cells in a sample. Such measurements may be employed in high-throughput screens for the identification of novel therapeutic compounds that modulate (i.e., stimulate or inhibit) apoptotic death of cells capable of expressing MAIAP.

For example, to identify a novel compound that stimulates apoptosis in tumor cells that overexpress MAIAP, cells that overexpress MAIAP (e.g., tumor cells or cells that are genetically engineered to overexpress MAIAP) may be treated with various test compounds, after which MAIAP mRNA or protein levels may be measured using well-known approaches, such as (but not limited to) RT-PCR (for mRNA) or ELISA (for protein). A decrease in MAIAP expression indicates a pro-apoptotic compound that may then be further tested using appropriate cell culture and animal models for its usefulness as an anti-cancer agent.

Conversely, to identify a novel compound that inhibits apoptosis, cultured cells that are known to undergo apoptosis when exposed to an appropriate pro-apoptotic stimulus are exposed to test compounds either before, after, or concurrent with exposure to the apoptotic stimulus. An increase in MAIAP mRNA or protein levels relative to a control apoptotic sample not treated with the compound indicates an anti-apoptotic compound that may then be further tested for its usefulness in treating diseases or conditions that involve excessive, pathological apoptosis, e.g. (but not limited to), neurodegenerative diseases, retinal degenerative diseases, cardiac degenerative diseases, and transplant rejection.

Various cell culture models of apoptosis are known in the art; any of these may be used to identify anti-apoptotic compounds with potential therapeutic utility. For example, cultured neurons and cardiomyocytes undergo apoptosis when subjected to hypoxic conditions, neurons undergo apoptosis when exposed to high concentrations of glutamine, NMDA, or other neuroexcitatory compounds, and cultured fibroblasts and many other types of cultured cells undergo apoptosis after serum or growth factor withdrawal, staurosporine exposure, DNA damage, or exposure to reactive oxygen species. One of ordinary skill in the art may readily determine which of the known cell culture models would be appropriate for the high-throughput screens of the invention.

In addition, apoptosis may be inhibited by expressing vector-encoded MAIAP within the experimental cells. MAIAP expression may be placed under one of the many known regulatable promoters, such as a promoter that becomes transcriptional active in the presence of a hormone (e.g., a steroid hormone such as estrogen), an antibiotic (such as tetracycline), metal ions (e.g., zinc), heat shock, or hypoxic conditions. An inducible promoter allows the generation of stable cell lines that become more resistant to apoptosis when MAIAP is inducibly expressed. Such cells may be used in high-throughput screens for identification of compounds that decrease MAIAP-mediated resistance to cell death, which may be monitored by any of the many apoptosis detection assays known in the art or disclosed herein.

ELISA for the Detection of Compounds that Modulate Apoptotic Cell Death

Enzyme-linked immunosorbant assays (ELISAs) are easily incorporated into high-throughput screens designed to test-large numbers of compounds for their ability to modulate levels of a given protein. When used in the methods of the invention, changes in the level of MAIAP protein in a sample, relative to a control, reflect changes in the apoptotic status of the cells within the sample. Protocols for ELISA may be found, for example, in Ausubel et al., *Current Protocols in Molecular Biology*, John Wiley & Sons, New York, N.Y., 1998. Lysates from cells treated with test compounds are prepared (see, for example, Ausubel et al., supra), and are loaded onto the wells of microtiter plates coated with "capture" antibodies against MAIAP. Unbound antigen is washed out, and a MAIAP-specific antibody, coupled to an agent to allow for detection, is added. Agents allowing detection include alkaline phosphatase (which can be detected following addition of colorimetric substrates such as p-nitrophenolphosphate), horseradish peroxidase (which can be detected by chemiluminescent substrates such as ECL, commercially available from Amersham) or fluorescent compounds, such as FITC (which can be detected by fluorescence polarization or time-resolved fluorescence). The amount of antibody binding, and hence the level of MAIAP protein within a lysate sample, is easily quantitated on a microtiter plate reader. An increase the level of MAIAP in a treated sample, relative to the level of MAIAP in an untreated sample, indicates a compound that stimulates apoptosis. Conversely, a decrease in the level of MAIAP in a treated sample, relative to the level of MAIAP in an untreated sample, indicates a compound that inhibits apoptosis.

Any person having ordinary skill in the art will understand that the appropriate controls should be included in each assay. The skilled artisan will know which controls to include, depending upon whether a pro-apoptotic compound or an anti-apoptotic compound is being sought, and depending upon the particular cell culture model being used for the assay.

Quantitative PCR of MAIAP mRNA as an Assay for Compounds that Modulate Apoptotic Cell Death The polymerase chain reaction (PCR), when coupled to a preceding reverse transcription step (RT-PCR), is a commonly used method for detecting vanishingly small quantities of a target mRNA. When performed within the linear range, with an appropriate internal control target (employing, for example, a housekeeping gene such as β-actin or GAPDH), such quantitative PCR provides an extremely precise and sensitive means of detecting slight modulations in mRNA levels. Moreover, this assay is easily performed in a 96-well format, and hence is easily incorporated into a high-throughput screening assay. The appropriate cells (depending upon whether the screen is for pro-apoptotic compounds or anti-apoptotic compounds) are cultured, treated with test compounds, and (if screening for anti-apoptotic compounds) exposed to an appropriate apoptotic stimulus. The cells are then lysed, the mRNA is reverse-transcribed, and the PCR is performed according to commonly used methods (such as those described in Ausubel et al., *Current Protocols in Molecular Biology*, John Wiley & Sons, New York, N.Y., 1998), using oligonucleotide primers that specifically hybridize with MAIAP mRNA. Changes in the levels of MAIAP RT-PCR product from samples exposed to test compounds, relative to control samples, indicate test compounds with apoptosis-modulating activity, i.e., an increase in the level of MAIAP RT-PCR product indicates a compound that inhibits apoptosis, and, conversely, a decrease in the level of MAIAP RT-PCR product indicates a compound that stimulates apoptosis.

Primer sequences for MAIAP-specific RT-PCR amplification may be selected using any one of the many known primer selection programs, e.g., Primer3 (http://www-genome.wi.mit.edu/cgi-bin/primer/primer3_www.cgi), or by other commonly-known approaches for selecting PCR primers.

Reporter Gene Assays for Compounds that Modulate Apoptotic Cell Death

Assays employing the detection of reporter gene products are extremely sensitive and readily amenable to automation, hence making them ideal for the design of high-throughput screens. Assays for reporter genes may employ, for example, colorimetric, chemiluminescent, or fluorometric detection of reporter gene products. Many varieties of plasmid and viral vectors containing reporter gene cassettes are easily obtained. Such vectors contain cassettes encoding reporter genes such as lacZ/β-galactosidase, green fluorescent protein, and luciferase, among others. A genomic DNA fragment carrying a MAIAP-specific transcriptional control region (e.g., a promoter and/or enhancer) is first cloned using standard approaches (such as those described by Ausubel et al., supra). The DNA carrying the MAIAP transcriptional control region is then inserted, by DNA subcloning, into a reporter vector, thereby placing a vector-encoded reporter gene under the control of the MAIAP transcriptional control region. The activity of the MAIAP transcriptional control region operably linked to the reporter gene can then be directly observed and quantitated as a function of reporter gene activity in a reporter gene assay.

In one embodiment, for example, the MAIAP transcriptional control region could be cloned upstream from a luciferase reporter gene within a reporter vector. This could be introduced into the test cells, along with an internal control reporter vector (e.g., a lacZ gene under the transcriptional regulation of the β-actin promoter). After the cells are exposed to the test compounds and apoptotic stimulus (if testing for anti-apoptotic compounds), reporter gene activity is measured and MAIAP reporter gene activity is normalized to internal control reporter gene activity. An increase in MAIAP reporter gene activity indicates a compound that inhibits apoptosis and a decrease in MAIAP reporter gene activity indicates a compound that stimulates apoptosis.

Interaction Trap Assays

Two-hybrid methods, and modifications thereof, may be used to identify novel proteins that interact with MAIAP, and hence may be, e.g., naturally occurring regulators of MAIAP or downstream targets of MAIAP. Such assays also may be used to screen for compounds that modulate the physical interactions of MAIAP with itself or with other proteins. Regulators of MAIAP, e.g. proteins that interfere with or enhance the interaction between MAIAP and other proteins may identified by the use of a three-hybrid system. Such assays are well-known to skilled artisans, and may be found, for example, in Ausubel et al., supra.

It will be readily apparent to those of ordinary skill in the art that the above-described assays may be modified for the purpose of identifying compounds that modulate the levels and/or biological activity of any of the tumor antigens disclosed herein.

TRAAM

We initially sequenced the 5' and 3' ends of a novel gene that we denoted "TRAAM"; see FIG. 17 for the 5' and 3' sequences and their encoded polypeptides; SEQ ID NOs: 1-4). The TRAAM clone encodes a novel protein that is structurally related to (yet distinct from) MUC-1, a glycoprotein that is aberrantly glycosylated in tumor cells of epithelial origin and is known to function as a tumor antigen. Our sequence suggested that the putative TRAAM polypeptide contains one partial and six full tandem repeats of twenty amino acids each. The nucleotide sequence matched expressed sequence tags (ESTs) in dbEST (AA865212 (SEQ ID NO: 36); AA641426 (SEQ ID NO: 37); AA399477 (SEQ ID NO: 38); AA486992 (SEQ ID NO: 39); AA076652 (SEQ ID NO: 40); AA293408 (SEQ ID NO: 41); Z25115 (SEQ ID NO: 42); AA079560 (SEQ ID NO: 43); AA534510 (SEQ ID NO: 44)), which were identified in various normal and tumor samples. Our Northern analyses demonstrated expression of this gene in all normal tissues studied. Preliminary analysis suggests that vaccination with GM-CSF-secreting tumor cells stimulates reactivity to this antigen: post-vaccination serum from two melanoma patients contained antibodies that specifically bound TRAAM.

Our initial TRAAM clone (TRAAM$_{KO08}$) was isolated from a phage expression library prepared from KO08 melanoma cells; this cell line was derived from a patient sample. To complete the TRAAM nucleotide sequence, we used a probe derived from TRAAM$_{KO08}$ to obtain a TRAAM clone (TRAAM$_{U987}$) from a cDNA library prepared from the U937 macrophage cell line. While we were completing the TRAAM$_{U987}$ sequence, it became apparent that the open reading frame (ORF) suggested by our TRAAM$_{KO08}$ 5' and 3' sequences did not fully line up with the longest ORF that we inferred from the full-length TRAAM$_{U987}$ sequence. This suggested the possibility that two distinct proteins might be encoded by the TRAAM gene. In fact, our translation (SEQ ID NO: 2; FIG. 17) of the TRAAM$_{K008}$ 5' sequence (SEQ ID NO: 1; FIG. 17) is similar to the translation of the longer TRAAM$_{U987}$ ORF (TRAAM$_{U987}$-ORF1; SEQ ID NO: 18; FIG. 7) and our translation (SEQ ID NO: 4; FIG. 17) of the TRAAM$_{K008}$ 3' sequence (SEQ ID NO: 3; FIG. 17) is similar to the translation of the shorter TRAAM$_{U987}$ ORF (TRAAM$_{U987}$-ORF2; SEQ ID NO: 19; FIG. 8). The translation of TRAAM$_{U987}$-ORF1 begins on nucleotide 1 of SEQ ID NO: 17 (FIG. 6), and the translation of TRAAM$_{U987}$-ORF2 begins on nucleotide 1208 of SEQ ID NO: 17 (FIG. 6).

To test the hypothesis that TRAAM$_{U987}$ encodes two polypeptides, we generated two peptides that correspond to tandem repeat regions within TRAAM$_{U987}$-ORF1 and TRAAM$_{U987}$-ORF2. The first peptide, which was derived from the TRAAM$_{U987}$-ORF1 amino acid sequence (SEQ ID NO: 18; FIG. 7) has the amino acid sequence SPSETPG-PRPAGPAGDEPAESPSETPGPRPAG-PAGDEPAKTPSETPGPS (SEQ ID NO: 20); we call this peptide "PSET". The second peptide, which was derived from the TRAAM$_{987}$-ORF$^2$ amino acid sequence (SEQ ID NO: 19; FIG. 8) has the amino acid sequence AHRRPQA-PAQQDLQGTSQPRAHRRPQA-PAQQDLQGTSQPRAHRRPQAPAQ (SEQ ID NO: 21); we call this peptide "TRAM."

Figure 9:
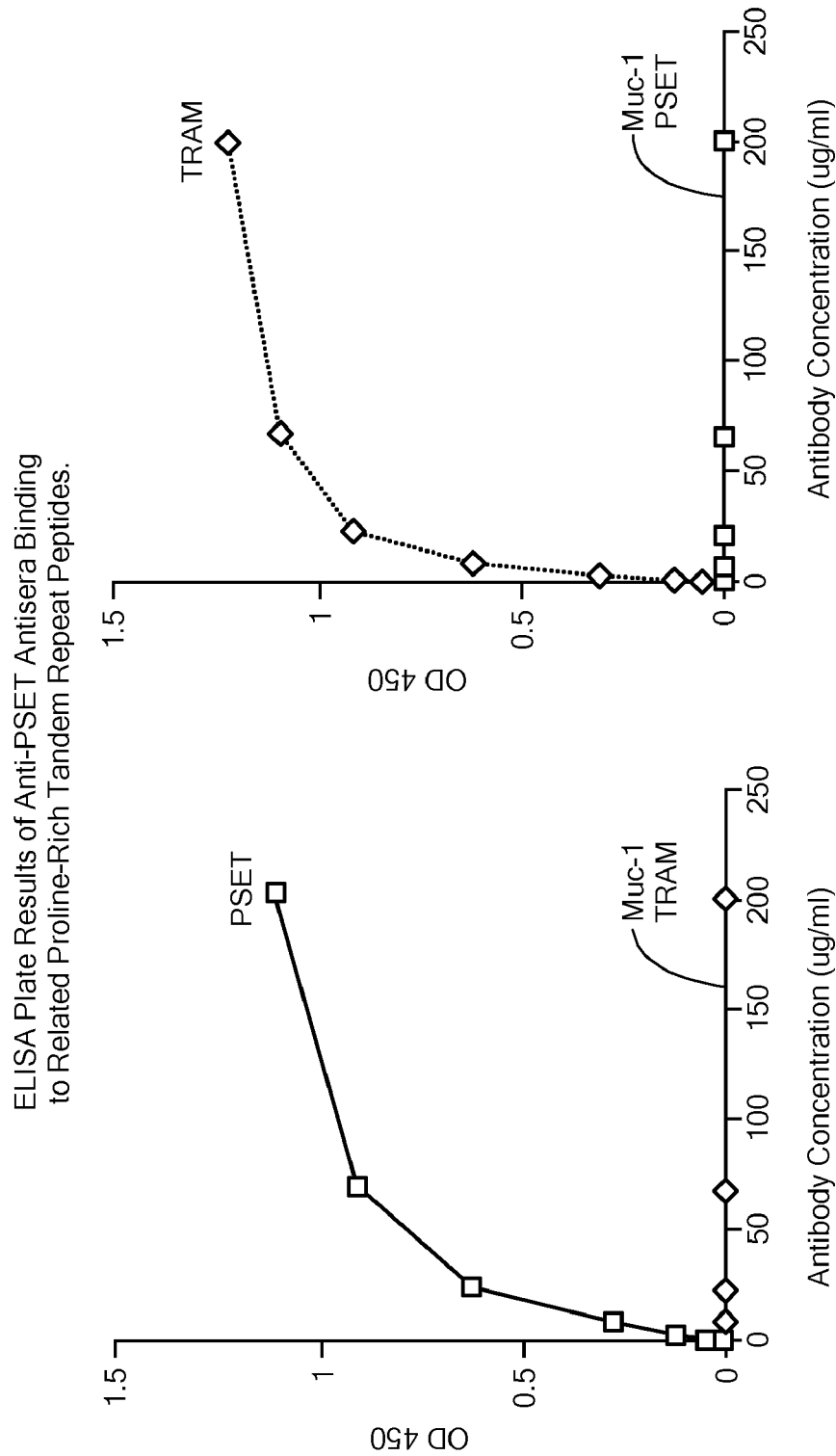
FIG. 9 is a series of graphs showing the results of ELISA assays using anti-PSET antiserum or anti-TRAM antiserum and PSET, TRAM, and MUC-1 peptides as antigen.
Figure 10:
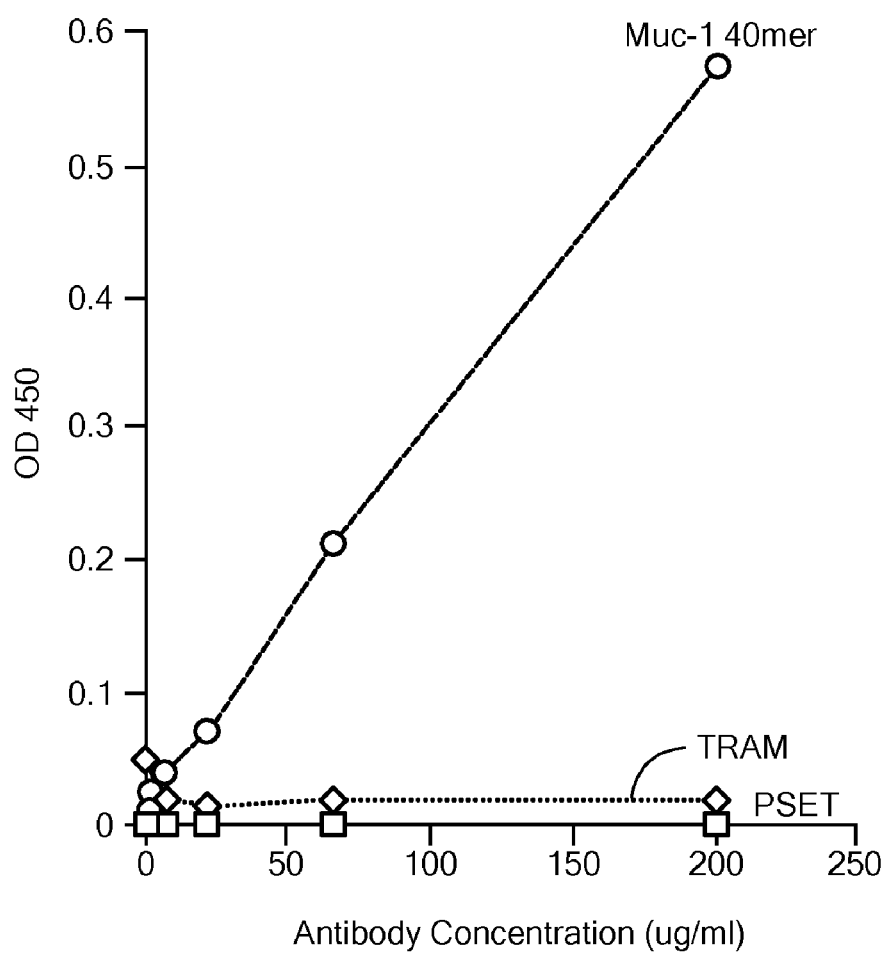
FIG. 10 is a graph showing the results of ELISA assays using anti-MUC-1 antiserum and PSET, TRAM, and MUC-1 peptides as antigen.

Rabbits were immunized with the two peptides and high-titer polyclonal antisera were obtained. The peptides and antibodies were used to set up ELISA assays. FIG. 9 shows the results of ELISA assays with anti-PSET or anti-TRAM antibodies and peptides encompassing the tandem repeats of PSET, TRAM, and MUC-1. The left panel of FIG. 9 shows that the antibodies generated against the PSET-derived peptide do not cross-react with the TRAM-derived peptide or the MUC-1-derived peptide. Likewise, the right panel of FIG. 9 shows that the antibodies generated against the TRAM-derived peptide do not cross-react with the PSET-derived peptide or the MUC-1-derived peptide. FIG. 10 is a diagram of a control ELISA showing that anti-MUC-1 antiserum does not detect PSET or TRAM.

The full-length TRAAM$_{U987}$ cDNA was cloned into a vector such that the encoded PSET and TRAM proteins each carry a histidine tag; the cDNA was then expressed in bacteria. Bacterial lysates contained a protein that was recognized only by the PSET-specific sera and a second protein that was recognized only by the TRAM-specific sera. This shows that two distinct protein products, PSET and TRAM, are translated from TRAAM$_{U987}$ in bacteria.

Western analyses using lysates prepared from KOO8 melanoma cells and U937 macrophages showed that anti-TRAAM antisera (from rabbits immunized with the TRAM peptide) recognized proteins that were distinct from proteins recognized by anti-PSET antisera (from rabbits immunized with the PSET peptide). Our results indicate that the TRAAM gene encodes at least two polypeptides, PSET and TRAM. We are in the process of generating a retroviral vector encoding full-length TRAAM$_{U987}$ to provide additional confirmation that the two translation products are expressed in eukaryotic cells. It is possible that there are differences between cancer and normal cells in this dual expression; such differences may prove to be valuable for diagnostic assays and therapeutic strategies. We are in the process of determining, by ELISA, whether either of these two proteins are recognized by patient sera.

In comparing our translation of our TRAAM$_{K008}$ 3' sequence with TRAAM$_{U987}$-ORF-2 (which contains the TRAM peptide), we observed that while TRAAM$_{K008}$ contained one partial and six full repeats of the twenty amino acid repeat sequence, TRAAM$_{U987}$ contained one partial and only four repeats of the repeat sequence. Since MUC-1 (which has a similar repeat sequence) from different individuals has been shown to contain a highly variable number (ranging from single digit numbers to triple digit numbers) of repeat sequences, it is likely that PSET-containing and TRAM-containing polypeptides encoded by the TRAAM gene (e.g., TRAAM-ORF1 and TRAAM-ORF2, respectively) will also contain a variable number of repeats. The consensus sequence for the twenty amino acid TRAM (TRAAM$_{U987}$-ORF1 and TRAAM$_{K008}$ carboxy-terminus) repeat sequence is: GT/m S Q/r P R A/p H R R P Q A P A R/Q Q D L Q (SEQ ID NO: 24). The sequence of the partial TRAM repeats is: A H R R P Q A P A Q Q D L Q (SEQ ID NO: 25). Other preferred TRAM repeat sequences are:

G T S Q P R A H R R P Q A P A R Q D L Q (SEQ ID NO: 26);

G M S Q P RA H R R P Q A P A R Q D L Q (SEQ ID NO: 27);

G T S Q P R A H RR P Q A P A Q Q D L Q (SEQ ID NO: 28); and

G T S Q P R P H R R P Q A P A R Q D L Q (SEQ ID NO: 29).

The consensus sequence for the PSET twenty amino acid repeat sequence is:

S P S E T P G P R/S P A G P A/T G/R D E P A E/k (SEQ ID NO: 29).

Preferred sequences are:

S P S E T P G P R P A G P A G D E P A E (SEQ ID NO: 31);

S P S E T P G P S P A G P T R D E P A E (SEQ ID NO: 32); and

S P S E T P G P S P A G P T R D E P A K (SEQ ID NO: 33).

Peptides corresponding to the TRAAM (e.g., PSET and TRAM) repeat sequences will be particularly useful as tumor antigens and as therapeutic peptides that block the activity of TRAAM gene products. Antisense nucleic acids that are complementary to the nucleotide sequences encoding the repeats will be useful for antisense inhibition of transcription and/or translation of the TRAAM gene.

3. KIAA0603/TBC

We isolated a cDNA clone, the sequence of which suggested that it encoded the human homolog of the mouse TBC-1 protein. While we were in the process of obtaining the full-length sequence of this clone, the gene KIAA0603 (Genbank Accession No. AB011175; Nagase et al., *DNA Res.* 5:31-39, 1998; SEQ ID NOs: 45 and 46), which corresponds to our sequence, was deposited in the database. Our sequence also corresponds to ESTs reported from normal and neoplastic tissues. We observed that serum from a second vaccinated patient also identified this protein as a tumor antigen.

4. TPR/UBP-3

TPR/UBP-3 (SEQ ID NO: 7) is a novel translocation in which the 5' partner encodes the TPR protein (a nucleoporin); the 3' partner encodes a novel gene (designated UBP-3; SEQ ID NO: 6) that is likely the human homolog of a ubiquitin-specific protease found in *Arabidopsis thaliana*.

Post-vaccination serum from eleven melanoma patients contained antibodies that specifically bound the TPR/UBP-3 fusion product.

5. BRAP-2/H$^+$-ATPase

BRAP-2/H$^+$-ATPase (SEQ ID NO: 8) is a novel translocation in which the 5' partner is similar to BRAP-2, a protein reported to be a binding partner of DDB p127 (the Xeroderma pigmentosum group E defective protein), as well as a binding partner of BRCA-1 (GenBank AF035620; *J. Biol. Chem.* 273:6183-6189, 1998; SEQ ID NOs: 47 and 48); there is a one-base-pair discrepancy between our sequence and the reported BRAP-2 sequence, which results in a different BRAP-2 carboxy terminus from that reported. The 3' partner is an accessory protein reported to be associated with the H+ vacuolar ATPase. Northern analysis shows expression of this ATPase subunit in all normal tissues examined. Nine post-vaccination serum samples contained antibodies that recognized the BRAP-2/H$^+$-ATPase fusion protein. Preliminary Western analysis suggests that the melanoma patient whose sera was used to clone this gene recognizes the ATPase subunit at high levels, but not BRAP-2. Recombinant BRAP-2 and the ATPase subunit have each been produced in bacteria as GST fusion proteins.

6. KOO8-1

KOO8-1 (SEQ ID NOs: 9 and 10) is a novel gene sequence with several matches in the EST data base (AA459487 (SEQ ID NO: 50); AA612844 (SEQ ID NO: 51); AA742366 (SEQ ID NO: 52); AA280738 (SEQ ID NO: 53); AA578562 (SEQ ID NO: 54); AA665027 (SEQ ID NO: 55); D81704 (SEQ ID NO: 56); AA748357 (SEQ ID NO: 57); D60753 (SEQ ID NO: 58); AA972891 (SEQ ID NO: 59)). There is a weak homology with ankyrin repeats at the protein level.

7. NOR-90

NOR-90 is a gene encoding a protein that has previously been reported as an autoantigen in patients with scleroderma, a connective tissue disease (J. Exp. Med. 174:1239-1244, 1991; Genebank Accession No. X56687; SEQ ID NO: 60). This protein is known to function as a transcription factor for rRNA synthesis. Our clone corresponds to a portion of NOR-90. Five out of seven post-vaccination serum samples contained antibodies that recognize NOR-90.

8. BR-1

BR-1 (SEQ ID NO: 14) is a novel gene sequence for which there are two EST matches: GB AA187982 (from HeLa cells; SEQ ID NO: 62) and GB AA354716 (from Jurkat T cells; SEQ ID NO: 63).

9. BR-2

BR-2 (SEQ ID NO: 15) is a novel gene sequence for which there are three EST matches: GB AA187982 (SEQ ID NO: 64), AA188110 (SEQ ID NO: 65), and EMB Z21827 (SEQ ID NO: 66). BR-1 and BR-2 may be alternative splice products of the same gene.

10. Gene AS

Gene AS (SEQ ID NO: 16) is a novel gene sequence that appears to be in the antisense orientation for the gene encoding tyrosinase-replated protein-2, a melanoma antigen.

In addition, TPR (Accession Number: EMB X66397; SEQ ID NO: 67), UBP-3 (SEQ ID NO: 6), and BRAP-2 (encoded either by our sequence, or by the previously-reported sequence) are considered to be tumor antigens for use in the methods of the invention. Novel gene sequences are shown in FIGS. 6 through 8 and 17.

Uses of the Invention

1. Diagnostic: Either DNA- or antibody-based tests may be used for detection of the translocations, alterations in the level of expression, or modifications (such as mutations) of the tumor antigen genes or gene products. Monitoring antibody or cellular responses to these antigens may be useful in determining disease burden, prognosis, and response to cancer therapy. For example, a patient's response to an anti-tumor vaccine may be monitored by measuring the levels of tumor antigen-specific antibodies or tumor antigen-specific cytotoxic T lymphocytes in a sample obtained from the patient before and after vaccination, using an appropriate assay such as ELISA (for antibody detection) or cytotoxic T lymphocyte functional assays, such as those measuring cytotoxicity, proliferation, or cytokine production.

2. Immunotherapies: The tumor antigens of the invention were identified as the targets of high titer IgG-specific antibody responses. There is a high likelihood that they will also be the target for helper and/or cytotoxic T cells, given the concurrent induction of humoral and cellular immunity in our vaccinated patients.

a. The tumor antigens may be used as components of generic vaccines in immunization strategies that employ, e.g.: peptides, whole proteins (alone, or with a wide variety of adjuvants including, but not limited to, QS21, alum, GMCSF, IL-2, IL-12), naked DNA, viral vectors (i.e., adenovirus, vaccinia virus, fowlpox) expressing antigen, dendritic cells (pulsed with peptide or protein or genetically modified to express the relevant tumor antigen), cell lines engineered to express these antigens with or without adjuvants (such as QS2 1, GM-CSF, IL-2, IL-12) as well as cell lines engineered to express immunostimulatory molecules (such as GM-SCF, B7-1, IL-2, IL-12).

b. Monoclonal antibodies against tumor antigens may be used not only for diagnosis (as in 1 above) but also therapeutically (for example, conjugated to a variety of toxins).

c. Antigen-specific T cells generated against these antigens are likely to be useful for adoptive immunotherapy.

3. Pharmacologic therapies: These antigens may represent targets for drug therapy. The tumor antigens encode proteins that are likely to be important to the cancer cell phenotype. For example, TBC-1 is a nuclear protein with structural homology to cell cycle regulators. As a second example, MAIAP, a member of the "inhibitor of apoptosis" family of proteins, may be overexpressed in some tumor cells. If so, inhibition of MAIAP, e.g., using antisense nucleic acids or small molecule inhibitors, may increase the effectiveness of apoptosis-inducing cancer therapies, such as chemotherapy or radiation therapy, for some types of tumors.

4. The tumor antigens may also be used as targets for high-throughput drug screens designed to isolate small molecule inhibitors of tumor antigen function, using known methods and as described herein. For example, high-throughput screens designed to detect inhibitors of MAIAP allow the identification of novel cancer therapeutics that may be used alone or in conjunction with other cancer therapies.

Synthesis of Tumor Antigen Polypeptides

Cloned tumor antigens may be overexpressed in vivo by introducing tumor antigen coding sequences into various types of cells, or in vitro, using cell-free expression systems that are known in the art. Tumor antigen gene products may then purified for biochemical characterization, antibody or vaccine production, or patient therapy. Purified tumor antigens are also useful for diagnostic assays that measure the presence of antibodies, e.g., in a patient's serum, that are specific for a given tumor antigen. The presence (or increased levels) of anti-tumor antigen antibodies in a patient's serum, relative to a reference sample, may indicate that the patient has a tumor or a tumor metastasis.

Eukaryotic and prokaryotic expression systems may be used to express tumor antigen proteins: tumor antigen gene sequences are introduced into a plasmid or other vector, which is then used to transform living cells. Constructs in which a tumor antigen cDNA containing the entire open reading frame, inserted in the correct orientation into an expression plasmid, may be used for protein expression. Alternatively, portions of tumor antigen gene sequences, including wild-type or mutant tumor antigen sequences, may be inserted. Prokaryotic and eukaryotic expression systems allow various immunogenic domains of tumor antigen proteins to be recovered as fusion proteins and then used for the generation of appropriate antibodies. In some cases, for example, when a tumor antigen is to be expressed directly within a patient's cells, it may be desirable to express the tumor antigen under the control of an inducible or tissue-specific promoter.

Typical expression vectors contain promoters that direct the synthesis of large amounts of mRNA corresponding to the inserted tumor antigen-encoding nucleic acid in the plasmid-bearing cells. They may also include eukaryotic or prokaryotic "origin of replication" sequences allowing for their autonomous replication within the host organism, sequences that encode genetic traits that allow vector-containing cells to be selected for in the presence of otherwise-toxic drugs (such as antibiotics), and sequences that increase the efficiency with which the synthesized mRNA is translated. Stable long-term vectors may be maintained as freely replicating entities within cells by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Expression of foreign sequences in bacteria such as *Escherichia coli* requires the insertion of a nucleic acid sequence encoding a polypeptide into a bacterial expression vector. Plasmid vectors in this category contain several elements required for the propagation of the plasmid in bacteria, and expression of inserted DNA of the plasmid by the plasmid-carrying bacteria. Propagation of only plasmid-bearing bacteria is achieved by introducing, into the plasmid, selectable marker-encoding sequences that allow plasmid-bearing bacteria to grow in the presence of otherwise-toxic drugs (e.g., antibiotics). The plasmid also bears a transcriptional promoter capable of producing large amounts of mRNA from the cloned gene. Such promoters may or may not be inducible promoters that initiate transcription upon induction. The plasmid also preferably contains a polylinker to simplify insertion of the gene in the correct orientation within the vector. In a simple *E. coli* expression vector utilizing the lac promoter, the expression vector plasmid contains a fragment of the *E. coli* chromosome containing the lac promoter and the neighboring lacZ gene. In the presence of the lactose analog IPTG, RNA polymerase normally transcribes the lacZ gene, producing lacZ mRNA, which is translated into the encoded protein, β-galactosidase. The lacZ gene can be cut out of the expression vector with restriction endonucleases and replaced by a tumor antigen gene sequence, or fragment, fusion, or mutant thereof. When this resulting plasmid is transfected into *E. coli*, addition of IPTG and subsequent transcription from the lac promoter produces mRNA encoding the polypeptide of interest, e.g., a tumor antigen, which is translated into a polypeptide, e.g., tumor antigen polypeptide.

Once the appropriate expression vectors containing a tumor antigen gene (or fragment, fusion, or mutant thereof) are constructed, they are introduced into an appropriate host cell by transformation, transfection, or transduction techniques that are known in the art, including calcium chloride transformation, calcium phosphate transfection, DEAE-dextran transfection, electroporation, microinjection, protoplast fusion and liposome-mediated transfection. The host cells that are transformed with the vectors of this invention may include (but are not limited to) *E. coli* or other bacteria, yeast, fungi, insect cells (using, for example, baculoviral vectors for expression), human, mouse, or other animal cells. Mammalian cells can also be used to express tumor antigen proteins using a vaccinia virus expression system described in F. Ausubel et al., *Current Protocols in Molecular Biology*, John Wiley & Sons, New York, N.Y., 1994.

In vitro expression of tumor antigen proteins, fusions, polypeptide fragments, or mutated versions thereof encoded by cloned DNA is also possible using the T7 late-promoter expression system. This system depends on the regulated expression of T7 RNA polymerase, an enzyme encoded in the DNA of bacteriophage T7. The T7 RNA polymerase transcribes DNA beginning within a specific 23-bp promoter sequence called the T7 late promoter. Copies of the T7 late promoter are located at several sites on the T7 genome, but none is present in *E. coli* chromosomal DNA. As a result, in T7-infected cells, T7 RNA polymerase catalyzes transcription of viral genes but not of *E. coli* genes. In this expression system, recombinant *E. coli* cells are first engineered to carry the gene encoding T7 RNA polymerase under the transcriptional regulation of the lac promoter. In the presence of IPTG, these cells transcribe the T7 polymerase gene at a high rate and synthesize abundant amounts of T7 RNA polymerase. These cells are then transformed with plasmid vectors that carry a copy of the T7 late promoter protein. When IPTG is added to the culture medium containing these transformed *E. coli* cells, large amounts of T7 RNA polymerase are produced. The polymerase then binds to the T7 late promoter on the plasmid expression vectors, catalyzing transcription of the inserted cDNA at a high rate. Since each *E. coli* cell contains many copies of the expression vector, large amounts of mRNA corresponding to the cloned cDNA can be produced in this system and the resulting protein can be radioactively labeled.

Plasmid vectors containing late promoters and the corresponding RNA polymerases from related bacteriophages such as T3, T5, and SP6 may also be used for in vitro production of proteins from cloned DNA. *E. coli* can also be used for expression using an M13 phage such as mGPI-2. Furthermore, vectors that contain phage lambda regulatory sequences, or vectors that direct the expression of fusion proteins, for example, a maltose-binding protein fusion protein or a glutathione-S-transferase fusion protein, also may be used for expression in *E. coli*.

Eukaryotic expression systems permit appropriate post-translational modifications to expressed proteins. Transient transfection of a eukaryotic expression plasmid allows the transient production of a tumor antigen polypeptide by a transfected host cell. Tumor antigen proteins may also be produced by a stably-transfected mammalian cell line. A number of vectors suitable for stable transfection of mammalian cells are available to the public (e.g., see Pouwels et al., *Cloning Vectors: A Laboratory Manual*, 1985, Supp. 1987), as are methods for constructing such cell lines (see e.g., F. Ausubel et al., *Current Protocols in Molecular*

*Biology*, John Wiley & Sons, New York, N.Y., 1994). In one example, cDNA encoding a tumor antigen protein, fusion, mutant, or polypeptide fragment is cloned into an expression vector that includes the dihydrofolate reductase (DHFR) gene. Integration of the plasmid and, therefore, integration of the tumor antigen-encoding gene into the host cell chromosome is selected for by inclusion of 0.01-300 µM methotrexate in the cell culture medium (described in F. Ausubel et al., supra). This dominant selection can be accomplished in most cell types. Recombinant protein expression can be increased by DHFR-mediated amplification of the transfected gene. Methods for selecting cell lines bearing gene amplifications are described in F. Ausubel et al., supra. These methods generally involve extended culture in medium containing gradually increasing levels of methotrexate. The most commonly used DHFR-containing expression vectors are pCVSEII-DHFR and pAdD26SV(A) (described in F. Ausubel et al., supra). The host cells described above or, preferably, a DHFR-deficient CHO cell line (e.g., CHO DHFR⁻ cells, ATCC Accession No. CRL 9096) are among those most preferred for DHFR selection of a stably-transfected cell line or DHFR-mediated gene amplification. Other drug markers may be analogously used.

Eukaryotic cell expression of proteins, such as tumor antigens, allows the production of large amounts of normal or mutant proteins for isolation and purification, and the use of cells expressing a tumor antigen protein provides a functional assay system for antibodies generated against the protein of interest. Expression of tumor antigen proteins, fusions, mutants, and polypeptide fragments in eukaryotic cells also enables studies of the functions of the normal complete proteins, specific portions of the proteins, or of naturally occurring polymorphisms and artificially produced mutated proteins. The tumor antigen-encoding DNA sequences can be altered using procedures known in the art, such as restriction endonuclease digestion, DNA polymerase fill-in, exonuclease deletion, terminal deoxynucleotide transferase extension, ligation of synthetic or cloned DNA sequences and site-directed sequence alteration using specific oligonucleotides together with PCR.

Another preferred eukaryotic expression system is the baculovirus system using, for example, the vector pBac-PAK9, which is available from Clontech (Palo Alto, Calif.). If desired, this system may be used in conjunction with other protein expression techniques, for example, the myc tag approach described by Evan et al. (*Mol. Cell Biol.* 5:3610-3616, 1985).

Once the recombinant protein is expressed, it can be isolated from the expressing cells by cell lysis followed by protein purification techniques, such as affinity chromatography. In this example, an anti-tumor antigen antibody, which may be produced by the methods described herein, can be attached to a column and used to isolate recombinant tumor antigen proteins. Lysis and fractionation of tumor antigen protein-harboring cells prior, to affinity chromatography may be performed by standard methods (see e.g., F. Ausubel et al., *Current Protocols in Molecular Biology*, John Wiley & Sons, New York, N.Y., 1994). Once isolated, the recombinant protein can, if desired, be purified further, e.g., by high performance liquid chromatography (HPLC; e.g., see Fisher, *Laboratory Techniques In Biochemistry And Molecular Biology*, Work and Burdon, Eds., Elsevier, 1980).

Polypeptides of the invention, particularly tumor antigen polypeptide fragments, can also be produced by chemical synthesis (e.g., by the methods described in *Solid Phase Peptide Synthesis*, 2nd ed., 1984, The Pierce Chemical Co., Rockford, Ill.). These general techniques of polypeptide expression and purification can also be used to produce and isolate useful tumor antigen polypeptide fragments or analogs, as described herein.

Those skilled in the art of molecular biology will understand that a wide variety of expression systems may be used to produce the recombinant tumor antigen polypeptides and fragments thereof. Tumor antigen polypeptides may be produced in prokaryotic hosts (e.g., *E. coli*) or in eukaryotic hosts (e.g., *S. cerevisiae*, insect cells such as Sf9 cells, or mammalian cells such as COS-1, NIH 3T3, or HeLa cells). These cells are commercially available from, for example, the American Type Culture Collection, Rockville, Md. (see also F. Ausubel et al., supra). The method of transformation and the choice of expression vehicle (e.g., expression vector) will depend on the host system selected. Transformation and transfection methods are described, e.g., in F. Ausubel et al., supra, and expression vehicles may be chosen from those provided, e.g., in Pouwels et al., *Cloning Vectors: A Laboratory Manual*, 1985, Supp. 1987.

Anti-Tumor Antigen Antibodies

In order to prepare purified polyclonal antibodies, tumor antigens, fragments of tumor antigens, or fusion proteins containing defined portions of tumor antigens can be synthesized in bacteria by expression of corresponding DNA sequences cloned into a suitable vector. Fusion proteins are commonly used as a source of antigen for producing antibodies. Two widely used expression systems for *E. coli* are lacZ fusions using the pUR series of vectors and trpE fusions using the pATH vectors. The proteins can be purified, and then coupled to a carrier protein and mixed with Freund's adjuvant (to stimulate the antigenic response by the animal of choice) and injected into rabbits or other laboratory animals. Alternatively, protein can be isolated from tumor antigen-expressing cultured cells. Following booster injections at bi-weekly intervals, the rabbits or other laboratory animals are then bled and the sera isolated. The sera can be used directly or can be purified prior to use, by various methods, including affinity chromatography employing reagents such as Protein A-Sepharose, Antigen Sepharose, and Anti-mouse-Ig-Sepharose. The sera can then be used to probe protein extracts from tumor antigen-expressing tissue, for example, by immunoprecipitation of tumor antigen from whole extracts, or by Western blotting of extracts that have been electrophoretically separated. Alternatively, synthetic peptide's can be made that correspond to the antigenic portions of the protein, and used to innoculate the animals.

In order to generate peptide or full-length protein for use in making tumor antigen-specific antibodies, a tumor antigen coding sequence can be expressed as a C-terminal fusion with glutathione S-transferase (GST; Smith et al., *Gene* 67:31-40, 1988). The fusion protein may be purified on glutathione-Sepharose beads, eluted with glutathione, and cleaved with thrombin (at an engineered cleavage site), and purified to the degree required to successfully immunize rabbits. Primary immunizations may be carried out with Freund's complete adjuvant and subsequent immunizations performed with Freund's incomplete adjuvant. Antibody titers may be monitored by Western blot and immunoprecipitation analyses using the thrombin-cleaved tumor antigen fragment of the GST-tumor antigen fusion protein. Immune sera may be affinity purified using CNBr-Sepharose-coupled tumor antigen protein. Antiserum specificity may be determined using a panel of unrelated GST fusion proteins.

It is also understood by those skilled in the art that monoclonal tumor antigen-specific antibodies may be produced by using tumor antigen isolated from tumor antigen-expressing cultured cells, or tumor antigen isolated from tissues (such as tumors). The cell extracts, or recombinant protein extracts containing tumor antigen, may for example, be injected with Freund's adjuvant into mice. After injection, spleens are removed from the mice and isolated spleen cells are suspended, e.g., in phosphate buffered saline (PBS). The spleen cells serve as a source of lymphocytes, some of which produce antibody of the appropriate specificity. These are then fused with permanently growing myeloma partner cells, and the products of the fusion are plated into tissue culture wells in the presence of a selective agent such as hypoxanthine, aminopterine, and thymidine (HAT). The wells are then screened by ELISA to identify those containing cells making antibody capable of binding a tumor antigen or polypeptide fragment or mutant thereof. These are then re-plated and after a period of growth, these wells are again screened to identify antibody-producing cells. Several cloning procedures are carried out until over 90% of the wells contain single clones which are positive for antibody production. From this procedure a stable line of clones that produce the antibody is established. The monoclonal antibody can then be purified by affinity chromatography using Protein A Sepharose, ion-exchange chromatography, as well as variations and combinations of these techniques. Truncated versions of monoclonal antibodies may also be produced by recombinant methods in which plasmids are generated which express the desired monoclonal antibody fragment(s) in a suitable host.

As an alternate or adjunct immunogen to GST fusion proteins, peptides corresponding to relatively unique hydrophilic regions of a tumor antigen may be generated and coupled to keyhole limpet hemocyanin (KLH) through an introduced C-terminal lysine. Antiserum to each of these peptides is similarly affinity purified on peptides conjugated to BSA, and specificity is tested by ELISA and Western blotting using peptide conjugates, and by Western blotting and immunoprecipitation using the tumor antigen of interest expressed as a GST fusion protein.

Alternatively, monoclonal antibodies that specifically bind the tumor antigen proteins described herein may be prepared using standard hybridoma technology (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., *In Monoclonal Antibodies and T Cell Hybridomas*, Elsevier, New York, N.Y., 1981; F. Ausubel et al., *Current Protocols in Molecular Biology*, John Wiley & Sons, New York, N.Y., 1994). Once produced, monoclonal antibodies are also tested for specific tumor antigen recognition by Western blot or immunoprecipitation analysis (by the methods described in F. Ausubel et al., supra).

Monoclonal and polyclonal antibodies that specifically recognize a tumor antigen (or fragments thereof), such as those described herein, are considered useful in the invention. For example, antibodies that specifically recognize a tumor antigen may be used to measure the level of that tumor antigen in a patient sample (such as blood). An increased level of the antigen, relative to a reference sample from a normal subject without a tumor, may indicate the presence of a tumor in a patient undergoing testing. Furthermore, an increased level of antigen, relative to an earlier sample taken from the same patient, may indicate an increase in tumor burden (i.e., metastasis).

Antibodies of the invention may be produced using tumor antigen amino acid sequences that do not reside within highly conserved regions, and that appear likely to be antigenic as analyzed by criteria such as those provided by the Peptide Structure Program (Genetics Computer Group Sequence Analysis Package, Program Manual for the GCG Package, Version 7, 1991) using the algorithm of Jameson and Wolf (*CABIOS* 4:181, 1988). These fragments can be generated by standard techniques, e.g., by the PCR, and cloned into the pGEX expression vector (F. Ausubel et al., *Current Protocols in Molecular Biology*, John Wiley & Sons, New York, N.Y., 1994). GST fusion proteins are expressed in *E. coli* and purified using a glutathione agarose affinity matrix as described in F. Ausubel et al., supra). To generate rabbit polyclonal antibodies, and to minimize the potential for obtaining antisera that is non-specific, or exhibits low-affinity binding to a tumor antigen, two or three fusions are generated for each protein, and each fusion is injected into at least two rabbits. Antisera are raised by injections in series, preferably including at least three booster injections.

In addition, antibodies of the invention may be produced using tumor antigen amino acid sequences that do reside within highly conserved regions. These antibodies may be screened as described above.

In addition to intact monoclonal and polyclonal anti-tumor antigen antibodies, the invention features various genetically engineered antibodies, humanized antibodies, and antibody fragments, including F(ab')2, Fab', Fab, Fv and sFv fragments. Antibodies can be humanized by methods known in the art, e.g., monoclonal antibodies with a desired binding specificity can be commercially humanized (Scotgene, Scotland; Oxford Molecular, Palo Alto, Calif.). Fully human antibodies, such as those expressed in transgenic animals, are also features of the invention (Green et al., *Nature Genetics* 7:13-21, 1994).

Ladner (U.S. Pat. Nos. 4,946,778 and 4,704,692) describes methods for preparing single polypeptide chain antibodies. Ward et al. (*Nature* 341:544-546, 1989) describe the preparation of heavy chain variable domains, termed "single domain antibodies," which have high antigen-binding affinities. McCafferty et al. (*Nature* 348:552-554, 1990) show that complete antibody V domains can be displayed on the surface of fd bacteriophage, that the phage bind specifically to antigen, and that rare phage (one in a million) can be isolated after affinity chromatography. Boss et al. (U.S. Pat. No. 4,816,397) describe various methods for producing immunoglobulins, and immunologically functional fragments thereof, which include at least the variable domains of the heavy and light chain in a single host cell. Cabilly et al. (U.S. Pat. No. 4,816,567) describe methods for preparing chimeric antibodies.

Use of Anti-Tumor Antigen Antibodies

Antibodies specific for tumor antigens may be used, as noted above, to detect tumor antigens in a patient sample (such as blood, a tumor biopsy, or other biological material obtained from a patient) or to inhibit the biological activities of tumor antigens. For example, nucleic acid encoding an antibody or portion of an antibody may be expressed within a cell to inhibit tumor antigen function.

In addition, the antibodies may be coupled to compounds for diagnostic and/or therapeutic uses. For example, the antibodies may be coupled to imaging compounds, such as radionucleotides, for imaging a tumor. Imaging methods are known to those skilled in the art (e.g., radiologists and nuclear physicians); they include, and are not limited to, X-rays, computerized tomography (CT) scans, magnetic resonance imaging (MRI), positron emission tomography (PET) scans, scintography, single photon emission computerized tomography (SPECT) scans, nuclear medicine scanning methods in general, and analogous approaches that allow detection and visualization of a tumor. Antibodies may also be coupled to radionuclides or toxic compounds (such as ricin) for specifically targeting anti-tumor therapy to a tumor, or to liposomes containing compounds for anti-tumor therapy.

Detection of Tumor Antigen Gene Expression

As noted, the antibodies described above may be used to monitor tumor antigen protein expression. In addition, in situ hybridization may be used to detect the expression of tumor antigen genes. In situ hybridization techniques, such as fluorescent in situ hybridization (FISH), rely upon the hybridization of a specifically labeled nucleic acid probe to the cellular RNA in individual cells or tissues. Therefore, such techniques allow the identification of mRNA within intact tissues, such as a patient biopsy. In this method, oligonucleotides or cloned nucleic acid (RNA or DNA) fragments corresponding to unique portions of tumor antigen genes are used to detect specific mRNA species that are differentially expressed in tumor vs. normal tissue. Numerous other gene expression detection techniques are known to those of skill in the art and may be employed within the methods of the invention.

Detection of Altered Expression Levels of Tumor Antigens and Mutations in Tumor Antigens Tumor antigen polypeptides and nucleic acid sequences find diagnostic use in the detection or monitoring of tumorigenesis and metastasis. Accordingly, an increase in the level of tumor antigen may indicate the development of a tumor or metastasis. Levels of tumor antigen may be assayed by any standard technique. Tumor antigen expression in a biological sample (e.g., a biopsy) may be monitored by standard Northern blot analysis or may be aided by PCR (see, e.g., F. Ausubel et al., *Current Protocols in Molecular Biology*, John Wiley & Sons, New York, N.Y., 1994; *PCR Technology: Principles and Applications for DNA Amplification*, H. A. Ehrlich, Ed., Stockton Press, NY; Yap et al. *Nucl. Acids. Res.* 19:4294, 1991).

A biological sample obtained from a patient may be analyzed for one or more mutations in tumor antigen nucleic acid sequences using a mismatch detection approach. Generally, these techniques involve PCR amplification of nucleic acid from the patient sample, followed by identification of the mutation (i.e., mismatch) by either altered hybridization; aberrant electrophoretic gel migration, binding or cleavage mediated by mismatch binding proteins, or direct nucleic acid sequencing. Any of these techniques may be used to facilitate mutant tumor antigen detection, and each is well known in the art; examples of particular techniques are described, without limitation, in Orita et al. (*Proc. Natl. Acad. Sci. USA* 86:2766-2770, 1989) and Sheffield et al. (*Proc. Natl. Acad. Sci. USA* 86:232-236, 1989).

Mismatch detection assays also provide an opportunity to diagnose a predisposition to developing a tumor before the onset of symptoms. For example, a patient heterozygous for a mutation in a tumor antigen gene may show no clinical symptoms and yet possess a higher than normal probability of developing cancer. Given this diagnosis, a patient may take precautions to minimize their exposure to adverse environmental factors (for example, excessive exposure to ultraviolet light) and to carefully monitor their medical condition (for example, through frequent physical examinations). The tumor antigen diagnostic assays described above may be carried out using any appropriate biological sample (for example, any biopsy sample, blood sample, or other tissue or body fluid sample that contains nucleic acid and/or protein).

Alternatively, a tumor antigen mutation, particularly as part of a diagnosis for predisposition to cancers associated with expression of a specific tumor antigen, may be tested using a DNA sample from any cell, for example, by mismatch detection techniques. Preferably, the DNA sample is subjected to PCR amplification prior to analysis.

In yet another approach, immunoassays are used to detect or monitor tumor antigen expression in a biological sample. Tumor antigen-specific polyclonal or monoclonal antibodies (produced as described above) may be used in any standard immunoassay format (e.g., enzyme-linked immunosorbent assay (ELISA), Western blot, or radioimmunoassay (RIA)) to measure tumor antigen polypeptide levels. These levels are compared to reference (wild-type) tumor antigen levels. For example, an increase in a tumor antigen, relative to reference levels, may indicate the presence of a tumor. Examples of immunoassays are described, e.g., in Ausubel et al., *Current Protocols in Molecular Biology*, John Wiley & Sons, New York, N.Y., 1994 through 1998.

Immunohistochemical techniques may also be utilized for tumor antigen detection. For example, a tumor biopsy may be obtained from a patient, sectioned, and stained for the presence of tumor antigens using an anti-tumor antigen antibody and any standard detection system (e.g., one which includes a secondary antibody conjugated to horseradish peroxidase). General guidance regarding such techniques may be found in, e.g., Bancroft and Stevens (*Theory and Practice of Histological Techniques*, Churchill Livingstone, 1982) and Ausubel et al. (*Current Protocols in Molecular Biology*, John Wiley & Sons, New York, N.Y., 1994 through 1998). Detection of a particular tumor antigen within the presence of a tumor may provide information concerning tumor prognosis and approaches to treatment.

Vaccination with Tumor Antigens for Tumor Therapy or Prophylaxis

Vaccination protocols may be designed to induce or enhance an immune response against a tumor antigen in order to treat an existing cancer, or prevent the development or recurrence of cancer. Reagents that are useful for vaccination may include, without limitation, full length tumor antigen polypeptides, or fragments thereof, or nucleic acids that encode tumor antigens (e.g., a viral or plasmid expression vector that carries a tumor antigen gene) or tumor antigen fragments.

a) Vaccination with Tumor Antigen Polypeptides

In order to produce a vaccination against one or more tumor antigens, it is necessary to obtain large amounts of pure tumor antigen protein from eukaryotic or prokaryotic cultured cells that express the protein. This can be achieved by methods that are described above and are known in the art. Induction of an immune response by administration of a tumor antigen protein to a subject may be achieved by conventional techniques that are well-known to those skilled in the art of vaccine production and delivery.

b) Vaccination by Gene Therapy

Gene therapy is another approach that may be used to induce an immune response in a subject to be treated for, or protected against, cancer. A tumor antigen-encoding gene, or a portion thereof, must be delivered to cells in a form that can be taken up and express sufficient protein to induce an effective immune response.

Transducing retroviral, adenoviral, and human immunodeficiency viral (HIV) vectors are suited for somatic cell gene therapy, because they show high efficiency of infection and stable integration and expression; see, e.g., Cayouette, M., and Gravel, C., (1997)*Hum. Gene Therapy*, 8:423-430; Kido, M., et al. (1996) *Curr. Eye Res.*, 15:833-844; Bloomer, U., et al. (1997) *J. Virol.,* 71:6641-6649; Naldini, L., et al. (1996) *Science* 272:263-267; Miyoshi, H., et al. (1997), *Proc. Nat. Acad. Sci., U.S.A.,* 94:10319-1032. For example, a full length tumor antigen gene, or portions thereof, can be cloned into a retroviral vector and transcribed via its endogenous promoter, or via the retroviral long terminal repeat, or via a promoter specific for the target cell type of interest. Other viral vectors that can be used include adenovirus, adeno-associated virus, vaccinia virus, bovine papilloma virus, or a herpes virus such as Epstein-Barr Virus.

Gene transfer in vivo may also be achieved by non-viral means. For example, viral or plasmid vectors encoding tumor antigens or fragments thereof may be injected directly into skeletal muscle or cardiac muscle by previously described methods (e.g., Wolff, J. A., et al., *Science,* 247: 1465-1468, 1990). Expression vectors injected into skeletal muscle in situ are taken up into muscle cell nuclei and used as templates for expression of their encoded proteins. Tumor antigen genes that are engineered to contain a signal peptide are secreted from tumor antigen-expressing muscle cells, after which they induce an immune response. Gene transfer into cells within the tissues of a living animal also may be achieved by lipofection (Felgner et al., *Proc. Natl. Acad. Sci. USA* 84: 7413, 1987; Ono et al., *Neurosci. Lett.* 117: 259, 1990; Brigham et al., *Am. J. Med. Sci.* 298:278, 1989; Staubinger et al., *Meth. Enz.* 101:512, 1983), or asialooroso-mucoid-polylysine conjugation (Wu et al., *J. Biol. Chem.* 263:14621, 1988; Wu et al., *J. Biol. Chem.* 264:16985, 1989).

Retroviral vectors, adenoviral vectors, adenovirus-associated viral vectors, or other viral vectors also may be used to deliver tumor antigen genes to cells ex vivo. Numerous vectors useful for this purpose are generally known (Miller, *Human Gene Therapy* 15-14, 1990; Friedman, *Science* 244: 1275-1281, 1989; Eglitis and Anderson, *BioTechniques* 6:608-614, 1988; Tolstoshev and Anderson, *Curr. Opin. Biotech.* 1:55-61, 1990; Sharp, *The Lancet* 337: 1277-1278, 1991; Cornetta et al., *Nucl. Acid Res. and Mol. Biol.* 36: 311-322, 1987; Anderson, *Science* 226: 401-409, 1984; Moen, *Blood Cells* 17: 407-416, 1991; Miller et al., *Biotech.* 7: 980-990, 1989; Le Gal La Salle et al., *Science* 259: 988-990, 1993; and Johnson, *Chest* 107: 77S-83S, 1995). Retroviral vectors are particularly well developed and have been used in clinical settings (Rosenberg et al., *N. Engl. J. Med* 323: 370, 1990; Anderson et al., U.S. Pat. No. 5,399, 346).

Gene transfer into cells ex vivo can also be achieved by delivery of non-viral vectors, such as expression plasmids, using methods such as calcium phosphate or DEAE dextran transfection, electroporation, and protoplast fusion. Liposomes may also be potentially beneficial for delivery of DNA into a cell.

Cells that are to be transduced or transfected ex vivo may be obtained from a patient (e.g., bone marrow stem cells or cells from a tumor biopsy) prior to transfection, and reintroduced after transfection. However, the cells also may be derived from a source other than the patient undergoing gene transfer.

In the constructs described above, tumor antigen mRNA expression can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in skeletal muscle cells may be used to direct tumor antigen gene expression for vaccination in situ. The enhancers used may include, without limitation, those that are characterized as tissue- or cell-specific in their expression. Alternatively, if a tumor antigen genomic clone is used as a therapeutic construct, regulation may be mediated by the cognate regulatory sequences or, if desired, by regulatory sequences derived from a heterologous source, including any of the promoters or regulatory elements described above.

Gene Therapy Approaches for Inhibiting Tumor Antigen Function

As described above for MAIAP, antisense-based strategies may be employed to explore tumor antigen gene function. Moreover, inhibition of tumor antigen function via antisense gene therapy may, in some cases, may provide an effective anti-tumor therapeutic approach.

The principle of antisense therapy is based on the hypothesis that sequence-specific suppression of gene expression (via transcription or translation) may be achieved by intracellular hybridization between genomic DNA or mRNA and a complementary antisense species. The formation of such a hybrid nucleic acid duplex interferes with transcription of the target tumor antigen-encoding genomic DNA, or processing/transport/translation and/or stability of the target tumor antigen mRNA.

Antisense nucleic acids may be delivered by a variety of approaches. For example, antisense oligonucleotides or antisense RNA may be directly administered (e.g., by intravenous injection) to a subject in a form that allows uptake into cells (e.g., tumor cells). Alternatively, viral or plasmid vectors that encode antisense RNA (or RNA fragments) may be introduced into cells in vivo or ex vivo. Antisense effects can be induced by sense sequences, however, the extent of phenotypic changes are highly variable. Phenotypic changes induced by effective antisense therapy are assessed according to changes in, e.g., protein levels, protein activity measurement, and target mRNA levels.

In a specific example, inhibition of tumor antigen function by antisense gene therapy may be accomplished by direct administration of antisense tumor antigen mRNA to a subject. The antisense tumor antigen mRNA may be produced and isolated by any standard technique, but is most readily produced by in vitro transcription using an antisense tumor antigen cDNA under the control of a high efficiency promoter (e.g., the T7 promoter). Administration of antisense tumor antigen mRNA to cells can be carried out by any of the methods for direct nucleic acid administration described above.

An alternative strategy for inhibiting tumor antigen function using gene therapy involves intracellular expression of an anti-tumor antigen antibody or a portion of an anti-tumor antigen antibody. For example, the gene (or gene fragment) encoding a monoclonal antibody that specifically binds to tumor antigen and inhibits its biological activity may be placed under the transcriptional control of a specific (e.g., tissue- or tumor-specific) gene regulatory sequence.

Administration of Tumor Antigen Polypeptides or Nucleic Acids that Comprise Tumor Antigen-Encoding or -Antisense Sequences Conventional pharmaceutical practice may be employed to provide suitable formulations or compositions to administer tumor antigen vaccinations or antisense nucleic acids for treatment of, or prophylaxis against, cancer. Tumor antigen polypeptides or fragments thereof, genes (or antisense nucleic acids) or fragments thereof, or tumor antigen-specific antibodies, may be administered within a pharmaceutically-acceptable diluent, carrier, or excipient, in unit dosage form. Administration may begin before a patient is symptomatic. Any appropriate route of administration may be employed, for example, administration may be parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in *Remington's Pharmaceutical Sciences*, (18$^{th}$ edition), ed. A. Gennaro, 1990, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for tumor antigens and tumor antigen-inhibitory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Vaccination with Irradiated, Autologous Melanoma Cells Engineered to Secrete Human GM-CSF Generates Potent Anti-Tumor Immunity in Patients with Metastatic Melanoma

GENERAL METHODS

Clinical Protocol

The details of the clinical study design and methods of vaccine production have been presented previously (Soiffer et al., *Hum. Gene Ther.*, 8:111-123, 1997; Ellem et al., *Cancer Immunol. Immunother*, 44:10-20, 1997; Simone et al., *Cancer Res.* 57:1537-1546, 1997.). In brief, surgically resected tumors were processed to single-cell suspension by collagenase and mechanical digestion and introduced into short-term culture. Replicating tumor cells were transduced with viral supernatants harvested from CRIP packaging cell lines transfected with MFG-S-human GM-CSF, irradiated with 15,000 cGy, and cryopreserved in liquid nitrogen. Transduced cells were certified to be free of replication-competent retrovirus (RCR), endotoxin, mycoplasma, and other microbial contaminants. GM-CSF secretion was determined by ELISA (R&D). A portion of the tumor culture for use in delayed-type hypersensitivity evaluation was irradiated but not transduced. Frozen cells were thawed and washed in HBSS prior to injection; vaccines were administered intradermally (0.5 ml) and subcutaneously (0.5 ml) into normal skin on the limbs and abdomen on a rotating basis. Non-transduced cells were injected intradermally (0.5 ml) into normal skin at the time of beginning vaccination and then at monthly intervals in order to measure the generation of delayed-type hypersensitivity. Patient sera were tested regularly for RCR; all samples were negative.

Immunologic Analyses and Histopathology

Peripheral blood mononuclear cells were obtained by centrifugation over Ficoll gradients. Tumor infiltrating lymphocytes were prepared by mechanical digestion of metastatic deposits. For cytokine assays, lymphocytes were co-cultured with irradiated, autologous melanoma cells in 24 well dishes in 2 mls of DME plus 10% fetal calf serum, antibiotics, 2-mercaptoethanol, and glutamine. Media was harvested at day eight and assayed for IL-3, IL-4, IL-5, IL-6, IL-10, GM-CSF, γ-IFN, TNF-α, and TNF-β production by ELISA using the appropriate monoclonal antibodies (Phariningen). For cytotoxicity assays, lymphocytes were bulk stimulated with irradiated, autologous tumor cells for one week in media plus 10 U/ml IL-2 and then tested using standard techniques against $^{51}$Cr labeled tumor targets (Kruisbeek et al., *Current Protocols in Immunology*, John Wiley & Sons, 1991).

For immunoblotting analysis, 0.5-2.0 mg of melanoma cell lysates (phosphate buffered saline supplemented with 0.5% NP-40, soybean trypsin inhibitor, leupeptin, pepstatin, aminocaproic acid, and PMSF) were electrophoresed on SDS-polyacrylamide 4-12% gradient gels, transferred to Immobilon membranes (Millipore), and blocked overnight at room temperature in 5% non-fat dry milk in PBS. Membranes were probed overnight at 4° C. in a 1:100 dilution of patient sera (in Tween 20/Tris buffered saline), washed, and incubated for one hour at room temperature with an anti-human IgG, Fcγ-specific antibody conjugated to alkaline phosphatase (Jackson Immuno Research). The membranes were then developed with NBT and BCIP (Promega).

For flow cytometry analysis, at least 100,000 melanoma cells were incubated with a 1:100 dilution of patient serum (in 1% non-fat milk) for three hours on ice, washed, and then stained with a 1:100 dilution of anti-human IgG, Fcγ-specific antibody conjugated to FITC. Lymphocytes were phenotyped with standard techniques using monoclonal antibodies against CD3, CD4, CD8, CD14, CD 19, CD45RA, CD45RO, and CD56 (Coulter).

For histopathology, tissues were formalin-fixed, paraffin-embedded, and stained with hematoxylin and eosin.

RESULTS

Patient Population, Vaccine Production, and Vaccine Administration

Thirty-three metastatic melanoma patients (stage 1V) ranging from 32 to 82 years of age (18 women, 15 men) were enrolled in the clinical protocol (Soiffer et al., *Hum. Gene Ther.*, 8:111-123, 1997). Twenty had received prior therapies. Patients underwent a surgical procedure to remove a metastatic lesion for vaccine preparation. Tumors were harvested from soft tissue (14 patients), lymph node (9 patients), lung (6 patients), liver (3 patients), and adrenal gland (1 patient). Resected lesions were processed by mechanical and enzymatic digestion into single-cell suspensions and introduced into short-term culture. Proliferating melanoma cells were transduced with a replication-defective retrovirus expressing GM-CSF, irradiated with 15,000 cGy (which induced cell cycle arrest, but did not inhibit secretion of CSF by cultured cells for at least seven days), and cryopreserved.

Two patients were excluded from the study after enrollment because of the absence of melanoma in the surgical specimen and two were excluded because vaccines could not be produced. In the remaining twenty-nine patients, vaccines were successfully generated, achieving GM-CSF secretion rates ranging from 84 to 965 ng per 10$^6$ cells per 24 hours. The duration of vaccine preparation was generally 8 weeks (the range was 8-32 weeks). Three successive patient cohorts were immunized intradermally and subcutaneously with $10^7$ irradiated tumor cells (each treatment) administrated at 28, 14, or 7 day intervals (dose levels 1, 2, and 3, respectively) for a total of 84 days (total of 3, 6, or 12 vaccinations). Four patients at dose level 3 received additional vaccinations (up to a total of 24) after the first course of therapy. Three patients were withdrawn from the study after tumor harvest and prior to vaccination because of rapid disease progression. Five patients were withdrawn from study after beginning vaccination because rapid disease progression prevented administration of the full course of immunizations. Twenty-one patients were withdrawn from study after beginning vaccination because rapid disease progression prevented administration of the full course of immunizations. Twenty-one patients completed therapy (three at dose level 1, four at dose level 2, and fourteen at dose level 3), were fully evaluable for toxicity and biologic activity, and comprised the study population reported here. Sites of metastatic disease were skin, subcutaneous tissue, lymph node, lung, liver, spleen, intestine, adrenal, kidney, and bone. The number of different organ systems involved with metastases was: one (8 patients), two (13 patients), three (7 patients), four (4 patients), and six (1 patient). Twenty patients received prior systemic therapies including IL-2, a-interferon, IL-12, IL-1, monoclonal antibody, BCG, tumor vaccine, and chemotherapy (DTIC, BCNU, taxol, cisplatin, carboplatin, vinblastine, fotomustine, cyclophophamide, and tamoxifen).

Toxicities

Vaccination elicited erythema and induration at injection sites. Reactions were associated with local pruritus that was easily controlled with emollients. Grade 1 fatigue and nasal congestion were occasionally noted. No hepatic, renal, pulmonary, cardiac, hematologic, gastrointestinal, or neurologic toxicities were observed. No patient experienced vitiligo or autoimmune events.

Vaccination Reactions

Injections of irradiated, autologous, GM-CSF secreting melanoma cells evoked striking local reactions in all patients, with the intensity and duration of the responses generally increasing in proportion to the number of vaccines administered. Clinically, the reactions were characterized by substantial erythema (up to 35 cm in diameter) and induration (up to 14 cm in diameter). Occasionally, the reactions became hemorrhagic. Vaccination responses tended to peak at approximately 48 hours following cell injection, but the elicited induration could persist for several weeks, particularly after multiple immunizations. An intriguing observation was the frequent development of recall reactions at sites of previous vaccination. Several patients continued to experience these reactions intermittently in a mild form even after completion of therapy (for up to two years), although no clear precipitants were identified.

Figure 11:
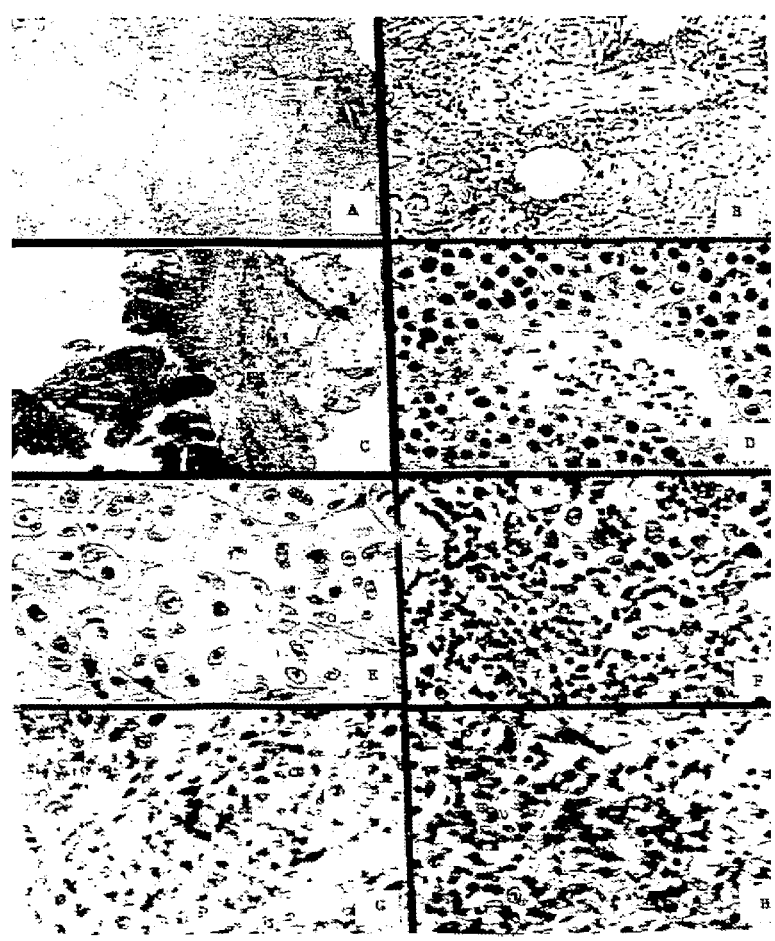
FIG. 11(A-H) is a series of photomicrographs of tissues from patients before and after vaccination with irradiated GM-CSF-secreting melanoma cells.

Vaccination sites in all patients were characterized histologically by an extensive infiltrate of dendritic cells, macrophages, eosinophils, and T lymphocytes which extended throughout the dermis and into the subcutaneous fat (FIG. 11A, injection site of irradiated GM-CSF-secreting melanoma cells following vaccination; note the extensive inflammatory reaction throughout all layers of the skin and the marked fibrosis in the subcutaneous fat). The infiltrates at dose levels 2 and 3 were usually more cellular than those at dose level 1 and also more frequently resulted in the development of flame figures (collections of deposited eosinophil granules) and endothelial cell damage in the superficial venules of the upper dermis. Eosinophil degranulation in nerve sheaths, lymphocytic infiltration of hair follicles, and fat necrosis were observed in several patients as well.

Delayed-Type Hypersensitivity Reactions

Although injections of irradiated, autologous, non-transfected melanoma cells failed to elicit significant responses in all patients at the time of early treatment, these injections evoked strong responses in all patients after several vaccinations were administered. Clinically, these delayed-type hypersensitivity reactions were characterized by extensive erythema (up to 10 cm) and induration (up to 6 cm) which peaked at 48 hours and then gradually resolved. Histopathologically, the reactions were characterized by dense infiltrates of T lymphocytes and degranulating eosinophils extending throughout the dermis (FIG. 11B, injection site of irradiated, non-transfected melanoma cells following vaccination). The infiltrates at dose levels 2 and 3 were usually greater than those at dose level 1.

Eosinophilia

In addition to the striking involvement of eosinophils in the reactions to injections of both irradiated, GM-CSF secreting and irradiated, non-transfected melanoma cells, significant increases in the numbers of peripheral blood eosinophils (but not other leukocytes) were also observed following immunization, with mean peak eosinophil counts of 705±715, 515±102, and 928±571 per $mm^3$ for dose levels 1, 2, and 3 respectively. The duration of eosinophilia tended to vary as a function of dose, with elevated counts persisting for several weeks more frequently at dose level 3 than at dose levels 1 or 2.

Since eosinophilia in many model systems is T cell-dependent, we investigated whether vaccination induced alterations in peripheral blood T cell cytokine production. For these studies, $1\times10^6$ peripheral blood mononuclear cells, obtained at various times during treatment, were cultured with $1\times10^4$ autologous, irradiated, non-transfected melanoma cells in the absence of supplemental growth factors; culture supernatants were harvested at day eight and assayed for cytokine content by ELISA (FIG. 12; "Tumor" represents the cytokines produced by the autologous, irradiated, non-transfected melanoma cells in the absence of lymphocytes). Vaccinations were administered on days 0, 28, and 56. In nine of ten patients studied, vaccination elicited substantial levels of T cell-derived IL-5, IL-3, and GM-CSF, in contrast to the variable production of IL-4, IL-6, IL-10, and TNF-β and the negligible induction of γ-interferon. The enhanced T cell secretion of IL-3, IL-S, and GM-CSF as a consequence of vaccination likely contributed, at least in part, to the augmented production of eosinophils, as these molecules have been shown to enhance the proliferation of eosinophilic precursors in vitro and in vivo. Moreover, the persistence of distinctive cytokine profiles for several months after completing treatment suggests that immunization stimulated the development of memory T cells.

Immune Responses in Metastases

To determine whether vaccination generated anti-melanoma immune responses capable of inducing anti-tumor effects, we examined the host reactions to metastatic lesions resected prior to and after completing therapy. Metastatic lesions procured before the beginning of immunization revealed in all patients either the absence of host reactivity or only a modest inflammatory reaction present focally within the tumor (FIG. 11E). Metastatic lesions resected after the completion of immunization, however, demonstrated a profound immune response in 11 of 16 patients from which tissue could be obtained (FIG. 11C; note extensive necrosis and fibrosis). These responses were found in metastatic lesions (up to 10 cm in diameter) derived from a variety of sites including skin, subcutaneous tissue, lymph node, lung, spleen, and intestine.

One important characteristic of the anti-melanoma immune reaction in each of the 11 responding patients was the diffuse infiltration of tumor masses by large numbers of T lymphocytes and plasma cells (FIG. 11F). Many CD4 and CD8 positive T lymphocytes were organized into rosettes around dying melanoma cells (satellitosis), a morphologic pattern indicative of lymphocyte-induced tumor apoptosis (FIG. 11G shows CD4-positive T cell reaction in metastasis following vaccination; FIG. 11H shows CD8-positive T cell reaction in metastasis following vaccination; tissues were formalin-fixed, paraffin-embedded, and stained with hematoxylin/eosin and anti-CD4 or anti-CD8). Plasma cells accounted for nearly 50% of the inflammatory cells and were intimately associated with the T lymphocytes and melanoma cells.

A second intriguing feature of the anti-melanoma response, observed in 4 patients, was the targeted destruction of the tumor vasculature, whereby lymphocytes, eosinophils, and neutrophils were closely associated with dying tumor blood vessels (FIG. 1D). Overall, the chronic inflammatory reactions evident in these 11 patients resulted in substantial tumor destruction (at least 80%) and the development of significant edema and fibrosis throughout the resected metastases. Of the five patients failing to develop inflammatory infiltrates in metastatic lesions as a consequence of vaccination, two were treated at dose level 1 and three had rapidly progressive disease resulting in death shortly after completion of therapy. No significant differences in the metastatic immune responses were observed between dose levels 2 and 3.

Characterization of Anti-Melanoma Cellular and Humoral Immunity

Figures 12, 13, 14:
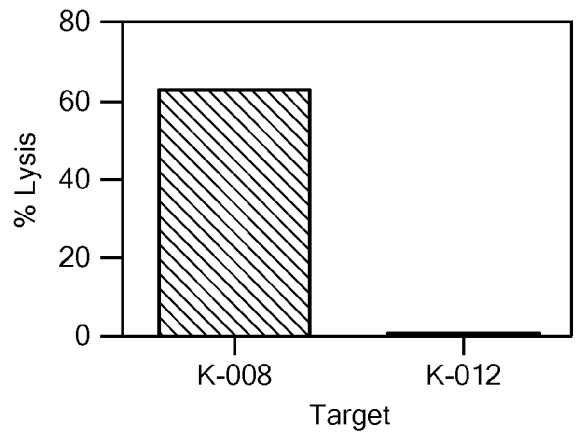
FIG. 12 is a chart showing that vaccination with irradiated GM-CSF-secreting melanoma cells stimulates cytokine production by peripheral blood lymphocytes.
FIG. 13 is a graph demonstrating the potent cytotoxicity of tumor infiltrating lymphocytes from a vaccinated patient.
FIG. 14 is a chart showing cytokine production by tumor infiltrating lymphocytes from a vaccinated patient.

The functional properties of the lymphocytes infiltrating the metastatic lesions were examined in two patients and found to be comparable. When single-cell suspensions of the excised metastases were introduced into culture in the presence of low doses of IL-2 (10 U/ml), the inflammatory cells lysed all of the residual, viable melanoma cells. To quantify cytotoxicity in a more formal way, we established additional primary cultures of the explanted metastases in which the non-adherent, inflammatory cells were removed; viable melanoma cells could be propagated in this way. Briefly, tumor infiltrating lymphocytes obtained from an abdominal wall metastasis removed following vaccination were cultured for one week with autologous melanoma cells (derived from the resected metastasis) in the presence of 10 U/ml IL-2. A four hour $^{51}$Cr release assay against the autologous tumor (KOO8) and a second melanoma line (effector:target ratio of 50:1) derived from another patient (K012, differing MHC class I profile) was performed. When the tumor infiltrating lymphocytes (bulk-cultured for one week with the autologous melanoma cells plus 10 U/ml IL-2) were tested in a standard 4 hour cytotoxicity assay against the explanted melanoma cells, highly significant lysis of the autologous melanoma cells, but not melanoma cells derived from another patient (differing MHC profile), was observed (FIG. 13).

The tumor infiltrating lymphocytes also demonstrated the ability to produce a broad range of cytokines in response to the autologous melanoma cells, a property which likely contributed to the enhanced T cell cytotoxicity and the prominent anti-tumor plasma cell response. ELISA analysis of the conditioned medium obtained by co-culturing the tumor infiltrating lymphocytes and autologous melanoma cells for one week in the presence of 10 U/ml of IL-2 revealed substantial levels of IL-4, IL-5, IL-6, IL-10, GM-CSF, and γ-interferon, but not TNF-β (FIG. 14; "Metastasis" refers to tumor cells cultured alone; similar results were found with a second patient examined). This cytokine profile indicates the coordinate expression of gene products which are associated with both Th1 and Th2 cells and suggests that multiple lymphocyte effector mechanisms can result in potent anti-tumor immune responses. Moreover, the substantial secretion of IL-10 is provocative, given the widely held view that this molecule is primarily immunosuppressive.

To determine whether the plasma cell infiltration of the metastatic lesions resulted in the generation of antibodies recognizing melanoma cells, we performed immunoblotting analysis using autologous melanoma cell lysates and sera obtained at various times during vaccination. Melanoma cell lysates were electrophoresed on 4-12% SDS-polyacrylamide gradient gels and immunoblotted with 1:100 dilutions of autologous serum obtained at various times during treatment. Membranes were developed with an alkaline phosphatase-conjugated anti-human IgG, Fcγ-specific antibody. Immunization stimulated the enhanced production of IgG anti-melanoma antibodies in seven patients examined thus far (FIG. 15; A, pre-treatment; B, one month after starting vaccination; C, two months after starting vaccination; D, three months after starting vaccination; similar results were obtained with six additional patients; increased reactivity was specific for autologous cells, as testing of allogeneic cell lysates revealed different patterns of reactivity). The reactivity of post-vaccination sera was characterized both by increased recognition of proteins detected by pre-immunization sera and the recognition of proteins not detected by pre-immunization sera.

Figures 15, 16:
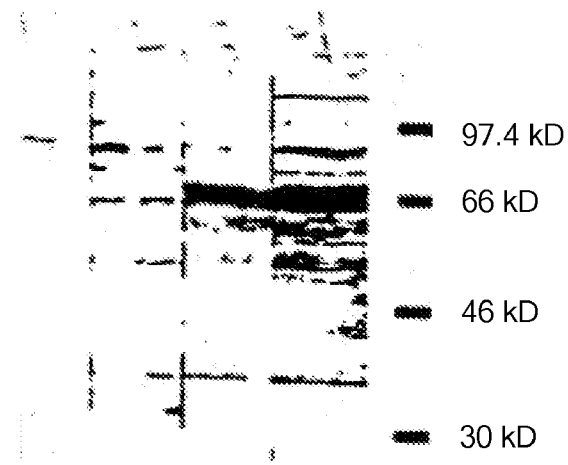
FIG. 15 is a Western blot demonstrating that vaccination with irradiated GM-CSF-secreting melanoma cells stimulates anti-melanoma antibody responses.
FIG. 16 is a chart that showing that vaccination with irradiated GM-CSF-secreting melanoma cells stimulates anti-melanoma antibody responses.

The induction of IgG antibodies recognizing surface melanoma cell determinants was also demonstrated in these patients by flow cytometry analysis. Briefly, melanoma cell lines were stained with 1:100 dilutions of sera obtained before and after vaccination, developed with an anti-human IgG, Fcγ-specific antibody, and analyzed by flow cytometry. Changes in reactivity as a function of vaccination are reported in FIG. 16 ("M," cell line established from a metastasis removed following treatment; "V," cell line established from a metastasis used to prepare the vaccine; +++, strong shift between pre- and post-immunization sera; ++, intermediate shift; +, small shift; ½+, borderline shift; 0, no shift; ND, not determined). Significant augmentation of reactivity to cultured melanoma cells as a function of vaccination was observed (FIG. 16). The specificity profiles of the antibodies elicited by immunization suggest the existence of several independent antigens.

Clinical Outcome

According to standard clinical criteria, one partial response (shrinkage of subcutaneous lesions), one mixed response, and three minor responses were observed. Three patients remain free of disease with follow-up of 33, 33, and 17 months, respectively; two were rendered disease-free by surgery (pathologic examination showed brisk lymphocyte and plasma cell infiltration with extensive tumor necrosis); one underwent radiation therapy to a scapular metastasis during vaccine preparation. Prior to beginning immunization, these patients had developed multiple new metastatic lesions.

Isolation of Melanoma Antigen-Encoding Clones Using Phage Expression Libraries

Library Construction

Polyadenylated mRNA is isolated using guanidinium isothiocyanate phenol-chloroform extraction in the presence of β-mercaptoethanol (Chomczynski and Sacchi, *Anal Chem.*, 162:156-159, 1987) followed by oligo(dT)-cellulose chromatography (Stratagene). Expression libraries are constructed using the lambda-derived unidirectional cloning vector UniZap according to procedures developed by the manufacturer (Stratagene). In brief, mRNA is reverse-transcribed with Moloney murine leukemia virus reverse transcriptase and 5-methyl dCTP using an oligo(dT) linker primer containing an Xho I site. The 5-methyl dCTP leads to methylation of the first strand, protecting it from digestion with Xho I. To generate the second cDNA strand, RNase H is used to nick the RNA strand; these breaks then serve as primers for DNA polymerase I to nick-translate the second strand of the cDNA. For the second strand synthesis dCTP (un-methylated) is used, so that the Xho I sites in the linker are accessible for digestion. The cDNA is then blunted with Pfu DNA polymerase and EcoR I adapters are ligated. The adapters are phosphorylated only on the blunt side to minimize their annealing to one another. A kinase reaction is then performed on the ligated adaptors so that the cDNA will be able to be cloned into the vector. Xho I digestion is carried out, resulting in fragments with 5' EcoR I and 3' Xho I ends. The cDNA is size fractionated on a Sephacryl S-500 column (we use fragments of 1200 base pairs and larger). The fractionated cDNA is then ligated into the UniZap vector and packaged into viral particles using Gigapack III gold extracts. The vector is initially propagated in XL1-Blue MRF' bacteria which are McrA⁻, McrB⁻ and which therefore will not restrict the hemimethylated DNA. It will be appreciated, by those of skill in the art, that analogous methods for isolating polyadenylated mRNA and constructing expression libraries may be used.

Isolation of Tumor Antigen Clones by Expression Library Screening Using Antibodies For immunologic screening, the closed insert is expressed as a fusion protein in *E. coli* using the beta-galactosidase promoter in the vector. The episome in XL1-Blue MRF' bacteria contains the lac repressor, which blocks transcription from the lacZ promoter in the absence of the inducer IPTG (isopropyl-1-thio-β-D-galactopyranoside) and thereby prevents potential toxicity of some inserts which might result in the inhibition of phage replication. Plated phage ($5 \times 10^4$ plaques per 150-cm dish) are propagated at 42° C. for 3.5 hours and then induced with IPTG treated membranes (Schleicher and Schuell) for four hours at 37° C. Replicate lifts are prepared. Membranes are then washed extensively with TTBS and blocked overnight in 5% w/v non-fat dry milk in PBS. Membranes are screened at room temperature overnight with various dilutions of patient post-vaccination serum in TTBS (to date we have tested 1:500, 1:1500, and 1:5000 with equivalent results). The serum is extensively pre-absorbed against lambda lysate of *E. coli*. The membranes are again extensively washed and then probed with a 1:1000 dilution of alkaline phosphatase conjugated anti human IgG Fc-specific (Jackson) which has also been extensively preabsorbed against lambda lysate of *E. coli*. Membranes are then developed with NBT and BCIP (Promega). Positive plaques are purified through secondary and tertiary screenings.

pBluescript phagemid can be removed from the UniZap vector by infection with a helper phage that allows excision to occur (Short et al., *Nuc. Acids Res.* 16:7583-7600, 1988; Alting-Mees et al., *Meth. Enzymol.* 216:483-495, 1992). Since this helper phage cannot replicate in a nonsuppressing host (SOLR cells) due to the presence of an amber mutation, simple purification of the excised phagemid is possible. The excised phagemids are then sequenced with T7 and T3 primers according to the instructions provided for the Sequenase kit. Sequences are compared against those in sequence databases using the BLAST and BEAUTY programs to determine whether they are related to or identical to known genes (Altschul et al., *J. Mol. Biol.*, 215:403-410, 1991; Worley et al., *Genome Res.*, 5:173-184, 1995). Full length cDNA sequences are then obtained using RACE (Clontech) to amplify the 5' and 3' ends (Frohman et al., *Proc. Natl. Acad. Sci. USA*, 85:8998-9002, 1988).

The expression profiles of melanoma antigens are assessed by Northern analysis or RT-PCR using a panel of melanoma tumor lines, cloned melanocytes (obtained from Clontech), various tumor tissues, and normal tissue obtained from autopsy material. The sequence of the normal counterpart is determined to delineate whether any mutation is associated with the tumor. For Northern blot analysis, 10 μg of total RNA prepared by guanidinium-isothiocyanate phenol extraction (TRIZOL, Gibco BRL) is electrophoresed in a 1% agarose formaldehyde gel and transferred to Zetabind membranes. We use Stratagene QuikHyb for hybridization in a hybridization oven at 65° C. Membranes are probed with a cDNA probe and β-actin probe labeled with $^{32}$P to high specific activity by the random hexamer method. Membranes are then washed twice with 2× standard saline citrate (SSC)/0.1% SDS at 60° C. for 15 minutes and then once with 0.1×SSC at 60° C. for 30 minutes. The membranes are developed by autoradiography. For RT-PCR analysis, 2 μg of total RNA is reverse-transcribed in a total volume of 20 μl with 4 μl of 5× reverse transcriptase buffer (Gibco BRL), 2 μl of a 20 mM solution of oligo (dT) primers, 20 U of RNasin (Promega), 2 μl of 0.1 M dithiothreitol, and 200 U of MoMLV reverse transcriptase (Giobco BRL). After heat killing the enzyme, 1 μl of 0.1 M RNase H (Pharmacia) is added and the reaction performed for 20 minutes at 37° C. One twentieth of the sample is then used in PCR reactions as follows: 5.0 μl 10×PCR buffer (350 mM KCl, 9 mM MgCl$_2$, 0.01% gelatin), 1 μl dNTPs, 1 μl 5' primer, 1 μl 3' primer, 0.5 μl Taq DNA polymerase, water to 50 μl. Typically, such PCR reactions are incubated for 30 cycles of 30 sec. at 95° C., 60 sec. at 55° C., and 2 minutes at 72° C.

Use of this screening method has allowed us to isolate clones encoding the tumor antigens described above, i.e., TRAAM, TPR/UBP3, UBP3, BRAP-2/H-ATPase, KOO8-1, MAIAP, Gene AS, BR-1, BR-2, KIAA0603, TPR, NOR-90, and BRAP-2.

Isolation of Tumor Antigen Clones by Expression Library Screening Using Cytotoxic T Cells In addition to antibody-based approaches for identifying novel tumor antigens revealed by vaccination with autologous, GM-CSF-secreting tumor cells, patient cytotoxic T lymphocytes (CTLs) may be used to isolate tumor antigen-encoding clones from expression libraries, using the cloning strategy developed by Boon et al. (*Ann. Rev. Immunol.* 12:337-365, 1994).

CTL clones may be obtained by the protocol of Herin et al. (*Int. J. Cancer,* 39:390-396, 1987). In brief, $1 \times 10^6$ tumor infiltrating lymphocytes are cultured in 24 well dishes with $1 \times 10^5$ irradiated, autologous melanoma cells in 2 ml of culture medium (DME plus 10 mM HEPES buffer, 10% fetal calf serum, 2 mM glutamine, $2 \times 10^{-5}$ M β-mercaptoethanol, minimal essential amino acids and antibiotics). On day three, 25 U/ml IL-2 is added and on day seven, cultures are re-stimulated. This process is repeated for four weeks, after which responding lymphocytes are transferred in 200 μl of medium to 96 well dishes at 1 cell per well together with 3000 irradiated autologous melanoma cells and $10^5$ irradiated allogeneic EBV-immortalized blasts as feeders. T cell functional responses evoked in response to tumor cells, such as cytotoxicity, proliferation, or cytokine production (such as GM-CSF and TNF-α) is then evaluated; such assays are well-known in the art.

Plasmid DNA from mammalian expression libraries cloned into the vector pCDM8 is divided into multiple pools and introduced into COS cells by DEAE-dextran precipitation, along with an expression plasmid encoding the relevant MHC class I molecule. The transfected COS cells are incubated for 48 hours at 37° C. and then co-cultured with lymphocytes plus IL-2. 24 hours later, tumor-specific T cell functional responses such as cytotoxicity, proliferation, or cytokine production (such as GM-CSF and TNF-α) are evaluated. DNA is extracted from transfected COS cells inducing responses from CTLs and the procedure is repeated until individual cDNA clones are obtained. The cDNA inserts are sequenced and further analyzed as described above.

The T cell antigenicity of tumor antigens isolated by the antibody screening method may be determined using the T cell functional assays described above. Similarly, tumor antigens identified by cytotoxic T cell-based screens may be tested for their humoral immunogenicity by testing the reactivity of patient sera to such antigens.

Determination of Tumor Antigen Immunogenicity

The relative immunogenicity of a tumor antigen cloned by the method of the invention may be tested by sub-cloning the tumor antigen-encoding cDNA into an expression vector (e.g., plasmid or viral), introducing the cDNA-bearing vector into a suitable cell line (e.g., by transfection, electroporation, or transduction), making lysates from the tumor antigen-expressing cells, and subjecting the lysates to Western blot analysis or ELISA using sera from patients vaccinated with the tumor antigen or with whole tumor cells.

Construction of Recombinant Retroviral Vectors Expressing Tumor Antigens

To clone cDNA sequences into pMFG (Dranoff et al., *Proc. Natl. Acad. Sci., U.S.A.*, 90:3539-3543, 1993), we construct oligonucleotides encompassing the ATG of the insert and adapt it into the vector Nco I site (unless a natural Nco I or BspHI site exists at the ATG of the cDNA). We then clone the remainder of the insert into the BamH I site of the pMFG vector in such a way so as to include as little sequence downstream of the stop codon as practical. After the integrity of the final construct is confirmed by sequencing, the plasmid is co-transfected by calcium phosphate precipitation with pSV2NEO into CRIP cells as previously described (Danos et al., *Proc. Natl. Acad. Sci. U.S.A.* 85:6460-6464, 1988). G418 selection is instituted at 36 hours, resistant clones picked, expanded, and eventually titered on NIH 3T3 cells using Southern analysis. The infected CRIP tumor cells are tested for the presence of helper virus using a very sensitive hisD mobilization assay (Hartman et al., *Proc. Natl. Acad. Sci. U.S.A.* 85:8047-8051, 1988). The method involves the construction of an indicator NIH 3T3 cell line transfected with a packageable retrovirus encoding the hisD gene (histidinol dehydrogenase from *Salmonella typhimurium*). Mammalian cells, including NIH 3T3 fibroblasts, when grown in histidine-free medium supplemented with histidinol, die from the combined effects of histidine deficiency and the inhibitory activities of histidinol on histidyl-tRNA synthetase. The expression of hisD, which catalyzes the dehydrogenation of histidinol to histidine, rescues transfected cells from this toxicity. Medium from the infected tumor cells is placed on the hisD transfected indicator cells. The medium is then harvested from the exposed hisD transfected cells and then placed on control NIH3T3 cells. The generation of hisD resistant cells in this control population is assessed. If helper virus is present in the infected tumor lines being tested, the retroviral vector encoding hisD is transferred to the control NIH 3T3 cells, giving rise to cells that are resistant when grown under histidinol selection.

Measurement of Antibody Responses

The development of antibody responses in patients vaccinated with tumor antigens ro with whole tumor cells may be assessed by Western analysis of CRIP cell lysates or other mammalian cell lines. Comparable dilutions of sera are evaluated; if reactivity is present pre-immunization, additional dilutions of post-vaccination sera may be examined in an attempt to perform semi-quantitative analysis. For immunoblotting, we prepare cell lysates as follows. Adherent cells are rinsed in PBS and then lysed in 300 μl of lysate buffer (138 mM NaCl, mM $NaH_2PO_4$, 1.5 mM $KH_2PO_4$, 2.7 mM KCl, pH 7.2, supplemented with 0.05 M aminocaproic acid, 100 μg/ml soybean trypsin inhibitor, 10 μg/ml leupeptin, 1 μg/ml pepstatin, 0.5% Nonidet P-40) per 10 cm dish. A Bradford assay is performed to determine protein content (Bradford, Anal. Biochem., 72:248-254, 1976). Prior to gel electrophoresis, the lysates are preabsorbed with normal sera. To do this, 100 μl of a 50% Protein A Sepharose bead suspension (Pharmacia) is washed with PBS and lysate buffer twice. 20 μl of normal human serum and 100 μl of lysate buffer are added to the beads on ice for 30 minutes and then the beads are washed four times with lysate buffer. Protein lysates from control CRIP cells and transfected CRIP lines are incubated with the beads at 4° C. overnight with gentle shaking. The samples are then centrifuged and the supernatants harvested.

The proteins (500-1000 μg per sample) are resolved on a 12.5% SDS-polyacrylamide gel under reducing conditions. The samples are transferred to Immobilon membranes via semi-dry electrophoretic transfer in CAPS buffer. The membranes are blocked overnight (5% w/v non-fat dry milk in PBS), washed twice in TTBS (50 mM Tris (Tris-hydroxymethyl-aminomethane), 138 mM NaCl, 2.7 mM KCl, 0.05% w/v Tween 20, pH 8.0), and then probed with patient serum (1:50 dilution) in TTBS at 4° C. overnight. The membrane is then washed with TTBS and incubated for one hour at room temperature with a 1:1000 dilution in TTBS of an anti-human IgG, Fc gamma-specific antibody conjugated to alkaline phosphatase (Jackson Immuno Research). Lastly, the membrane is extensively washed with TTBS and then developed with nitroblue tetrazolium (NBT) and 5-bromo-4-chloro-3-indolyl phosphate (BCIP) (Promega).

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

What is claimed is:

1. An isolated MAIAP nucleic acid, wherein said nucleic acid encodes the MAIAP polypeptide set forth in SEQ ID NO: 12.

2. The MAIAP nucleic acid of claim 1, wherein said nucleic acid comprises the nucleotide sequence set forth in SEQ ID NO: 11.

3. The nucleic acid of claim 2, wherein said nucleic acid is DNA or RNA.

4. A vector comprising the nucleic acid of claim 2.

5. An isolated cell comprising the nucleic acid of claim 2.

* * * * *